(12) United States Patent
Sangi

(10) Patent No.: US 9,278,975 B2
(45) Date of Patent: Mar. 8, 2016

(54) PYRAZOLO[1,5-A]PYRIMIDINES AS ANTIVIRAL AGENTS

(71) Applicant: Gilead Sciences, Inc., Foster City, CA (US)

(72) Inventor: Michael Sangi, Oakland, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 14/566,340

(22) Filed: Dec. 10, 2014

(65) Prior Publication Data

US 2015/0166546 A1    Jun. 18, 2015

Related U.S. Application Data

(62) Division of application No. 13/722,962, filed on Dec. 20, 2012, now Pat. No. 8,946,238.

(60) Provisional application No. 61/579,625, filed on Dec. 22, 2011, provisional application No. 61/618,510, filed on Mar. 30, 2012.

(51) Int. Cl.
| | |
|---|---|
| C07D 487/04 | (2006.01) |
| A61K 31/519 | (2006.01) |
| C07D 487/08 | (2006.01) |
| A61K 31/538 | (2006.01) |
| C07F 9/6561 | (2006.01) |
| A61K 31/675 | (2006.01) |
| A61K 45/06 | (2006.01) |

(52) U.S. Cl.
CPC ............ *C07D 487/04* (2013.01); *A61K 31/519* (2013.01); *A61K 31/538* (2013.01); *A61K 31/675* (2013.01); *A61K 45/06* (2013.01); *C07D 487/08* (2013.01); *C07F 9/6561* (2013.01)

(58) Field of Classification Search
CPC .................................................... C07D 487/04
See application file for complete search history.

(56) References Cited

U.S. PATENT DOCUMENTS

| 6,342,501 | B1 | 1/2002 | Townsend et al. |
|---|---|---|---|
| 7,304,068 | B2 | 12/2007 | Gudmundsson et al. |
| 8,486,938 | B2 | 7/2013 | Babaoglu et al. |
| 8,809,330 | B2 | 8/2014 | Babaoglu et al. |
| 8,946,238 | B2 | 2/2015 | Boojamra et al. |
| 8,980,878 | B2 | 3/2015 | Siegel et al. |
| 2007/0287700 | A1 | 12/2007 | Bond et al. |
| 2010/0215616 | A1 | 8/2010 | Romine et al. |
| 2010/0316607 | A1 | 12/2010 | Or et al. |
| 2011/0319412 | A1 | 12/2011 | Sakagami et al. |
| 2013/0164280 | A1 | 6/2013 | Boojamra et al. |
| 2013/0273037 | A1 | 10/2013 | Siegel et al. |
| 2014/0072554 | A1 | 3/2014 | Babaoglu et al. |
| 2014/0154240 | A1 | 6/2014 | Babaoglu et al. |
| 2015/0166546 | A1 | 6/2015 | Boojamra et al. |

FOREIGN PATENT DOCUMENTS

| CN | 1297447 A | 5/2001 |
|---|---|---|
| DE | 10247271 A1 | 8/2004 |
| WO | WO-96/00730 A1 | 1/1996 |
| WO | WO-99/41253 A1 | 8/1999 |
| WO | WO-00/42043 A1 | 7/2000 |
| WO | WO-01/46189 A1 | 6/2001 |
| WO | WO-03/078435 A1 | 9/2003 |
| WO | WO-03/095455 A2 | 11/2003 |
| WO | WO-2005061513 A1 | 7/2005 |
| WO | WO-2007077186 A1 | 7/2007 |
| WO | WO-2008070447 A2 | 6/2008 |
| WO | WO-2009/076679 A2 | 6/2009 |
| WO | WO-2009079011 A1 | 6/2009 |
| WO | WO-2009106539 A1 | 9/2009 |
| WO | WO-2009126691 A1 | 10/2009 |
| WO | WO-2010033701 A2 | 3/2010 |
| WO | WO-2010/048950 A1 | 5/2010 |
| WO | WO-2010065674 A1 | 6/2010 |
| WO | WO-2010075376 A2 | 7/2010 |
| WO | WO-2010080357 A1 | 7/2010 |
| WO | WO-2010099527 A1 | 9/2010 |
| WO | WO-2010101246 A1 | 9/2010 |
| WO | WO-2010144646 A2 | 12/2010 |
| WO | WO-2010148006 A1 | 12/2010 |
| WO | WO-2011/015658 A1 | 2/2011 |
| WO | WO-2011059887 A1 | 5/2011 |
| WO | WO-2011099832 A2 | 8/2011 |
| WO | WO-2011/149856 A1 | 12/2011 |
| WO | WO-2011/163518 A1 | 12/2011 |
| WO | WO-2012/012776 A1 | 1/2012 |
| WO | WO-2013/096681 A1 | 6/2013 |
| WO | WO-2013/158776 A1 | 10/2013 |

OTHER PUBLICATIONS

Office Action mailed Dec. 4, 2012 for U.S. Appl. No. 13/167,618.
Notice of Allowance mailed Mar. 12, 2013 for U.S. Appl. No. 13/167,618.
Notice of Allowability mailed Jun. 18, 2013 for U.S. Appl. No. 13/167,618.
Office Action mailed Mar. 12, 2014 for U.S. Appl. No. 13/905,410.
Office Action mailed Sep. 2, 2014 for U.S. Appl. No. 13/905,410.
Notice of Allowance and Fee(s) Due dated Nov. 10, 2014 for U.S. Appl. No. 13/905,410.
2nd Notice of Allowance and Fee(s) Due dated Jan. 21, 2015 for U.S. Appl. No. 13/905,410.
Notice of Allowance and Fee(s) Due dated Dec. 13, 2013 for U.S. Appl. No. 14/069,685.
2nd Notice of Allowance and Fee(s) Due dated Apr. 14, 2014 for U.S. Appl. No. 14/069,685.

(Continued)

*Primary Examiner* — Paul Zarek
(74) *Attorney, Agent, or Firm* — Steven R. Eck

(57) ABSTRACT

The invention provides compounds and pharmaceutically acceptable salts and esters and compositions thereof, for treating viral infections. The compounds and compositions are useful for treating Pneumovirinae virus infection including Human respiratory syncytial virus infections.

1 Claim, No Drawings

(56) References Cited

OTHER PUBLICATIONS

Notice of Allowability mailed May 27, 2014 for U.S. Appl. No. 14/069,685.
Notice of Alowance and Fee(s) Due dated Jun. 29, 2015 for U.S. Appl. No. 14/566,340.
Restriction Requirement, dated Dec. 6, 2013, for U.S. Appl. No. 13/865,069.
Office Action, dated Mar. 17, 2014, for U.S. Appl. No. 13/865,069.
Final Rejection, dated Aug. 4, 2014, for U.S. Appl. No. 13/865,069.
Notice of Allowance and Fees Due, dated Oct. 22, 2014, for U.S. Appl. No. 13/865,069.
International Search Report and Written Opinion for PCT International Application No. PCT/US2011/041688, mailed Sep. 30, 2011 (11 pages).
International Preliminary Report on Patentability for PCT International Application No. PCT/US2011/041688, dated Dec. 28, 2012 (6 pages).
International Search Report for PCT International Application No. PCT/US2012/071065, mailed Mar. 11, 2013 (3 pages).
Written Opinion for PCT International Application No. PCT/US2012/071065, mailed Mar. 11, 2013 (7 pages) (rec'd Jan. 16, 2014 fr EPO as ISA).
International Preliminary Report on Patentability for PCT International Applicaiton No. PCT/US2012/071065, dated Jul. 3, 2014 (9 pages).
International Search Report and Written Opinion for PCT International Application No. PCT/US2013/037001, mailed Aug. 29, 2013 (13 pages).
International Preliminary Report on Patentability for PCT International Application No. PCT/US2013/037001, mailed Oct. 30, 2014. (10 pages).
Search Report for ARIPO Application No. AP/P/2013/006686, dated Nov. 13, 2014.
Patent Examination Report No. 1, dated Mar. 7, 2014, for Australian Patent Application No. 2011270798.
Patent Examination Report No. 2, dated Aug. 26, 2014, for Australian Patent Application No. 2011270798.
Office Action issued by the Bolivian Patent Office for Application No. SP-0188-2011, dated Apr. 21, 2015-Non-English w/Agent Summary.
Statement of Bolivian Opposition, Jan. 29, 2013, for BO Patent Application No. SP-0188-2011.
Office Action, rec'd Apr. 2, 2015 for CL Application No. CL3632-2012 (5 pages) (in SP).
Notification of the First Office Action, Mar. 3, 2014, for CN Patent Application No. 201180030620.4 (with English translation).
Notification of the Second Office Action, Nov. 4, 2014, for CN Patent Application No. 201180030620.4 (with English translation).
Notification of the Third Office Action, Apr. 2, 2015, for CN Patent Application No. 201180030620.4 (with English translation), 11 pages.
Office Action for Columbian Patent Application No. 12-217,437 dated Jan. 3, 2014 (no refs cited).
Eurasian Office Action for EA Patent Application No. 201291172 (with English translation), dated Jan. 10, 2014.
Eurasiam 2nd Office Action for EA Patent Application No. 201291172 (with English translation), rec'd Aug. 22, 2014, dated Jun. 10, 2014.
Eurasian 3rd Office Action for EA Patent Application No. 201291172 (with English translation), rec'd Feb. 3, 2015, dated Jan. 16, 2015.
Notification of readiness to grant a Eurasian Patent for EA Patent Application No. 2012291172, mailed Apr. 20, 2015.
Communication pursuant to Article 94(3) EPC for EP Application No. 11729018.9, dated May 23, 2014.
Communication under Rule 71(3) EPC for EP Application No. 11729018.9, dated Jul. 8, 2015.
JP Application No. 2013-516776, Office Action dated Apr. 15, 2015 (English translation).
Office Action for MX Patent Application No. MX/a/2012/015292, dated Mar. 31, 2014.
First Examination Report for NZ Patent Application No. 604345, dated Aug. 9, 2013.
Further Examination Report for NZ Patent Application No. 604345, dated Nov. 24, 2014.
First Examination Report for NZ Patent Application No. 704655, dated Feb. 27, 2015.
Substantive Examination Report for PH Patent Application No. 1/2012/502528, dated Jul. 16, 2014 (rec'd Aug. 6, 2014 Cooley).
Substantive Examination Report for PH Patent Application No. 1/2012/502528, dated Dec. 23, 2014 (rec'd Jan. 12, 2015 by Cooley).
Pakistan Examination Report for PK Patent Application No. 469/2011, dated Jul. 26, 2012.
Taiwan Office Action with Search Report (+ English translation) for TW Patent Application No. 100122237, dated Jan. 7, 2014.
Taiwan Office Action for Taiwan Patent Application No. 100122237, dated Jun. 13, 2014.
Office action Issued by the Ukranian Patent Office for Application No. a 2012 13827, dated Jul. 7, 2015, 6 pages (with English Translation).
Vietnam National Office of Intellectual Property (NOIP)'s Opinion dated Jun. 30, 2014, with English Translation for VN Patent Application No. 1-2013-00161.
Communication pursuant to Rules 161(1) and 162 EPC dated Aug. 7, 2014, for EP Patent Application No. 12814092.8.
First Examination Report for New Zealand Application No. 625737 dated Mar. 27, 2015.
EPO Communication in EP Application No. EP 13718996.5 dated Dec. 23, 2014.
Notification Prior to Examination for Israeli Patent Application No. 235062, dated Jan. 1, 2015.
Asinex Compounds (Nov. 2008-Mar. 2011) Alsnex Ltd., 20 Geroev Panfilovtzev Str., Bldg. 1 Moscow 125480, Russia, 27 pages.
Boulatov, Roman et al., "Functional Analogues of the Dioxygen Reduction Site in Cytochrome Oxidase: Mechanistic Aspects and Possible Effects of CuB," J. Am. Soc. 124(10):11923-11935, 2002.
Chapman et al., "RSV604, a Novel Inhibitor of Respiratory Syncytial Virus Replication," Antimicrobial Agents and Chemotherapy 51(9):3346-3353, 2007.
"Chemivate Limited Screening Compounds," Chemivate Limited, Jun. 2007 XP002708502, retrieved from the Internet: URL:http://chemivate.com/chemivate/Downloads/ChemivateJun07.pdf [retrieved on Aug. 1, 2013].
Cihlar et al., "Design and Profiling of GS-9148, a Novel Nucleotide Analog Active against Nucleoside-Resistant Variants fo Human Immunodeficiency Virus Type 1, and its Orally Bioavailable Phosphonoamidate Prodrug, GS-9131," Antimicrobial Agents and Chemotherapy 52(2):655-665, 2008.
Cockerill, G. Stuart et al., "The Discovery and development of a novel inhibitor of RSV," Division of Mewdlcinal Chemistry Program, 231st ACS National Meeting, Atlanta, GA, 2006.
Dall'Aqua, William F. et al. "Properties of Human IgG1s Engineered for Enhanced Binding to the Neonatal Fc Receptor (FcRn)," *The Journal of Biological Chemistry*, 281(33):23514-23524, 2006.
Database Chemcats (Online), Acciession No. 0056408351, Chemical Abstract Service, Columbus, Ohio, US, XP002658304, 15 pages, 2011.
Dominy, Jr., John E., "Synthesis of Amino Acid Cofactor in Cysteine Dioxygenase Is Regulated by Substrate and Represents a Novel Post-translation Regulation of Activity," Journal of Biological Chemistry, 283(18):12188-12201, 2008.
Douglas et al., "Small Molecules VP-14637 and JNJ-2408068 Inhibit Respiratory Syncytial Virus Fusion by Similar Mechanisms," Antimicrobial Agents and Chemotherapy 49(6):2460-2466, 2005.
Grimes et al., "Copper(II)-Catalyzed Conversion of Aryl/Heteroaryl Boronic Acids, Boronates, and Trifluoroborates into the Corresponding Azides: Substrate Scope and Limitations," *Synthesis (Stuttg)* 2010(9):1441-1448.
Morrison et al., "Salts of Amines," Organic Chemistry, 6th Edition, p. 823, 1992.
Pandey, Gunjan et al., "Branching of o—nitrobenzoate degradation pathway in Arthrobacter protophormiae RKJI 00: identification of new intermediates," *FEMS Microbiology Letters* 229(2):231-236, 2003.

(56) References Cited

OTHER PUBLICATIONS

Roymans et al., "Treatment of Respiratory Synctial Virus Infection: Past, Present and Future," http://cdn.intechopen.com/pdfs-wm/24399.pdf, pp. 197-234, 2011.

Sandritter et al., "Part 1: Respiratory syncytial virus-immunoglobulin intravenous (RSV-IGIV) for respiratory syncytial viral infections," J. Pediatric Helath Care, 11:6:284-291, Nov.-Dec. 1997.

Sin et al., "Part 7: Structure-Activity relationships associated with a series of isatin oximes that demonstrate antiviral activity in vivo," Biooganic & Medicinal Chemistry Letters 19:4857-4862, 2009.

Sun et al., "Respiratory Syncytial Virus Entry Inhibitors Targeting the F Protein," Viruses 5:211-225, 2013.

The Random House Distionary of the English Language, Second Edition, Definition of "obligate"(1987).

Wu, H. et al., In: Current Topics in Microbiology and Immunology, Dessain, S.K. (ed.), Springer-Verlag Berlin Heidelberg, p. 118, 2008.

PYRAZOLO[1,5-A]PYRIMIDINES AS ANTIVIRAL AGENTS

CROSS REFERENCE TO RELATED APPLICATIONS

This application is a divisional of U.S. patent application Ser. No. 13/722,962, filed Dec. 20, 2012, which claims the benefit under 35 U.S.C. §119(e) of U.S. Provisional Application No. 61/579,625, filed Dec. 22, 2011, and U.S. Provisional Application No. 61/618,510, filed Mar. 30, 2012. The foregoing applications are incorporated herein by reference in their entireties.

BACKGROUND

Pneumovirinae viruses are negative-sense, single-stranded, RNA viruses that are responsible for many prevalent human and animal diseases. The Pneumovirinae subfamily of viruses is a part of the family Paramyxoviridae and includes human respiratory syncytial virus (HRSV). Almost all children will have had an HRSV infection by their second birthday. HRSV is the major cause of lower respiratory tract infections in infancy and childhood with 0.5% to 2% of those infected requiring hospitalization. The elderly and adults with chronic heart, lung disease or those that are immunosuppressed also have a high risk for developing severe HRSV disease (http://www.cdc.gov/rsv/index.html). No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumovirinae therapeutics.

SUMMARY

Provided herein are methods and compounds for the treatment of infections caused by the Pneumovirinae virus family.

Accordingly, one embodiment provides a compound of formula I:

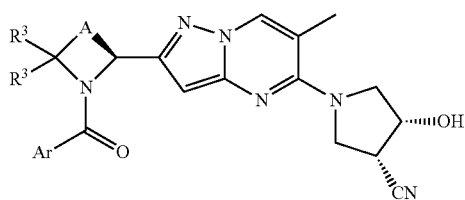

I or a salt or ester, thereof;
wherein:
A is $—(C(R^4)_2)_n—$ wherein any one $C(R^4)_2$ of said $—(C(R^4)_2)_n—$ may be optionally replaced with $—O—$, $—S—$, $—S(O)_p—$, NH or $NR^a$;
n is 3, 4, 5 or 6;
each p is 1 or 2;
Ar is a $C_2$-$C_{20}$ heterocyclyl group or a $C_6$-$C_{20}$ aryl group, wherein the $C_2$-$C_{20}$ heterocyclyl group or the $C_6$-$C_{20}$ aryl group is optionally substituted with 1, 2, 3, 4 or 5 $R^6$;

each $R^3$, $R^4$ and $R^6$ is independently H, oxo, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, $—C(=O)R^{11}$, $—C(=O)OR^{11}$, $—C(=O)NR^{11}R^{12}$, $—C(=O)SR^{11}$, $—S(O)_p(OR^{11})$, $—SO_2NR^{11}R^{12}$, $—NR^{11}S(O)_p(OR^{11})$, $NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl;

or two $R^4$ on adjacent carbon atoms, when taken together, may optionally form a double bond between the two carbons to which they are attached or may form a $(C_3$-$C_7)$cycloalkyl ring wherein one carbon atom of said $(C_3$-$C_7)$cycloalkyl ring may be optionally replaced by $—O—$, $—S—$, $—S(O)_p—$, $—NH—$ or $—NR^a—$;

or four $R^4$ on adjacent carbon atoms, when taken together, may optionally form an optionally substituted $C_6$ aryl ring;

or two $R^4$ on the same carbon atom, when taken together, may optionally form a $(C_3$-$C_7)$cycloalkyl ring wherein one carbon atom of said $(C_3$-$C_7)$cycloalkyl ring may be optionally replaced by $—O—$, $—S—$, $—S(O)_p—$, $—NH—$ or $—NR^a—$;

or two $R^6$ on adjacent carbon atoms, when taken together, may optionally form a $(C_3$-$C_7)$cycloalkyl ring wherein one carbon atom of said $(C_3$-$C_7)$cycloalkyl ring may be optionally replaced by $—O—$, $—S—$, $—S(O)_p—$, $—NH—$ or $—NR^a—$;

each $R^a$ is independently $(C_1$-$C_8)$alkyl, $(C_1$-$C_8)$haloalkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl wherein any $(C_1$-$C_8)$alkyl, $(C_1$-$C_8)$haloalkyl, $(C_2$-$C_8)$alkenyl or $(C_2$-$C_8)$alkynyl of $R^a$ is optionally substituted with one or more OH, $NH_2$, $CO_2H$, $C_2$-$C_{20}$ heterocyclyl, and wherein any aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl of $R^a$ is optionally substituted with one or more (e.g. 1, 2, 3, 4 or 5) OH, $NH_2$, $CO_2H$, $C_2$-$C_{20}$ heterocyclyl or $(C_1$-$C_8)$alkyl;

each $R^{11}$ or $R^{12}$ is independently H, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl, $(C_4$-$C_8)$carbocyclylalkyl, $—C(=O)R^a$, $—S(O)_pR^a$ or aryl$(C_1$-$C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with $—O—$, $—S—$, $—S(O)_p—$, $—NH—$, $—NR^a—$ or $—C(O)—$; and wherein each $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl or $(C_4$-$C_8)$carbocyclylalkyl of each $R^6$, $R^{11}$ or $R^{12}$ is, independently, optionally substituted with one or more (e.g. 1, 2, 3, 4 or 5) oxo, halogen, hydroxy, $NH_2$, CN, $N_3$, $N(R^a)_2$, $NHR^a$, SH, $SR^a$, $S(O)_pR^a$, $OR^a$, $(C_1$-$C_8)$alkyl, $(C_1$-$C_8)$haloalkyl, $—C(O)R^a$, $—C(O)H$, $—C(=O)OR^a$, $—C(=O)OH$, $—C(=O)N(R^a)_2$, $—C(=O)NHR^a$, $—C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $=OC(=O)R^a$, $—OP(O)(OH)_2$ or $R^a$;

provided the compound is not:

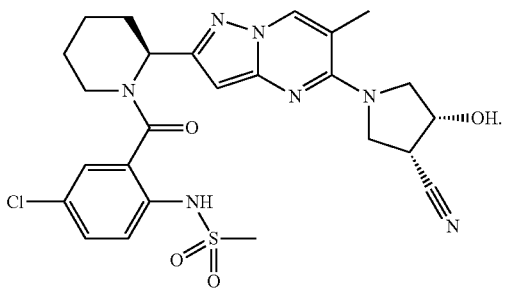

Another embodiment provides a compound of formulas 1-111 (i.e., compounds 1-111), as described in examples 1 and 2, or a salt or ester thereof.

Another embodiment provides a compound of formula I (e.g., compounds 112-209) or a stereoisomer (e.g. enantiomer, diasteromer, atropisomer) or a salt or ester thereof.

Another embodiment provides a compound of formulas 1-111 or a stereoisomer (e.g., enantiomer, diasteromer, atropisomer) or a salt or ester thereof.

Another embodiment provides a pharmaceutical composition comprising a compound of formula I or a pharmaceutically acceptable salt thereof, and a pharmaceutically acceptable carrier.

Another embodiment provides a pharmaceutical composition comprising a compound of formulas 1-111 or a pharmaceutically acceptable salt thereof, and a pharmaceutically acceptable carrier.

Another embodiment provides a method of treating a Pneumovirinae infection in a mammal (e.g., a human) in need thereof comprising administering a therapeutically effective amount of a compound of formula I or a pharmaceutically acceptable salt or ester thereof.

Another embodiment provides a method of treating a Pneumovirinae infection in a mammal (e.g., a human) in need thereof comprising administering a therapeutically effective amount of a compound of formulas 1-111, or a pharmaceutically acceptable salt or ester thereof.

Another embodiment provides a method of treating a Pneumovirinae infection in a mammal (e.g., a human) in need thereof comprising administering a therapeutically effective amount of a, tautomer, polymorph, pseudopolymorph, amorphous form, hydrate or solvate of a compound of a compound of formula I, or a pharmaceutically acceptable salt or ester thereof.

Another embodiment provides a method of treating a Pneumovirinae infection in a mammal (e.g., a human) in need thereof comprising administering a therapeutically effective amount of a, tautomer, polymorph, pseudopolymorph, amorphous form, hydrate or solvate of a compound of formulas 1-111, or a pharmaceutically acceptable salt or ester thereof.

Another embodiment provides a method of treating a respiratory syncytial virus infection in a mammal (e.g., a human) in need thereof comprising administering a therapeutically effective amount of a compound of formula I, or a pharmaceutically acceptable salt or ester thereof.

Another embodiment provides a method of treating a respiratory syncytial virus infection in a mammal (e.g., a human) in need thereof comprising administering a therapeutically effective amount of a compound of formulas 1-111, or a pharmaceutically acceptable salt or ester thereof.

Another embodiment provides a method of treating a respiratory syncytial virus infection in a mammal (e.g., a human) in need thereof comprising administering a therapeutically effective amount of a tautomer, polymorph, pseudopolymorph, amorphous form, hydrate or solvate of a compound of formula I, or a pharmaceutically acceptable salt or ester thereof.

Another embodiment provides a method of treating a respiratory syncytial virus infection in a mammal (e.g. a human) in need thereof comprising administering a therapeutically effective amount of a tautomer, polymorph, pseudopolymorph, amorphous form, hydrate or solvate of a compound of formulas 1-111, or a pharmaceutically acceptable salt or ester thereof.

Another embodiment provides a method of treating a Pneumovirinae infection in a mammal (e.g. a human) in need thereof comprising administering a therapeutically effective amount of a compound of formula I or a pharmaceutically acceptable salt or ester thereof, and a pharmaceutically acceptable diluent or carrier.

Another embodiment provides a method of treating a Pneumovirinae infection in a mammal (e.g. a human) in need thereof comprising administering a therapeutically effective amount of a compound of formulas 1-111 or a pharmaceutically acceptable salt or ester thereof, and a pharmaceutically acceptable diluent or carrier.

Another embodiment provides a method of treating a Pneumovirinae infection in a mammal (e.g. a human) in need thereof comprising administering a therapeutically effective amount of a compound of formula I or a pharmaceutically acceptable salt or ester thereof, in combination with at least one additional therapeutic agent.

Another embodiment provides a method of treating a Pneumovirinae infection in a mammal (e.g. a human) in need thereof comprising administering a therapeutically effective amount of a compound of formulas 1-111 or a pharmaceutically acceptable salt or ester thereof, in combination with at least one additional therapeutic agent.

Another embodiment provides a method of treating a Pneumovirinae infection in a mammal (e.g. a human) in need thereof, comprising administering a therapeutically effective amount of a combination pharmaceutical agent comprising:
  a) a first pharmaceutical composition comprising a compound of formula I or a pharmaceutically acceptable salt or ester thereof; and
  b) a second pharmaceutical composition comprising at least one additional therapeutic agent active against infectious Pneumovirinae viruses.

Another embodiment provides a method of treating a Pneumovirinae infection in a mammal (e.g. a human) in need thereof, comprising administering a therapeutically effective amount of a combination pharmaceutical agent comprising:
  a) a first pharmaceutical composition comprising a compound of formulas 1-111 or a pharmaceutically acceptable salt or ester thereof; and
  b) a second pharmaceutical composition comprising at least one additional therapeutic agent active against infectious Pneumovirinae viruses.

Another embodiment provides a method of treating a Pneumovirinae infection in a mammal (e.g. a human) in need thereof, comprising administering a therapeutically effective amount of a combination pharmaceutical agent comprising:
  a) a therapeutic agent selected from a compound a of formula I and pharmaceutically acceptable salts and esters thereof; and
  b) a therapeutic agent active against infectious Pneumovirinae viruses.

Another embodiment provides a method of treating a Pneumovirinae infection in a mammal (e.g. a human) in need thereof, comprising administering a therapeutically effective amount of a combination pharmaceutical agent comprising:

a) a therapeutic agent selected from a compound of formulas 1-111 and pharmaceutically acceptable salts and esters thereof; and b) a therapeutic agent active against infectious Pneumovirinae viruses.

Another embodiment provides a method of treating a respiratory syncytial virus infection in a mammal (e.g. a human) in need thereof, comprising administering a therapeutically effective amount of a combination pharmaceutical agent comprising:

a) a first pharmaceutical composition comprising a compound of formula I or a pharmaceutically acceptable salt or ester thereof; and b) a second pharmaceutical composition comprising at least one additional therapeutic agent active against infectious respiratory syncytial viruses.

Another embodiment provides a method of treating a respiratory syncytial virus infection in a mammal (e.g. a human) in need thereof, comprising administering a therapeutically effective amount of a combination pharmaceutical agent comprising:

a) a first pharmaceutical composition comprising a compound of formulas 1-111 or a pharmaceutically acceptable salt or ester thereof; and b) a second pharmaceutical composition comprising at least one additional therapeutic agent active against infectious respiratory syncytial viruses.

Another embodiment provides a method of treating a respiratory syncytial virus infection in a mammal (e.g. a human) in need thereof, comprising administering a therapeutically effective amount of a combination pharmaceutical agent comprising:

a) a therapeutic agent selected from a compound of formula I and pharmaceutically acceptable salts and esters thereof; and b) a therapeutic agent active against infectious Pneumovirinae viruses.

Another embodiment provides a method of treating a respiratory syncytial virus infection in a mammal (e.g. a human) in need thereof, comprising administering a therapeutically effective amount of a combination pharmaceutical agent comprising:

a) a therapeutic agent selected from a compound of formulas 1-111 and pharmaceutically acceptable salts and esters thereof; and b) a therapeutic agent active against infectious Pneumovirinae viruses.

Another embodiment provides a compound of formula I or a pharmaceutically acceptable salt or ester thereof, for use in medical therapy.

Another embodiment provides a compound of formulas 1-111 or a pharmaceutically acceptable salt or ester thereof for use in medical therapy.

Another embodiment provides a compound of formula I or a pharmaceutically acceptable salt or ester thereof, for use in the prophylactic or therapeutic treat a viral infection caused by a Pneumovirinae virus or a respiratory syncytial virus.

Another embodiment provides a compound of formulas 1-111 or a pharmaceutically acceptable salt or ester thereof, for use in the prophylactic or therapeutic treat a viral infection caused by a Pneumovirinae virus or a respiratory syncytial virus.

Another embodiment provides the use of a compound of formula I or a pharmaceutically acceptable salt or ester thereof, for the manufacture of a medicament useful for the treatment of a viral infection caused by a Pneumovirinae virus or a respiratory syncytial virus in a mammal (e.g. a human).

Another embodiment provides the use of a compound of formulas 1-111 or a pharmaceutically acceptable salt or ester thereof for the manufacture of a medicament useful for the treatment of a viral infection caused by a Pneumovirinae virus or a respiratory syncytial virus in a mammal (e.g. a human).

Another embodiment provides processes and novel intermediates disclosed herein which are useful for preparing a compound of formula I or a compound of formulas 1-111.

Another embodiment provides novel methods for synthesis, analysis, separation, isolation, purification, characterization, and testing of the compounds as disclosed herein.

DETAILED DESCRIPTION

Definitions

Unless stated otherwise, the following terms and phrases as used herein are intended to have the following meanings:

When trade names are used herein, applicants intend to independently include the tradename product and the active pharmaceutical ingredient(s) of the tradename product.

The term "alkyl" refers to a straight or branched hydrocarbon. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, and octyl (—($CH_2$)$_7CH_3$).

The term "alkoxy" refers to a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—C($CH_3$)$_3$ or —OtBu) and the like.

The term "haloalkyl" refers to an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —CF$_3$, —CHF$_2$, —CFH$_2$, —CH$_2$CF$_3$, and the like.

The term "alkenyl" refers to a straight or branched hydrocarbon with at least one site of unsaturation, i.e. a carbon-carbon, sp$^2$ double bond. For example, an alkenyl group can have 2 to 20 carbon atoms (i.e., C$_2$-C$_{20}$ alkenyl), 2 to 8 carbon atoms (i.e., C$_2$-C$_8$ alkenyl), or 2 to 6 carbon atoms (i.e., C$_2$-C$_6$ alkenyl). Examples of suitable alkenyl groups include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

The term "alkynyl" refers to a straight or branched hydrocarbon with at least one site of unsaturation, i.e. a carbon-carbon, sp triple bond. For example, an alkynyl group can have 2 to 20 carbon atoms (i.e., C$_2$-C$_{20}$ alkynyl), 2 to 8 carbon atoms (i.e., C$_2$-C$_8$ alkyne), or 2 to 6 carbon atoms (i.e., C$_2$-C$_6$ alkynyl). Examples of suitable alkynyl groups include, but are not limited to, acetylenic (—C≡CH), propargyl (—CH$_2$C≡CH), and the like.

The term "halogen" or "halo" refers to F, Cl, Br, or I.

The term "aryl" refers to an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

The term "arylalkyl" refers to an acyclic alkyl radical in which one of the hydrogen atoms bonded to a carbon atom, typically a terminal or sp$^a$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The term "heterocycle" or "heterocyclyl" as used herein includes by way of example and not limitation those heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

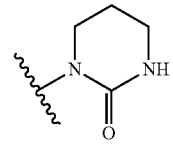 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

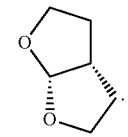

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

The term "carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

The term "cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 7 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or spiro. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, bicyclo[3.1.0]hex-6-yl and the like.

The term "carbocyclylalkyl" refers to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

Selected substituents comprising the compounds of formula I may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with, for example any phosphate or phosphonate prodrug compounds of the invention, include but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

It is to be noted that all tautomers, atropisomers, polymorphs, pseudopolymorphs of compounds disclosed herein and pharmaceutically acceptable salts and esters thereof are embraced by the present invention.

A compound disclosed herein and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds disclosed herein A compound disclosed herein and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds disclosed herein and their pharmaceutically acceptable salts.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound disclosed herein present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular disclosed herein, the specific activity of the composition, the delivery device employed, the physical characteristics of the composition, its intended use, as well as patient considerations such as severity of the disease state, patient cooperation, etc., and can readily be determined by one skilled in the art and in reference to the information provided herein.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

Physiologically acceptable salts (e.g. pharmaceutically acceptable salt) of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4$. Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$. Each R is independently selected from H and $(C_1-C_8)$alkyl.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

It is to be understood that the compositions herein comprise compounds disclosed herein in their un-ionized, as well as zwitterionic form, and combinations with stoichiometric amounts of water as in hydrates.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds disclosed herein have chiral centers, e.g. chiral carbon. The compounds of the invention include enriched or resolved optical isomers at any or all asymmetric, chiral atoms. In other words, the chiral centers apparent from the depictions are provided as the chiral isomers. Individual enantiomers or diasteromers, isolated or synthesized, substantially free of their enantiomeric or diastereomeric partners, are all within the scope of the invention. The stereoisomeric mixtures can separated into their individual, substantially optically pure isomers through well-known techniques such as, for example, the separation of diastereomeric salts formed with optically active adjuncts, e.g., acids or bases followed by conversion back to the optically active substances. Typically, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. Enantiomers" refer to two stereoisomers of a compound which are non-superimposable mirror images of one another.

It is to be understood that for compounds disclosed herein when a bond is drawn in a non-stereochemical manner (e.g. flat) the atom to which the bond is attached includes all stereochemical possibilities. It is also to understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, the compounds disclosed herein are greater than 50% a single enantiomer. In another embodiment, the compounds disclosed herein are at least 80% a single enantiomer. In another embodiment, the compounds disclosed herein are at least 90% a single enantiomer In another embodiment, the compounds disclosed herein are at least 98% a single enantiomer. In another embodiment, the compounds disclosed herein are at least 99% a single enantiomer. In another embodiment, the compounds disclosed herein are greater than 50% a single diastereomer. In another embodiment, the compounds disclosed herein are at least 80% a single diastereomer. In another embodiment, the compounds disclosed herein are at least 90% a single diastereomer. In another embodiment, the compounds disclosed herein are at least 98% a single diastereomer. In another embodiment, the compounds disclosed herein are at least 99% a single diastereomer.

In one embodiment compounds are represented by formula I and Ia (and salts and esters, thereof) as shown below wherein one position of chirality is marked with an asterisk.

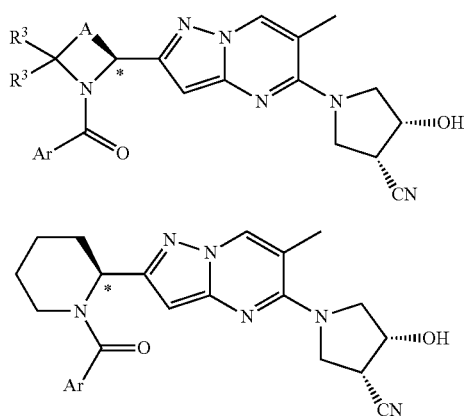

The stereochemistry at the carbon marked with an asterisk as shown above for formula I is the (S) stereochemistry provided that A is ranked the lowest (3) or highest (1) of the three substituents of the asterisk carbon following the Cahn-Ingold-Prelog system or the (R) stereochemistry provided that A is ranked number 2 of the three substituents of the asterisk carbon following the Cahn-Ingold-Prelog system (March, J., Advanced Organic Chemistery, 4$^{th}$ Addition, John Wiley and Sons, pages 109-111). The stereochemistry at the carbon marked with an asterisk as shown above for formula Ia is the (S) stereochemistry. In one embodiment, the compounds of formula I and Ia are greater than 50% a single stereoisomer at the asterisk position. In another embodiment, the compounds of formula I and Ia are at least 60% a single stereoisomer at the asterisk position. In another embodiment, the compounds of formula I and Ia are at least 70% a single stereoisomer at the asterisk position. In another embodiment, the compounds of formula I and Ia are at least 80% a single stereoisomer at the asterisk position. In another embodiment, the compounds of formula I and Ia are at least 90% a single stereoisomer at the asterisk position. In another embodiment, the compounds of formula I and Ia are at least 95% a single stereoisomer at the asterisk position.

In one embodiment compounds are represented by formula I and Ia (and salts and esters, thereof) as shown below wherein three positions of chirality are marked with an asterisk.

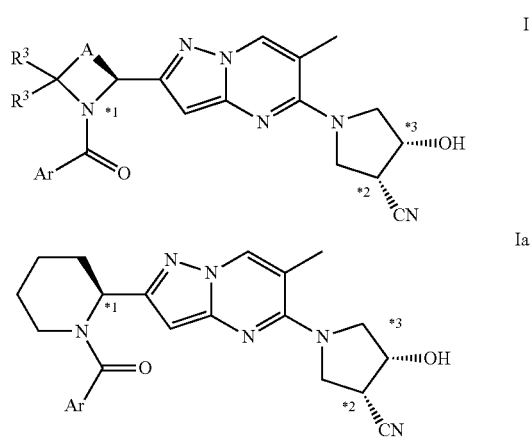

The stereochemistry at the carbon marked with an asterisk 1 (*1) as shown above for formula I is the (S) stereochemistry provided that A is ranked the lowest (3) or highest (1) of the three substituents of the asterisk 1 (*1) carbon following the Cahn-Ingold-Prelog system or the (R) stereochemistry provided that A is ranked number 2 of the three substituents of the asterisk 1 (*1) carbon following the Cahn-Ingold-Prelog system. The stereochemistry at the carbon marked with an asterisk 1 (*1) as shown above for formula Ia is the (S) stereochemistry. The stereochemistry at the carbon marked with an asterisk 2 (*2) as shown above for formula I and formula Ia is the (S) stereochemistry. The stereochemistry at the carbon marked with an asterisk 3 (*3) as shown above for formula I and formula Ia is the (R) stereochemistry. In one embodiment, the compounds of formula I and Ia are greater than 50% a single stereoisomer at each of the asterisk positions. In another embodiment, the compounds of formula I and Ia are at least 60% a single stereoisomer at each of the asterisk positions. In another embodiment, the compounds of formula I and Ia are at least 70% a single stereoisomer at each of the asterisk positions. In another embodiment, the compounds of formula I and Ia are at least 80% a single stereoisomer at each of the asterisk positions. In another embodiment, the compounds of formula I and Ia are at least 90% a single stereoisomer at each of the asterisk positions. In another embodiment, the compounds formula I and Ia are at least 95% a single stereoisomer at each of the asterisk positions.

In one embodiment compounds are represented by formulas II or IIa or salts or esters thereof, wherein one position of chirality is marked with an asterisk.

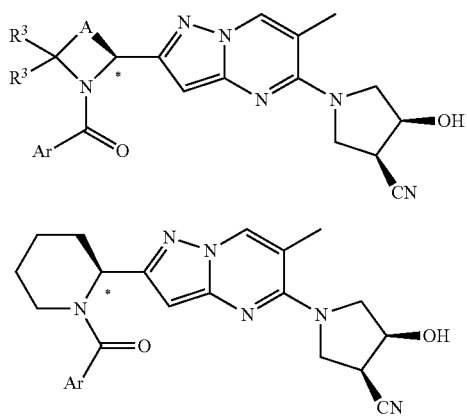

The stereochemistry at the carbon marked with an asterisk as shown above for formula II is the (S) stereochemistry provided that A is ranked the lowest (3) or highest (1) of the three substituents of the asterisk carbon following the Cahn-Ingold-Prelog system or the (R) stereochemistry provided that A is ranked number 2 of the three substituents of the asterisk carbon following the Cahn-Ingold-Prelog system. The stereochemistry at the carbon marked with an asterisk as shown above for formula IIa is the (S) stereochemistry. In one embodiment, the compounds of formula II and IIa are greater than 50% a single stereoisomer at the asterisk position. In another embodiment, the compounds of formula II and IIa are at least 60% a single stereoisomer at the asterisk position. In another embodiment, the compounds of formula II and IIa are at least 70% a single stereoisomer at the asterisk position. In another embodiment, the compounds of formula II and IIa are at least 80% a single stereoisomer at the asterisk position. In another embodiment, the compounds of formula II and IIa are at least 90% a single stereoisomer at the asterisk position. In another embodiment, the compounds of formula II and IIa are at least 95% a single stereoisomer at the asterisk position.

One embodiment provides compounds of formula II and IIa (and salts and esters, thereof) as shown below wherein three positions of chirality are marked with an asterisk.

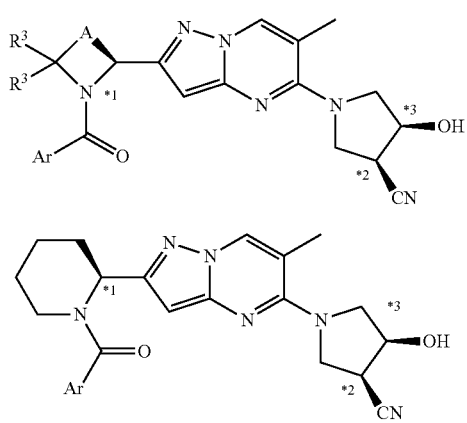

The stereochemistry at the carbon marked with an asterisk 1 (*1) as shown above for formula II is the (S) stereochemistry provided that A is ranked the lowest (3) or highest (1) of the three substituents of the asterisk 1 (*1) carbon following the Cahn-Ingold-Prelog system or the (R) stereochemistry provided that A is ranked number 2 of the three substituents of the asterisk 1 (*1) carbon following the Cahn-Ingold-Prelog system. The stereochemistry at the carbon marked with an asterisk 1 (*1) as shown above for formula IIa is the (S) stereochemistry. The stereochemistry at the carbon marked with an asterisk 2 (*2) as shown above for formula II and formula IIa is the (R) stereochemistry. The stereochemistry at the carbon marked with an asterisk 3 (*3) as shown above for formula I and formula Ia is the (S) stereochemistry. In one embodiment, the compounds of formula II and IIa are greater than 50% a single stereoisomer at each of the asterisk positions. In another embodiment, the compounds of formula II and IIa are at least 60% a single stereoisomer at each of the asterisk positions. In another embodiment, the compounds of formula I and Ia are at least 70% a single stereoisomer at each of the asterisk positions. In another embodiment, the compounds of formula II and IIa are at least 80% a single stereoisomer at each of the asterisk positions. In another embodiment, the compounds of formula II and IIa are at least 90% a single stereoisomer at each of the asterisk positions. In another embodiment, the compounds of formula II and IIa are at least 95% a single stereoisomer at each of the asterisk positions.

One embodiment provides for compounds of formulas III or IIIa or salts or esters thereof. Compounds of formula III and IIIc are shown below wherein one position of chirality is marked with an asterisk.

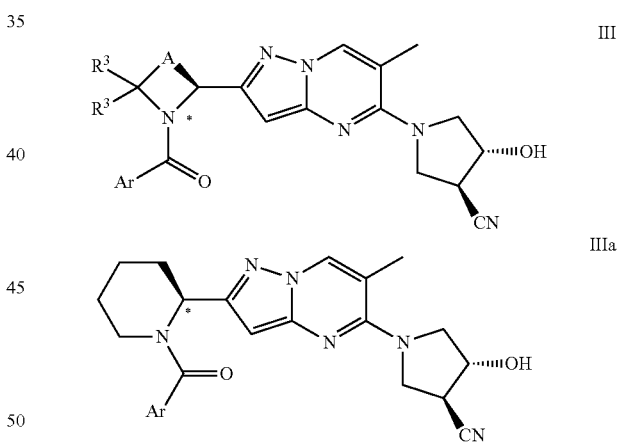

The stereochemistry at the carbon marked with an asterisk as shown above for formula III is the (S) stereochemistry provided that A is ranked the lowest (3) or highest (1) of the three substituents of the asterisk carbon following the Cahn-Ingold-Prelog system or the (R) stereochemistry provided that A is ranked number 2 of the three substituents of the asterisk carbon following the Cahn-Ingold-Prelog system. The stereochemistry at the carbon marked with an asterisk as shown above for formula IIIa is the (S) stereochemistry. In one embodiment, the compounds of formula III and IIIa are greater than 50% a single stereoisomer at the asterisk position. In another embodiment, the compounds of formula III and IIIa are at least 60% a single stereoisomer at the asterisk position. In another embodiment, the compounds of formula III and IIIa are at least 70% a single stereoisomer at the asterisk position. In another embodiment, the compounds of formula III and IIIa are at least 80% a single stereoisomer at the asterisk position. In another embodiment, the compounds of formula III and IIIa are at least 90% a single stereoisomer at the asterisk position. In another embodiment, the compounds of formula III and IIIa are at least 95% a single stereoisomer at the asterisk position.

One embodiment provides compounds of formula III and IIIa (and salts and esters, thereof) as shown below wherein three positions of chirality are marked with an asterisk.

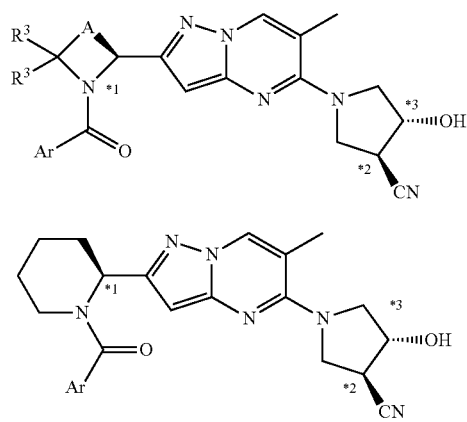

III

IIIa

The stereochemistry at the carbon marked with an asterisk 1 (*1) as shown above for formula III is the (S) stereochemistry provided that A is ranked the lowest (3) or highest (1) of the three substituents of the asterisk 1 (*1) carbon following the Cahn-Ingold-Prelog system or the (R) stereochemistry provided that A is ranked number two of the three substituents of the asterisk 1 (*1) carbon following the Cahn-Ingold-Prelog system. The stereochemistry at the carbon marked with an asterisk 1 (*1) as shown above for formula IIIa is the (S) stereochemistry. The stereochemistry at the carbon marked with an asterisk 2 (*2) as shown above for formula III and formula IIIa is the (R) stereochemistry. The stereochemistry at the carbon marked with an asterisk 3 (*3) as shown above for formula III and formula IIIa is the (R) stereochemistry. In one embodiment, the compounds of the invention of formula III and IIIa are greater than 50% a single stereoisomer at each of the asterisk positions. In another embodiment, the compounds of the invention of formula III and IIIa are at least 60% a single stereoisomer at each of the asterisk positions. In another embodiment, the compounds of the invention of formula III and IIIa are at least 70% a single stereoisomer at each of the asterisk positions. In another embodiment, the compounds of the invention of formula III and IIIa are at least 80% a single stereoisomer at each of the asterisk positions. In another embodiment, the compounds of the invention of formula III and IIIa are at least 90% a single stereoisomer at each of the asterisk positions. In another embodiment, the compounds of the invention of formula III and IIIa are at least 95% a single stereoisomer at each of the asterisk positions.

One embodiment provides for compounds of formulas IV or IVa or salts or esters thereof. Compounds of formula IV and IVa are shown wherein one position of chirality is marked with an asterisk.

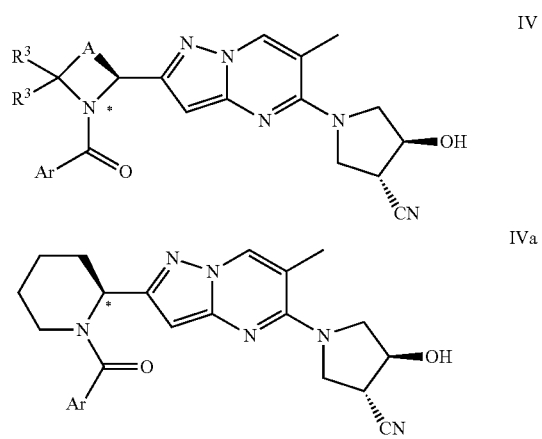

IV

IVa

The stereochemistry at the carbon marked with an asterisk as shown above for formula IV is the (S) stereochemistry provided that A is ranked the lowest (3) or highest (1) of the three substituents of the asterisk carbon following the Cahn-Ingold-Prelog system or the (R) stereochemistry provided that A is ranked number 2 of the three substituents of the asterisk carbon following the Cahn-Ingold-Prelog system. The stereochemistry at the carbon marked with an asterisk as shown above for formula IVa is the (S) stereochemistry. In one embodiment, the compounds of formula IV and IVa are greater than 50% a single stereoisomer at the asterisk position. In another embodiment, the compounds of formula IV and IVa are at least 60% a single stereoisomer at the asterisk position. In another embodiment, the compounds of formula IV and IVa are at least 70% a single stereoisomer at the asterisk position. In another embodiment, the compounds of formula IV and IVa are at least 80% a single stereoisomer at the asterisk position. In another embodiment, the compounds of formula IV and IVa are at least 90% a single stereoisomer at the asterisk position. In another embodiment, the compounds of formula IV and IVa are at least 95% a single stereoisomer at the asterisk position.

One embodiment provides compounds of formula IV and IVa (and salts and esters, thereof) as shown below wherein three positions of chirality are marked with an asterisk.

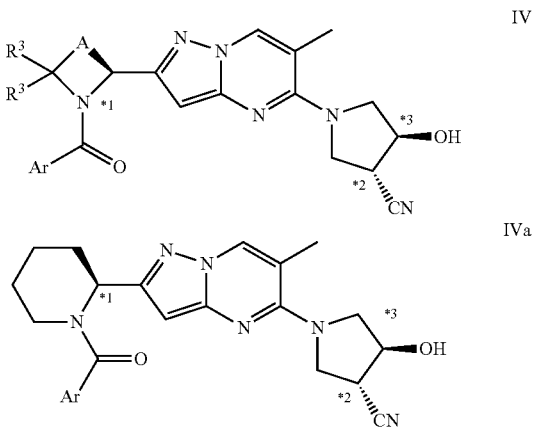

IV

IVa

The stereochemistry at the carbon marked with an asterisk 1 (*1) as shown above for formula IV is the (S) stereochemistry provided that A is ranked the lowest (3) or highest (1) of the three substituents of the asterisk 1 (*1) carbon following the Cahn-Ingold-Prelog system or the (R) stereochemistry provided that A is ranked number 2 of the three substituents of the asterisk 1 (*1) carbon following the Cahn-Ingold-Prelog System. The stereochemistry at the carbon marked with an asterisk 1 (*1) as shown above for formula IVa is the (S) stereochemistry. The stereochemistry at the carbon marked with an asterisk 2 (*2) as shown above for formula IV and formula IVa is the (S) stereochemistry. The stereochemistry at the carbon marked with an asterisk 3 (*3) as shown above for formula IV and formula IVa is the (S) stereochemistry. In one embodiment, the compounds of formula IV and IVa are greater than 50% a single stereoisomer at each of the asterisk positions. In another embodiment, the compounds of formula IV and IVa are at least 60% a single stereoisomer at each of the asterisk positions. In another embodiment, the compounds of formula IV and IVa are at least 70% a single stereoisomer at each of the asterisk positions. In another embodiment, the compounds of formula IV and IVa are at least 80% a single stereoisomer at each of the asterisk positions. In another embodiment, the compounds of formula IV and IVa are at least 90% a single stereoisomer at each of the asterisk positions. In another embodiment, the compounds of formula IV and IVa are at least 95% a single stereoisomer at each of the asterisk positions.

Each of the compounds of formulas 1-24 described herein have a core represented by formula V wherein a position of chirality is marked with an asterisk (wherein R represents an amine).

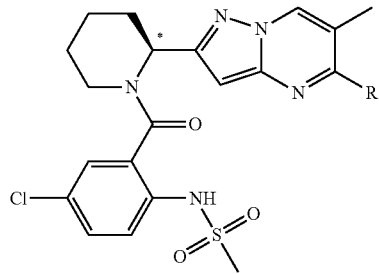

V

The stereochemistry at the carbon marked with an asterisk as shown for formula V is the (S) stereochemistry. In one embodiment, the compounds of formulas 1-24 are greater than 50% a single stereoisomer at the asterisk position. In another embodiment, the compounds of formulas 1-24 are at least 60% a single stereoisomer at the asterisk position. In another embodiment, the compounds of formulas 1-24 are at least 70% a single stereoisomer at the asterisk position. In another embodiment, the compounds of formulas 1-24 are at least 80% a single stereoisomer at the asterisk position. In another embodiment, the compounds of formulas 1-24 are at least 90% a single stereoisomer at the asterisk position. In another embodiment, the compounds of formulas 1-24 are at least 95% a single stereoisomer at the asterisk position.

Each of the compounds of formula 25-111 described herein have a core represented by formula VI wherein two positions of chirality are marked with an asterisk.

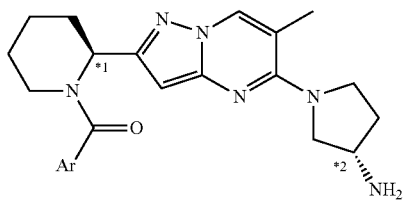

VI

The stereochemistry at the carbon marked with an asterisk 1 (*1) as shown for formula VI is the (S) stereochemistry. The stereochemistry at the carbon marked with an asterisk 2 (*2) as shown for formula VI is the (S) stereochemistry. In one embodiment, the compounds of formulas 25-111 are greater than 50% a single stereoisomer at each of the asterisk positions. In another embodiment, the compounds of formulas 25-111 are at least 60% a single stereoisomer at each of the asterisk positions. In another embodiment, the compounds of formulas 25-111 are at least 70% a single stereoisomer at each of the asterisk positions. In another embodiment, the compounds of formulas 25-111 are at least 80% a single stereoisomer at each of the asterisk positions. In another embodiment, the compounds of formulas 25-111 are at least 90% a single stereoisomer at each of the asterisk positions. In another embodiment, the compounds of formulas 25-111 are at least 95% a single stereoisomer at each of the asterisk positions.

The compounds disclosed herein also include molecules that incorporate isotopes of the atoms specified in the particular molecules. Non-limiting examples of these isotopes include D, T, $^{14}C$, $^{13}C$ and $^{15}N$.

Whenever a compound described herein is substituted with more than one of the same designated group, e.g., "R" or "$R^1$", then it will be understood that the groups may be the same or different, i.e., each group is independently selected. Wavy lines, ∼∼∼, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention.

DETAILED DESCRIPTION OF EXEMPLARY EMBODIMENTS

Reference will now be made in detail to certain embodiments, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the full scope of the present invention as described herein.

Specific values listed below for radicals, substituents, and ranges, are for illustration only; they do not exclude other defined values or other values within defined ranges for the radicals and substituents. Specific values listed are values for compounds of formula I, II, III, IV as well as sub-formulas of these formulas (e.g. formula Ia, IIa, IIIa and IVa).

A specific group of compounds of formula I are compounds of formula Ia.

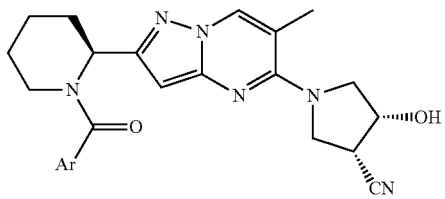

Ia and salts and esters, thereof.

A specific value for $R^3$ is H.

A specific value for n is 3.

A specific value for $R^4$ is H.

A specific value for A is —$(CH_2)_3$—.

A specific value for Ar is phenyl, pyridyl, 1,2,3,4-tetrahydronaphthyl, indazolyl, 1,6-naphthyridyl, 2,3,-dihydroindanyl, quinolyl, indolyl, 4H-benzo][d][1,3]dioxanyl, pyrazolo[1,5-a]pyridinyl, imidazo[1,2-a]pyridinyl, 1,2,3,4-tetrahydroquinolyl, benzo[d][1,3]dioxolyl, quinoxalyl, isoquinolyl, naphthyl, thiophenyl, pyrazolyl, 4,5,6,7-tetrahydrobenzothiophenyl or pyrazolo[3,4,b]pyridinyl, wherein any phenyl, pyridyl, 1,2,3,4-tetrahydronaphthyl, indazolyl, 1,6-naphthyridyl, 2,3,-dihydroindanyl, quinolyl, indolyl, 4H-benzo][d][1,3]dioxanyl, pyrazolo[1,5-a]pyridinyl, imidazo[1,2-a]pyridinyl, 1,2,3,4-tetrahydroquinolyl, benzo[d][1,3]dioxolyl, quinoxalyl, isoquinolyl, naphthyl, thiophenyl, pyrazolyl, 4,5,6,7-tetrahydrobenzothiophenyl or pyrazolo[3,4,b]pyridinyl of Ar is optionally substituted with 1 to 5 $R^6$.

A specific value for Ar is phenyl, monocyclic-hetereocycle or bicyclic-heterocycle, wherein any phenyl, monocyclic-hetereocycle or bicyclic-heterocycle of Ar is optionally substituted with 1 to 5 $R^6$.

A specific value for Ar is phenyl, monocyclic-hetereocycle or bicyclic-heterocycle, wherein the monocyclic-heterocycle or bicyclic-heterocycl consists or 1-10 carbon atoms and 1-5 heteroatoms within the ring system and wherein any phenyl, monocyclic-hetereocycle or bicyclic-heterocycle of Ar is optionally substituted with 1 to 5 $R^6$.

A specific value for Ar is phenyl optionally substituted by 1, 2, 3, 4, or 5 $R^6$ groups.

A specific value for Ar is phenyl optionally substituted by 1, 2, 3, or 4 $R^6$ groups.

A specific value for Ar is phenyl optionally substituted by 1, 2, or 3 $R^6$ groups.

A specific value for Ar is naphthyl optionally substituted by 1, 2, 3, 4, or 5 $R^6$ groups.

A specific value for Ar is naphthyl optionally substituted by 1, 2, 3, or 4 $R^6$ groups.

A specific value for Ar is naphthyl optionally substituted by 1, 2, or 3 $R^6$ groups.

A specific value for Ar is phenyl optionally substituted by 1, 2, 3, 4, or 5 $R^6$ groups selected from halogen, alkyl, alkoxy, —$CH_2OH$, $CF_3$, —O—$CF_3$, —O—$CF_2$, —O—($C_3$-$C_6$ cycloalkyl), —$SO_2NH_2$, —$SO_2NH(C_1$-$C_6$ alkyl), —$SO_2N(C_1$-$C_6$ alkyl)$_2$, —$SO_2$—$C_1$-$C_6$ alkyl, —S(=O)—$C_1$-$C_6$ alkyl, an oxadiazole optionally substituted by $CH_3$, and a triazole ring optionally substituted by $CH_3$; or two $R^6$ groups on the phenyl ring together with the atoms to which they are attached form a benzodioxole, benzodioxine, or dihydroindene ring.

A specific value for Ar is phenyl substituted by 1, 2, 3, or 4 $R^6$ groups selected from halogen, alkyl, alkoxy, —$CH_2OH$, $CF_3$, —O—$CF_3$, —O—$CF_2$, —O—($C_3$-$C_6$ cycloalkyl), —$SO_2NH_2$, —$SO_2NH(C_1$-$C_6$ alkyl), —$SO_2N(C_1$-$C_6$ alkyl)$_2$, —$SO_2$—$C_1$-$C_6$ alkyl, —S(=O)—$C_1$-$C_6$ alkyl, an oxadiazole optionally substituted by $CH_3$, and a triazole ring optionally substituted by $CH_3$; or two $R^6$ groups on the phenyl ring together with the atoms to which they are attached form a benzodioxole, benzodioxine, or dihydroindene ring.

A specific value for Ar is phenyl optionally substituted by 1, 2, or 3 $R^6$ groups selected from halogen, alkyl, alkoxy, —$CH_2OH$, $CF_3$, —O—$CF_3$, —O—$CF_2$, —O—($C_3$-$C_6$ cycloalkyl), —$SO_2NH_2$, —$SO_2NH(C_1$-$C_6$ alkyl), —$SO_2N(C_1$-$C_6$ alkyl)$_2$, —$SO_2$—$C_1$-$C_6$ alkyl, —S(=O)—$C_1$-$C_6$ alkyl, an oxadiazole optionally substituted by $CH_3$, and a triazole ring optionally substituted by $CH_3$; or two $R^6$ groups on the phenyl ring together with the atoms to which they are attached form a benzodioxole, benzodioxine, or dihydroindene ring.

A specific value for Ar is naphthyl optionally substituted by 1, 2, 3, 4, or 5 $R^6$ groups selected from halogen, alkyl, alkoxy, —$CH_2OH$, $CF_3$, —O—$CF_3$, —O—$CF_2$, —O—($C_3$-$C_6$ cycloalkyl), —$SO_2NH_2$, —$SO_2NH(C_1$-$C_6$ alkyl), —$SO_2N(C_1$-$C_6$ alkyl)$_2$, —$SO_2$—$C_1$-$C_6$ alkyl, —S(=O)—$C_1$-$C_6$ alkyl, an oxadiazole optionally substituted by $CH_3$, and a triazole ring optionally substituted by $CH_3$; or two $R^6$ groups on the phenyl ring together with the atoms to which they are attached form a benzodioxole, benzodioxine, or dihydroindene ring.

A specific value for Ar is naphthyl optionally substituted by 1, 2, 3, or 4 $R^6$ groups selected from halogen, alkyl, alkoxy, —$CH_2OH$, $CF_3$, —O—$CF_3$, —O—$CF_2$, —O—($C_3$-$C_6$ cycloalkyl), —$SO_2NH_2$, —$SO_2NH(C_1$-$C_6$ alkyl), —$SO_2N(C_1$-$C_6$ alkyl)$_2$, —$SO_2$—$C_1$-$C_6$ alkyl, —S(=O)—$C_1$-$C_6$ alkyl, an oxadiazole optionally substituted by $CH_3$, and a triazole ring optionally substituted by $CH_3$; or two $R^6$ groups on the phenyl ring together with the atoms to which they are attached form a benzodioxole, benzodioxine, or dihydroindene ring.

A specific value for Ar is naphthyl optionally substituted by 1, 2, or 3 $R^6$ groups selected from halogen, alkyl, alkoxy, —$CH_2OH$, $CF_3$, —O—$CF_3$, —O—$CF_2$, —O—($C_3$-$C_6$ cycloalkyl), —$SO_2NH_2$, —$SO_2NH(C_1$-$C_6$ alkyl), —$SO_2N(C_1$-$C_6$ alkyl)$_2$, —$SO_2$—$C_1$-$C_6$ alkyl, —S(=O)—$C_1$-$C_6$ alkyl, an oxadiazole optionally substituted by $CH_3$, and a triazole ring optionally substituted by $CH_3$; or two $R^6$ groups on the phenyl ring together with the atoms to which they are attached form a benzodioxole, benzodioxine, or dihydroindene ring.

A specific value for Ar is pyridine optionally substituted by 1, 2, 3, 4, or 5 $R^6$ groups.

A specific value for Ar is pyridine optionally substituted by 1, 2, 3, or 4 $R^6$ groups.

A specific value for Ar is pyridine optionally substituted by 1, 2, or 3 $R^6$ groups.

A specific value for Ar is pyridine optionally substituted by 1, 2, 3, 4, or 5 $R^6$ groups independently selected from halogen, alkyl, alkoxy, —$CH_2OH$, phenyl and $CF_3$.

A specific value for Ar is pyridine optionally substituted by 1, 2, 3, or 4 $R^6$ groups. independently selected from halogen, alkyl, alkoxy, —$CH_2OH$, phenyl and $CF_3$.

A specific value for Ar is pyridine optionally substituted by 1, 2, or 3 $R^6$ groups. independently selected from halogen, alkyl, alkoxy, —$CH_2OH$, phenyl and $CF_3$.

Individual embodiments provide compounds of the formula I wherein Ar is, respectively, indazole, imidazopyridazine, benzothiophene, benzoimidazole, indazole, quinoline, isoquinaline, quinoxaline, tetrahydroquinoline, indole, triazolopyrimidine, pyrazolopyridine, naphthyridine, in which, in each embodiment the Ar group is either unsubstituted or substituted by 1, 2, 3, 4, or 5 R$^6$ groups.

Individual embodiments provide compounds of the formula I wherein Ar is, respectively, indazole, imidazopyridazine, benzothiophene, benzoimidazole, indazole, quinoline, isoquinaline, quinoxaline, tetrahydroquinoline, indole, triazolopyrimidine, pyrazolopyridine, naphthyridine, in which, in each embodiment the Ar group is either unsubstituted or substituted by 1, 2, 3, or 4 R$^6$ groups.

Individual embodiments provide compounds of the formula I wherein Ar is, respectively, indazole, imidazopyridazine, benzothiophene, benzoimidazole, indazole, quinoline, isoquinaline, quinoxaline, tetrahydroquinoline, indole, triazolopyrimidine, pyrazolopyridine, naphthyridine, in which, in each embodiment the Ar group is either unsubstituted or substituted by 1, 2, or 3 R$^6$ groups.

Individual embodiments provide compounds of the formula I wherein Ar is, respectively, indazole, imidazopyridazine, benzothiophene, benzoimidazole, indazole, quinoline, isoquinaline, quinoxaline, tetrahydroquinoline, indole, triazolopyrimidine, pyrazolopyridine, naphthyridine, in which, in each embodiment the Ar group is either unsubstituted or substituted by 1, 2, or 3 substituents selected from halogen, alkyl, alkoxy, CF$_3$, —O—CF$_3$, and —O—CF$_2$.

A specific value for Ar is indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine, wherein indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine are not substituted.

A specific value for Ar is indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine, wherein indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine are each optionally substituted by 1, 2, 3, 4, or 5 R$^6$ groups.

A specific value for Ar is indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine, wherein indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine are each optionally substituted by 1, 2, 3, or 4 R$^6$ groups.

A specific value for Ar is indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine, wherein indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine are each optionally substituted by 1, 2, or 3, or 4 R$^6$ groups.

A specific value for Ar is indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine, wherein indazole, imidazopyridazine, benzothiophene, benzoimidazole, indazole, quinoline, isoquinaline, quinoxaline, tetrahydroquinoline, indole, triazolopyrimidine, pyrazolopyridine or naphthyridine are each optionally substituted by 1, 2, or 3 substituents selected from halogen, alkyl, alkoxy, CF$_3$, —O—CF$_3$, and —O—CF$_2$.

A specific value for R$^6$ is OR$^{11}$, CN, S(O)$_p$R$^a$, halogen, (C$_1$-C$_8$)alkyl, C$_6$-C$_{20}$ aryl or C$_2$-C$_{20}$ heterocyclyl, (C$_3$-C$_7$)cycloalkyl or (C$_4$-C$_8$)carbocyclylalkyl, wherein any (C$_1$-C$_8$) alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_4$-C$_8$)carbocyclylalkyl of R$^6$ is optionally substituted with one or more oxo, halogen, hydroxy, NH$_2$, CN, N$_3$, N(R$^a$)$_2$, NHR$^a$, SH, SR$^a$, S(O)$_p$R$^a$, OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, NHS(O)$_p$R$^a$, NR$^a$S(O)$_p$R$^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N(R$^a$)$_2$, NR$^a$C(O)NH$_2$, NHC(O)NHR$^a$, NHC(O)N(R$^a$)$_2$, NHC(O)NH$_2$, =NH, =NOH, =NOR$^a$, NHS(O)$_p$NHR$^a$, NR$^a$S(O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, =OC(=O)R$^a$, —OP(O)(OH)$_2$ or R$^a$.

Another specific value for R$^6$ is OR$^{11}$, CN, S(O)$_p$R$^a$, halogen, (C$_1$-C$_8$)alkyl, C$_6$-C$_{20}$ aryl, C$_2$-C$_{20}$ heterocyclyl, (C$_3$-C$_7$)cycloalkyl, (C$_4$-C$_8$)carbocyclylalkyl, NR$^{11}$C(O)R$^{11}$ or NR$^{11}$S(O)$_p$R$^a$, wherein any (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_4$-C$_8$)carbocyclylalkyl of R$^6$ is optionally substituted with one or more oxo, halogen, hydroxy, NH$_2$, CN, N$_3$, N(R$^a$)$_2$, NHR$^a$, SH, SR$^a$, S(O)$_p$R$^a$, OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, NHS(O)$_p$R$^a$, NR$^a$S(O)$_p$R$^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N(R$^a$)$_2$, NR$^a$C(O)NH$_2$, NHC(O)NHR$^a$, NHC(O)N(R$^a$)$_2$, NHC(O)NH$_2$, =NH, NOH, =NOR$^a$, NR$^a$S(O)$_p$NHR$^a$, NR$^a$S(O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, =OC(=O)R$^a$, —OP(O)(OH)$_2$ or R$^a$.

A specific value for Ar is:

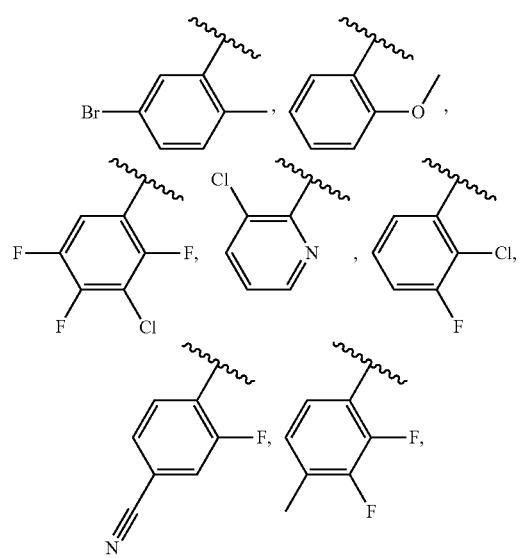

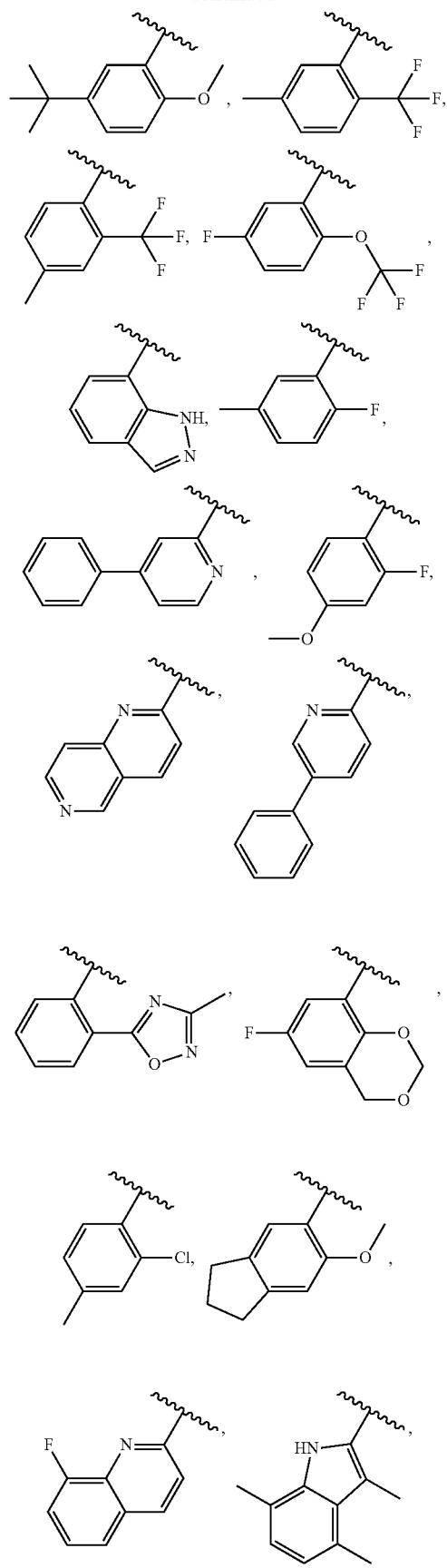
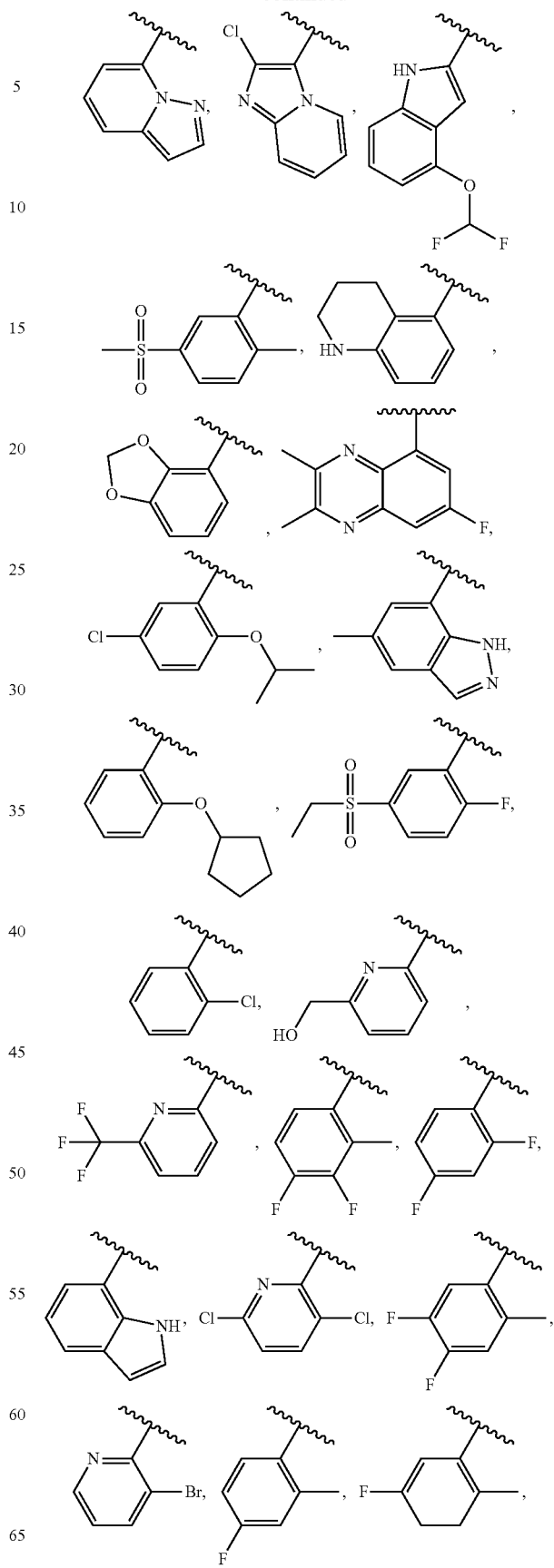

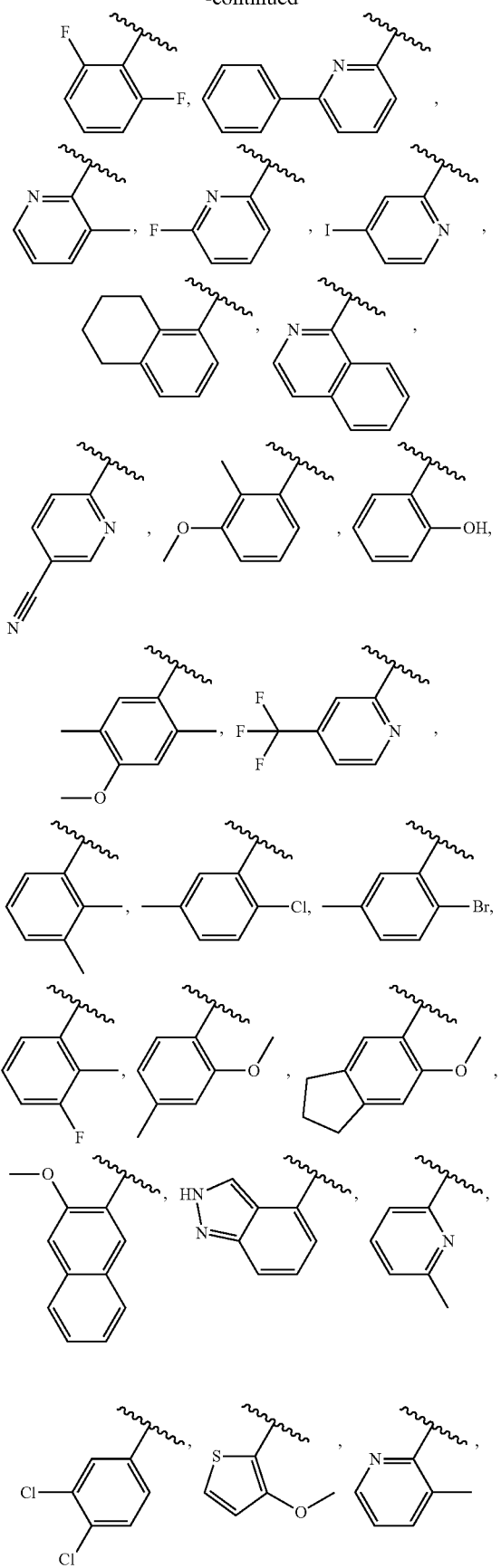
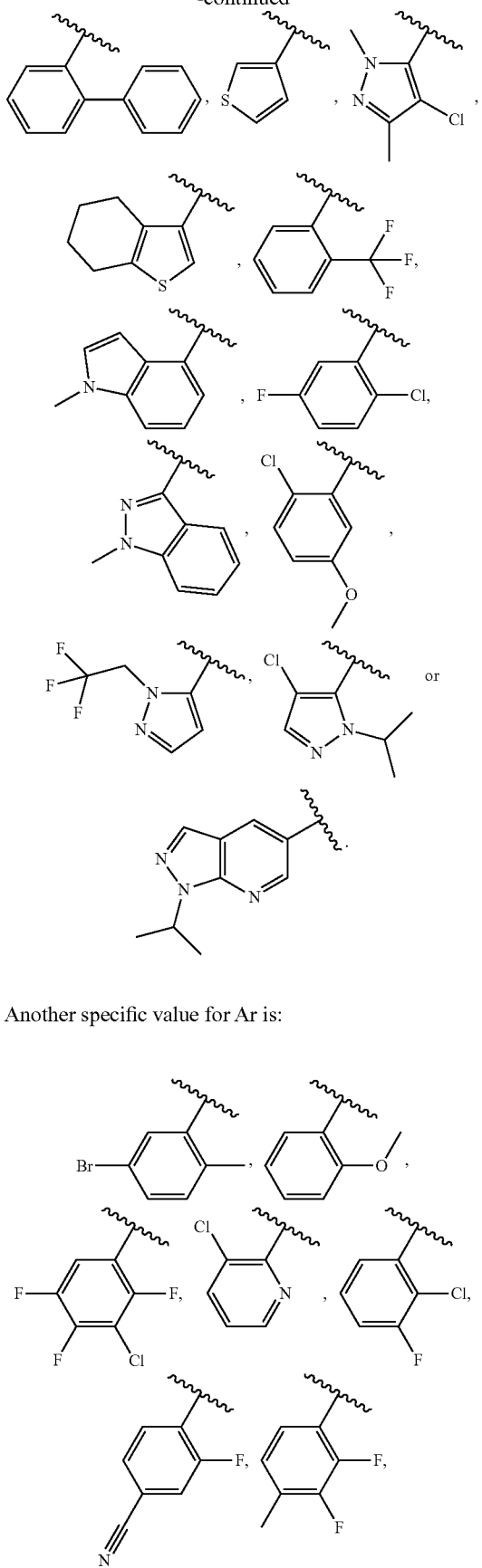
Another specific value for Ar is:

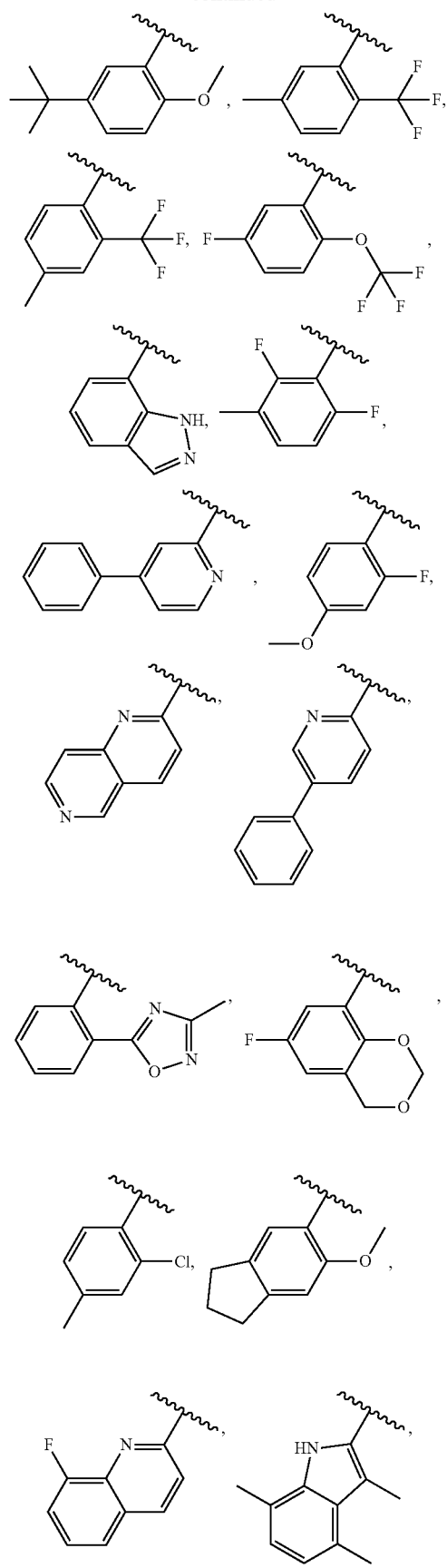
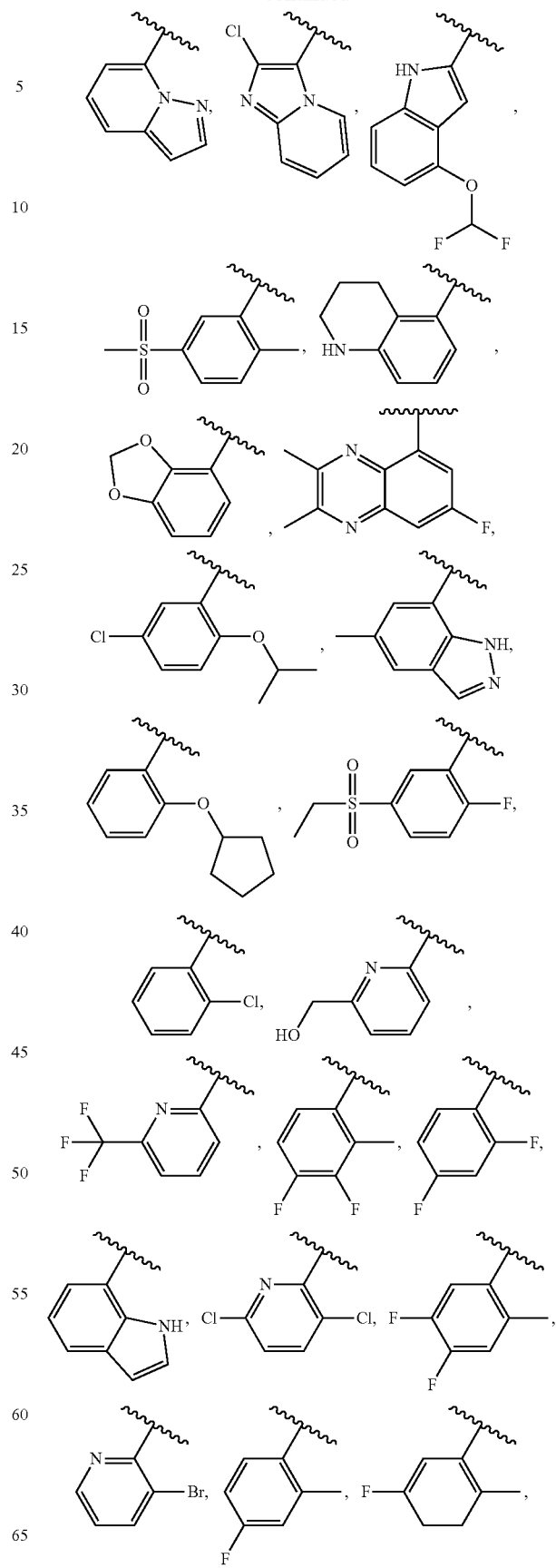

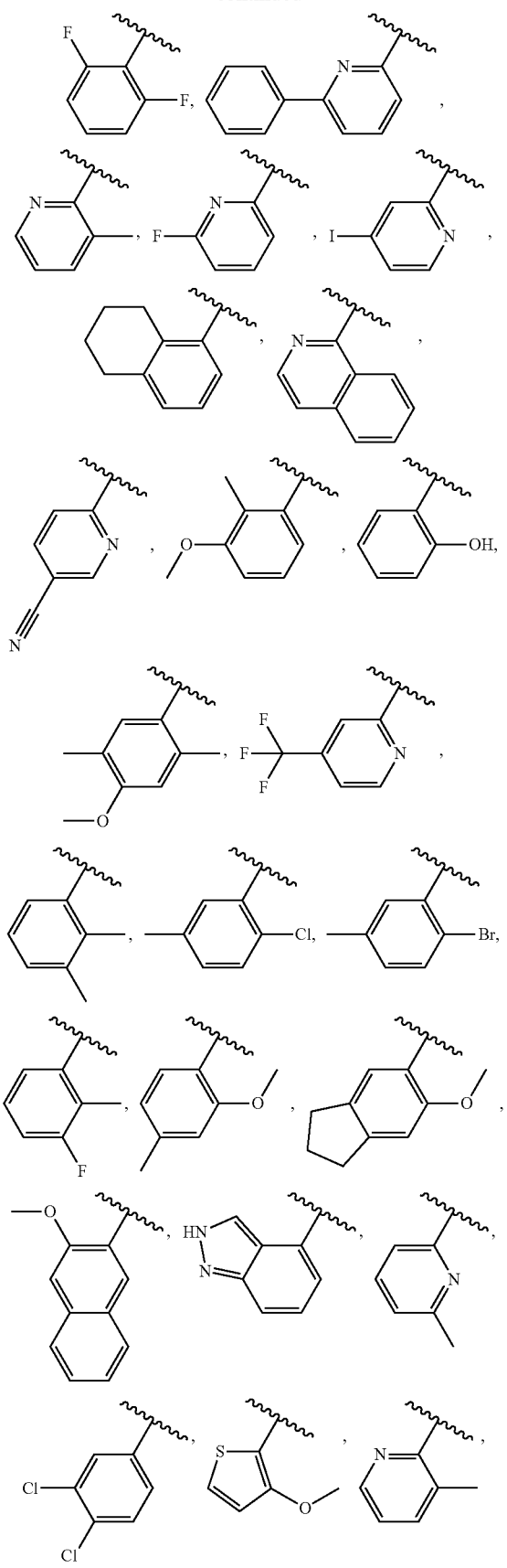
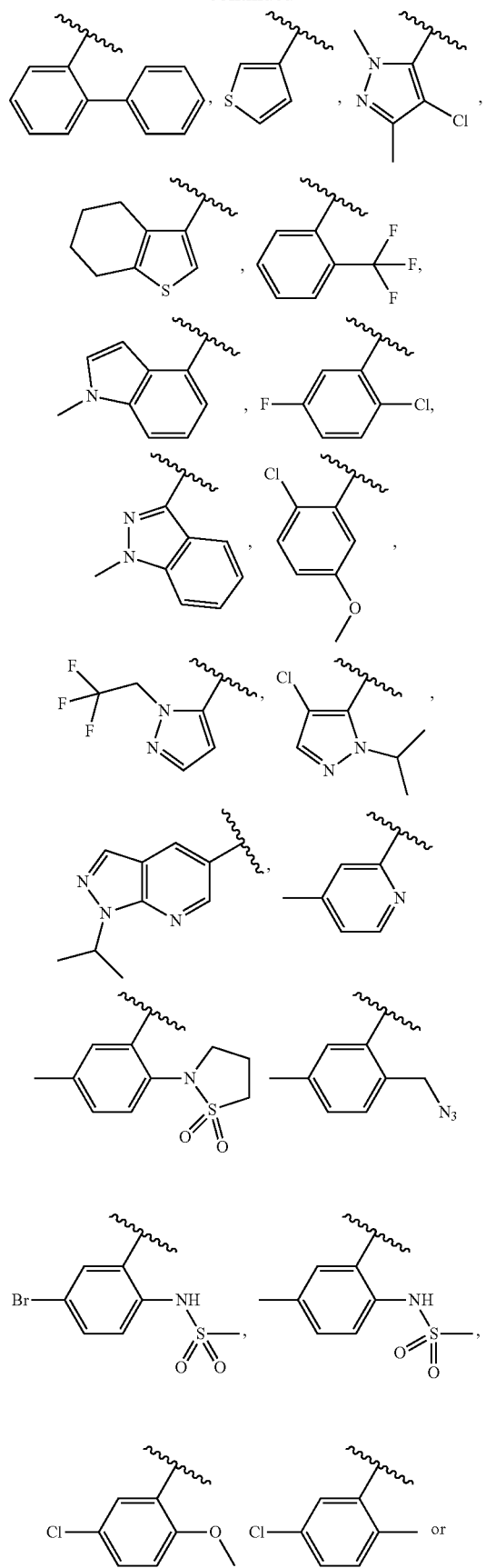

-continued

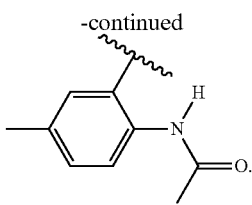

In one embodiment the invention provides a compound of formula I:

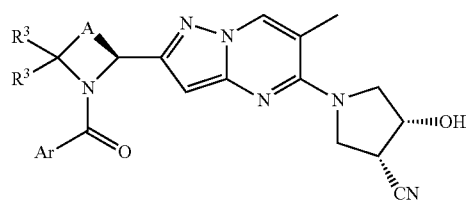

or a salt or ester, thereof;
wherein:

A is —(C($R^4$)$_2$)$_n$— wherein any one C($R^4$)$_2$ of said —(C($R^4$)$_2$)$_n$— may be optionally replaced with —O—, —S—, —S(O)$_p$, NH or N$R^a$;

n is 3, 4, 5 or 6;

each p is 1 or 2;

Ar is a $C_2$-$C_{20}$ heterocyclyl group or a $C_6$-$C_{20}$ aryl group, wherein the $C_2$-$C_{20}$ heterocyclyl group or the $C_6$-$C_{20}$ aryl group is optionally substituted with 1, 2, 3, 4 or 5 $R^6$;

each $R^3$, $R^4$ or $R^6$ is independently H, oxo, O$R^{11}$, N$R^{11}R^{12}$, N$R^{11}$C(O)$R^{11}$, N$R^{11}$C(O)O$R^{11}$, N$R^{11}$C(O)N$R^{11}R^{12}$, N$_3$, CN, NO$_2$, S$R^{11}$, S(O)$_p$$R^a$, N$R^{11}$S(O)$_p$$R^a$, —C(=O)O$R^{11}$, —C(=O)N$R^{11}R^{12}$, —C(=O)S$R^{11}$, —S(O)$_p$(O$R^{11}$), —SO$_2$N$R^{11}R^{12}$, —N$R^{11}$S(O)$_p$(O$R^{11}$), N$R^{11}$SO$_p$N$R^{11}R^{12}$, N$R^{11}$C(=N$R^{11}$)N$R^{11}R^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl;

or two $R^4$ on adjacent carbon atoms, when taken together, may optionally form a double bond between the two carbons to which they are attached or may form a ($C_3$-$C_7$)cycloalkyl ring wherein one carbon atom of said ($C_3$-$C_7$)cycloalkyl ring may be optionally replaced by —O—, —S—, —S(O)$_p$—, —NH— or —N$R^a$—;

four $R^4$ on adjacent carbon atoms, when taken together, may optionally form an optionally substituted $C_6$ aryl ring;

two $R^4$ on the same carbon atom, when taken together, may optionally form a ($C_3$-$C_7$)cycloalkyl ring wherein one carbon atom of said ($C_3$-$C_7$)cycloalkyl ring may be optionally replaced by —O—, —S—, —S(O)$_p$—, —NH— or —N$R^a$—;

two $R^6$ on adjacent carbon atoms, when taken together, may optionally form a ($C_3$-$C_7$)cycloalkyl ring wherein one carbon atom of said ($C_3$-$C_7$)cycloalkyl ring may be optionally replaced by —O—, —S—, —S(O)$_p$—, —NH— or —N$R^a$—;

each $R^a$ is independently ($C_1$-$C_8$)alkyl, ($C_1$-$C_8$)haloalkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl wherein any ($C_1$-$C_8$)alkyl, ($C_1$-$C_8$)haloalkyl, ($C_2$-$C_8$)alkenyl or ($C_2$-$C_8$)alkynyl of $R^a$ is optionally substituted with one or more OH, NH$_2$, CO$_2$H, $C_2$-$C_{20}$ heterocyclyl, and wherein any aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl of $R^a$ is optionally substituted with one or more OH, NH$_2$, CO$_2$H, $C_2$-$C_{20}$ heterocyclyl or ($C_1$-$C_8$)alkyl;

each $R^{11}$ or $R^{12}$ is independently H, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl, ($C_4$-$C_8$)carbocyclylalkyl, —C(=O)$R^a$, —S(O)$_p$$R^a$, or aryl($C_1$-$C_8$)alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S—, —S(O)$_p$—, —NH—, —N$R^a$— or —C(O)—; and wherein each ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl or ($C_4$-$C_8$)carbocyclylalkyl of each $R^6$, $R^{11}$ or $R^{12}$ is, independently, optionally substituted with one or more oxo, halogen, hydroxy, NH$_2$, CN, N$_3$, N($R^a$)$_2$, NH$R^a$, SH, S$R^a$, S(O)$_p$$R^a$, O$R^a$, ($C_1$-$C_8$)alkyl, ($C_1$-$C_8$)haloalkyl, —C(O)$R^a$, —C(O)H, —C(=O)O$R^a$, —C(=O)OH, —C(=O)N($R^a$)$_2$, —C(=O)NH$R^a$, —C(=O)NH$_2$, NHS(O)$_p$$R^a$, N$R^a$S(O)$_p$$R^a$, NHC(O)$R^a$, N$R^a$C(O)$R^a$, NHC(O)O$R^a$, N$R^a$C(O)O$R^a$, N$R^a$C(O)NH$R^a$, N$R^a$C(O)N($R^a$)$_2$, N$R^a$C(O)NH$_2$, NHC(O)NH$R^a$, NHC(O)N($R^a$)$_2$, NHC(O)NH$_2$, =NH, =NOH, =NO$R^a$, N$R^a$S(O)$_p$NH$R^a$, N$R^a$S(O)$_p$N($R^a$)$_2$, N$R^a$S(O)$_p$NH$_2$, NHS(O)$_p$NH$R^a$, NHS(O)$_p$N($R^a$)$_2$, NHS(O)$_p$NH$_2$, —OC(=O)$R^a$, —OP(O)(OH)$_2$ or $R^a$;

provided the compound is not:

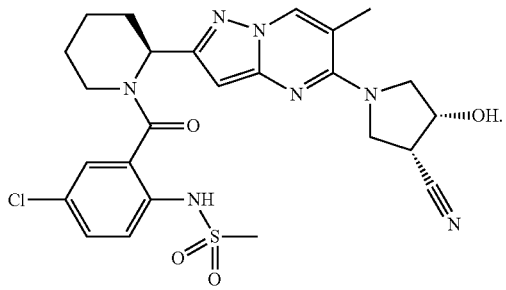 [SMILES: Cc1cn2nc([C@@H]3CCCCN3C(=O)c3cc(Cl)ccc3NS(C)(=O)=O)cc2nc1N1C[C@@H](C#N)[C@@H](O)C1]

A specific group of compounds of formula I are compounds of formula Ia:

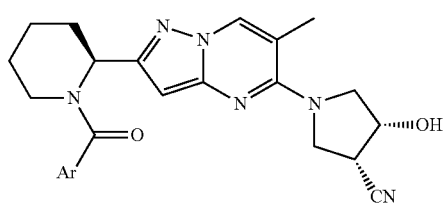

Ia and salts and esters, thereof; provided the compound does not include:

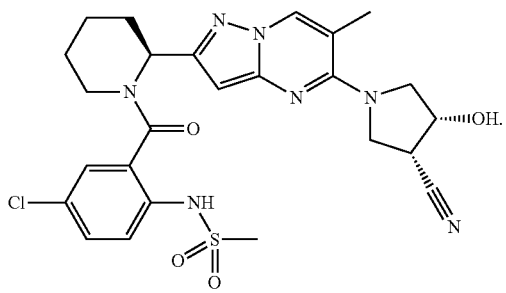

In one embodiment the compounds of formula I or Ia do not include:
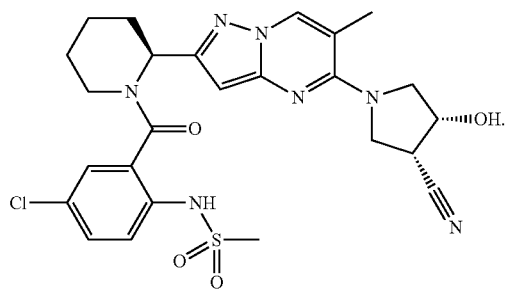
In one embodiment a compound of formula I is selected from:
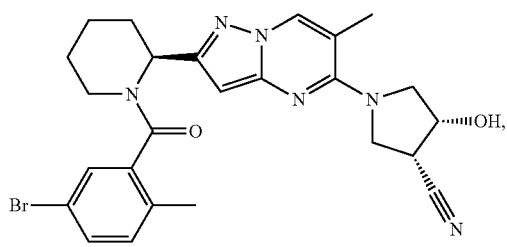
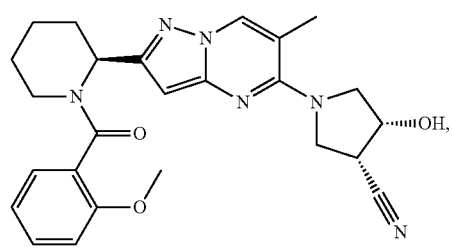
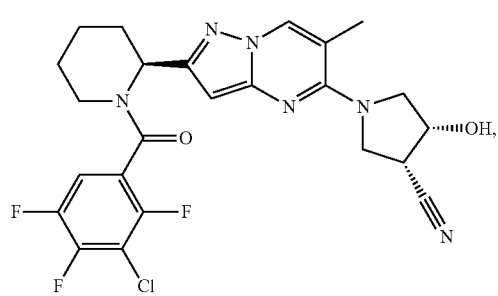
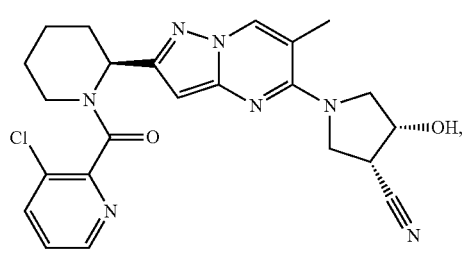
-continued
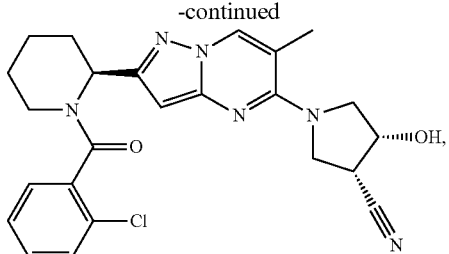
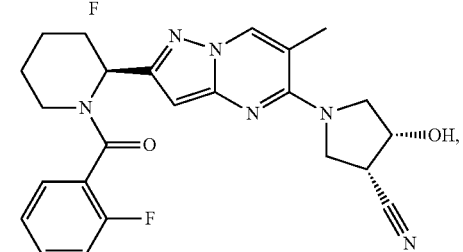
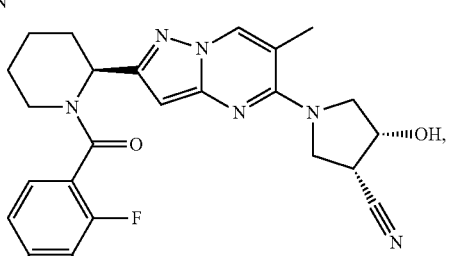
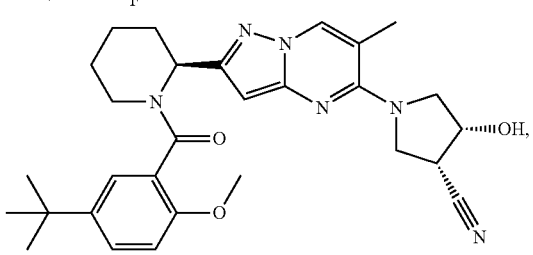
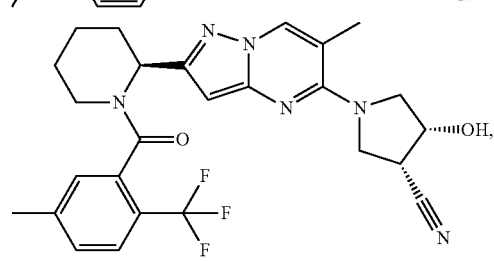
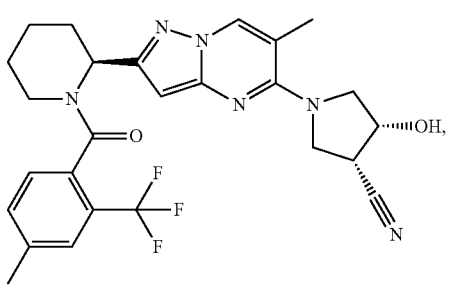

37
-continued
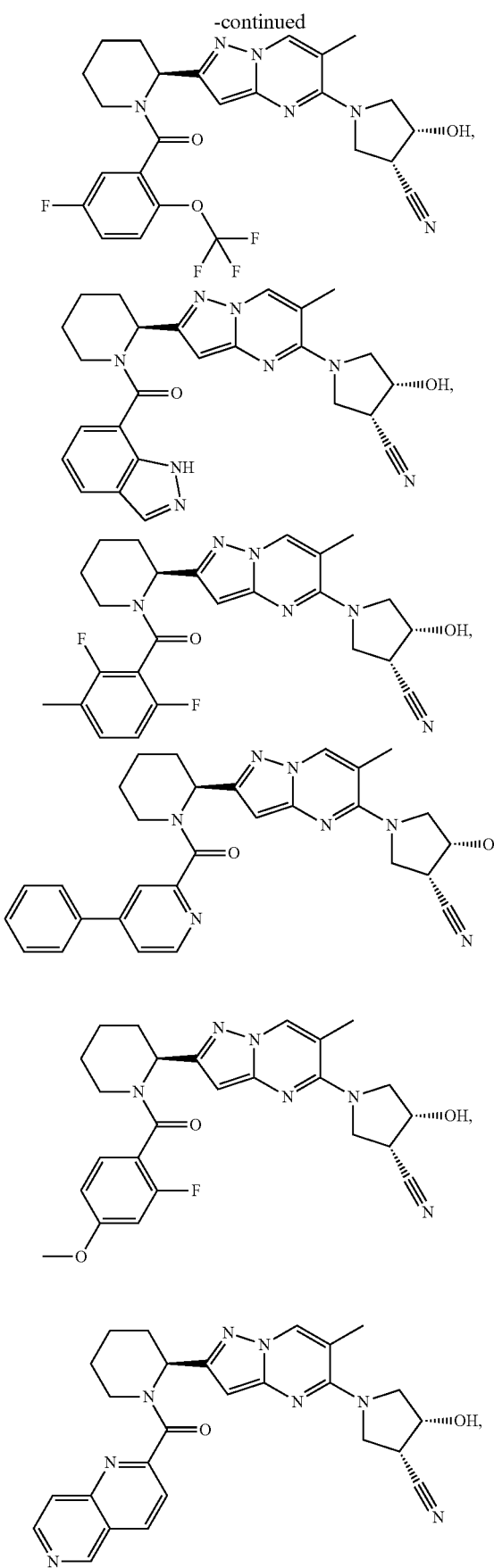
38
-continued
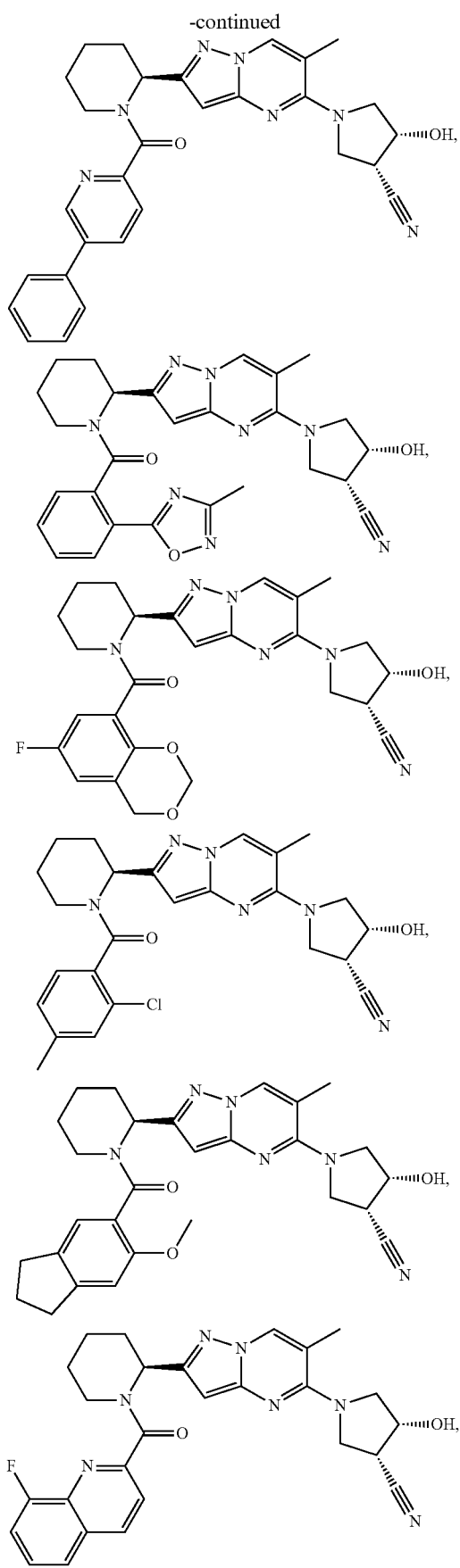

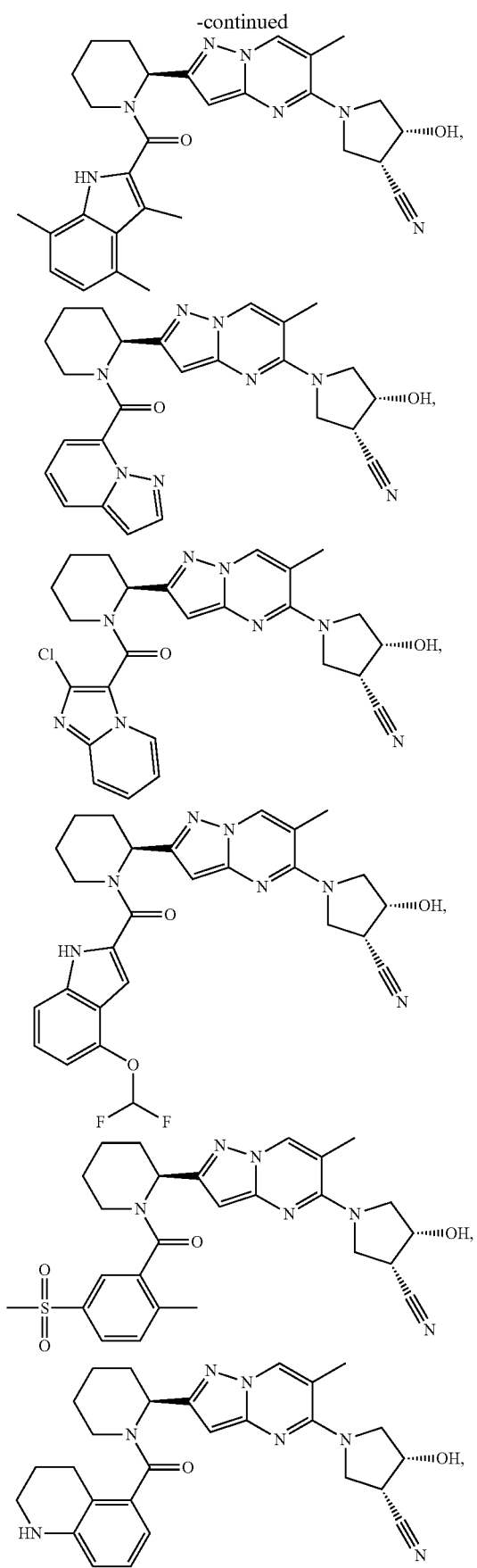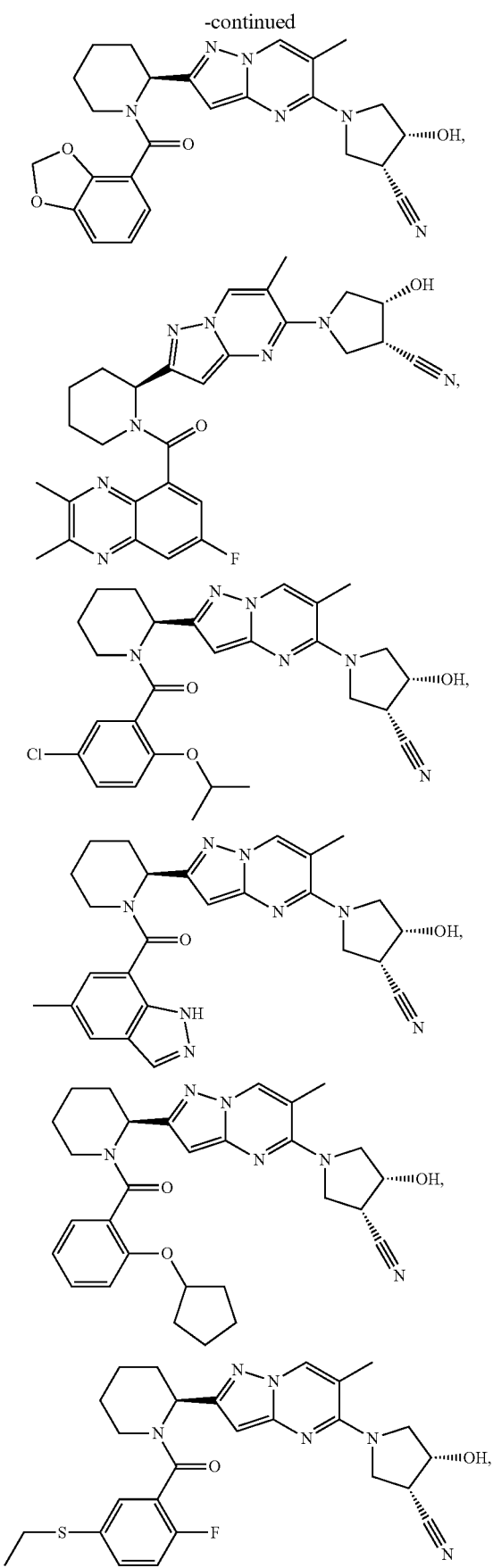

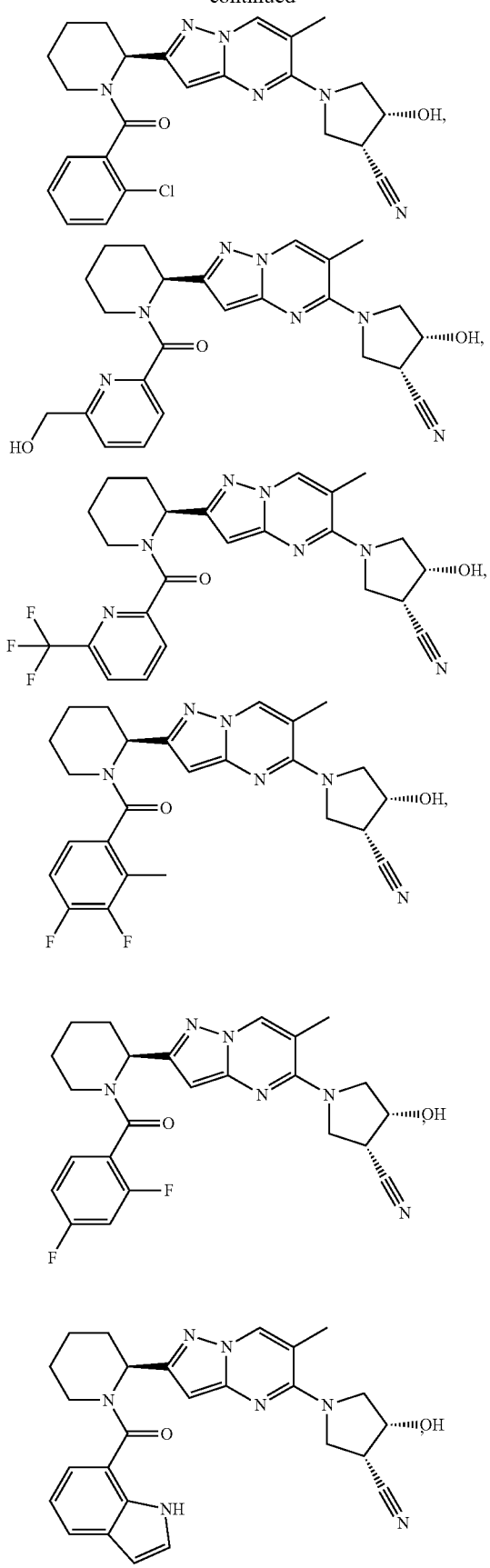
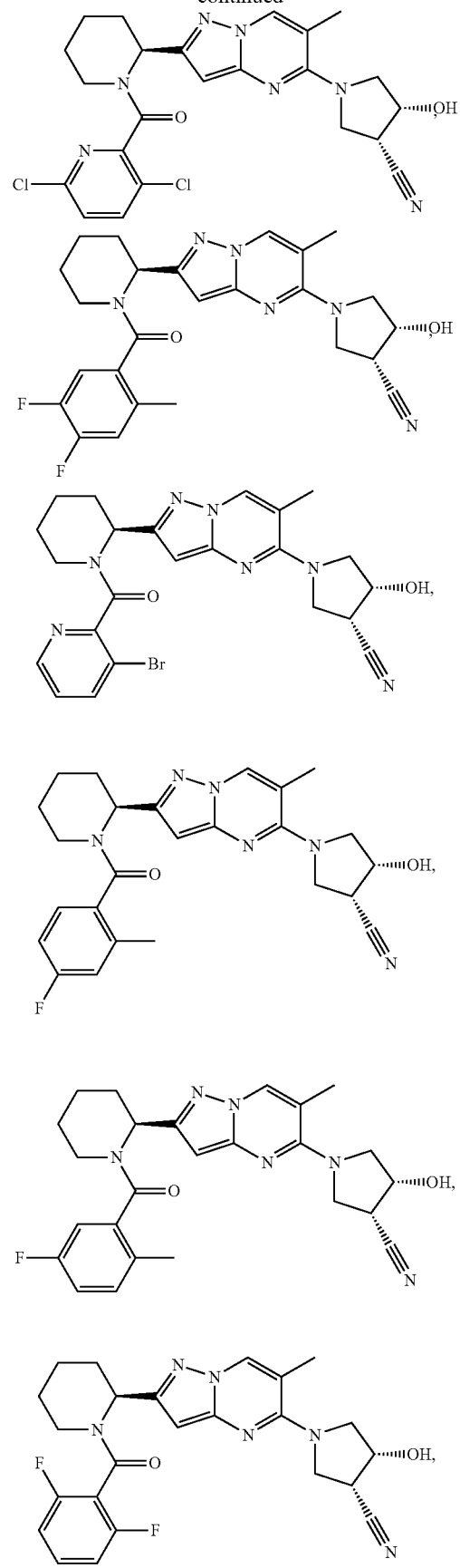

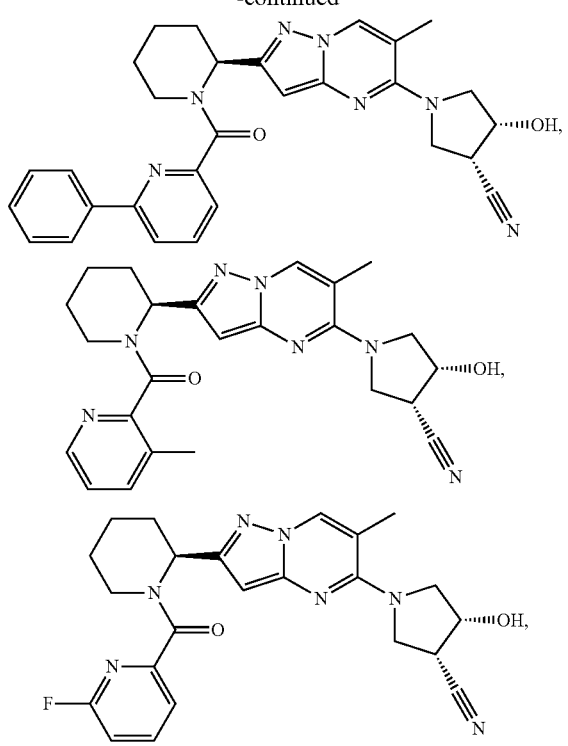
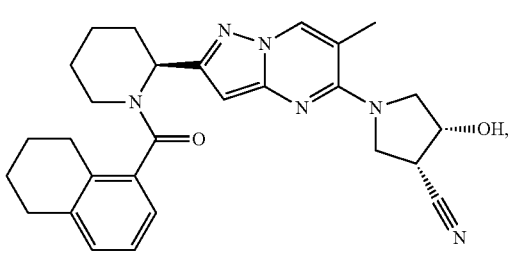
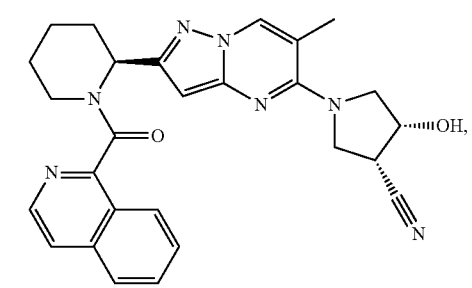
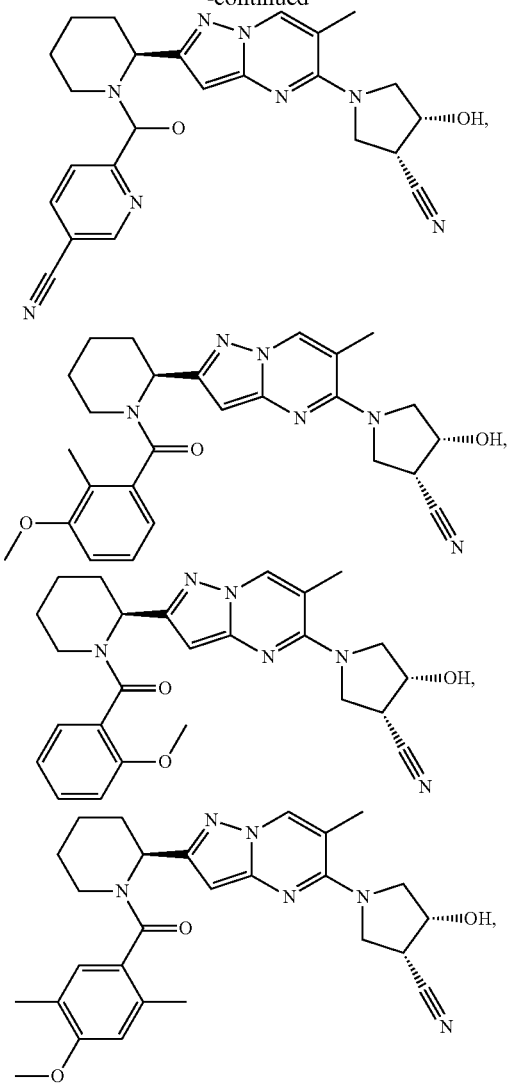
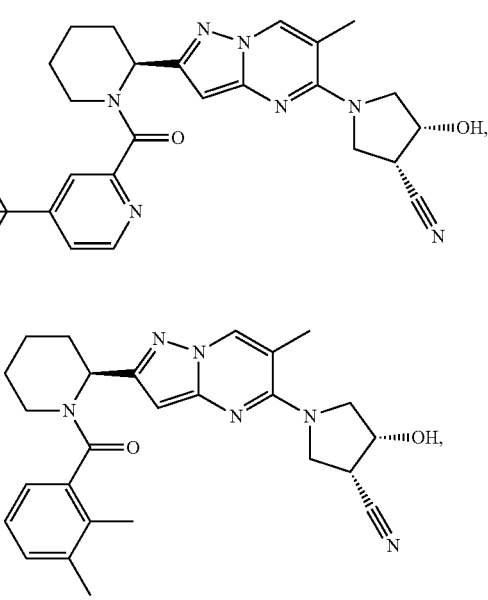

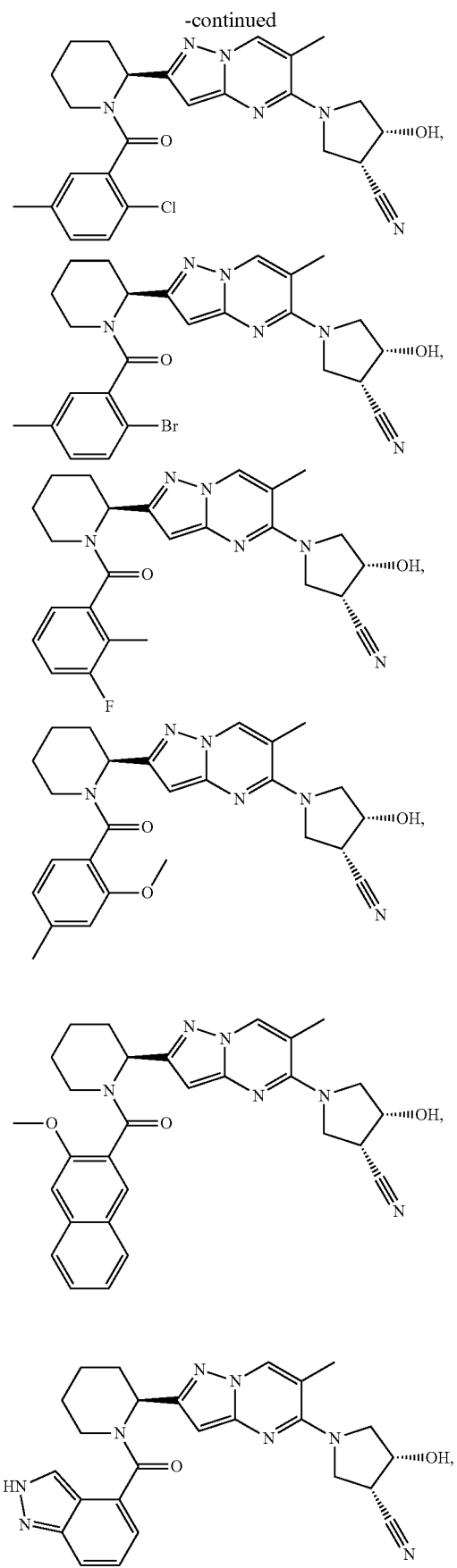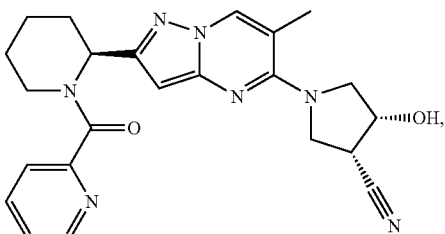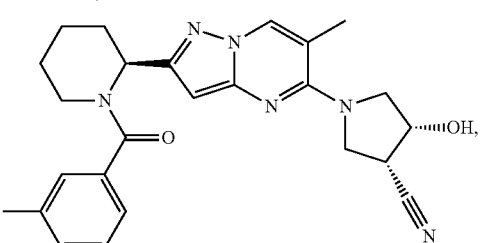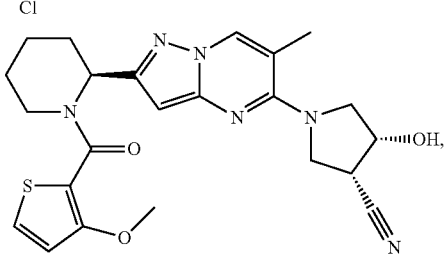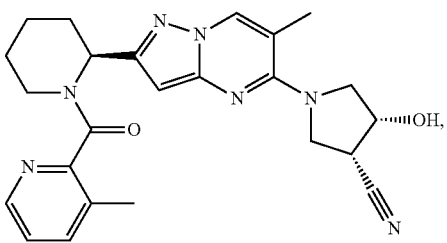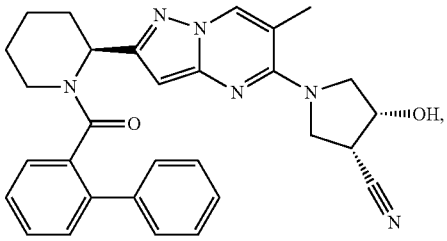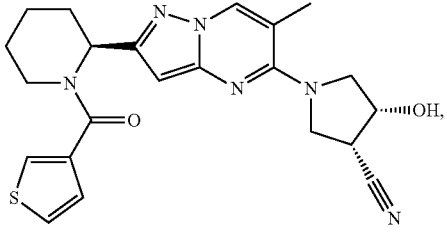

-continued
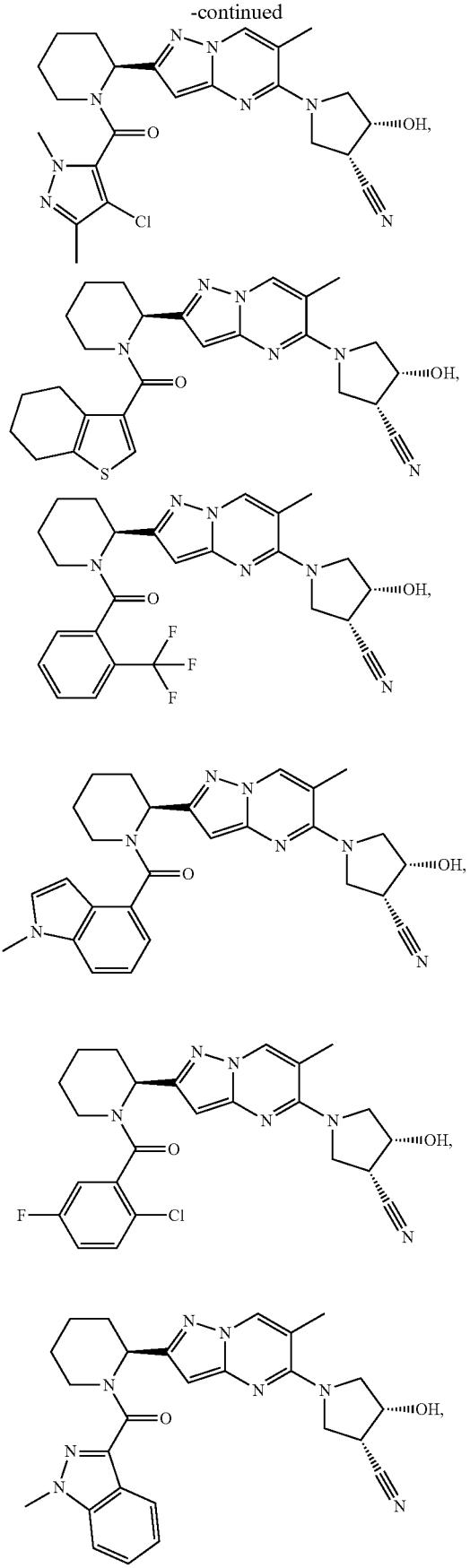
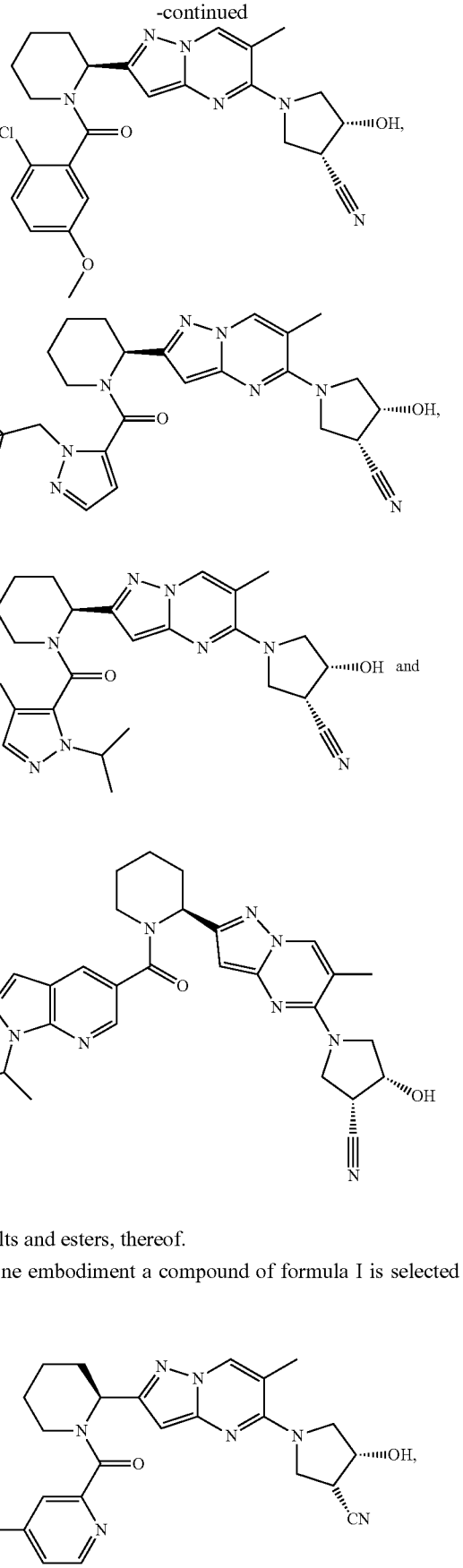
and salts and esters, thereof.
In one embodiment a compound of formula I is selected from:
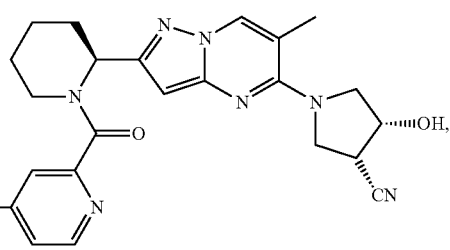

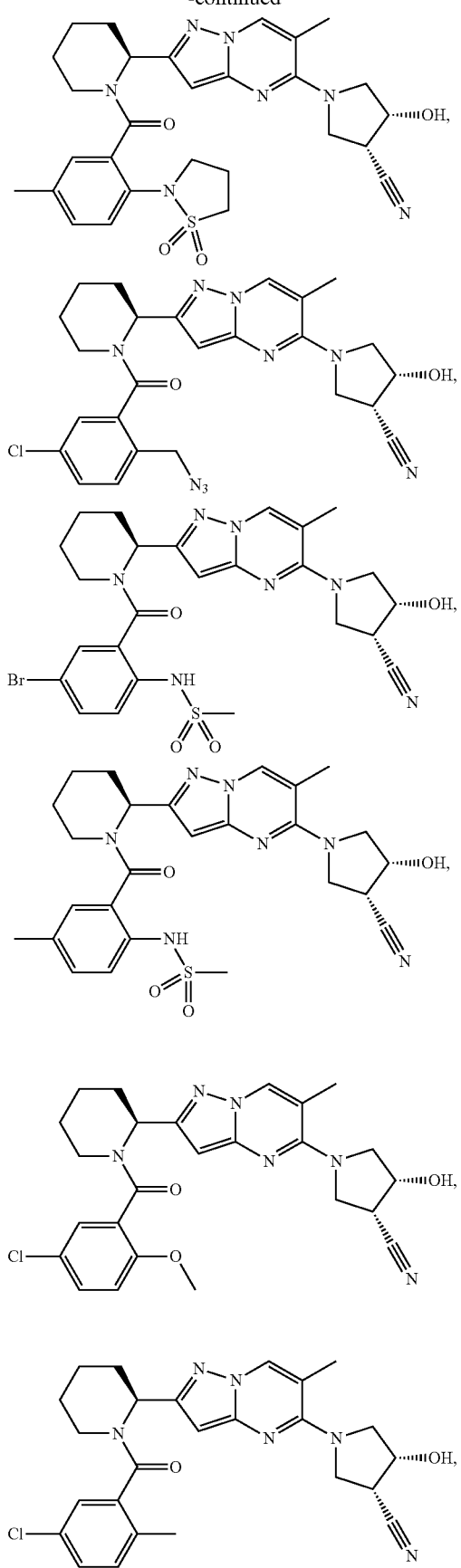
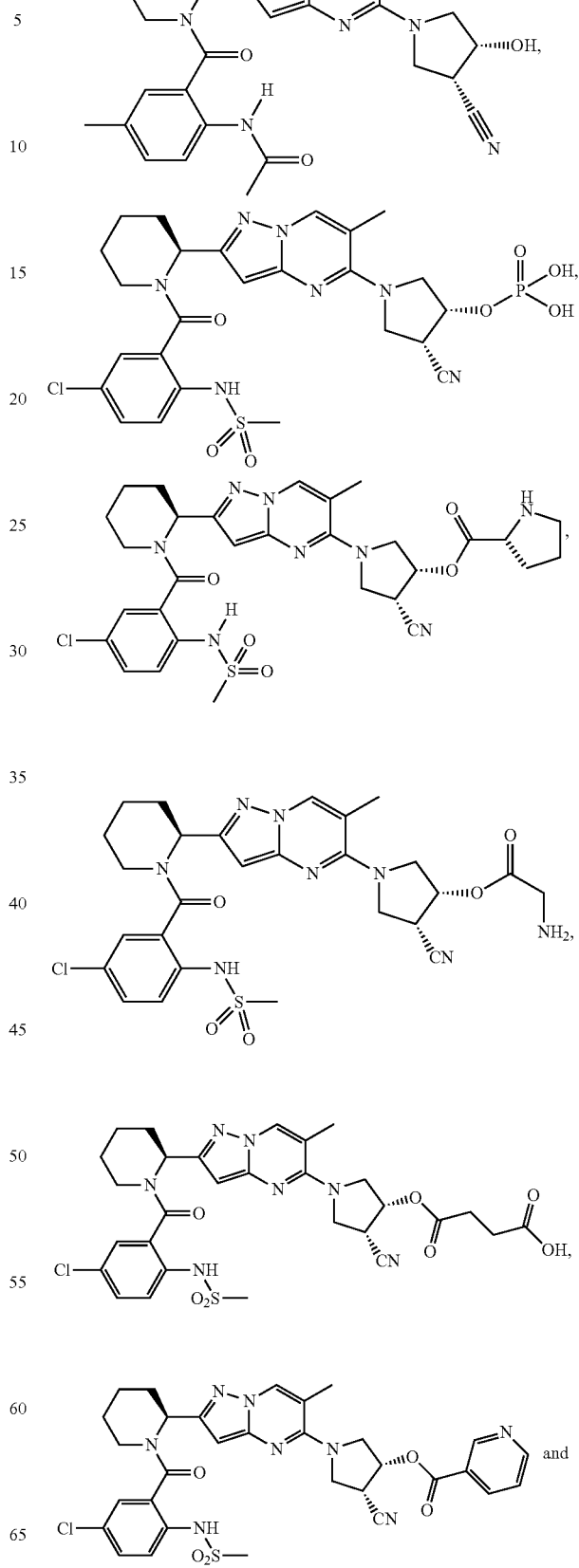

-continued

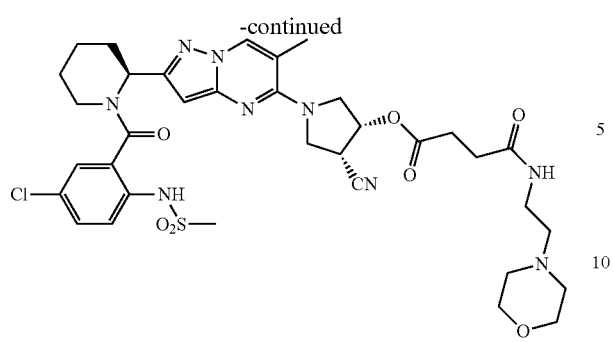

and salts and esters, thereof.

One embodiment provides a compound of formula II or IIa:

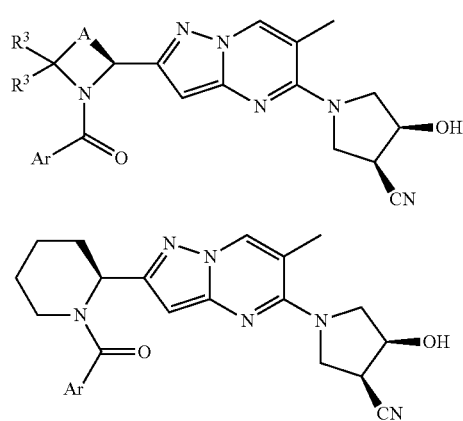

or a salt or ester, thereof, provided the compound is not

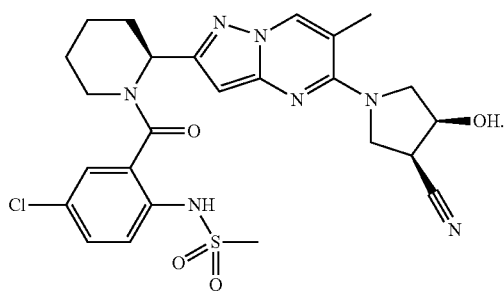 [SMILES: Cc1cn2nc([C@@H]3CCCCN3C(=O)c3cc(Cl)ccc3NS(C)(=O)=O)cc2nc1N1C[C@@H](O)[C@@H](C#N)C1]

In one embodiment the compounds of formula II or IIa do not include:

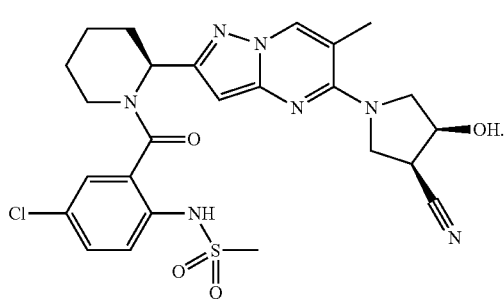 [SMILES: Cc1cn2nc([C@@H]3CCCCN3C(=O)c3cc(Cl)ccc3NS(C)(=O)=O)cc2nc1N1C[C@@H](O)[C@@H](C#N)C1]

One embodiment provides a compound of formula III or IIIa:

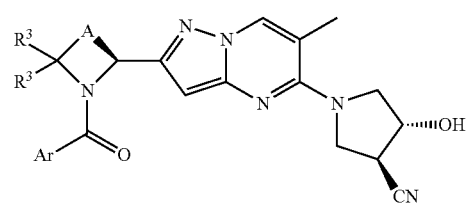

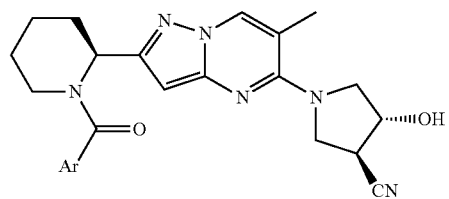

or a salt or ester, thereof, provided the compound is not:

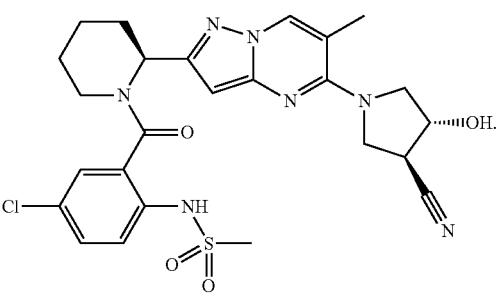 [SMILES: Cc1cn2nc([C@@H]3CCCCN3C(=O)c3cc(Cl)ccc3NS(C)(=O)=O)cc2nc1N1C[C@H](O)[C@@H](C#N)C1]

In one embodiment the compounds of formula III or IIIc do not include:

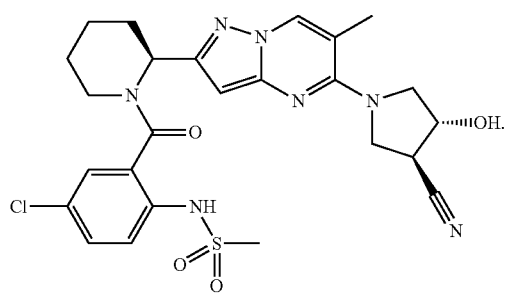 [SMILES: Cc1cn2nc([C@@H]3CCCCN3C(=O)c3cc(Cl)ccc3NS(C)(=O)=O)cc2nc1N1C[C@H](O)[C@@H](C#N)C1]

One embodiment provides a compound of formula IV or IVa:

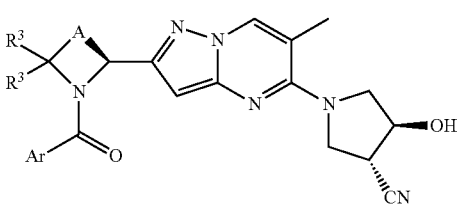

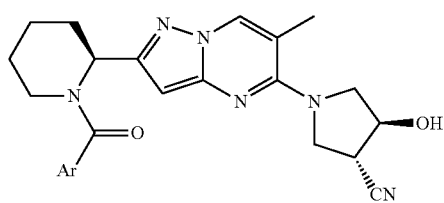

or a salt or ester, thereof, provided the compound is not

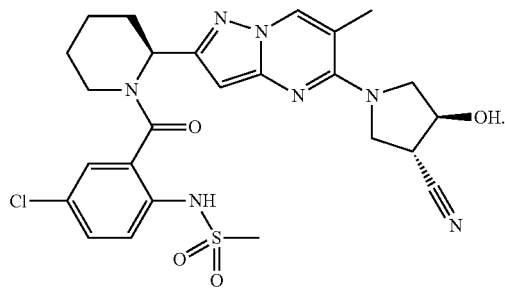 [SMILES: Cc1cn2nc([C@@H]3CCCCN3C(=O)c3cc(Cl)ccc3NS(C)(=O)=O)cc2nc1N1C[C@@H](O)[C@H](C#N)C1]

In one embodiment the compounds of formula IV or IVa do not include:

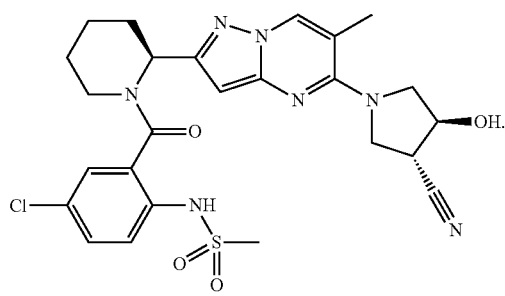 [SMILES: Cc1cn2nc([C@@H]3CCCCN3C(=O)c3cc(Cl)ccc3NS(C)(=O)=O)cc2nc1N1C[C@@H](O)[C@H](C#N)C1]

One embodiment provides for a mixture of a compound of formula III with a corresponding compound of formula IV. The mixture of the compound of formula III with the corresponding compound of formula IV is thus a mixture of trans diastereomers wherein the trans substituents are the substituents connected to the carbon marked with an asterisk 2 (*2) and the carbon marked with an asterisk 2 (*3). The invention also provides a mixture of a compound of formula IIIc with a corresponding compound of formula IVa. The mixture of the compound of formula IIIa with the corresponding compound of formula IVa is thus a mixture of trans diastereomers wherein the trans substituents are the substituents connected to the carbon marked with an asterisk 2 (*2) and the carbon marked with an asterisk 2 (*3).

One embodiment does not include:

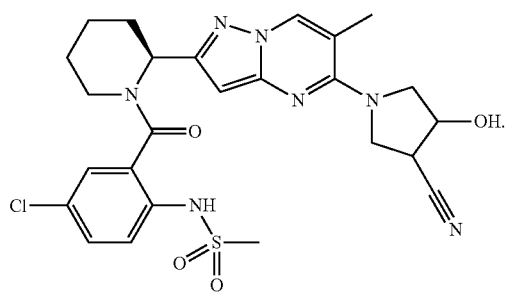 [SMILES: Cc1cn2nc([C@@H]3CCCCN3C(=O)c3cc(Cl)ccc3NS(C)(=O)=O)cc2nc1N1CC(O)C(C#N)C1]

In one embodiment a compound is selected from:

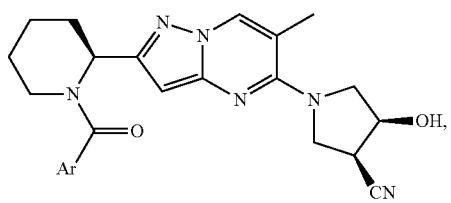

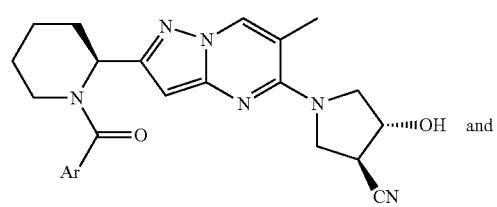

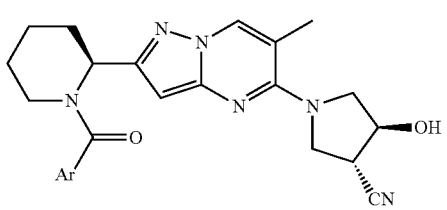

and salts and esters, thereof, or a mixture of a compound of formula IIIa and a corresponding compound of formula IVa or a salt or ester, thereof; wherein Ar is selected from:

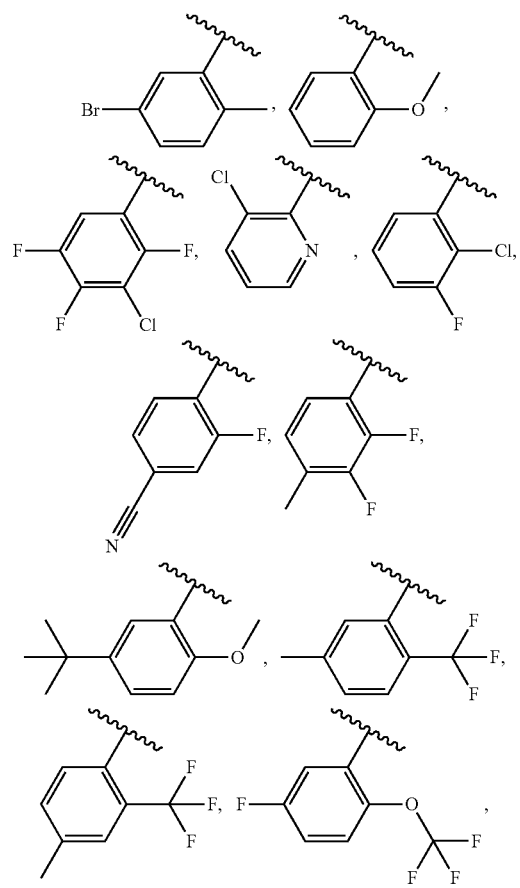

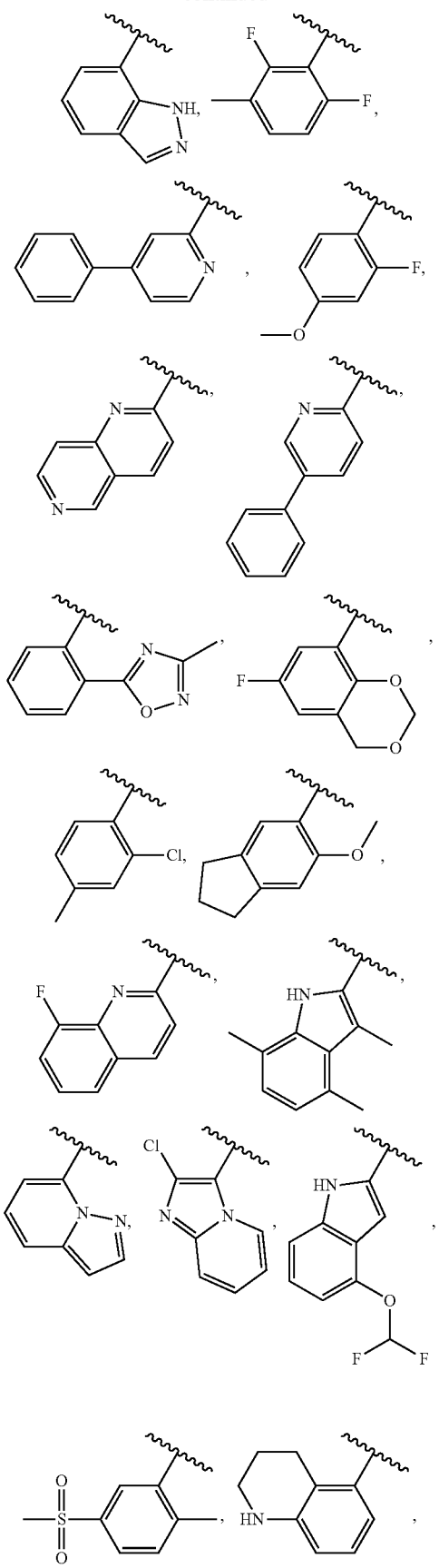
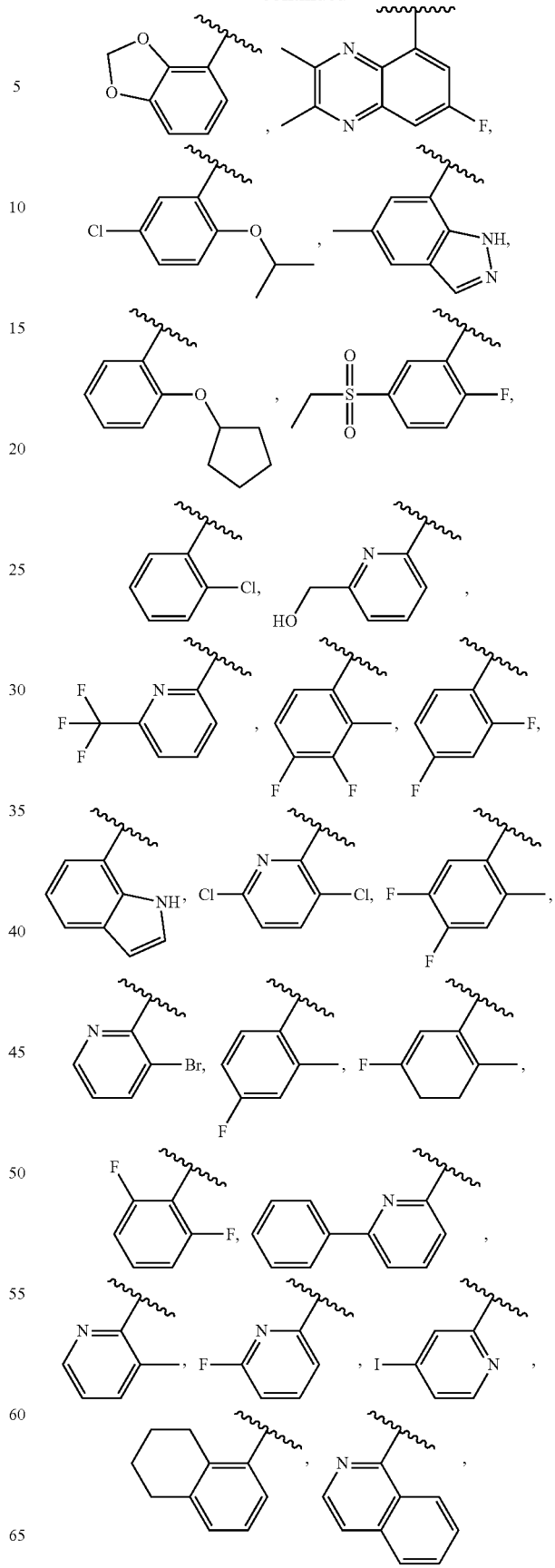

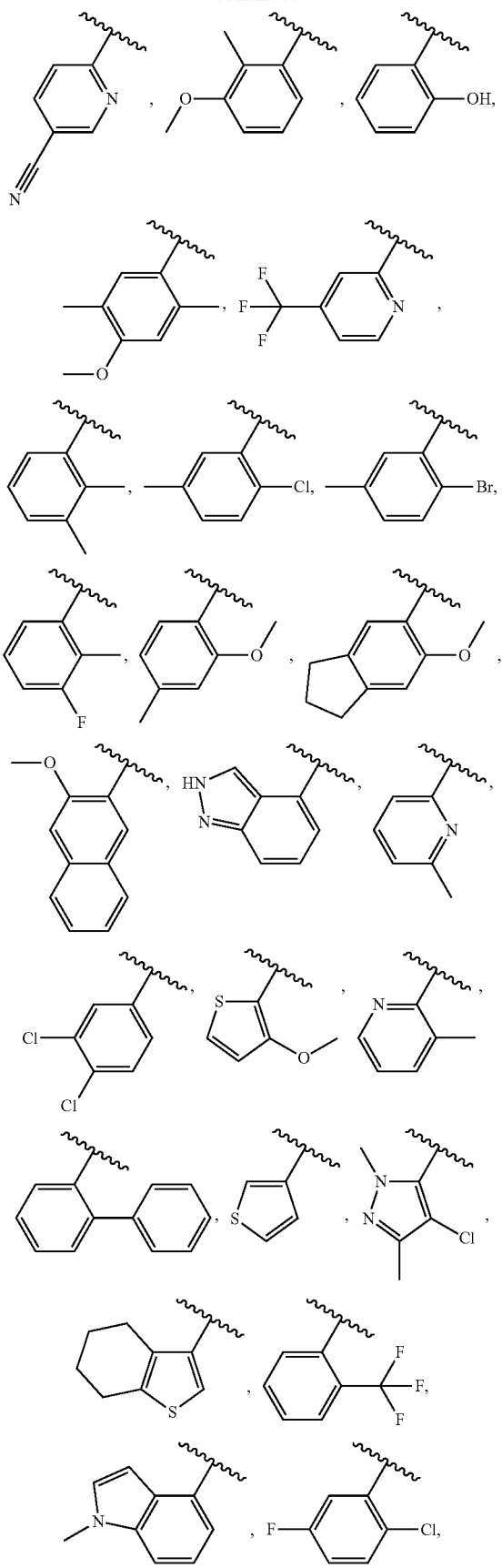
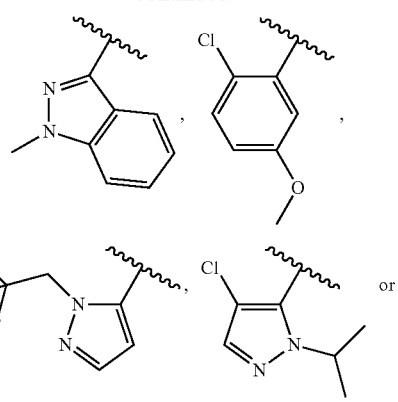
In one embodiment a compound is selected from:
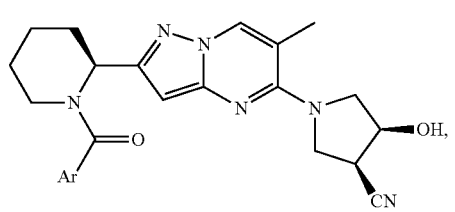
IIa
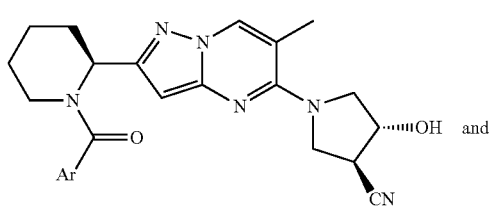
IIIa
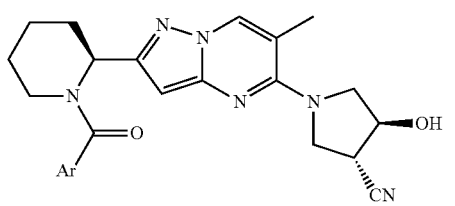
IVa
and salts and esters, thereof, or a mixture of a compound of formula IIIa and a corresponding compound of formula IVa or a salt or ester, thereof; wherein Ar is selected from:
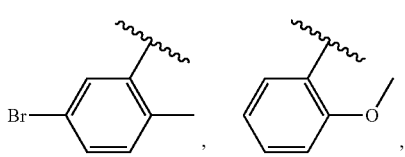

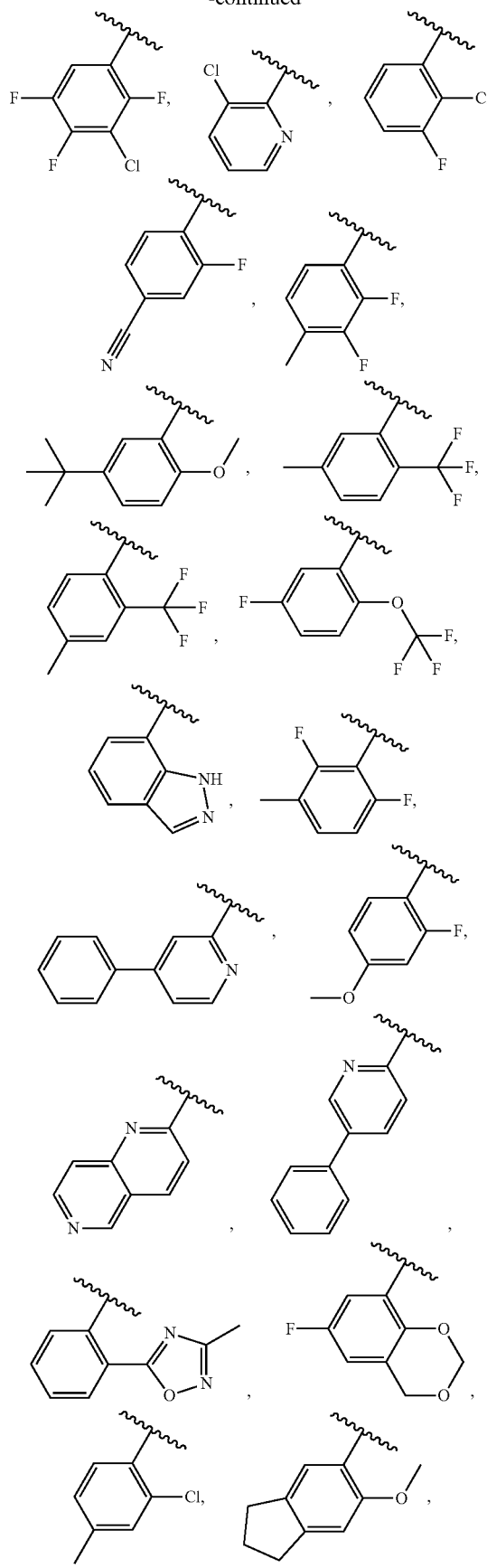
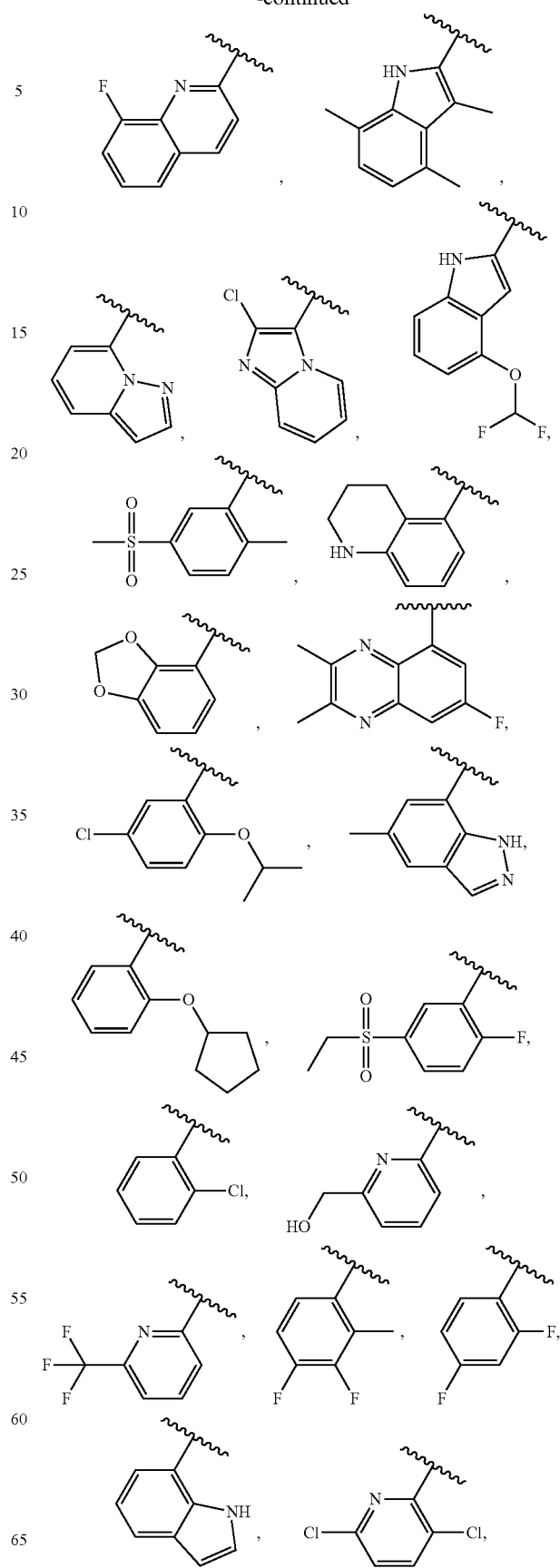

-continued
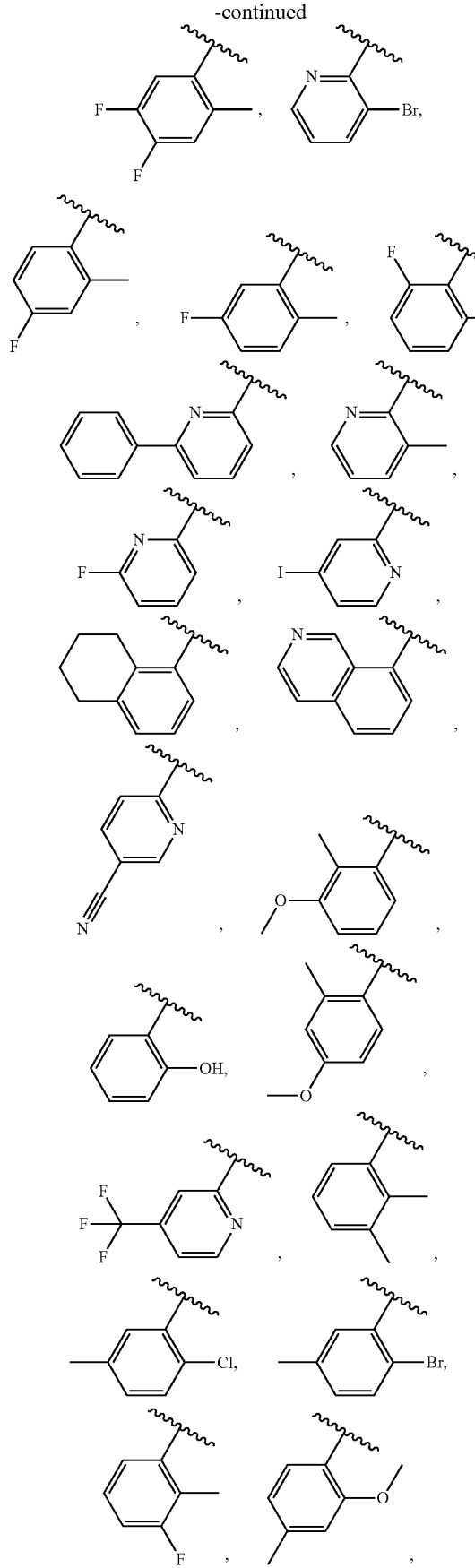
-continued
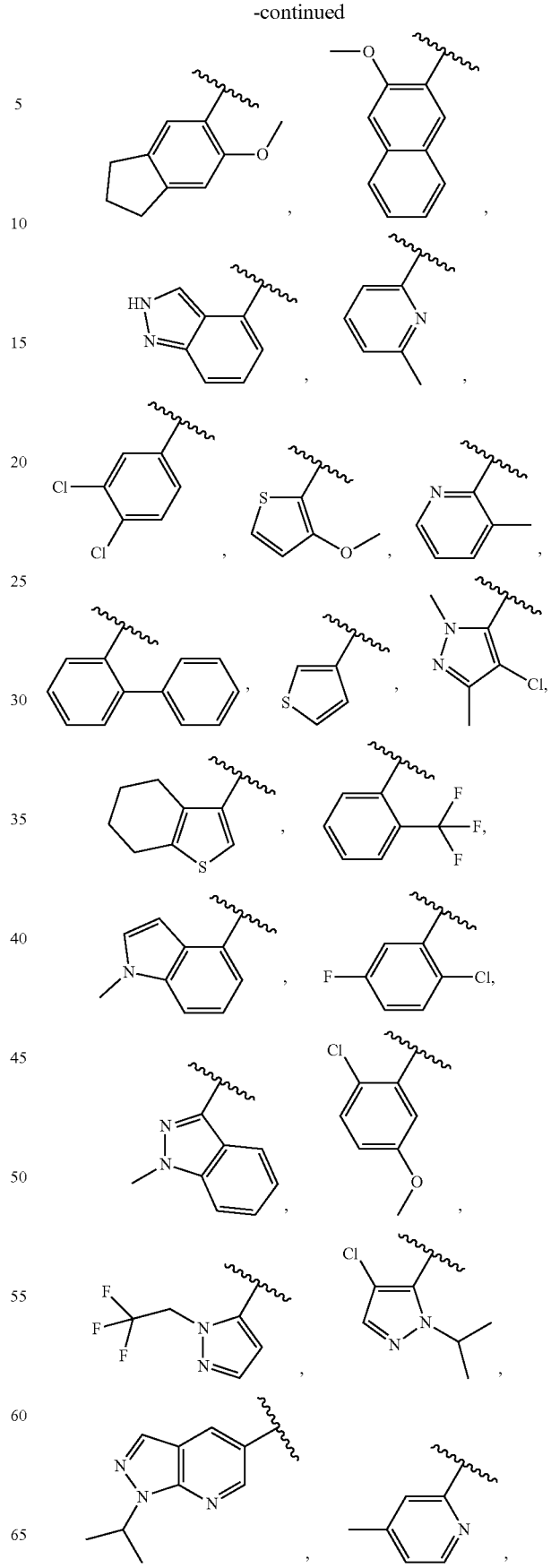

-continued

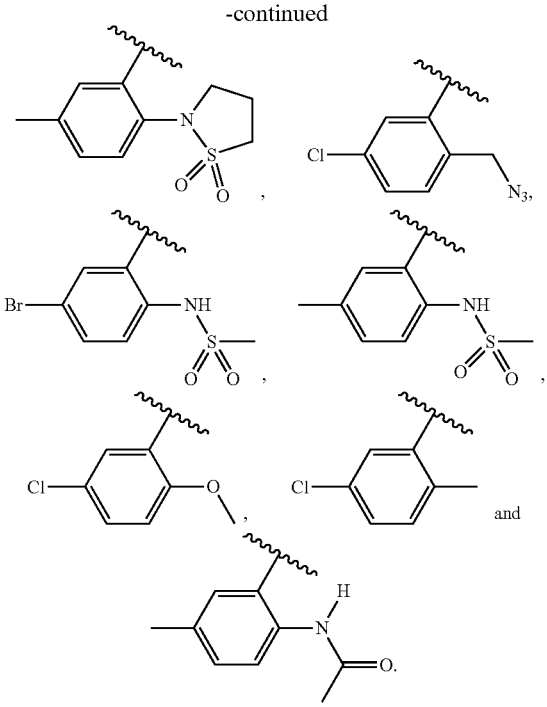

One embodiment provides a pharmaceutical composition comprising a compound of formula II, IIa, III, IIIa, IV or IVa or a pharmaceutically acceptable salt or ester thereof, and a pharmaceutically acceptable carrier.

One embodiment provides a pharmaceutical composition comprising a mixture of a compound of formula III and a corresponding compound of formula IV or pharmaceutically acceptable salts or esters thereof, and a pharmaceutically acceptable carrier.

One embodiment provides a pharmaceutical composition comprising a mixture of a compound of formula IIIa and a corresponding compound of formula IVa or pharmaceutically acceptable salts or esters thereof, and a pharmaceutically acceptable carrier.

One embodiment provides a method of treating a Pneumovirinae infection in a mammal (e.g. a human) in need thereof by administering a therapeutically effective amount of a compound of formula II, IIa, III, IIIc, IV or IVa or a pharmaceutically acceptable salt or ester thereof.

One embodiment provides a method of treating a Pneumovirinae infection in a mammal (e.g. a human) in need thereof by administering a therapeutically effective amount of a mixture of a compound of formula III and a corresponding compound of formula IV or pharmaceutically acceptable salts or esters thereof.

One embodiment provides a method of treating a Pneumovirinae infection in a mammal (e.g. a human) in need thereof by administering a therapeutically effective amount of a mixture of a compound of formula IIIa and a corresponding compound of formula IVa or pharmaceutically acceptable salts or esters thereof.

One embodiment provides a method of treating a Pneumovirinae infection in a mammal (e.g. a human) in need thereof by administering a therapeutically effective amount of a, tautomer, polymorph, pseudopolymorph, amorphous form, hydrate or solvate of a compound of formula II, IIa, III, IIIc, IV or IVa or a pharmaceutically acceptable salt or ester thereof.

One embodiment provides a method of treating a Pneumovirinae infection in a mammal (e.g. a human) in need thereof by administering a therapeutically effective amount of a, tautomer, polymorph, pseudopolymorph, amorphous form, hydrate or solvate of a compound a mixture of a compound of formula III and a corresponding compound of formula IV or pharmaceutically acceptable salts or esters thereof.

One embodiment provides a method of treating a Pneumovirinae infection in a mammal (e.g. a human) in need thereof by administering a therapeutically effective amount of a, tautomer, polymorph, pseudopolymorph, amorphous form, hydrate or solvate of a mixture of a compound of formula IIIc and a corresponding compound of formula IVa or pharmaceutically acceptable salts or esters thereof.

One embodiment provides a method of treating a respiratory syncytial virus infection in a mammal (e.g. a human) in need thereof by administering a therapeutically effective amount of a compound of formula II, IIa, III, IIIa, IV or IVa or a pharmaceutically acceptable salt or ester thereof.

One embodiment provides a method of treating a respiratory syncytial virus infection in a mammal (e.g. a human) in need thereof by administering a therapeutically effective amount of a mixture of a compound of formula III and a corresponding compound of formula IV or pharmaceutically acceptable salts or esters thereof.

One embodiment provides a method of treating a respiratory syncytial virus infection in a mammal (e.g. a human) in need thereof by administering a therapeutically effective amount of a mixture of a compound of formula IIIa and a corresponding compound of formula IVa or pharmaceutically acceptable salts or esters thereof.

One embodiment provides a method of treating a respiratory syncytial virus infection in a mammal (e.g. a human) in need thereof by administering a therapeutically effective amount of a tautomer, polymorph, pseudopolymorph, amorphous form, hydrate or solvate of a compound of formula II, IIa, III, IIIa, IV or IVa or a pharmaceutically acceptable salt or ester thereof.

One embodiment provides a method of treating a respiratory syncytial virus infection in a mammal (e.g. a human) in need thereof by administering a therapeutically effective amount of a tautomer, polymorph, pseudopolymorph, amorphous form, hydrate or solvate of a mixture of a compound of formula III and a corresponding compound of formula IV or pharmaceutically acceptable salts or esters thereof.

One embodiment provides a method of treating a respiratory syncytial virus infection in a mammal (e.g. a human) in need thereof by administering a therapeutically effective amount of a tautomer, polymorph, pseudopolymorph, amorphous form, hydrate or solvate of a mixture of a compound of formula IIIa and a corresponding compound of formula IVa or pharmaceutically acceptable salts or esters thereof.

One embodiment provides a method of treating a Pneumovirinae infection in a mammal (e.g. a human) in need thereof by administering a therapeutically effective amount of a compound of formula II, IIa, III, IIIa, IV or IVa or a pharmaceutically acceptable salt or ester thereof, and a pharmaceutically acceptable diluent or carrier.

One embodiment provides a method of treating a Pneumovirinae infection in a mammal (e.g. a human) in need thereof by administering a therapeutically effective amount of a mixture of a compound of formula III and a corresponding compound of formula IV or pharmaceutically acceptable salts or esters thereof, and a pharmaceutically acceptable diluent or carrier.

One embodiment provides a method of treating a Pneumovirinae infection in a mammal (e.g. a human) in need thereof by administering a therapeutically effective amount of a mixture of a compound of formula IIIa and a corresponding compound of formula IVa or pharmaceutically acceptable salts or esters thereof, and a pharmaceutically acceptable diluent or carrier.

One embodiment provides a method of treating a Pneumovirinae infection in a mammal (e.g. a human) in need thereof by administering a therapeutically effective amount of a compound of formula II, IIa, III, IIIa, IV or IVa or a pharmaceutically acceptable salt or ester thereof, in combination with at least one additional therapeutic agent.

One embodiment provides a method of treating a Pneumovirinae infection in a mammal (e.g. a human) in need thereof by administering a therapeutically effective amount of a mixture of a compound of formula III and a corresponding compound of formula IV or pharmaceutically acceptable salts or esters thereof, in combination with at least one additional therapeutic agent.

One embodiment provides a method of treating a Pneumovirinae infection in a mammal (e.g. a human) in need thereof by administering a therapeutically effective amount of a mixture of a compound of formula IIIa and a corresponding compound of formula IVa or pharmaceutically acceptable salts or esters thereof, in combination with at least one additional therapeutic agent.

One embodiment provides a method of treating a Pneumovirinae infection in a mammal (e.g. a human) in need thereof, by administering a therapeutically effective amount of a combination pharmaceutical agent comprising:
 a) a first pharmaceutical composition comprising a compound of formula II, IIa, III, IIIa, IV or IVa or a pharmaceutically acceptable salt or ester thereof; and
 b) a second pharmaceutical composition comprising at least one additional therapeutic agent active against infectious Pneumovirinae viruses.

One embodiment provides a method of treating a Pneumovirinae infection in a mammal (e.g. a human) in need thereof, by administering a therapeutically effective amount of a combination pharmaceutical agent comprising:
 a) a first pharmaceutical composition comprising a mixture of a compound of formula III and a corresponding compound of formula IV, or pharmaceutically acceptable salts or esters thereof; and
 b) a second pharmaceutical composition comprising at least one additional therapeutic agent active against infectious Pneumovirinae viruses.

One embodiment provides a method of treating a Pneumovirinae infection in a mammal (e.g. a human) in need thereof, by administering a therapeutically effective amount of a combination pharmaceutical agent comprising:
 a) a first pharmaceutical composition comprising a mixture of a compound of formula IIIa and a corresponding compound of formula IVa or pharmaceutically acceptable salts or esters thereof; and
 b) a second pharmaceutical composition comprising at least one additional therapeutic agent active against infectious Pneumovirinae viruses.

One embodiment provides a method of treating a Pneumovirinae infection in a mammal (e.g. a human) in need thereof, by administering a therapeutically effective amount of a combination pharmaceutical agent comprising:
 a) a compound of formula II, IIa, III, IIIa, IV or IVa or a pharmaceutically acceptable salt or ester thereof; and
 b) a therapeutic agent active against infectious Pneumovirinae viruses.

One embodiment provides a method of treating a Pneumovirinae infection in a mammal (e.g. a human) in need thereof, by administering a therapeutically effective amount of a combination pharmaceutical agent comprising:
 a) a mixture of a compound of formula III and a corresponding compound of formula IV or pharmaceutically acceptable salts or esters thereof; and
 b) a therapeutic agent active against infectious Pneumovirinae viruses.

One embodiment provides a method of treating a Pneumovirinae infection in a mammal (e.g. a human) in need thereof, by administering a therapeutically effective amount of a combination pharmaceutical agent comprising:
 a) a mixture of a compound of formula IIIa and a corresponding compound of formula IVa or pharmaceutically acceptable salts or esters thereof; and
 b) a therapeutic agent active against infectious Pneumovirinae viruses.

One embodiment provides a method of treating a respiratory syncytial virus infection in a mammal (e.g. a human) in need thereof, by administering a therapeutically effective amount of a combination pharmaceutical agent comprising:
 a) a first pharmaceutical composition comprising a compound of formula II, IIa, III, IIIa, IV or IVa or a pharmaceutically acceptable salt or ester thereof; and
 b) a second pharmaceutical composition comprising at least one additional therapeutic agent active against infectious respiratory syncytial viruses.

One embodiment provides a method of treating a respiratory syncytial virus infection in a mammal (e.g. a human) in need thereof, by administering a therapeutically effective amount of a combination pharmaceutical agent comprising:
 a) a mixture of a compound of formula III and a corresponding compound of formula IV or pharmaceutically acceptable salts or esters thereof; and
 b) a second pharmaceutical composition comprising at least one additional therapeutic agent active against infectious respiratory syncytial viruses.

One embodiment provides a method of treating a respiratory syncytial virus infection in a mammal (e.g. a human) in need thereof, by administering a therapeutically effective amount of a combination pharmaceutical agent comprising:
 a) a mixture of a compound of formula IIIa and a corresponding compound of formula IVa or a pharmaceutically acceptable salt thereof a pharmaceutically acceptable salt or ester thereof; and
 b) a second pharmaceutical composition comprising at least one additional therapeutic agent active against infectious respiratory syncytial viruses.

One embodiment provides a method of treating a respiratory syncytial virus infection in a mammal (e.g. a human) in need thereof, by administering a therapeutically effective amount of a combination pharmaceutical agent comprising:
 a) a compound of formula II, IIa, III, IIIa, IV or IVa or a pharmaceutically acceptable salt or ester thereof; and
 b) a therapeutic agent active against infectious respiratory syncytial viruses.

One embodiment provides a method of treating a respiratory syncytial virus infection in a mammal (e.g. a human) in need thereof, by administering a therapeutically effective amount of a combination pharmaceutical agent comprising:

a) a mixture of a compound of formula III and a corresponding compound of formula IV or pharmaceutically acceptable salts or esters thereof; and b) a therapeutic agent active against infectious respiratory syncytial viruses.

One embodiment provides a method of treating a respiratory syncytial virus infection in a mammal (e.g. a human) in need thereof, by administering a therapeutically effective amount of a combination pharmaceutical agent comprising:

a) a mixture of a compound of formula IIIa and a corresponding compound of formula IVa or pharmaceutically acceptable salts or esters thereof; and b) a therapeutic agent active against infectious respiratory syncytial viruses.

One embodiment provides a compound of formula II, IIa, III, IIIa, IV or IVa or a pharmaceutically acceptable salt or ester thereof for use in medical therapy.

One embodiment provides a mixture of a compound of formula III and a corresponding compound of formula IV a pharmaceutically acceptable salts or esters thereof, for use in medical therapy.

One embodiment provides a mixture of a compound of formula IIIa and a corresponding compound of formula IVa or pharmaceutically acceptable salts or esters thereof, for use in medical therapy.

One embodiment provides a compound of formula II, IIa, III, IIIa, IV or IVa or a pharmaceutically acceptable salt or ester thereof, for use in the prophylactic or therapeutic treat a viral infection caused by a Pneumovirinae virus or a respiratory syncytial virus.

One embodiment provides a mixture of a compound of formula III and a corresponding compound of formula IV or pharmaceutically acceptable salts or esters thereof, for use in the prophylactic or therapeutic treat a viral infection caused by a Pneumovirinae virus or a respiratory syncytial virus.

One embodiment provides a mixture of a compound of formula IIIa and a corresponding compound of formula IVa or pharmaceutically acceptable salts or esters thereof, for use in the prophylactic or therapeutic treat a viral infection caused by a Pneumovirinae virus or a respiratory syncytial virus.

One embodiment provides the use of a compound of formula II, IIa, III, IIIa, IV or IVa or a pharmaceutically acceptable salt or ester thereof, for the manufacture of a medicament useful for the treatment of a viral infection in a mammal (e.g. a human) caused by a Pneumovirinae virus or a respiratory syncytial virus.

One embodiment provides the use of a mixture of a compound of formula III and a corresponding compound of formula IV or pharmaceutically acceptable salts or esters thereof, for the manufacture of a medicament useful for the treatment of a viral infection in a mammal (e.g. a human) caused by a Pneumovirinae virus or a respiratory syncytial virus.

One embodiment provides the use of a mixture of a compound of formula IIIa and a corresponding compound of formula IVa or pharmaceutically acceptable salts or esters thereof, for the manufacture of a medicament useful for the treatment of a viral infection in a mammal (e.g. a human) caused by a Pneumovirinae virus or a respiratory syncytial virus.

In one embodiment a compound is selected from:

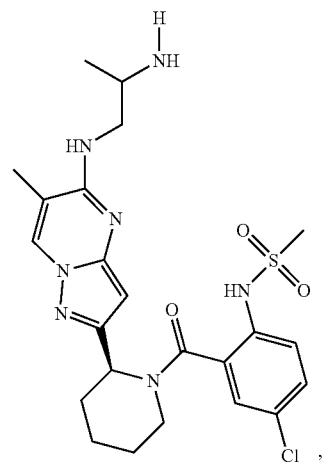

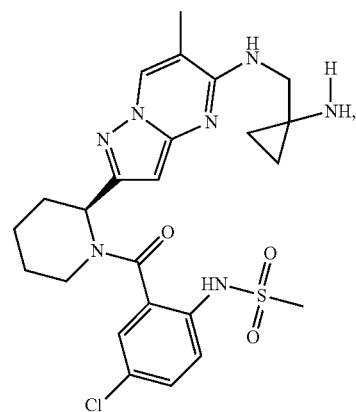

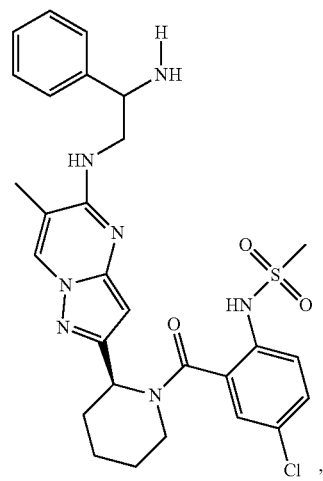

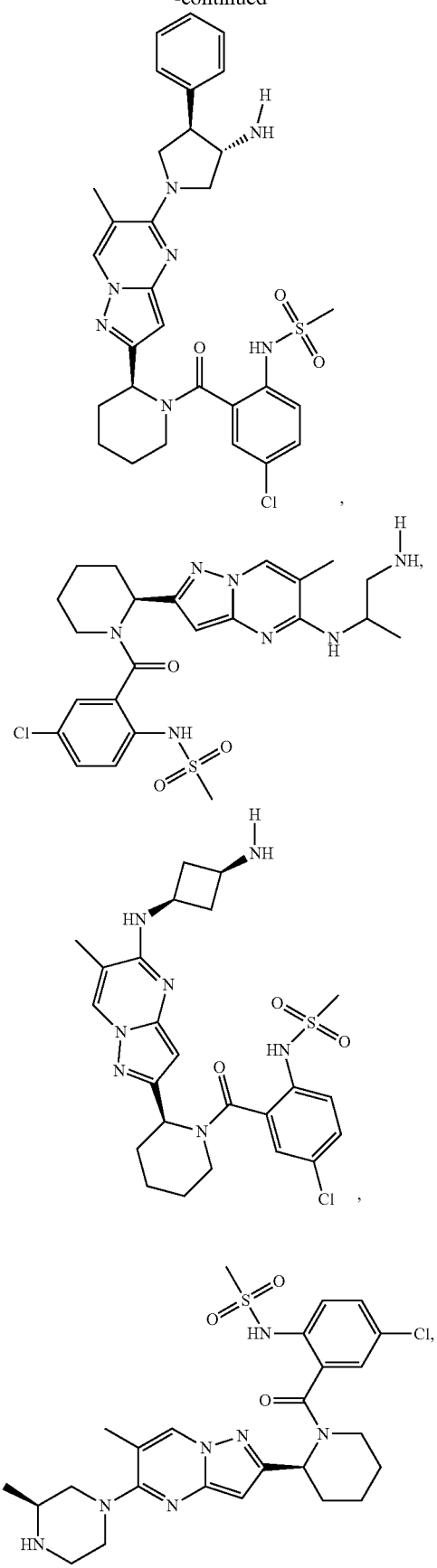

-continued
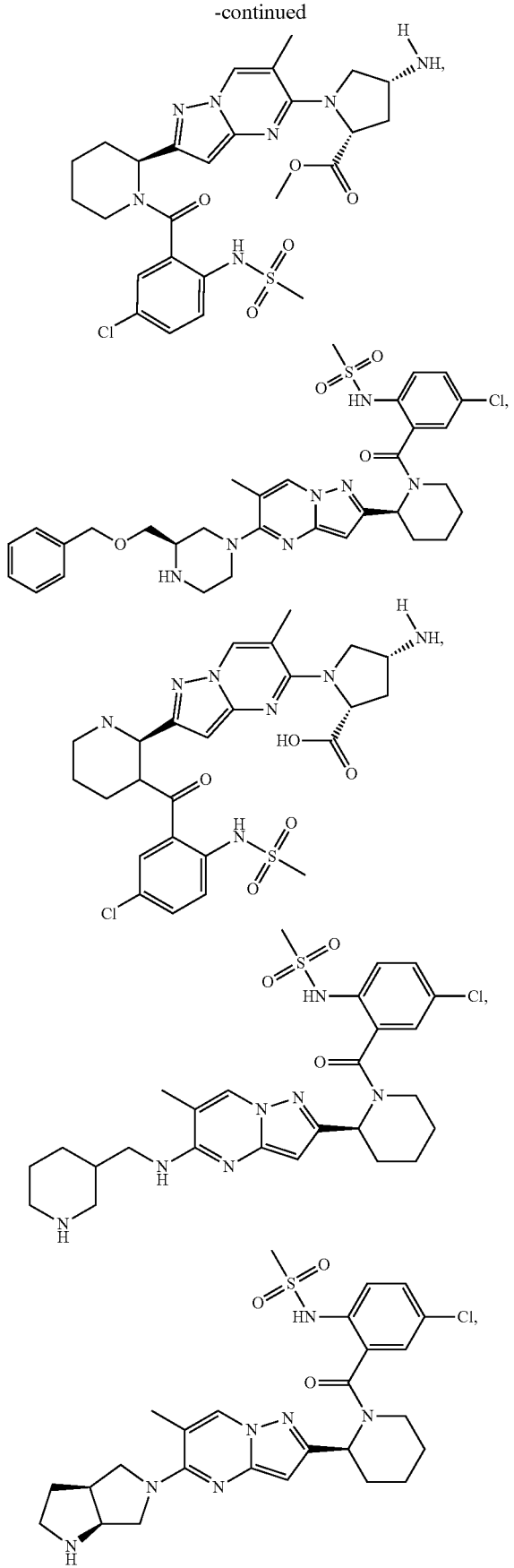
-continued
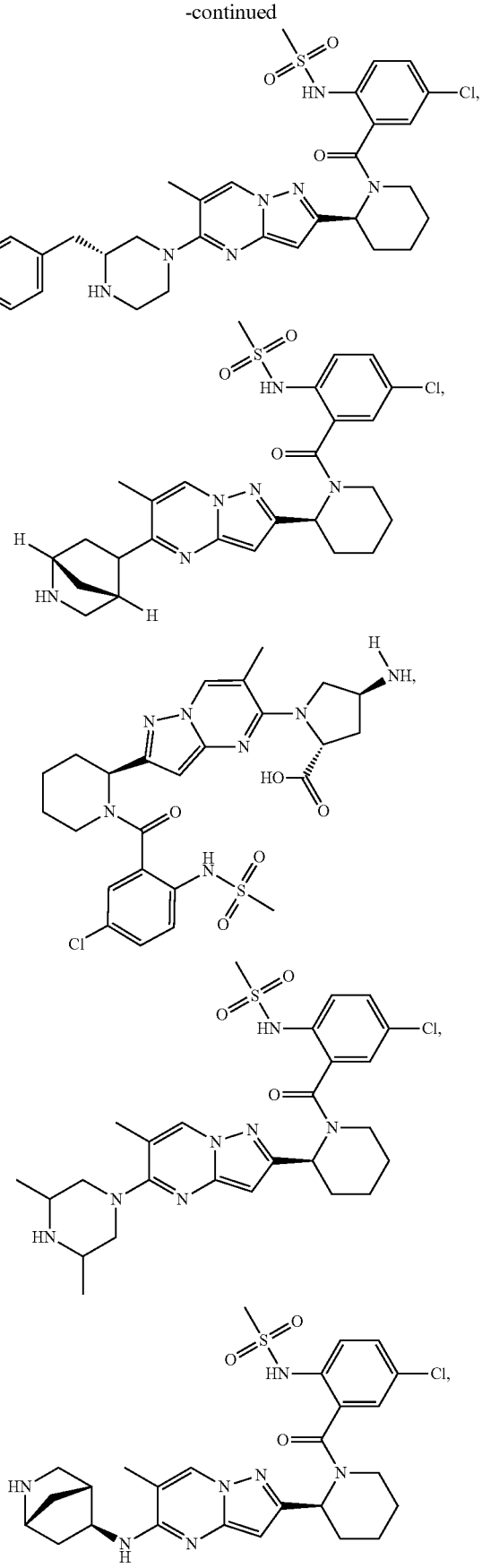

73
-continued
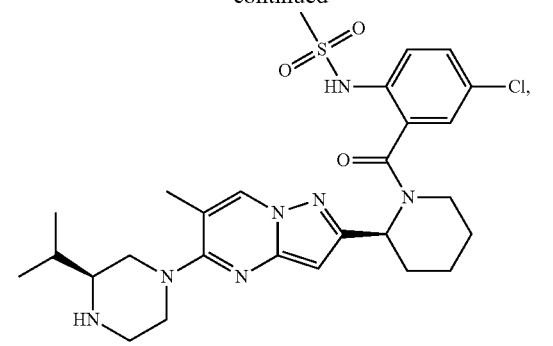
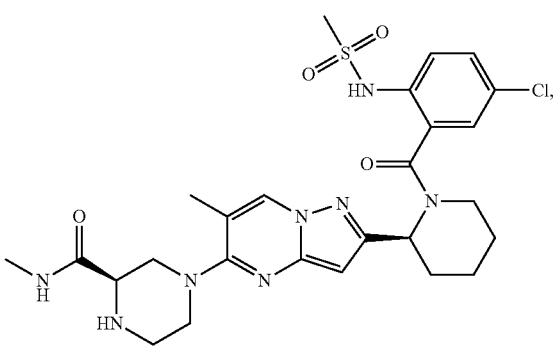
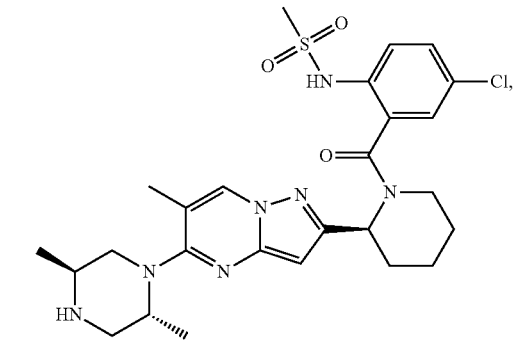
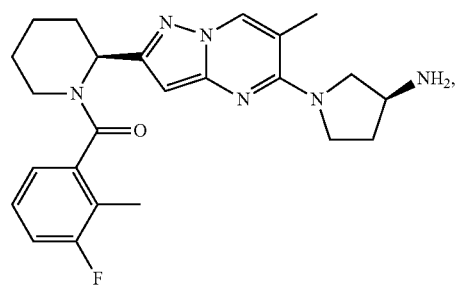
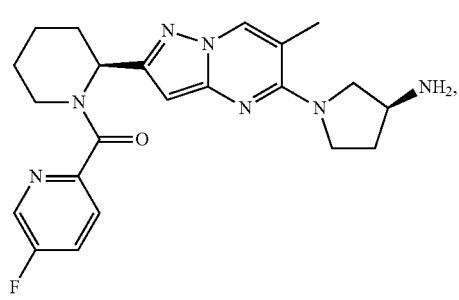
74
-continued
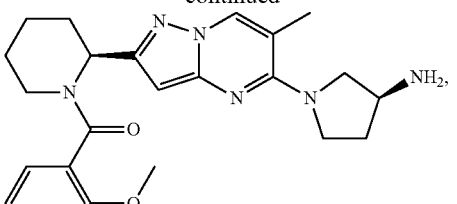
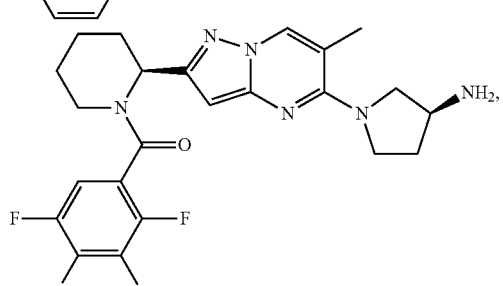
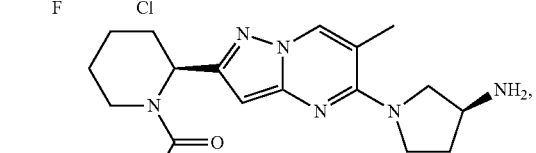
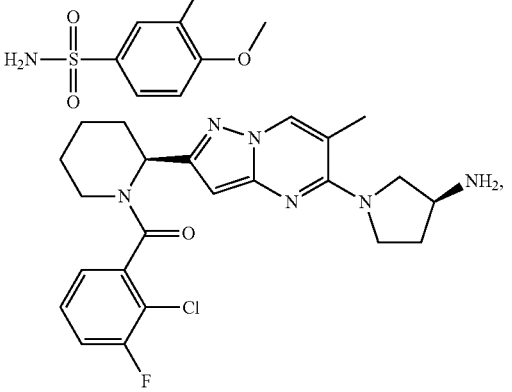
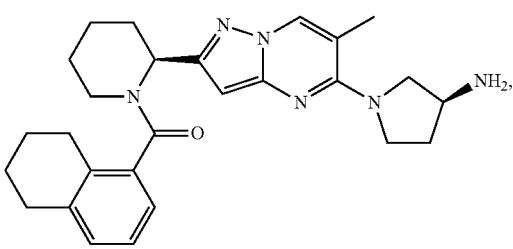
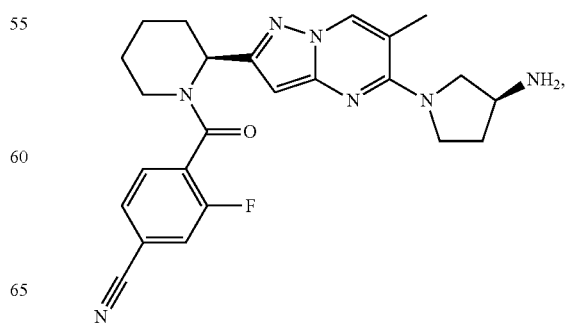

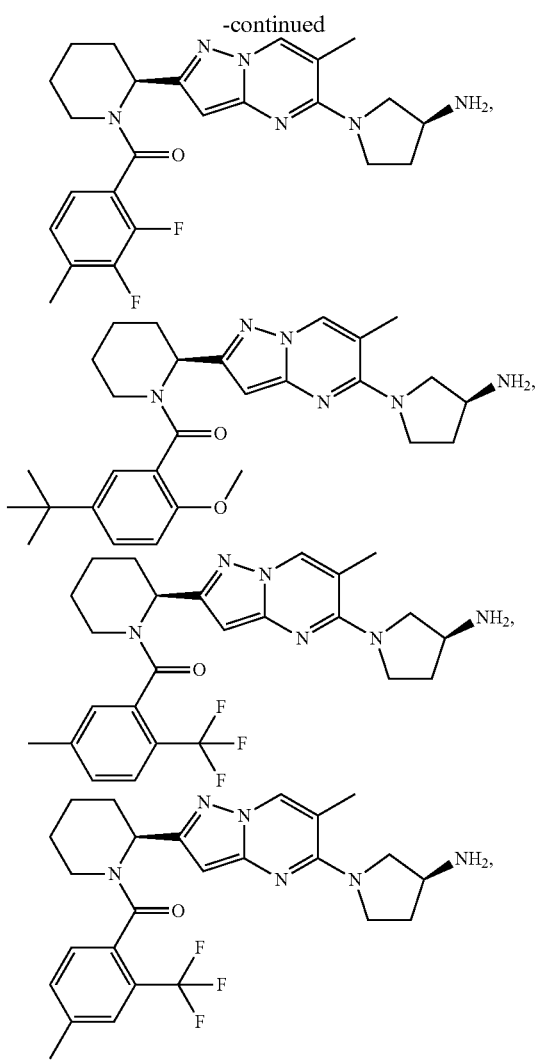
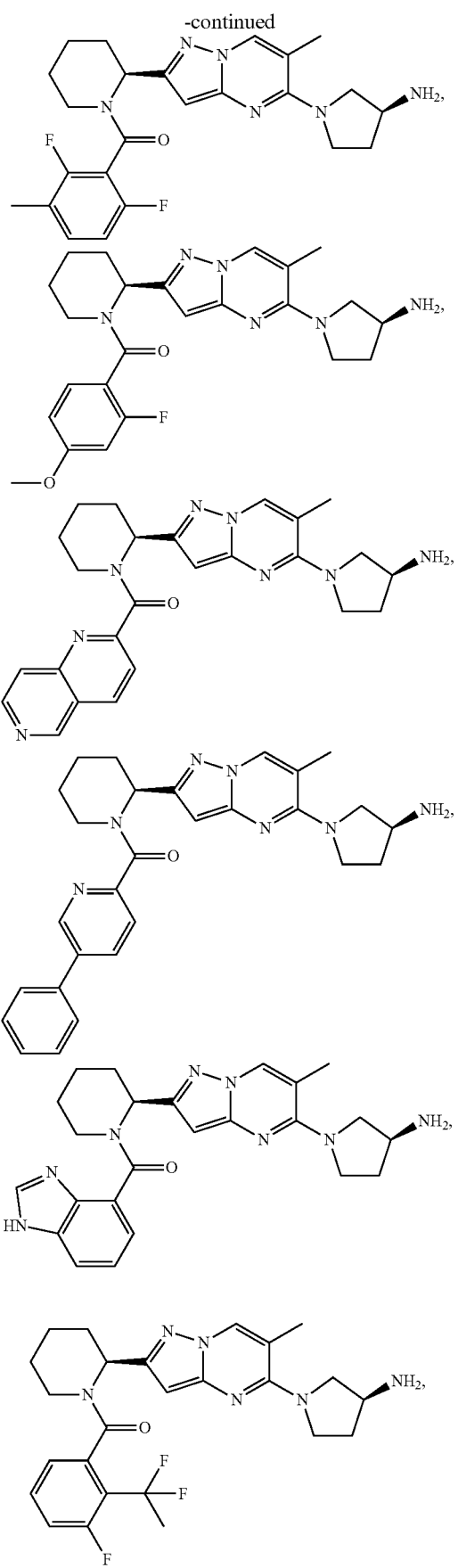

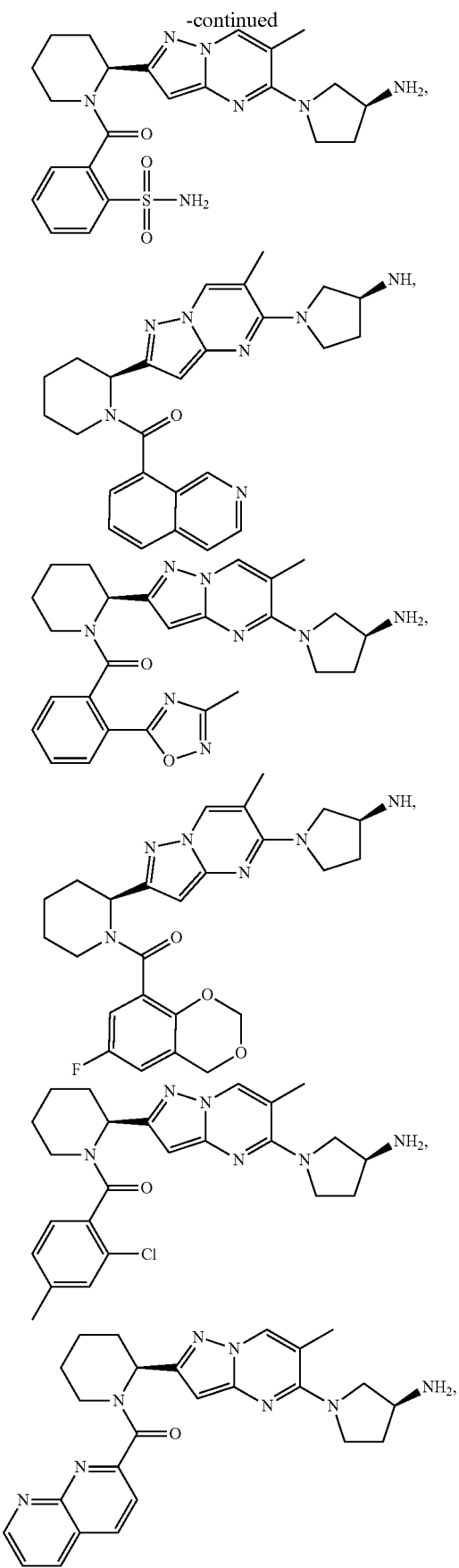

79
-continued
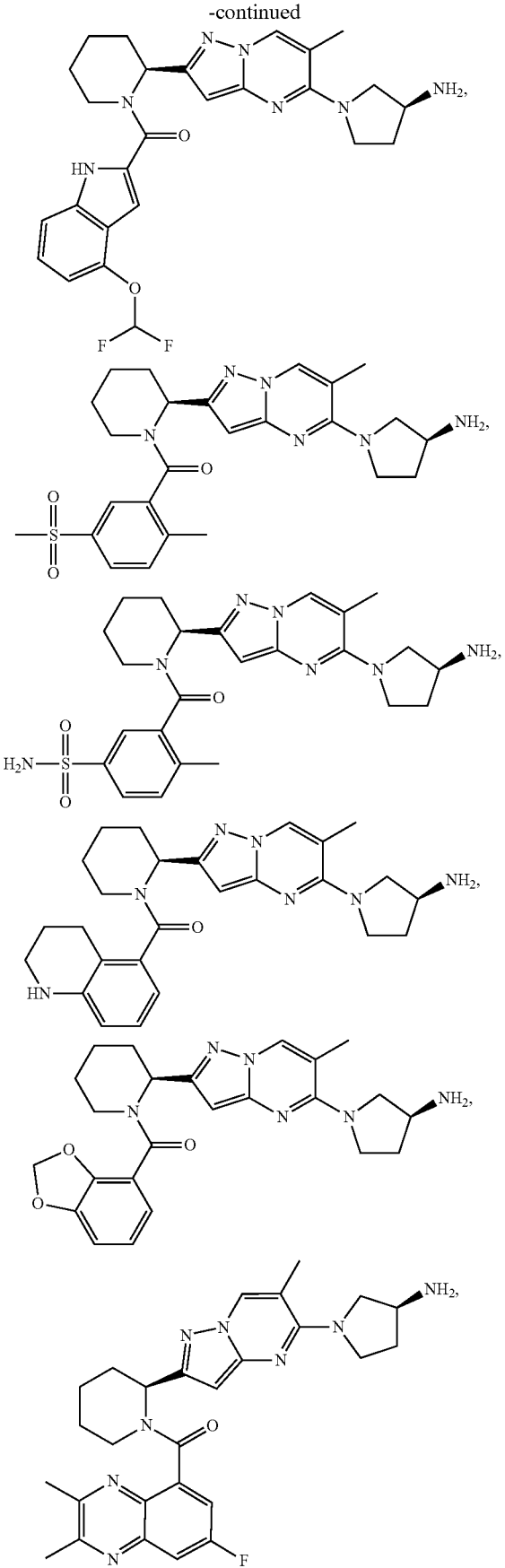
80
-continued
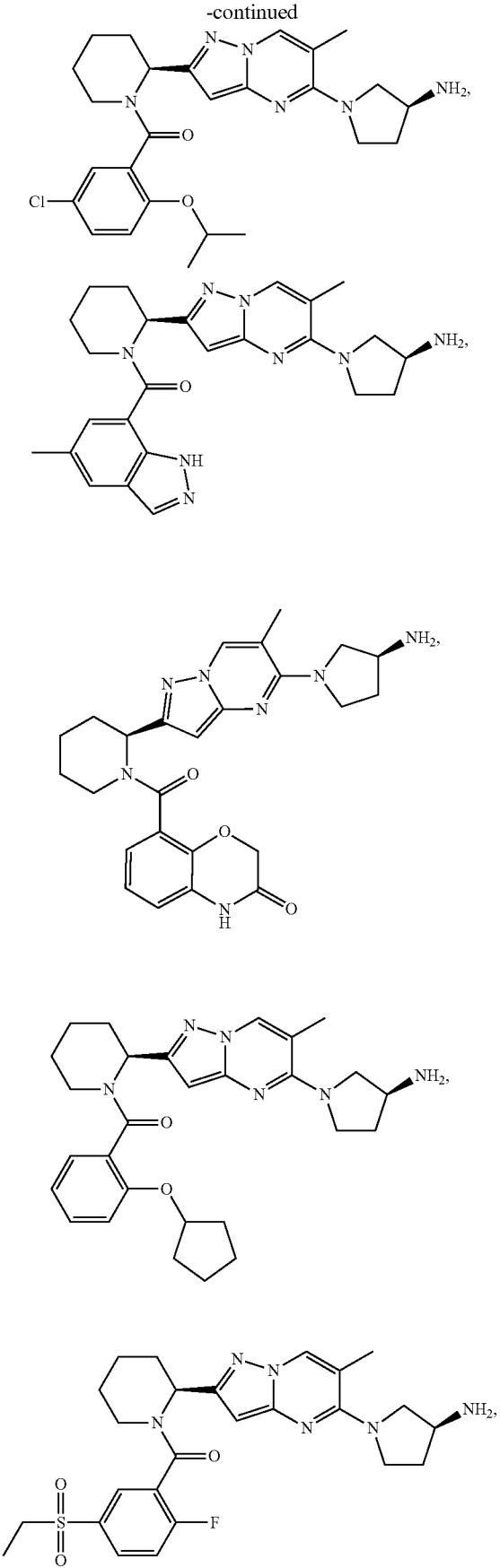

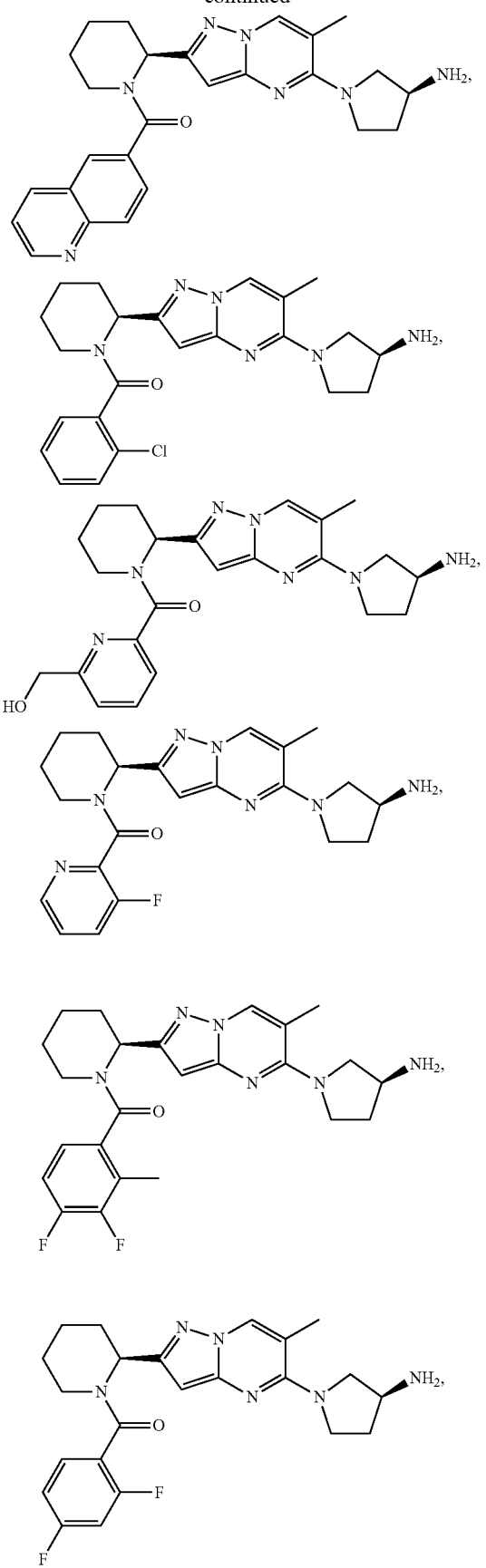
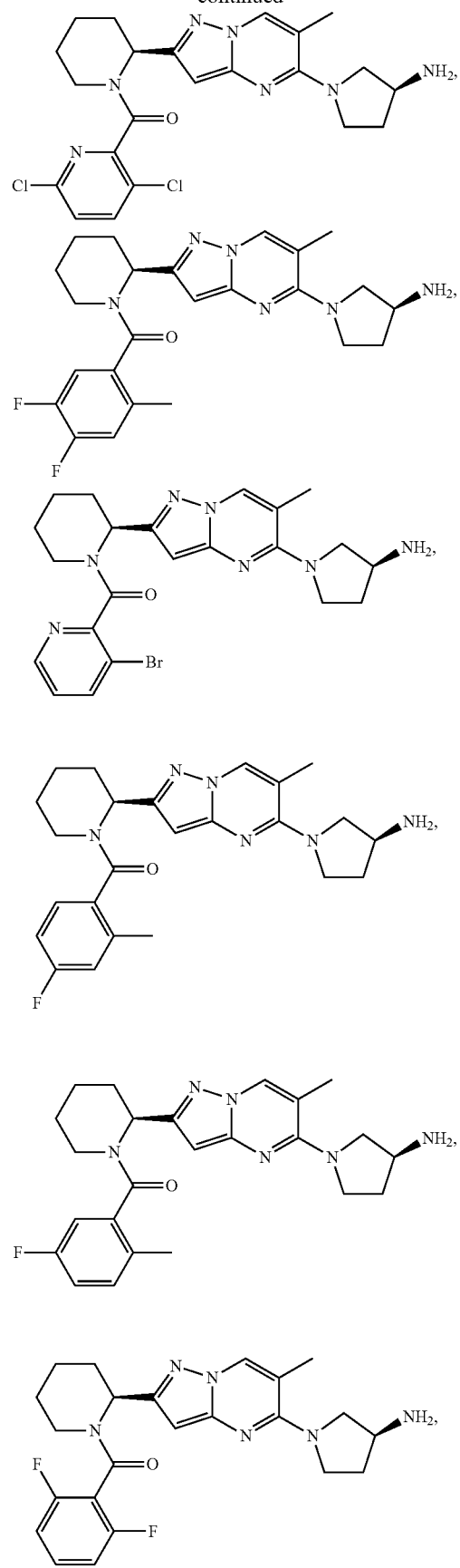

-continued
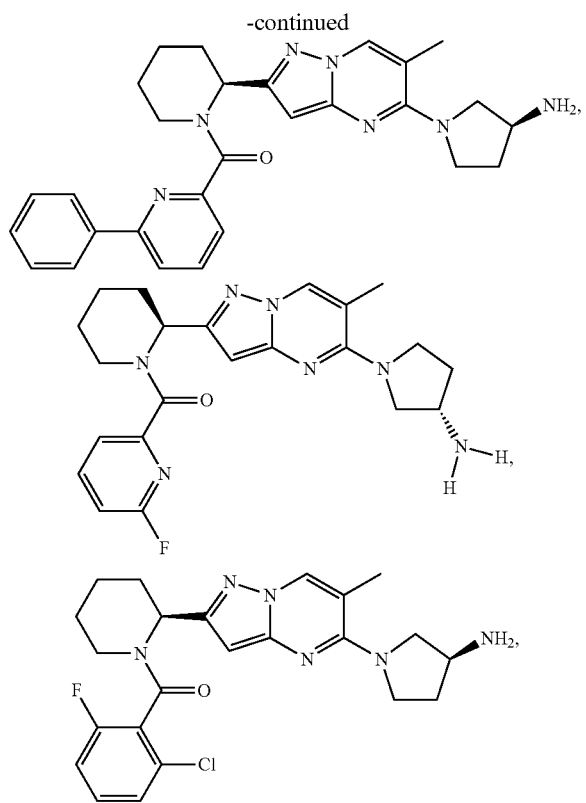
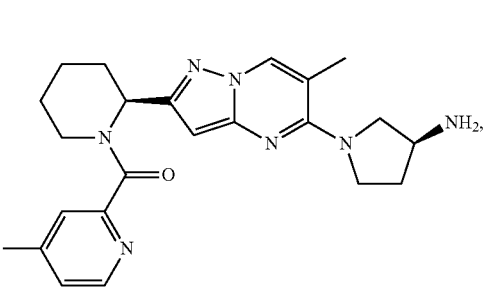
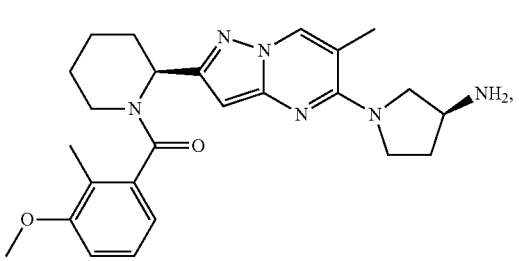
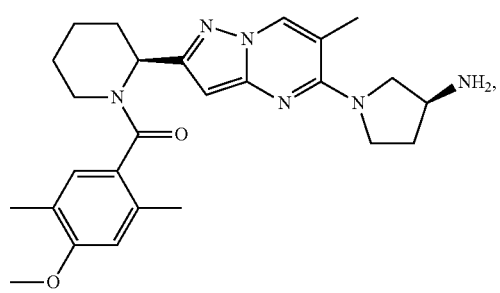
-continued
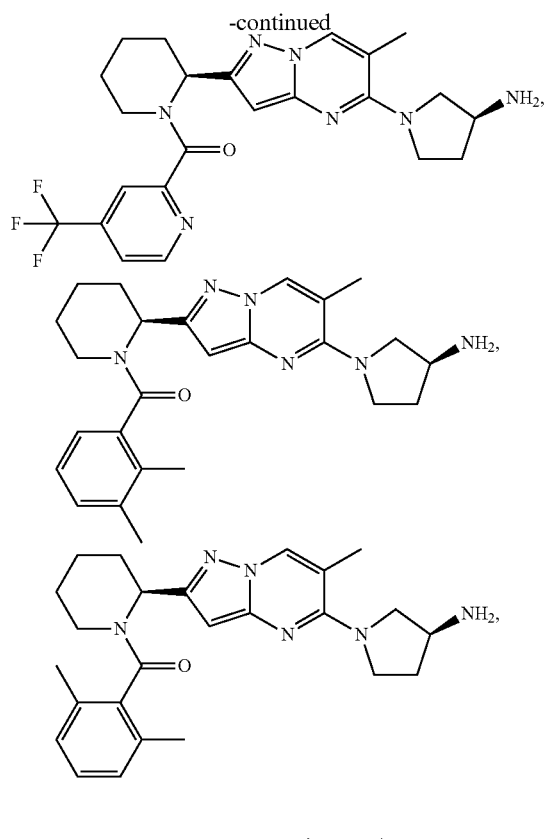
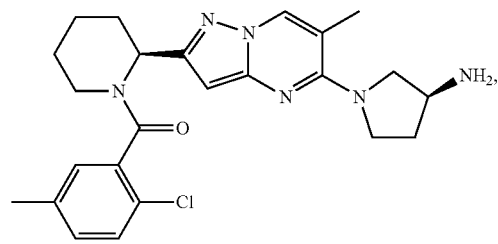
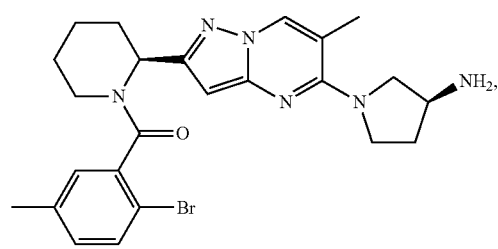
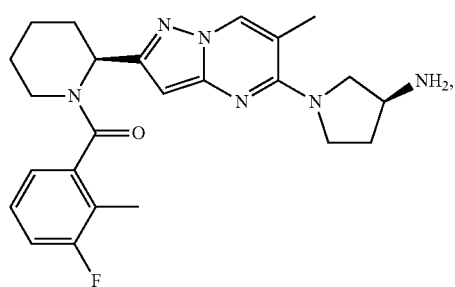

85
-continued
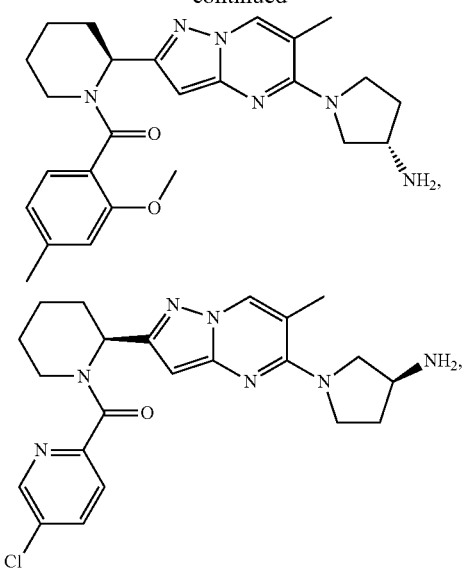
86
-continued
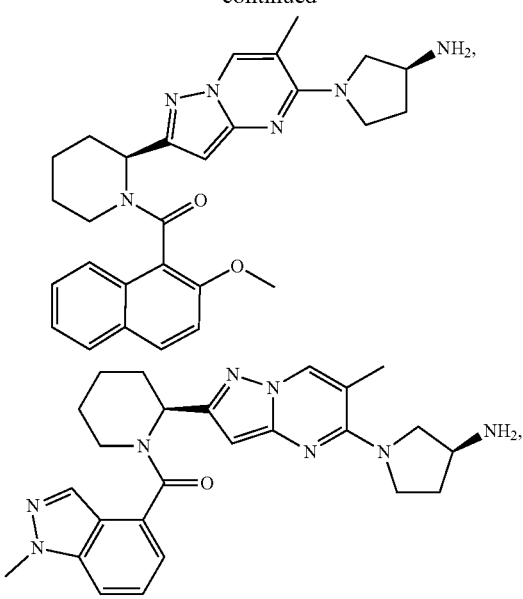
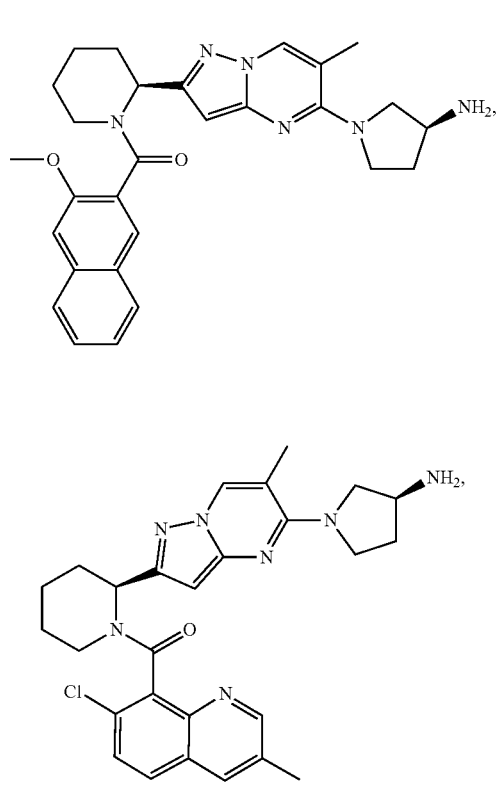
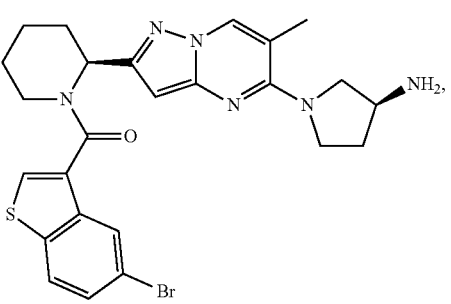
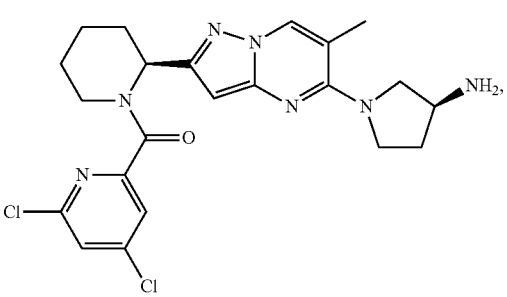
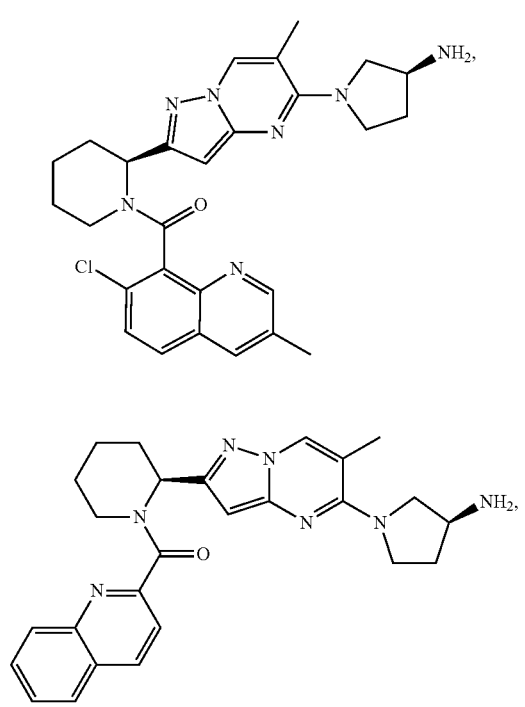
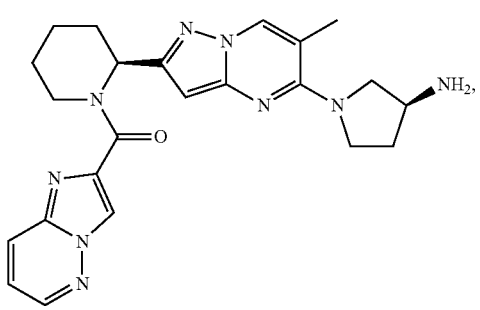

-continued
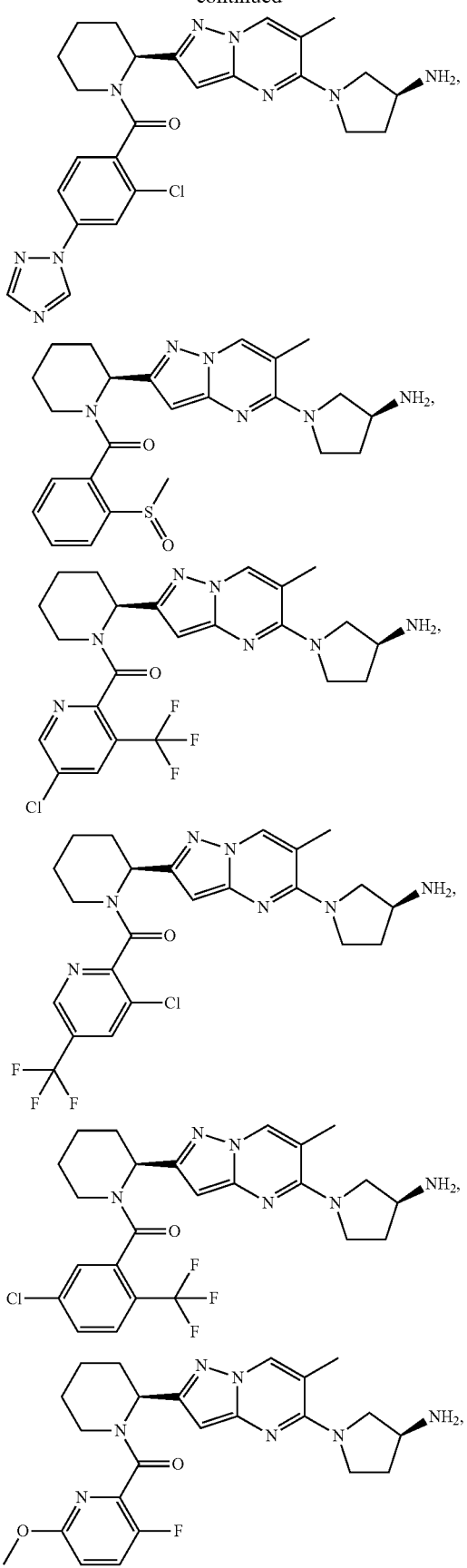
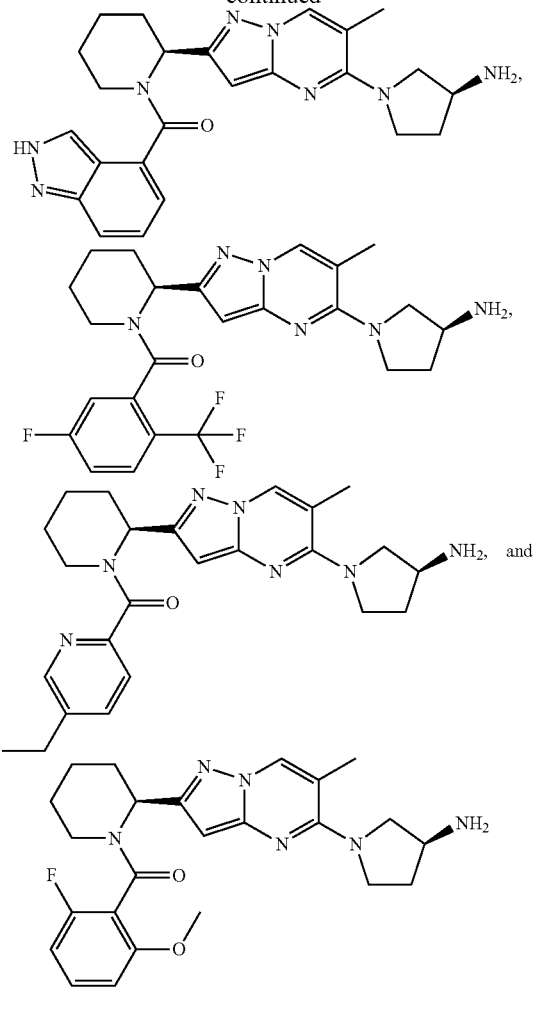
and salts and esters thereof.
One embodiment provides a compound selected from:
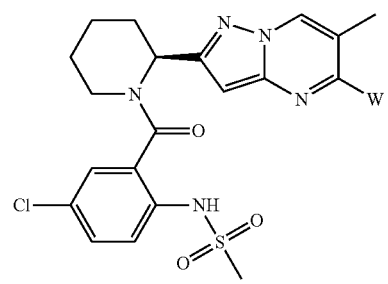
wherein W is:
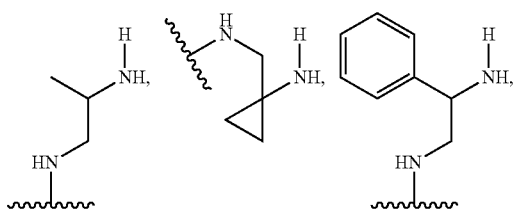

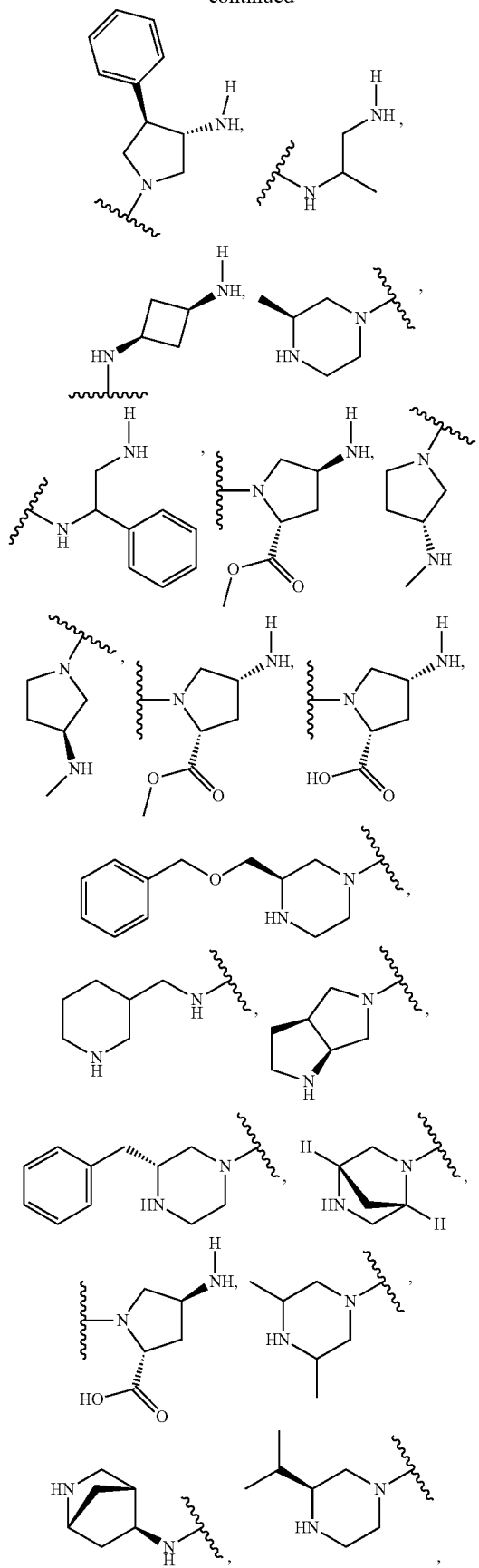
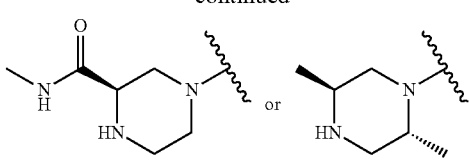
or a salt, or stereoisomer thereof.
In another embodiment the compound is selected from:
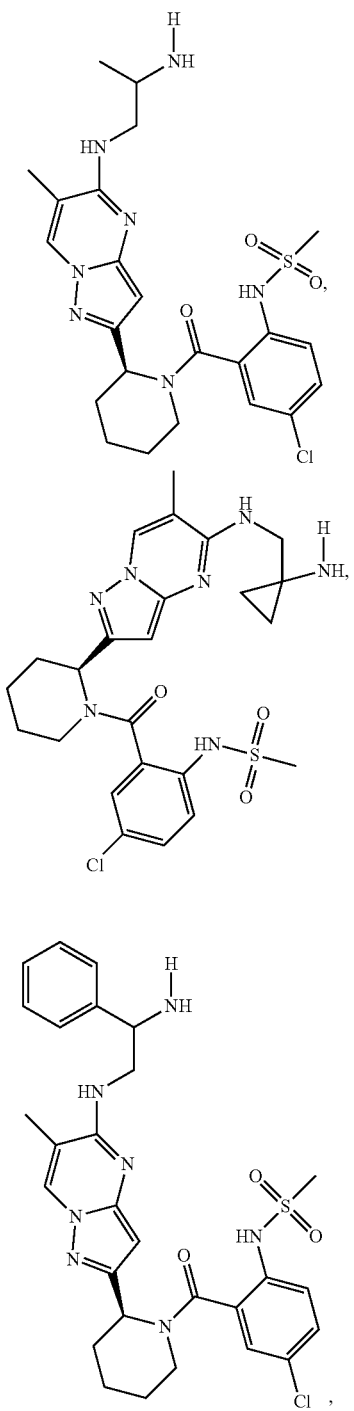

91
-continued
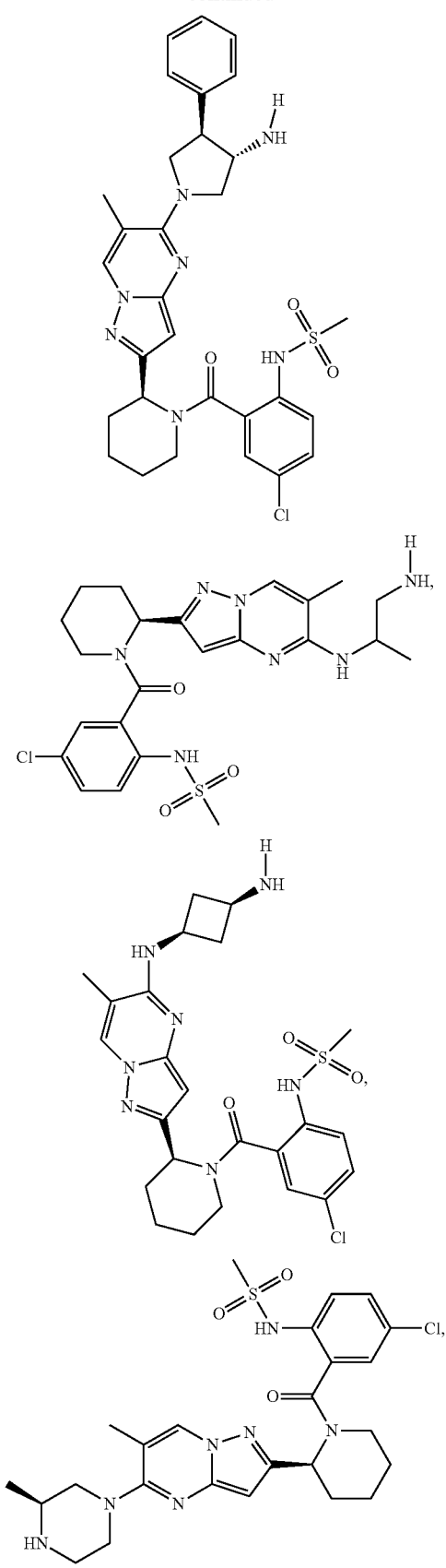
92
-continued
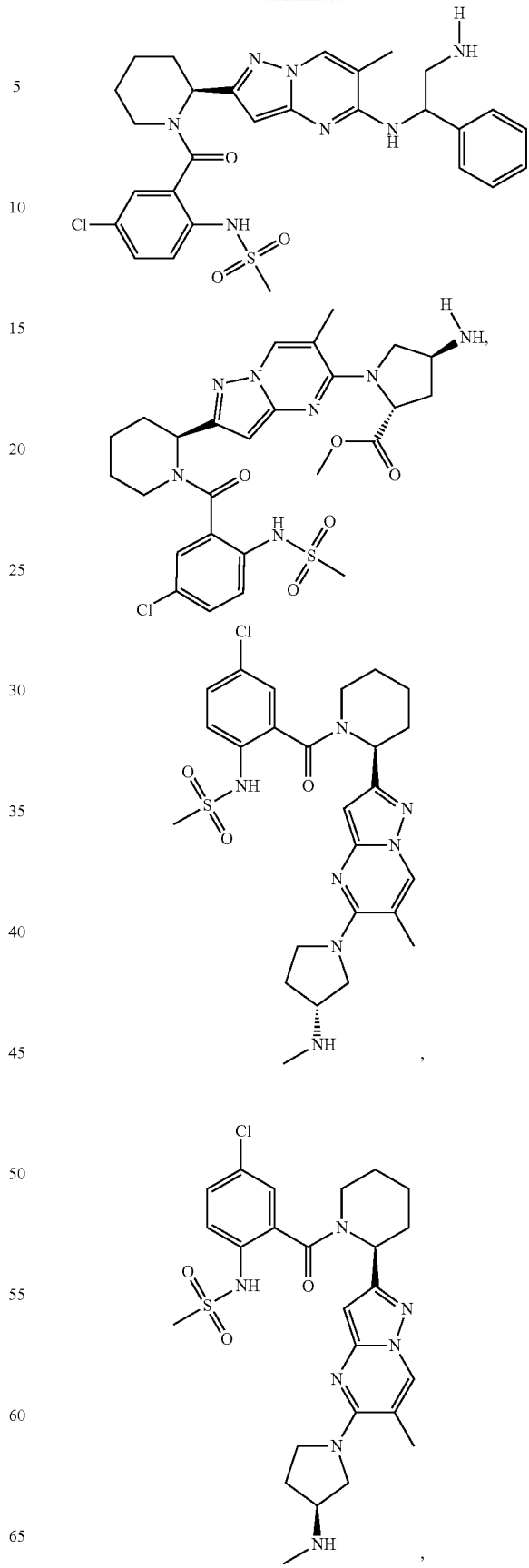

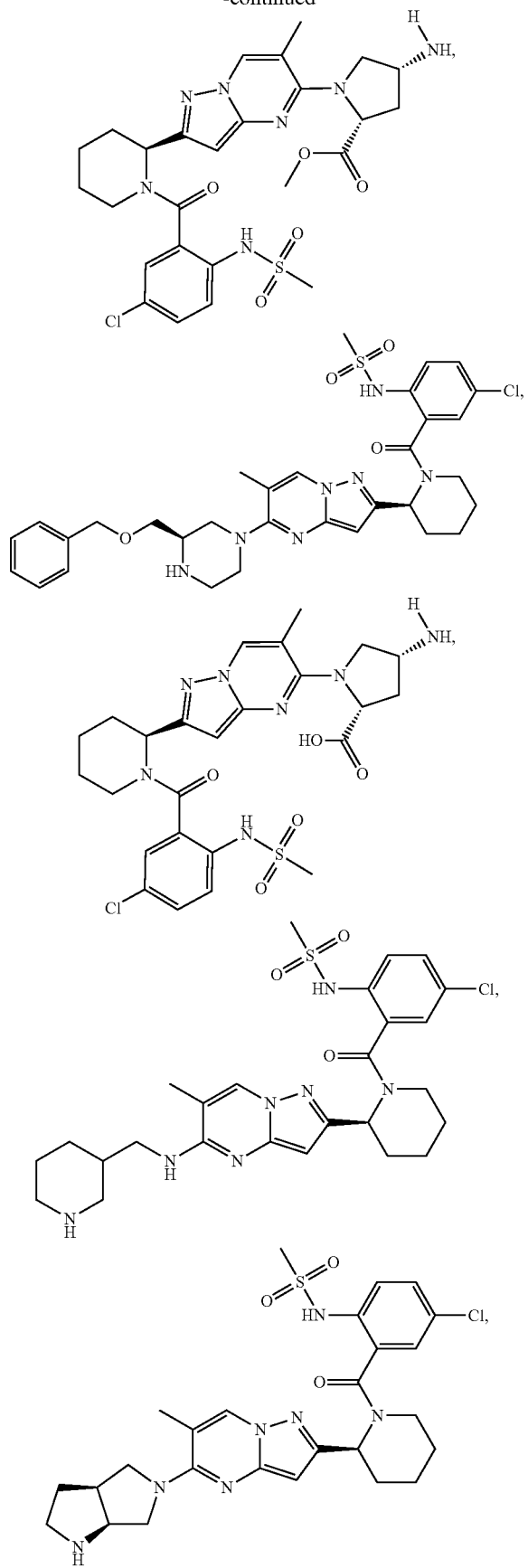
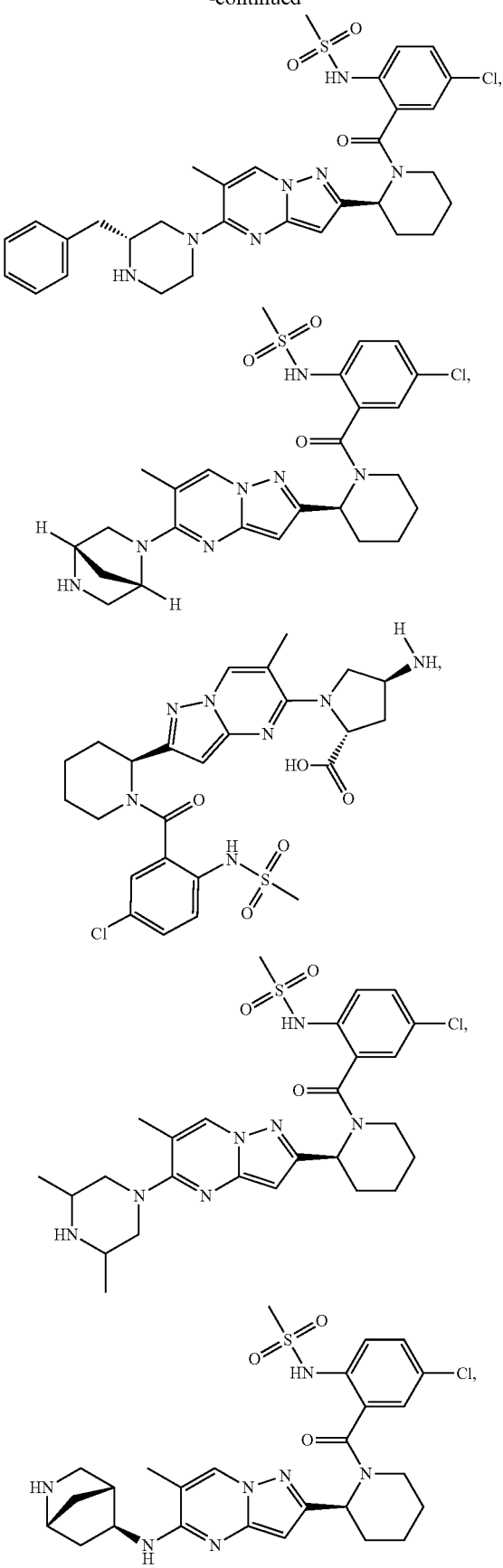

-continued
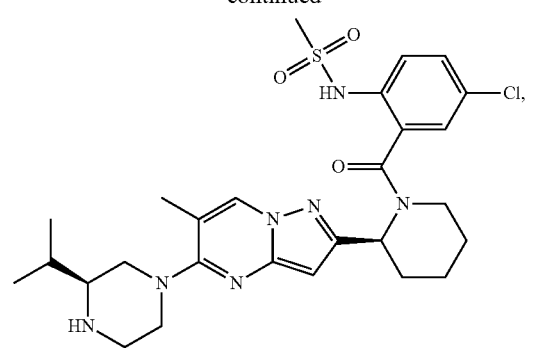
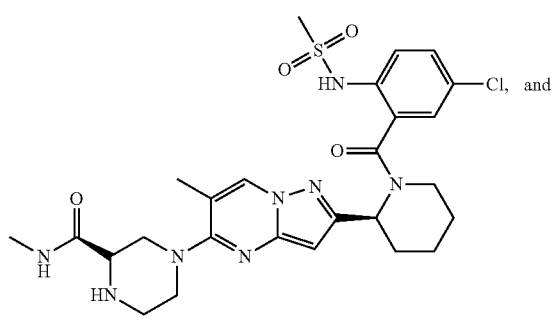
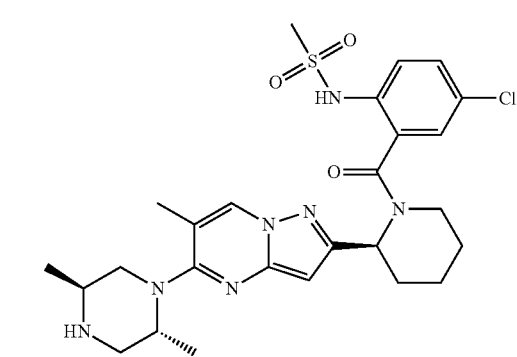
and salts and esters thereof.
One embodiment provides a compound of formula:
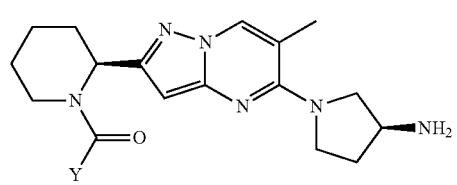
wherein Y is selected from:
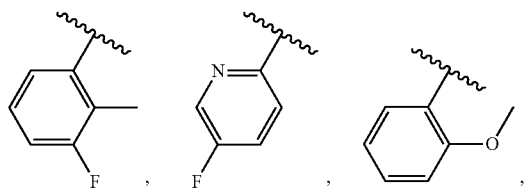
-continued
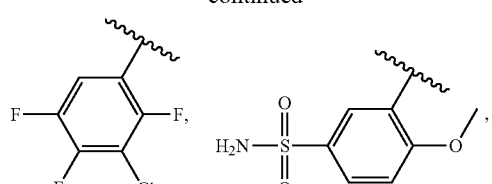
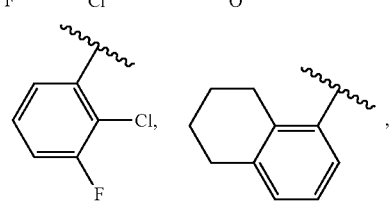
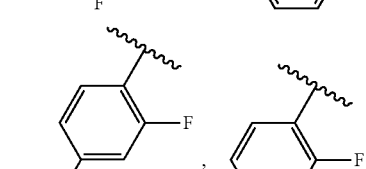
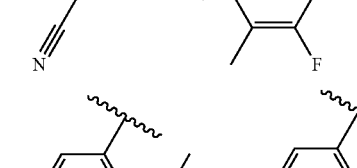
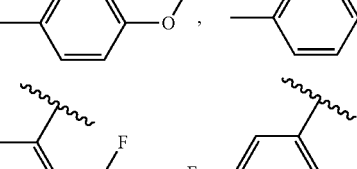
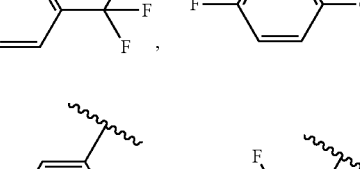
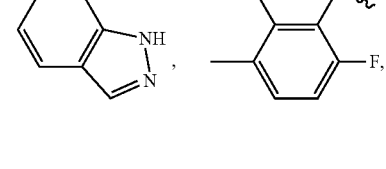
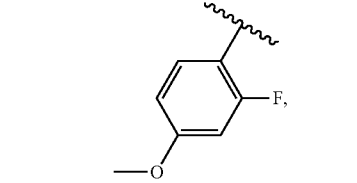
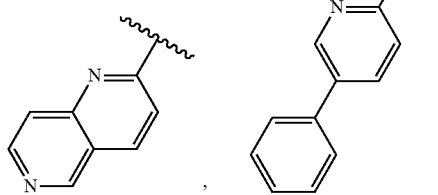

-continued
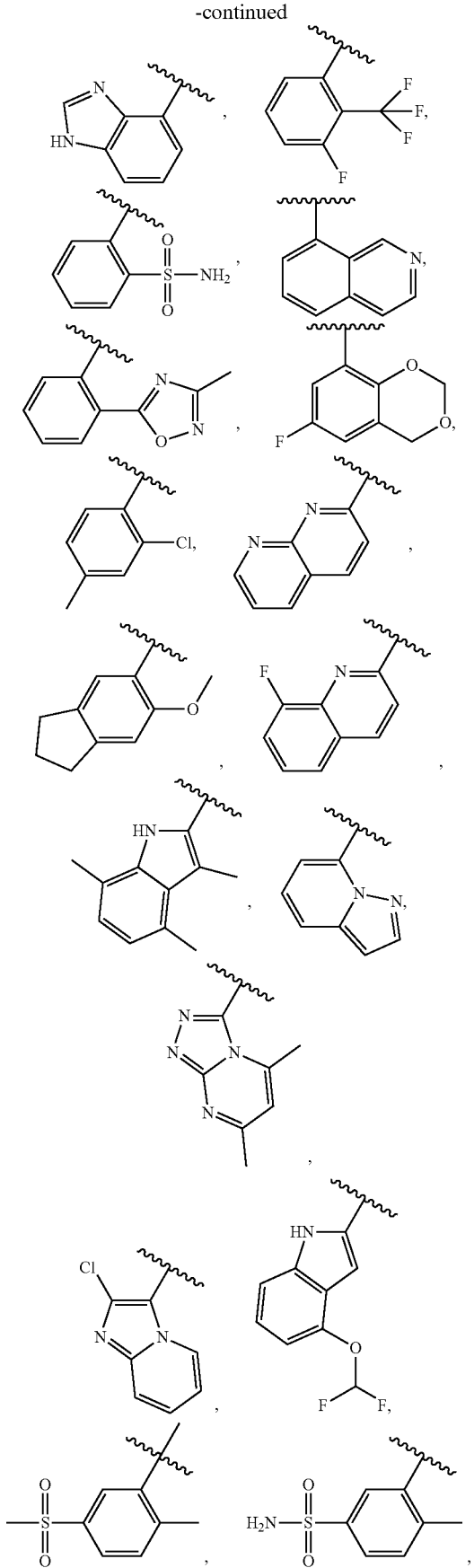
-continued
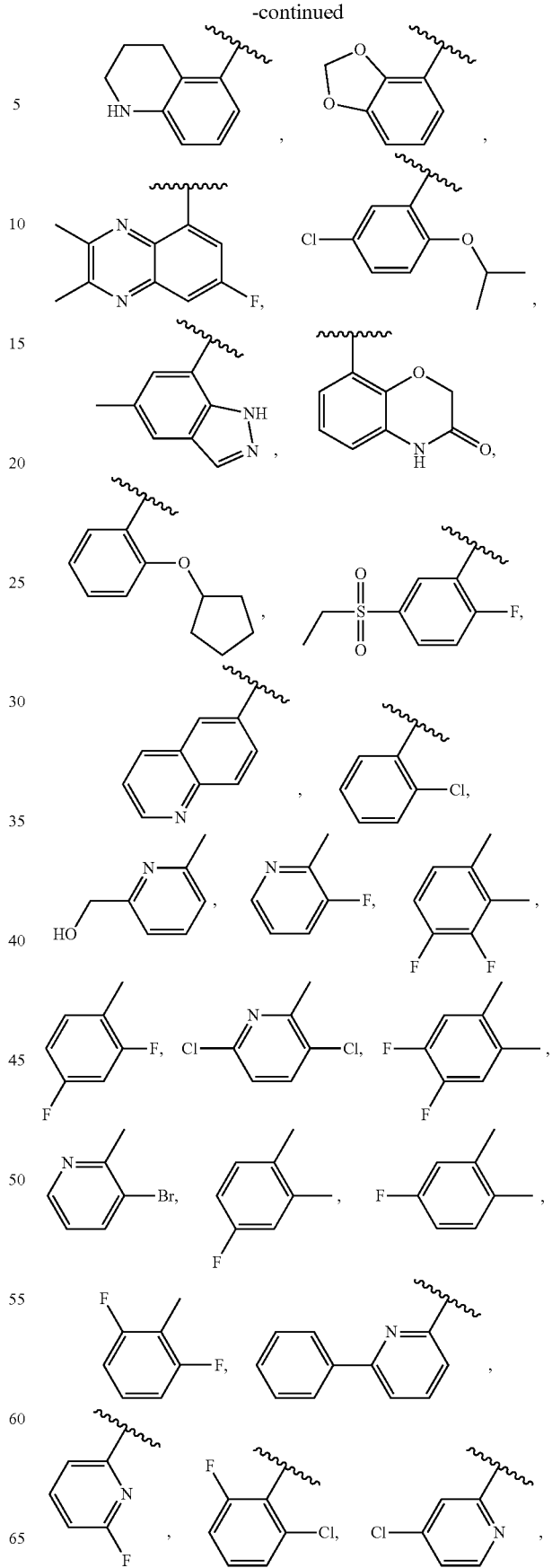

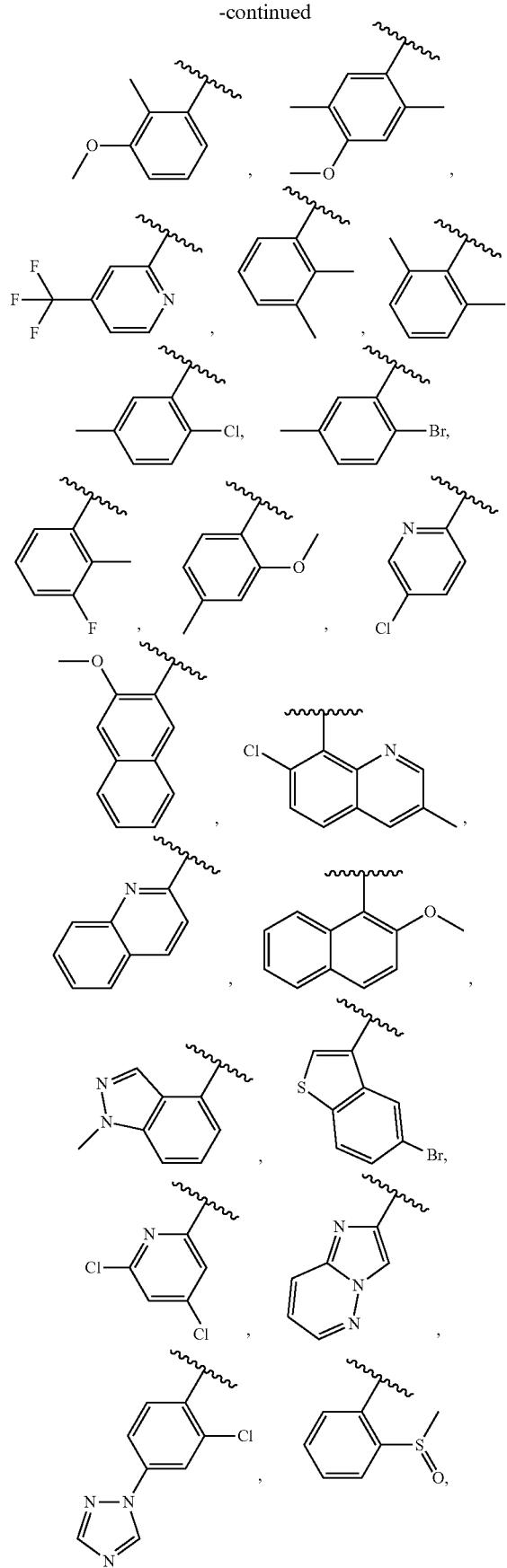
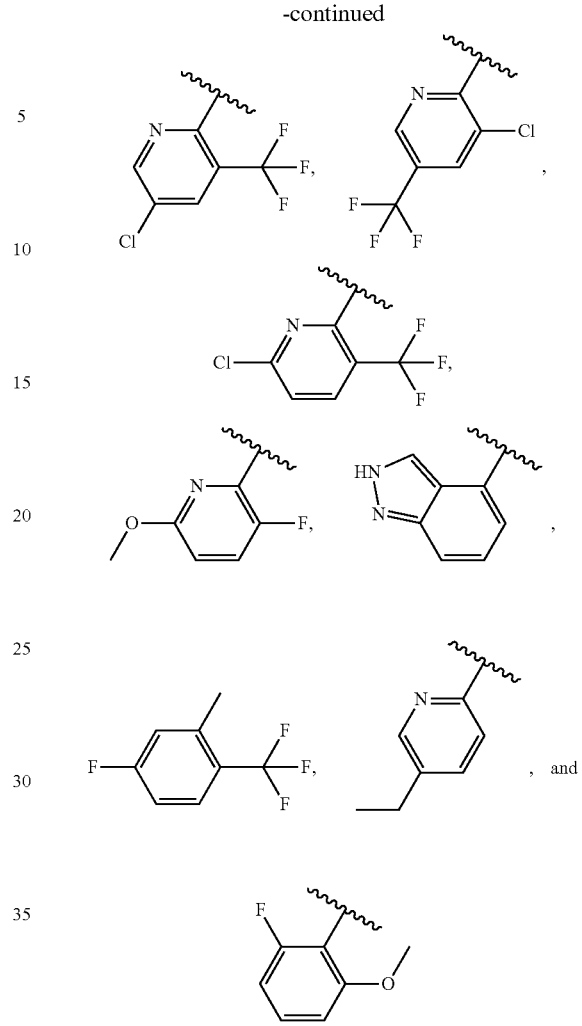
or a salt, or stereoisomer thereof.
In another embodiment the compound is selected from:
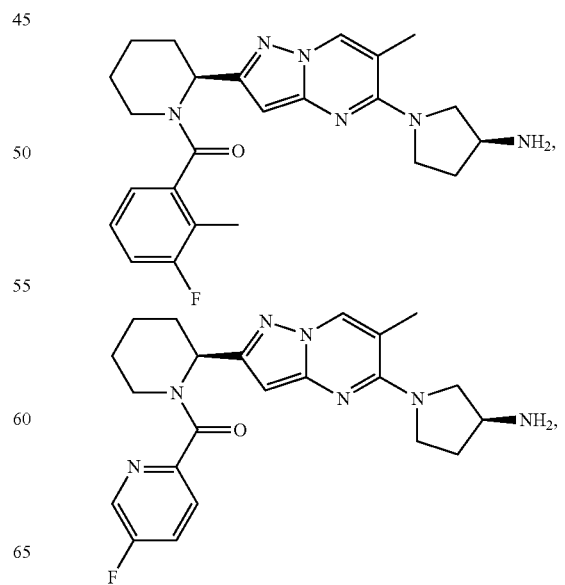

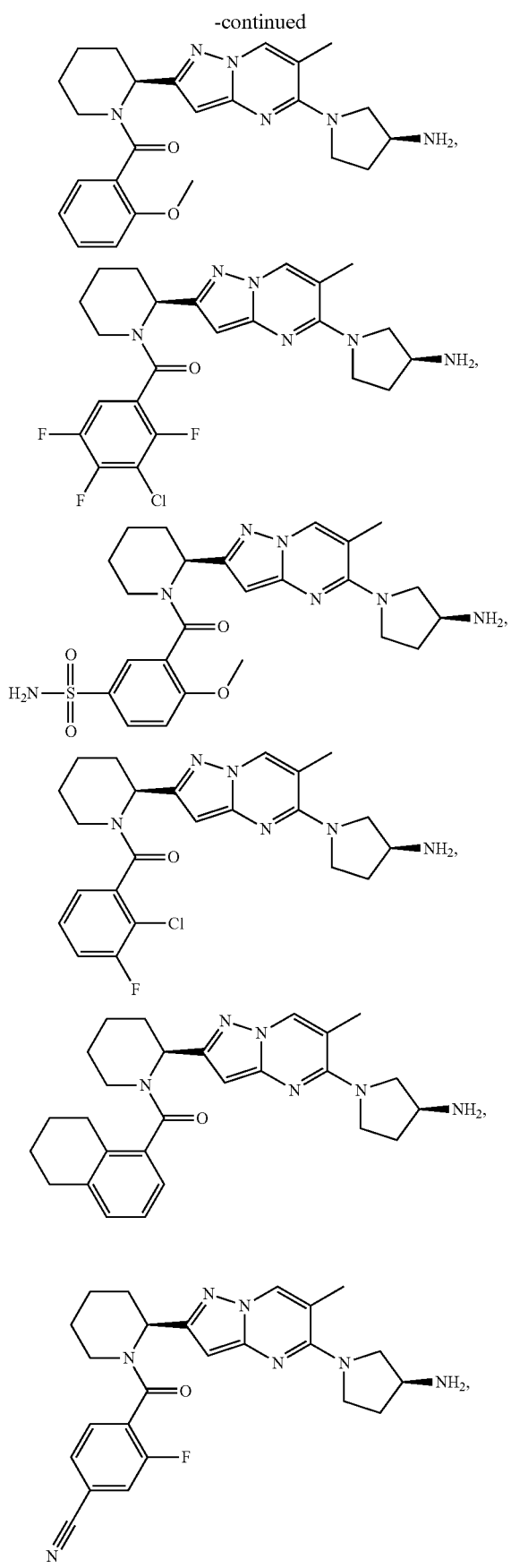
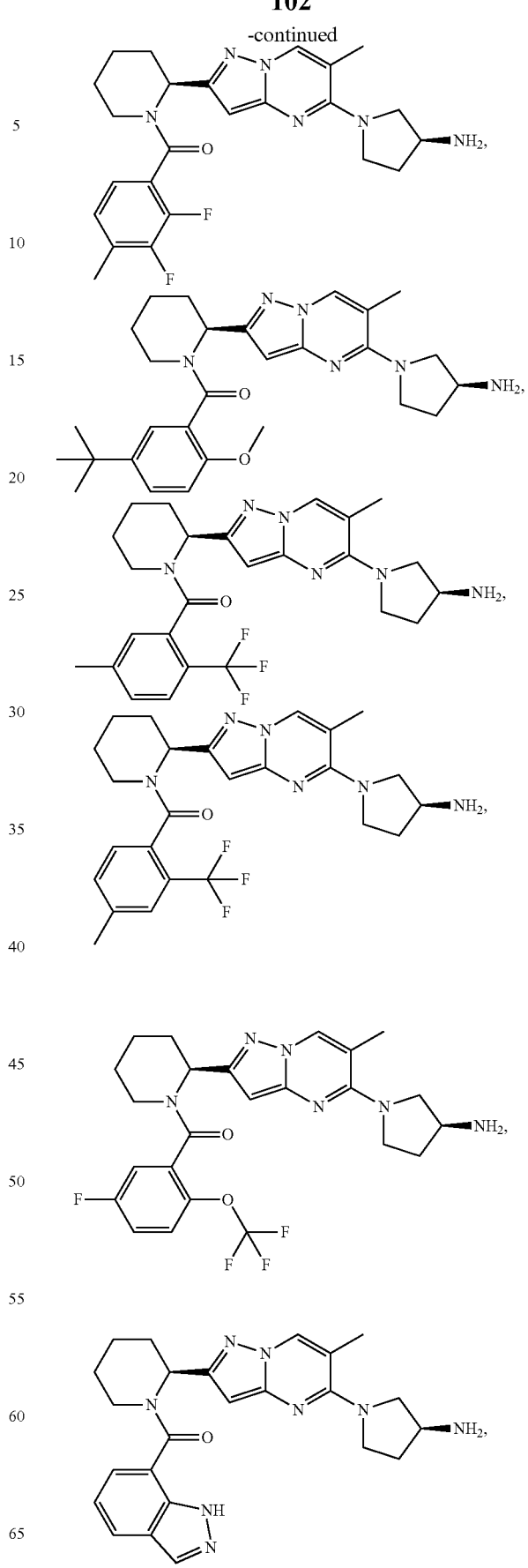

103
-continued
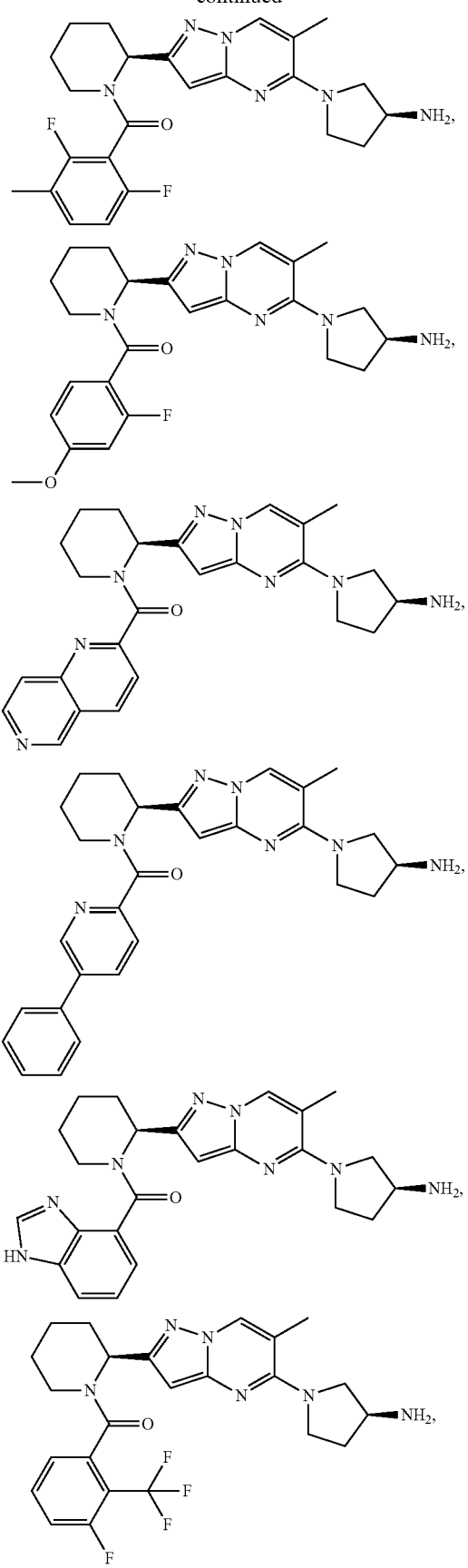
104
-continued
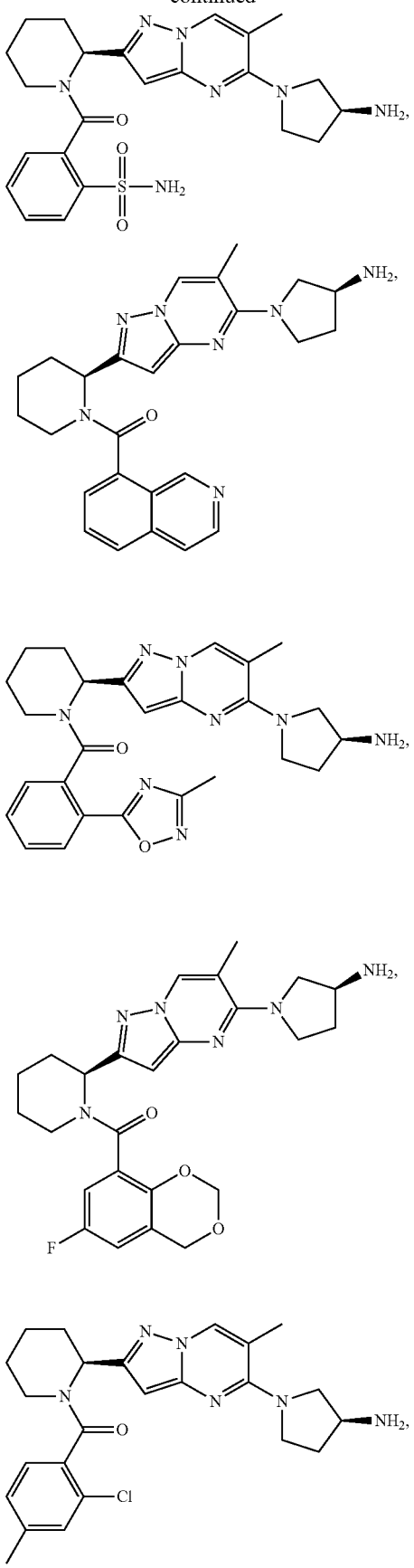

105
-continued
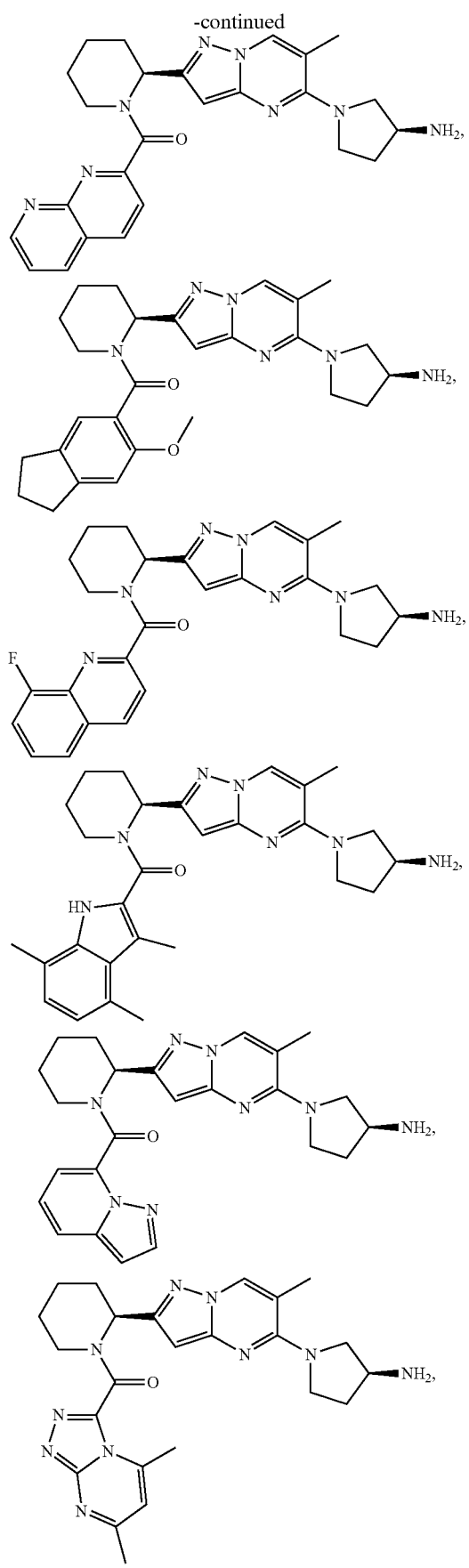
106
-continued
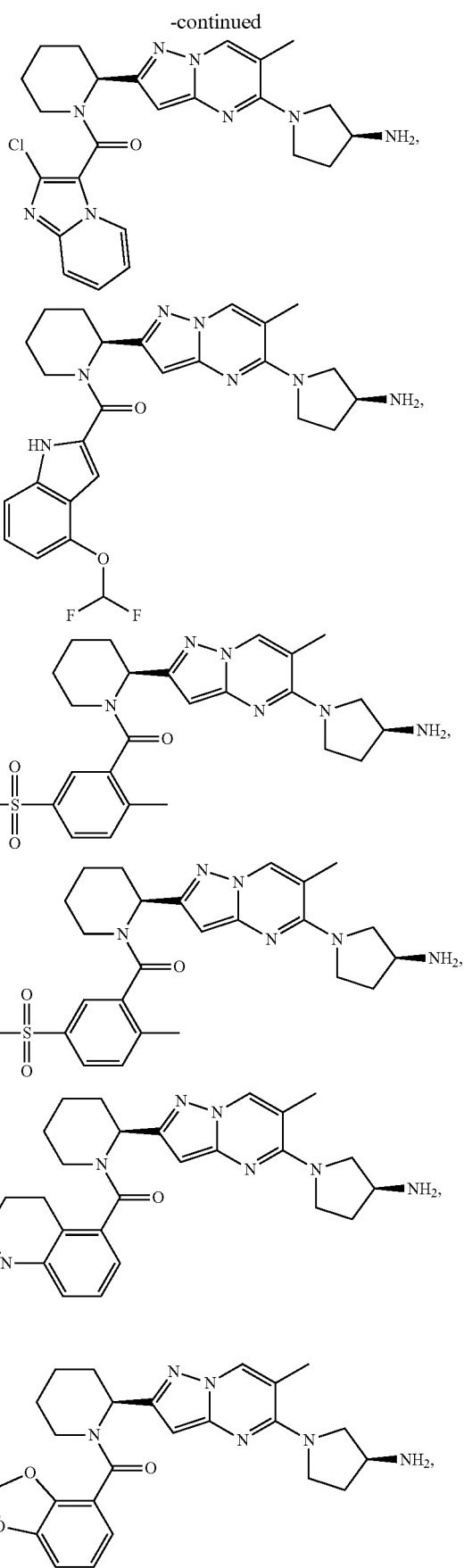

107
-continued
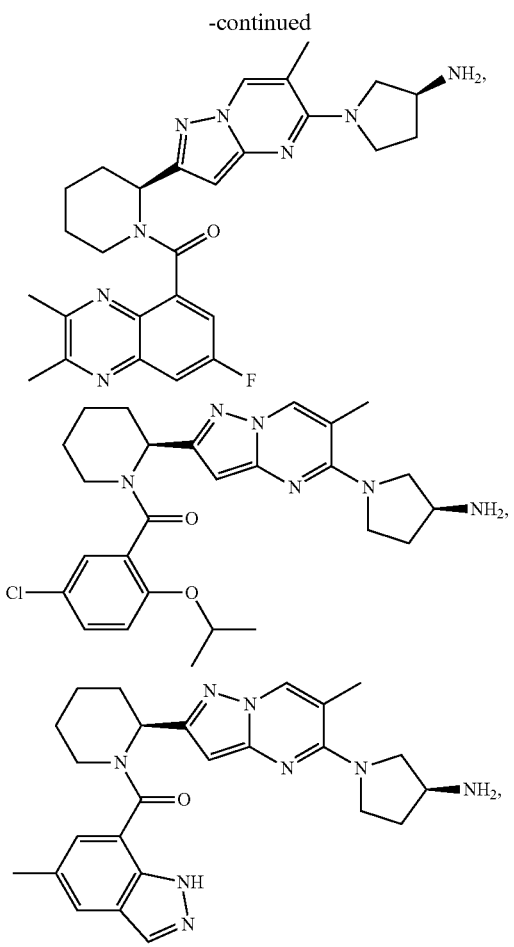
108
-continued
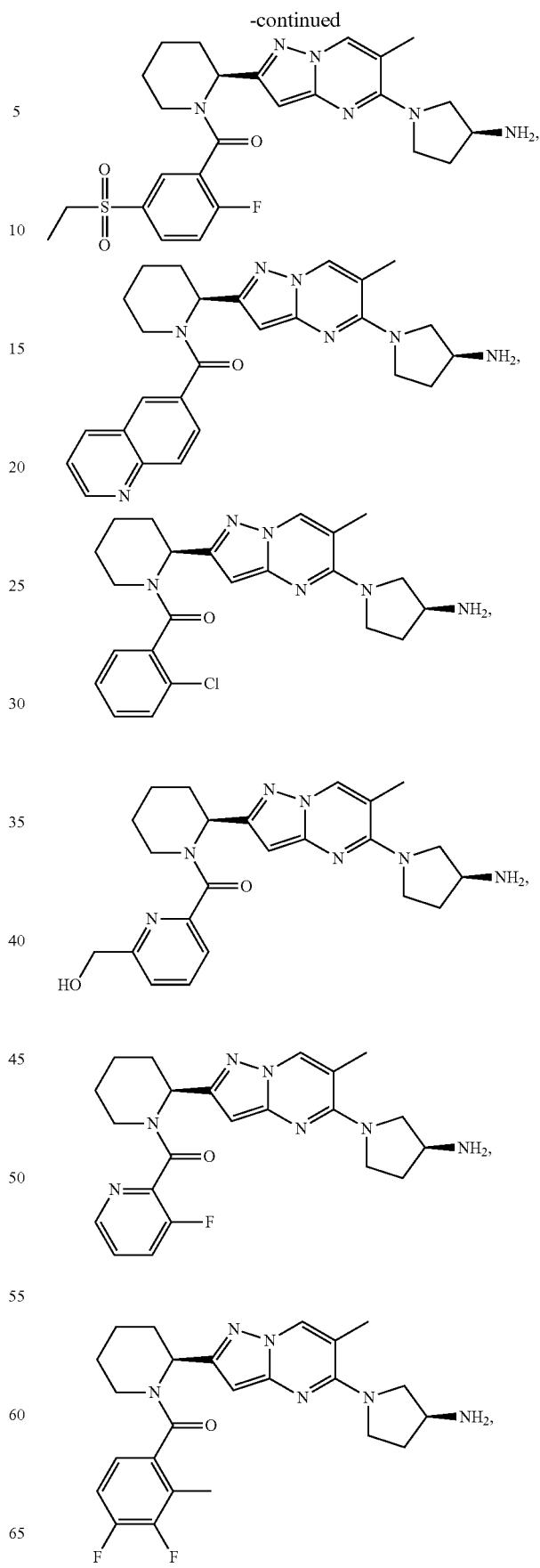

109
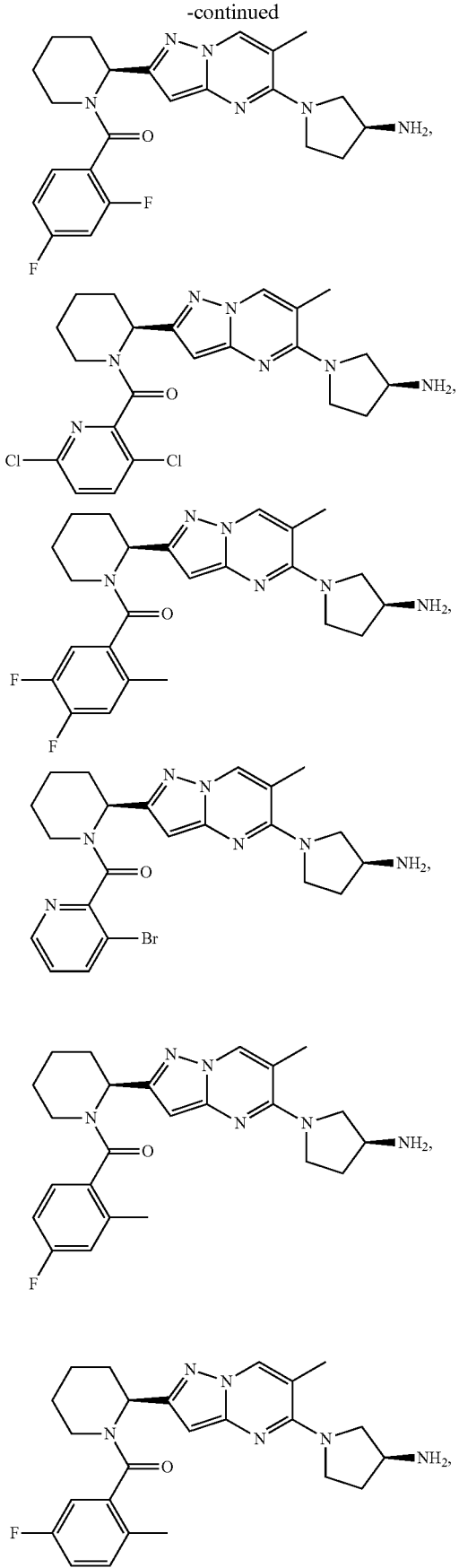
110
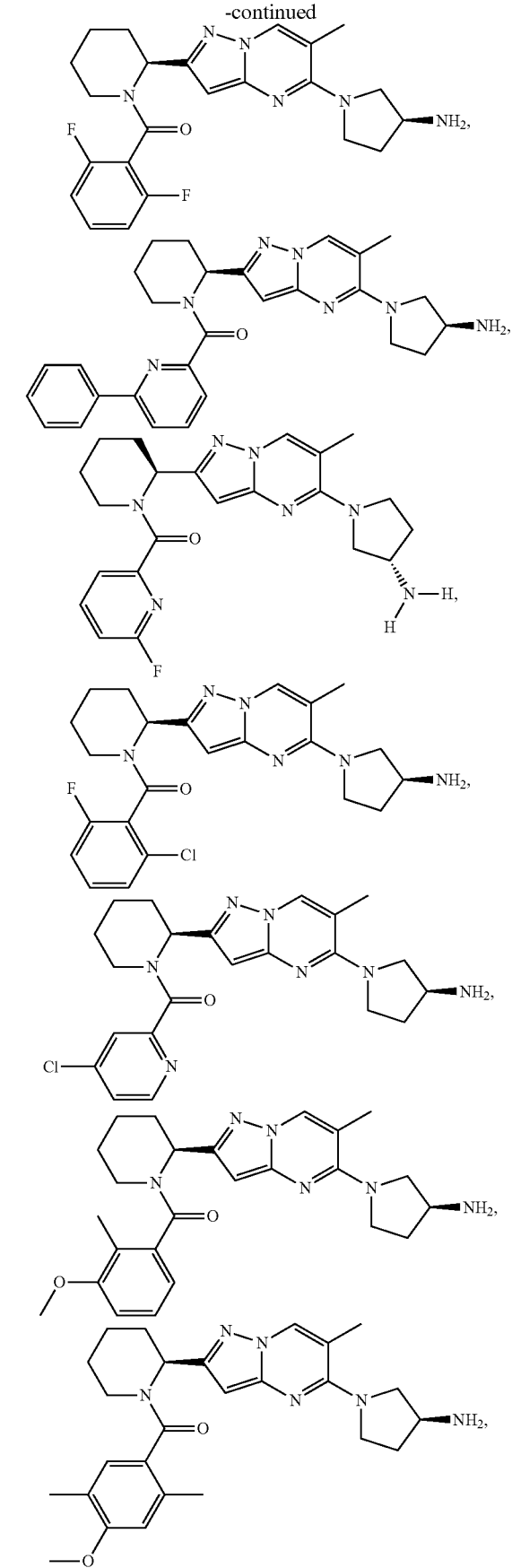

111
-continued
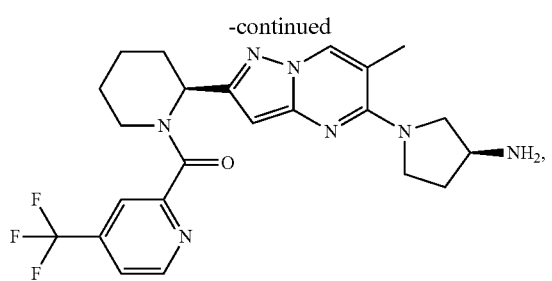
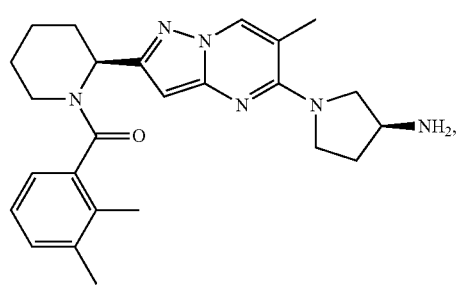
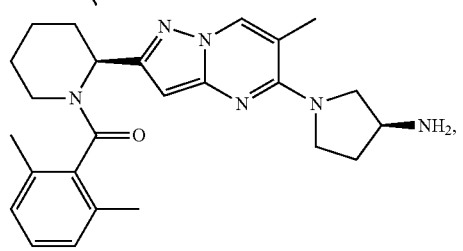
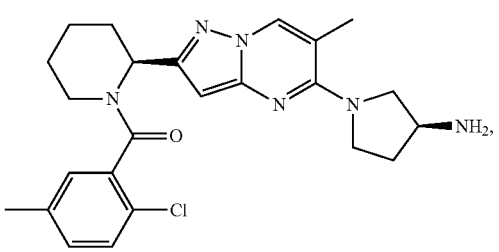
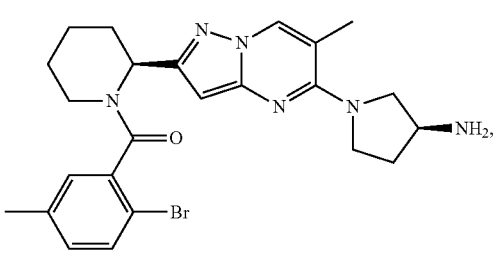
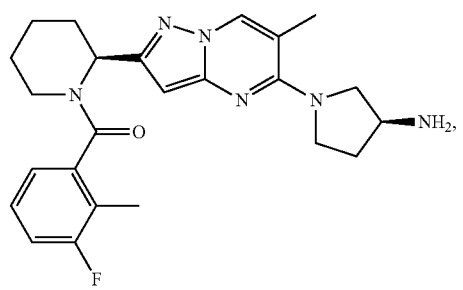
112
-continued
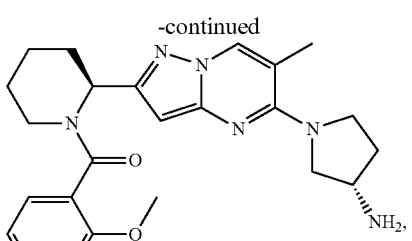
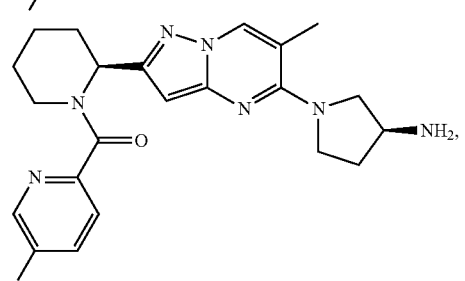
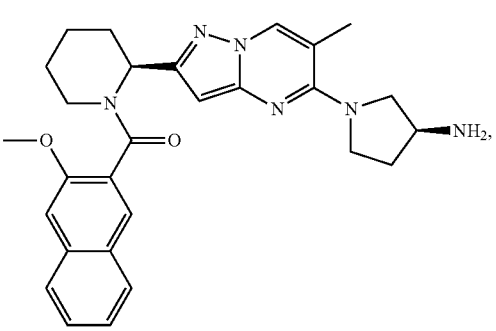
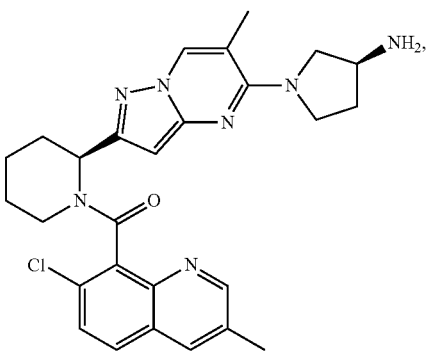
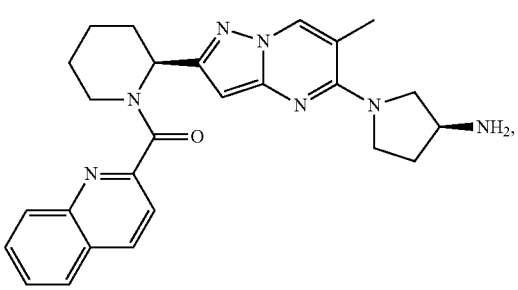

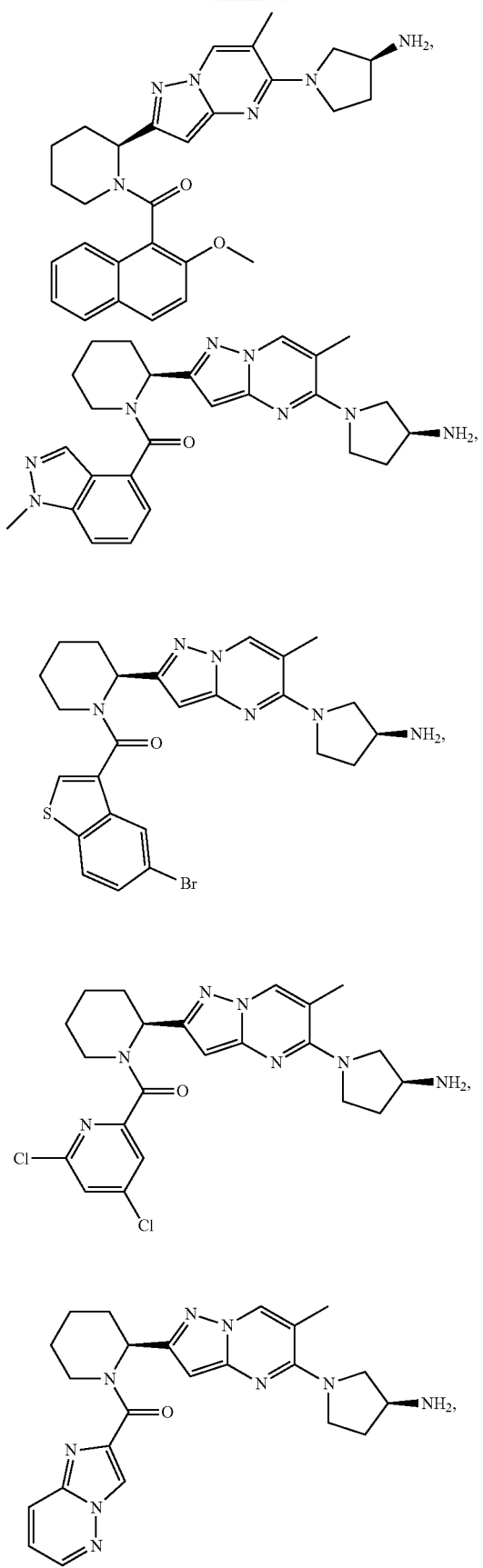
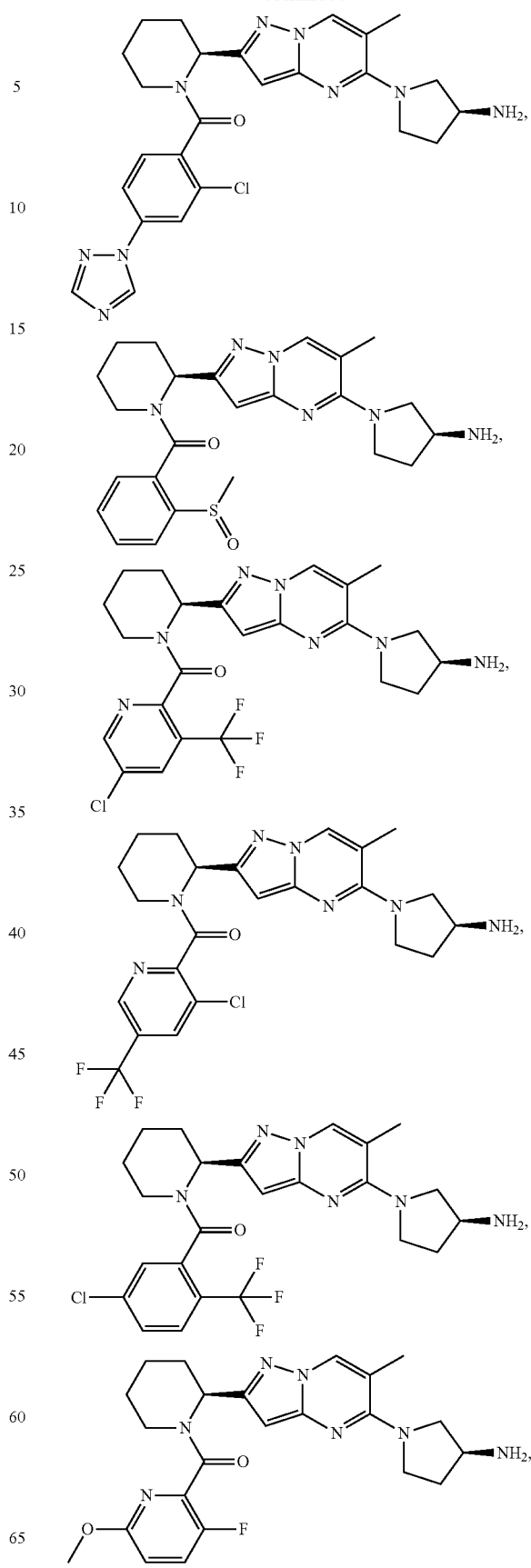

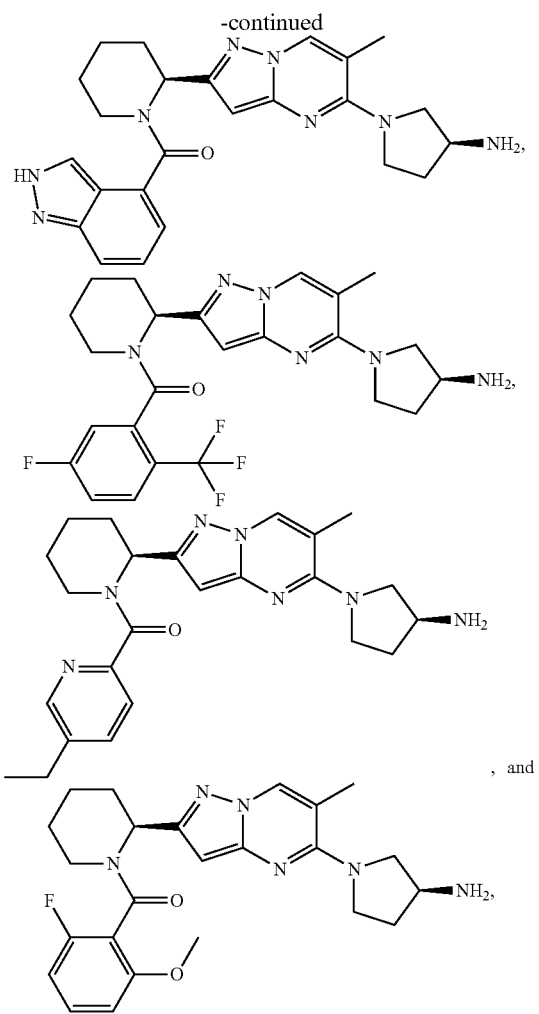

and salts and esters thereof.

Esters of Compounds of the Invention.

The compounds disclosed herein also include "esters" of the compounds of the invention. Accordingly, one example of esters of the compounds of the invention include esters wherein a hydroxyl group of the compound of the invention is an ester. These esters of the invention are typically labile and thus the ester may be converted to the corresponding hydroxyl group in vivo (e.g. after administration). Esters include those esters based on carbon and phosphorus.

Typical esters include: $(R^aO)_2P(=O)O-$, $(HO)_2P(=O)O-$, $(C_1-C_8)alkyl(C=O)O-$, $C_6-C_{20}aryl(C=O)O-$, $C_2-C_{20}heterocyclyl(C=O)O-$ or $(C_4-C_8)carbocyclylalkyl(C=O)O-$ wherein each $(C_1-C_8)alkyl(C=O)O-$, $C_6-C_{20}aryl(C=O)O-$, $C_2-C_{20}heterocyclyl(C=O)O-$ or $(C_4-C_8)carbocyclylalkyl(C=O)O-$, is independently, optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)alkyl$, $(C_1-C_8)haloalkyl$, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $-OC(=O)R^a$, $-OP(O)(OH)_2$ or $R^a$;

each $R^a$ is independently $(C_1-C_8)alkyl$, $(C_1-C_8)haloalkyl$, $(C_2-C_8)alkenyl$, $(C_2-C_8)alkynyl$, $aryl(C_1-C_8)alkyl$, $C_6-C_{20}$ aryl, $C_2-C_{20}$ heterocyclyl, $(C_3-C_7)cycloalkyl$ or $(C_4-C_8)carbocyclylalkyl$ wherein any $(C_1-C_8)alkyl$, $(C_1-C_8)haloalkyl$, $(C_2-C_8)alkenyl$ or $(C_2-C_8)alkynyl$ of $R^a$ is optionally substituted with one or more OH, $NH_2$, $CO_2H$, $C_2-C_{20}$ heterocyclyl, and wherein any $aryl(C_1-C_8)alkyl$, $C_6-C_{20}$ aryl, $C_2-C_{20}$ heterocyclyl, $(C_3-C_7)cycloalkyl$ or $(C_4-C_8)carbocyclylalkyl$ of $R^a$ is optionally substituted with one or more OH, $NH_2$, $CO_2H$, $C_2-C_{20}$ heterocyclyl or $(C_1-C_8)alkyl$; and each p is 1 or 2.

It is to be understood that the point of connection of the esters $(R^aO)_2P(=O)O-$, $(HO)_2P(=O)O-$, $(C_1-C_8)alkyl(C=O)O-$, $C_6-C_{20}aryl(C=O)O-$, $C_2-C_{20}heterocyclyl(C=O)O-$ and $(C_4-C_8)carbocyclylalkyl(C=O)O-$ to the compound of the invention is through the oxygen of the ester.

In one embodiment the compounds of formula I include compounds of formula Ib

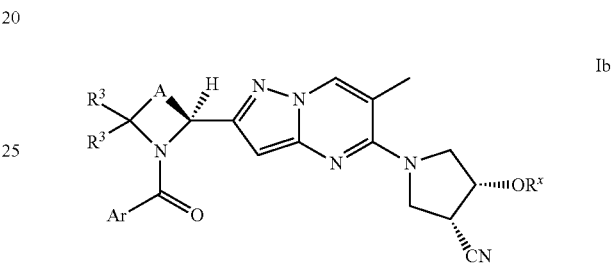

Ib or a salt or ester, thereof;

wherein:

A is $-(C(R^4)_2)_n-$ wherein any one $C(R^4)_2$ of said $-(C(R^4)_2)_n-$ may be optionally replaced with $-O-$, $-S-$, $-S(O)_p-$, NH or $NR^a$;

n is 3, 4, 5 or 6;

each p is 1 or 2;

Ar is a $C_2-C_{20}$ heterocyclyl group or a $C_6-C_{20}$ aryl group, wherein the $C_2-C_{20}$ heterocyclyl group or the $C_6-C_{20}$ aryl group is optionally substituted with 1, 2, 3, 4 or 5 $R^6$;

each $R^3$, $R^4$ or $R^6$ is independently H, oxo, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $NR^{11}C(=NR^{11})NR^{11}R^{12}$, halogen, $(C_1-C_8)alkyl$, $(C_2-C_8)alkenyl$, $(C_2-C_8)alkynyl$, $aryl(C_1-C_8)alkyl$, $C_6-C_{20}$ aryl, $C_2-C_{20}$ heterocyclyl, $(C_3-C_7)cycloalkyl$ or $(C_4-C_8)carbocyclylalkyl$;

two $R^4$ on adjacent carbon atoms, when taken together, may optionally form a double bond between the two carbons to which they are attached or may form a $(C_3-C_7)cycloalkyl$ ring wherein one carbon atom of said $(C_3-C_7)cycloalkyl$ ring may be optionally replaced by $-O-$, $-S-$, $-S(O)_p-$, $-NH-$ or $-NR^a-$;

four $R^4$ on adjacent carbon atoms, when taken together, may optionally form an optionally substituted $C_6$ aryl ring;

two $R^4$ on the same carbon atom, when taken together, may optionally form a $(C_3-C_7)cycloalkyl$ ring wherein one carbon atom of said $(C_3-C_7)cycloalkyl$ ring may be optionally replaced by $-O-$, $-S-$, $-S(O)_p-$, $-NH-$ or $-NR^a-$;

two $R^6$ on adjacent carbon atoms, when taken together, may optionally form a $(C_3-C_7)cycloalkyl$ ring wherein one carbon atom of said $(C_3-C_7)cycloalkyl$ ring may be optionally replaced by $-O-$, $-S-$, $-S(O)_p-$, $-NH-$ or $-NR^a-$;

each $R^a$ is independently $(C_1-C_8)$alkyl, $(C_1-C_8)$haloalkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl wherein any $(C_1-C_8)$alkyl, $(C_1-C_8)$haloalkyl, $(C_2-C_8)$alkenyl or $(C_2-C_8)$alkynyl of $R^a$ is optionally substituted with one or more OH, $NH_2$, $CO_2H$, $C_2-C_{20}$ heterocyclyl, and wherein any aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl of $R^a$ is optionally substituted with one or more OH, $NH_2$, $CO_2H$, $C_2-C_{20}$ heterocyclyl or $(C_1-C_8)$alkyl;

each $R^{11}$ or $R^{12}$ is independently H, $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$heterocyclyl, $(C_3-C_7)$cycloalkyl, $(C_4-C_8)$carbocyclylalkyl, —C(=O)$R^a$, —S(O)$_p R^a$, or aryl$(C_1-C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S—, —S(O)$_p$, —NH—, —NR$^a$— or —C(O)—;

wherein each $(C_1-C_8)$alkyl, $(C_2-C_8)$alkenyl, $(C_2-C_8)$alkynyl, aryl$(C_1-C_8)$alkyl, $C_6-C_{20}$ aryl, $C_2-C_{20}$ heterocyclyl, $(C_3-C_7)$cycloalkyl or $(C_4-C_8)$carbocyclylalkyl of each $R^6$, $R^{11}$ or $R^{12}$ is, independently, optionally substituted with one or more oxo, halogen, hydroxy, $NH_2$, CN, $N_3$, $N(R^a)_2$, $NHR^a$, SH, $SR^a$, $S(O)_p R^a$, $OR^a$, $(C_1-C_8)$alkyl, $(C_1-C_8)$haloalkyl, —C(O)$R^a$, —C(O)H, —C(=O)$OR^a$, —C(=O)OH, —C(=O)N$(R^a)_2$, —C(=O)NHR$^a$, —C(=O)NH$_2$, NHS(O)$_p R^a$, NR$^a$S(O)$_p R^a$, NHC(O)$R^a$, NR$^a$C(O)$R^a$, NHC(O)OR$^a$, NR$^a$C(O)OR$^a$, NR$^a$C(O)NHR$^a$, NR$^a$C(O)N$(R^a)_2$, NR$^a$C(O)NH$_2$, NHC(O)NHR$^a$, NHC(O)N$(R^a)_2$, NHC(O)NH$_2$, =NH, =NOH, =NOR$^a$, NR$^a$S(O)$_p$NHR$^a$, NR$^a$S(O)$_p$N$(R^a)_2$, NR$^a$S(O)$_p$NH$_2$, NHS(O)$_p$NHR$^a$, NHS(O)$_p$N$(R^a)_2$, NHS(O)$_p$NH$_2$, —OC(=O)$R^a$, —OP(O)(OH)$_2$ or $R^a$; and $R^x$ is H, $(R^a O)_2 P(=O)$—, $(HO)_2 P(=O)O$—, $(C_1-C_8)$alkyl(C=O)—, $C_6-C_{20}$aryl(C=O)—, $C_2-C_{20}$heterocyclyl(C=O)— or $(C_4-C_8)$carbocyclylalkyl(C=O)—, wherein each $(C_1-C_8)$alkyl(C=O)—, $C_6-C_{20}$aryl(C=O)—, $C_2-C_{20}$heterocyclyl(C=O)— or $(C_4-C_8)$carbocyclylalkyl(C=O)— is independently, optionally substituted with one or more oxo, halogen, hydroxy, $NH_2$, CN, $N_3$, $N(R^a)_2$, $NHR^a$, SH, SR$^a$, S(O)$_p R^a$, OR$^a$, $(C_1-C_8)$alkyl, $(C_1-C_8)$haloalkyl, —C(O)$R^a$, —C(O)H, —C(=O)$OR^a$, —C(=O)OH, —C(=O)N$(R^a)_2$, —C(=O)NHR$^a$, —C(=O)NH$_2$, NHS(O)$_p R^a$, NR$^a$S(O)$_p R^a$, NHC(O)$R^a$, NR$^a$C(O)$R^a$, NHC(O)OR$^a$, NR$^a$S(O)$_p R^a$, NR$^a$C(O)OR$^a$, NR$^a$C(O)NHR$^a$, NR$^a$C(O)N$(R^a)_2$, NR$^a$C(O)NH$_2$, NHC(O)NHR$^a$, NHC(O)N$(R^a)_2$, NHC(O)NH$_2$, =NH, =NOH, =NOR$^a$, NR$^a$S(O)$_p$NHR$^a$, NR$^a$S(O)$_p$N$(R^a)_2$, NR$^a$S(O)$_p$NH$_2$, NHS(O)$_p$NHR$^a$, NHS(O)$_p$N$(R^a)_2$, NHS(O)$_p$NH$_2$, —OC(=O)$R^a$, —OP(O)(OH)$_2$ or $R^a$;

provided the compound is not:

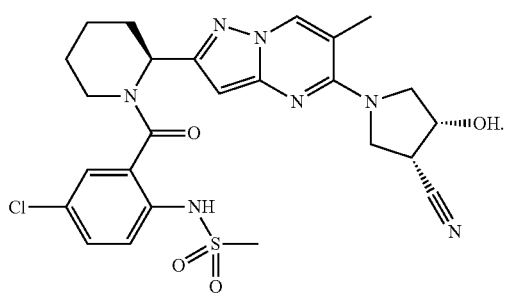

A specific value for $R^x$ is H, $(HO)_2P(=O)$—, $(C_1-C_8)$alkyl(C=O)— or $C_2-C_{20}$heterocyclyl(C=O)—, wherein each $(C_1-C_8)$alkyl(C=O)— or $C_2-C_{20}$heterocycyl(C=O)— is independently, optionally substituted with one or more oxo, halogen, hydroxy, $NH_2$, CN, $N_3$, $N(R^a)_2$, $NHR^a$, SH, $SR^a$, $S(O)_p R^a$, $OR^a$, $(C_1-C_8)$alkyl, $(C_1-C_8)$haloalkyl, —C(O)$R^a$, —C(O)H, —C(=O)$OR^a$, —C(=O)OH, —C(=O)N$(R^a)_2$, —C(=O)NHR$^a$, —C(=O)NH$_2$, NHS(O)$_p R^a$, NR$^a$S(O)$_p R^a$, NHC(O)$R^a$, NR$^a$C(O)$R^a$, NHC(O)OR$^a$, NR$^a$C(O)OR$^a$, NR$^a$C(O)NHR$^a$, NR$^a$C(O)N$(R^a)_2$, NR$^a$C(O)NH$_2$, NHC(O)NHR$^a$, NHC(O)N$(R^a)_2$, NHC(O)NH$_2$, =NH, =NOH, =NOR$^a$, NR$^a$S(O)$_p$NHR$^a$, NR$^a$S(O)$_p$N$(R^a)_2$, NR$^a$S(O)$_p$NH$_2$, NHS(O)$_p$NHR$^a$, NHS(O)$_p$N$(R^a)_2$, NHS(O)$_p$NH$_2$, OC(=O)$R^a$, —OP(O)(OH)$_2$ or $R^a$.

Another specific value for IV is H, $(HO)_2P(=O)$—, $(C_1-C_8)$alkyl(C=O)— or $C_2-C_{20}$heterocyclyl(C=O)—, wherein each $(C_1-C_8)$alkyl(C=O)— or $C_2-C_{20}$heterocyclyl(C=O)— is independently, optionally substituted with one or more $NH_2$, —C(=O)OH or NR$^a$C(O)$R^a$.

Another specific value for $R^x$ is:

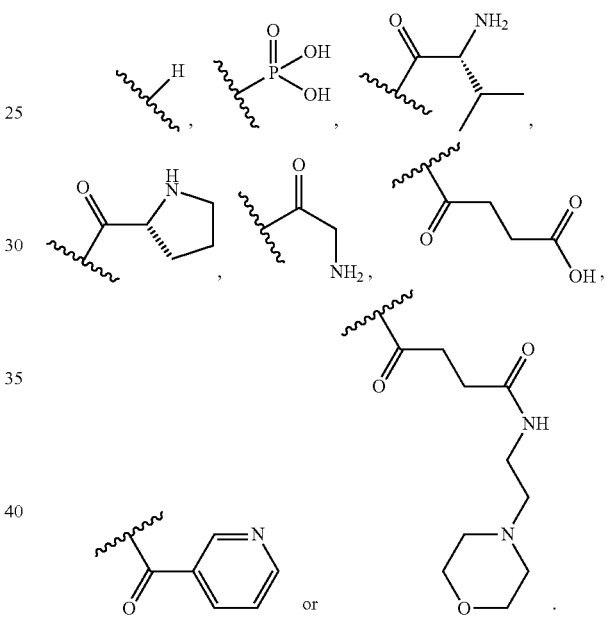

Preparation of Compounds of the Invention.

The compounds of formulas I and Ia were be prepared by the procedures described in examples 3, 4 and 6-31. The compounds of formulas 1-24 (i.e. compounds of formula V) were prepared by the procedures described in example 1 and example 4. The compounds of formulas 25-111 (i.e. compounds of formula VI) were prepared by the procedures described in examples 2, 4 and 5.

The compounds of formula II and IIa can be prepared following the procedures described in examples 3, 4, 5 and 6 by using intermediate 9b instead of intermediate 9a.

The compounds of formulas III, IIIa, IV and IVa can be prepared following the procedures described in examples 3, 4, 5 and 6 by using the enantiomers of trans-3-cyano-4-hydroxypyrrolidine instead of the cis enantiomers. The enantiomers of trans-3-cyano-4-hydroxypyrrolidine can be prepared following literature procedures (Schauss, S. E., et al., Organic Letters, 2(7), 2000, pages 1001-1004).

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumovirinae infections as described below.

In another aspect, the invention is a novel, efficacious, safe, nonirritating and physiologically compatible inhalable composition comprising a compound of formula I or a compound of formulas 1-111, or a pharmaceutically acceptable salt thereof, suitable for treating Pneumovirinae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 μm. Preferably, the compound of formula I or formulas 1-111 is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 µm and about 5 µm using a nebulizer able to aerosolize the formulation of the compound of formula I or formulas 1-111 into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than 5 µM, the particles are deposited in the upper airways decreasing the amount of drug delivered to the site of inflammation and bronchoconstriction in the lower respiratory tract. If the MMAD of the aerosol is smaller than about 1 µm, then the particles have a tendency to remain suspended in the inhaled air and are subsequently exhaled during expiration.

When formulated and delivered according to the method of the invention, the aerosol formulation for nebulization delivers a therapeutically efficacious dose of the compound of formula I or formulas 1-111 to the site of Pneumovirinae infection sufficient to treat the Pneumovirinae infection. The amount of drug administered must be adjusted to reflect the efficiency of the delivery of a therapeutically efficacious dose of the compound of formula I or formulas 1-111. In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of formula I or formulas 1-111 into the airways. In a preferred embodiment, at least about 30 to about 50% of the active compound is delivered. More preferably, about 70 to about 90% of the active compound is delivered.

In another embodiment of the instant invention, a compound of formula I or formulas 1-111 or a pharmaceutically acceptable salt thereof, is delivered as a dry inhalable powder. The compounds of the invention are administered endobronchially as a dry powder formulation to efficacious deliver fine particles of compound into the endobronchial space using dry powder or metered dose inhalers. For delivery by DPI, the compound of formula I or formulas 1-111 is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well known in the art. In one embodiment, excipients are added to the compound of formula I or formulas 1-111 before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of formula I or formulas 1-111 is delivered as a dry powder using a device such as a dry powder inhaler or other dry powder dispersion devices. Non-limiting examples of dry powder inhalers and devices include those disclosed in U.S. Pat. No. 5,458,135; U.S. Pat. No. 5,740,794; U.S. Pat. No. 5,775,320; U.S. Pat. No. 5,785,049; U.S. Pat. No. 3,906,950; U.S. Pat. No. 4,013,075; U.S. Pat. No. 4,069,819; U.S. Pat. No. 4,995,385; U.S. Pat. No. 5,522,385; U.S. Pat. No. 4,668,218; U.S. Pat. No. 4,667,668; U.S. Pat. No. 4,805,811 and U.S. Pat. No. 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 µm and about 5 µm, and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of formula I or formulas 1-111, or a pharmaceutically acceptable salt thereof, is delivered as a dry powder using either type of dry powder inhaler as described herein, wherein the MMAD of the dry powder, exclusive of any excipients, is predominantly in the range of 1 µm to about 5 µm.

In another preferred embodiment, a compound of formula I or formulas 1-111 is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234. In preferred embodiments, a compound of formula I or formulas 1-111, or a pharmaceutically acceptable salt thereof, is delivered as a dry powder using a metered dose inhaler wherein the MMAD of the dry powder, exclusive of any excipients, is predominantly in the range of about 1-5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. For the treatment of Pneumovirinae virus infections, preferably, the other active therapeutic agent is active against Pneumovirinae virus infections, particularly respiratory syncytial virus infections. Non-limiting examples of these other active therapeutic agents are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof.

Many of the infections of the Pneumovirinae viruses are respiratory infections. Therefore, additional active therapeutics used to treat respiratory symptoms and sequelae of infection may be used in combination with the compounds of formula I or formulas 1-111. The additional agents are preferably administered orally or by direct inhalation. For example, other preferred additional therapeutic agents in combination with the compounds of formula I or formulas 1-111 for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of formula I or compounds of formulas 1-111 are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diprorionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflamatory agents working through anti-inflamatory cascade mechanisms are also useful as additional therapeutic agents in combination with the compounds of formula I or the compounds of formulas 1-111 for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluorophenyl)-1-(3-phenyl-propyl)-5-pyridin-4-yl-1H-imidazol-2- yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with the compounds of formula I or formulas 1-111 are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of formula I or formulas 1-111 are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of formula I or formulas 1-111 for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-py-ridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azo-nia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of formula I or formulas 1-111 may also be combined with mucolytic agents to treat both the infection and symptoms of respiratory infections. A non-limiting example of a mucolytic agent is ambroxol. Similarly, the compounds of formula I or formulas 1-111 may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, J. Pediatrics 2007, 266). The compounds of formula I or formulas 1-111 may also be combined with nebulized hypertonic saline particularly when the Pneumovirinae virus infection is complicated with bronchiolitis. The combination of the compounds of formula I or formulas 1-111 with hypertonic saline may also comprise any of the additional agents discussed above. In a preferred aspect, nebulized about 3% hypertonic saline is used.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

Another embodiment provides for methods of treating Pneumovirinae virus infection in a patient, comprising: administering to the patient a therapeutically effective amount of a compound of formula I or formulas 1-111, or a pharmaceutically acceptable salt, solvate, and/or ester thereof.

Another embodiment provides for methods of treating Pneumovirinae virus infection in a patient, comprising: administering to the patient a therapeutically effective amount of a compound of formula I or formulas 1-111, or a pharmaceutically acceptable salt, solvate, and/or ester thereof, and at least one additional active therapeutic agent.

Another embodiment provides for methods of treating Human respiratory syncytial virus infection in a patient, comprising: administering to the patient a therapeutically effective amount of a compound of formula I or formulas 1-111, or a pharmaceutically acceptable salt, solvate, and/or ester thereof, and at least one additional active therapeutic agent.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver, lung or other metabolic organ, or within cells in general.

Tissue Distribution

It has also been discovered that certain compounds of the invention show high lung to plasma ratios which may be beneficial for therapy. One particular group of compounds of the invention that demonstrate this property are compounds that include an amine functional group.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| $Ac_2O$ | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DIPEA | N,N-diisopropylethylamine |
| DMA | dimethylacetamide |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HATU | 2-(1H-7-azabenzotriazol-1-yl)-1,1,3,3-tetramethyl uronium hexafluorophosphate Methanaminium |
| HMDS | hexamethyldisilazane |
| HPLC | High pressure liquid chromatography |
| IPA | isopropyl alcohol |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| $MH^+$ | mass plus 1 |
| $MH^-$ | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

The invention will now be illustrated by the preparation of the following non-limiting compounds of the invention. It is to be understood that individual steps described herein may be combined. It is also to be understood that separate batches of a compound may be combined and then carried forth in the next synthetic step.

Example 1

Procedure for the Preparation of Compounds of Formulas 1-24

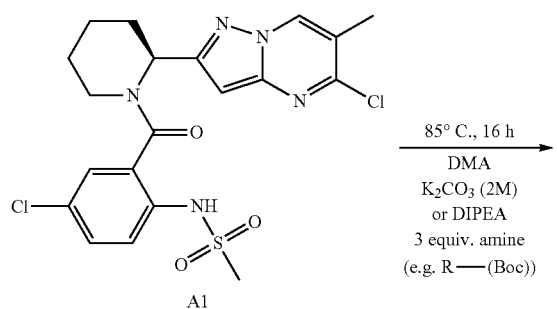

A1

85° C., 16 h
DMA
K₂CO₃ (2M)
or DIPEA
3 equiv. amine
(e.g. R—(Boc))

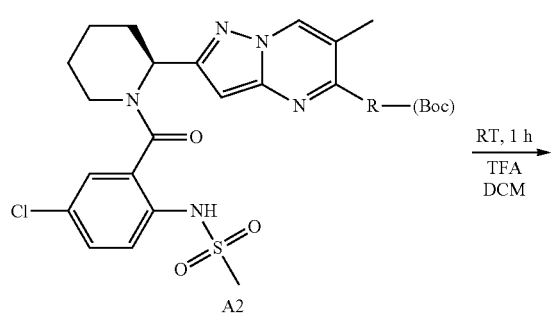

A2

RT, 1 h
TFA
DCM

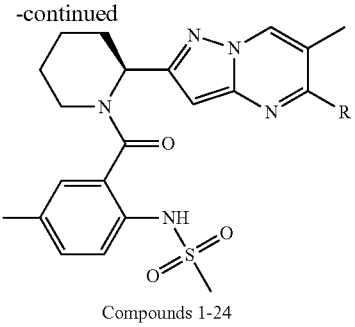

Compounds 1-24

R—(Boc) represents a diamine wherein one of the amine groups is protected with a Boc group
R represents a diamine In 50 mL, singled necked, round bottomed flask was placed (s)-N-(4-chloro-2-(2-(5-chloro-6-methylpyrazolo[1,5-a]pyrimidine-2-yl)piperidine-1-carbonyl)phenyl)methane-sulfonamide (A1), (1200 mg, 2.49 mmol) in DMA (10.8 mL). The amines (R-(Boc)) (0.12 mmol) were placed in separate 2-ml vials. Then, into each vial was dispensed a solution of A1 (0.2 mL, 0.041 mmol) followed by 0.1 mL of K₂CO₃ (2M) or DIPEA. The resulting reaction mixtures were placed on a hot plate at 85° C. for 16 h. Then, to each reaction mixture was added EtOAc (4 mL), washed with saturated NaHCO₃ (2 mL×2), and concentrated in Genevac to give A2 as a solid. The crude product A2 was redissolved in dichloromethane (0.5 mL) followed by the addition of TFA (0.2 mL). After the reaction mixture was stirred at room temperature for 1 h, it was loaded onto the CUBCX column. The mixture was washed with MeOH:EtOAc (1:4, 4 mL) and MeOH:dichloromethane (1:4, 4 mL), eluted with 7N NH₄OMe:EtOAc (3:7, 4 mL), and concentrated to afford the final compound (i.e. compounds 1-24).

| Compound Formula | Compound | calculated MW | observed MW |
|---|---|---|---|
| 1 | 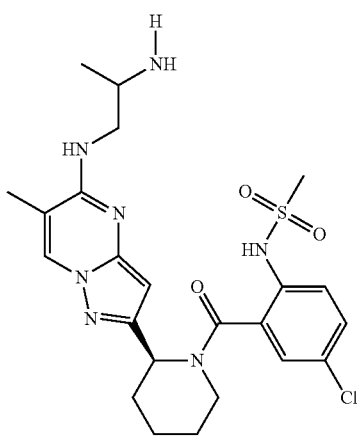 [SMILES: Cc1cn2nc([C@@H]3CCCCN3C(=O)c3cc(Cl)ccc3NS(C)(=O)=O)cc2nc1NCC(C)N] | 520.056 | 520.5 |

-continued
| Compound Formula | Compound | calculated MW | observed MW |
|---|---|---|---|
| 2 | 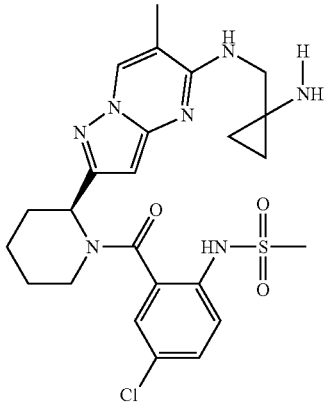 [SMILES: Cc1cn2nc([C@@H]3CCCCN3C(=O)c3cc(Cl)ccc3NS(C)(=O)=O)cc2nc1NCC1(N)CC1] | 532.067 | 532.5 |
| 3 | 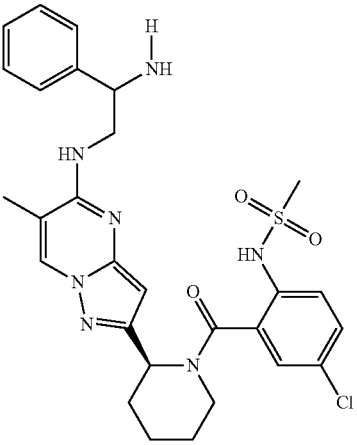 [SMILES: Cc1cn2nc([C@@H]3CCCCN3C(=O)c3cc(Cl)ccc3NS(C)(=O)=O)cc2nc1NCC(N)c1ccccc1] | 582.127 | 582.6 |
| 4 | 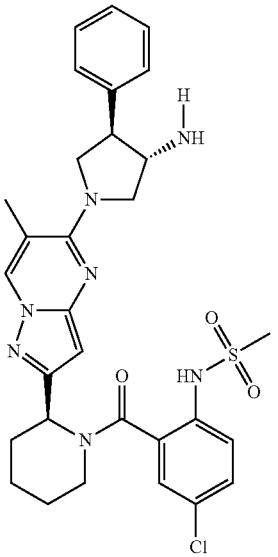 [SMILES: Cc1cn2nc([C@@H]3CCCCN3C(=O)c3cc(Cl)ccc3NS(C)(=O)=O)cc2nc1N1C[C@@H](N)[C@H](c2ccccc2)C1] | 608.165 | 608.6 |

-continued
| Compound Formula | Compound | calculated MW | observed MW |
|---|---|---|---|
| 5 | 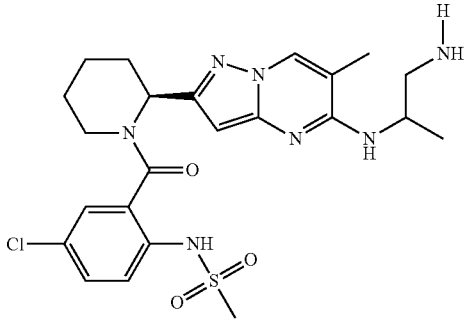 [SMILES: Cc1cn2nc([C@@H]3CCCCN3C(=O)c3cc(Cl)ccc3NS(C)(=O)=O)cc2nc1NC(C)CN] | 520.056 | 520.2 |
| 6 | 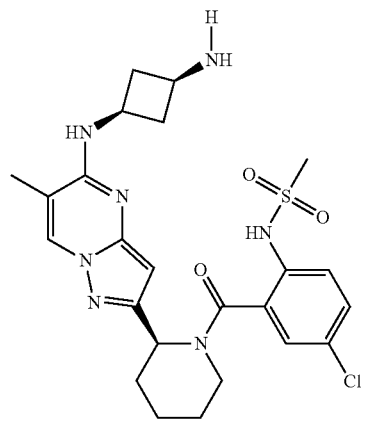 [SMILES: Cc1cn2nc([C@@H]3CCCCN3C(=O)c3cc(Cl)ccc3NS(C)(=O)=O)cc2nc1N[C@H]1C[C@@H](N)C1] | 532.067 | 532.5 |
| 7 | 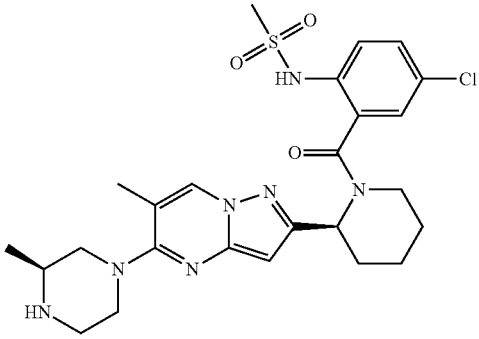 [SMILES: Cc1cn2nc([C@@H]3CCCCN3C(=O)c3cc(Cl)ccc3NS(C)(=O)=O)cc2nc1N1CCN[C@@H](C)C1] | 546.094 | 546.6 |
| 8 | 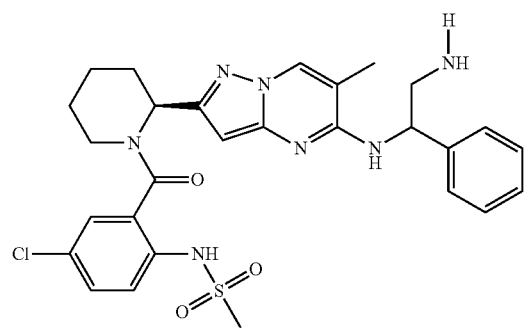 [SMILES: Cc1cn2nc([C@@H]3CCCCN3C(=O)c3cc(Cl)ccc3NS(C)(=O)=O)cc2nc1NC(CN)c1ccccc1] | 582.127 | 582.5 |

-continued
| Compound Formula | Compound | calculated MW | observed MW |
|---|---|---|---|
| 9 | 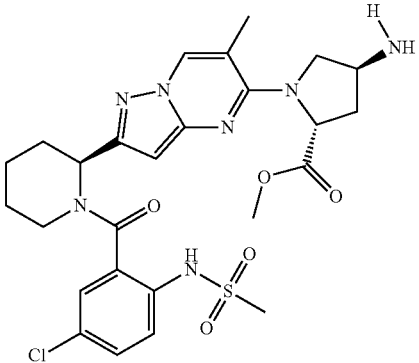 [SMILES: COC(=O)[C@H]1C[C@H](N)CN1c1nc2cc([C@@H]3CCCCN3C(=O)c3cc(Cl)ccc3NS(C)(=O)=O)nn2cc1C] | 590.103 | 590.6 |
| 10 | 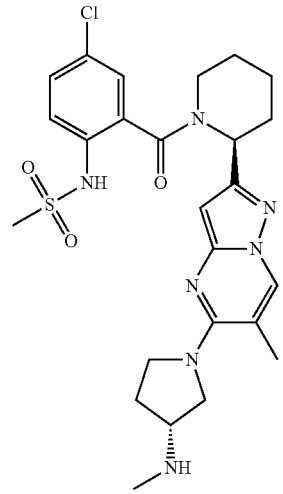 | 546.094 | 546.6 |
| 11 | 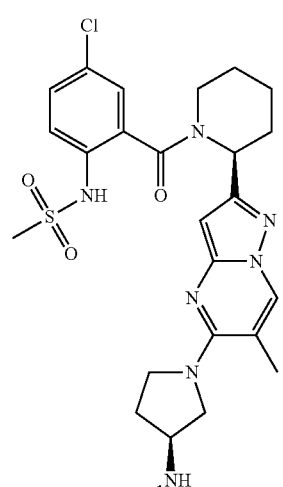 | 546.094 | 546.6 |

-continued

| Compound Formula | Compound | calculated MW | observed MW |
|---|---|---|---|
| 12 | | 590.103 | 590.6 |
| 13 | | 652.218 | 652.7 |
| 14 | | 576.076 | 576.5 |
| 15 | | 560.121 | 560.6 |

-continued

| Compound Formula | Compound | calculated MW | observed MW |
|---|---|---|---|
| 16 | | 558.105 | 558.6 |
| 17 | | 622.192 | 622.7 |
| 18 | | 544.078 | 544.6 |
| 19 | | 576.076 | 576.6 |

-continued

| Compound Formula | Compound | calculated MW | observed MW |
|---|---|---|---|
| 20 | | 560.121 | 560.6 |
| 21 | | 558.105 | 558.5 |
| 22 | | 574.148 | 574.6 |
| 23 | | 589.119 | 589.6 |

| Compound Formula | Compound | calculated MW | observed MW |
|---|---|---|---|
| 24 | | 560.121 | 560.5 |

Example 2

General Procedure for the Preparation of Compounds of Formulas 25-111

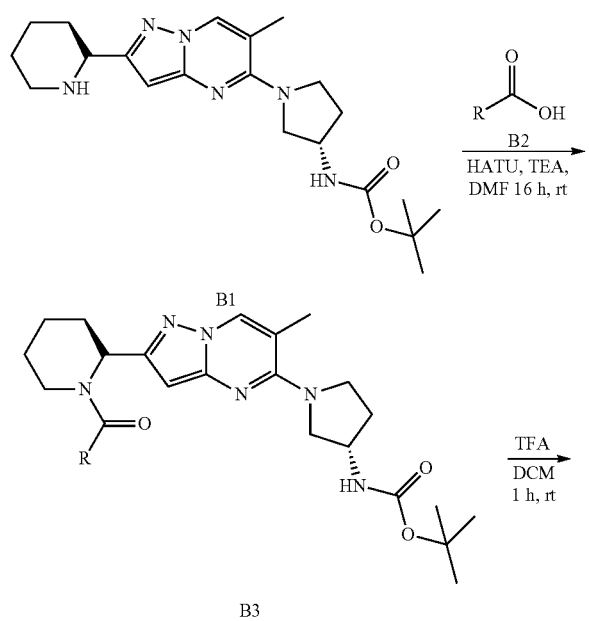

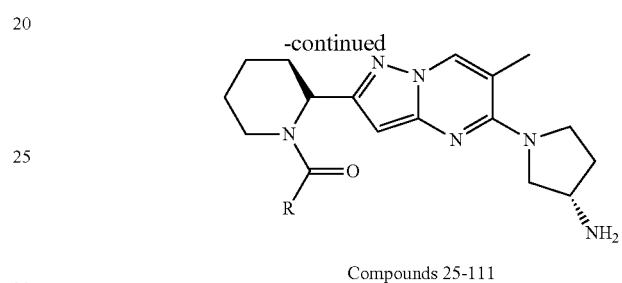

Compounds 25-111

In 50 mL, singled necked, round bottomed flask was placed tert-butyl (S)-1-(6-methyl-2-((S)-piperidin-2-yl)pyrazolo[1,5-a]pyrimidin-5-yl)pyrrolidin-3-ylcarbamate (B1) (2640 mg, 6.59 mmol) and TEA (1.83 mL, 13.2 mmol) in DMF (8.8 mL). The carboxylic acids B2 (between 0.10 mmol and 0.50 mmol) were placed in 132 separate 2-ml vials. Then, into each vial was dispensed a solution of B1 (0.050 mmol) followed by the addition of HATU (38 mg, 0.10 mmol). The resulting reaction mixtures were placed on an orbital shaker at room temperature for 16 h. Then, to each reaction mixture was added EtOAc (4 mL), washed with sat. NaHCO$_3$ (2 mL×2), and concentrated in Genevac to give B3 as a solid. The crude product B3 was redissolved in dichloromethane (0.5 mL) followed by the addition of TFA (0.2 mL). After the reaction mixture was stirred at room temperature for 1 h, it was loaded onto the CUBCX column. The mixture was washed with MeOH:EtOAc (1:4, 4 mL) and MeOH:dichloromethane (1:4, 4 mL), eluted with 7N NH$_4$OMe:EtOAc (3:7, 4 mL), and concentrated to afford the final compound (i.e. compounds 25-111).

| Compound formula | Structure | calculated MW | observed MW |
|---|---|---|---|
| 25 | 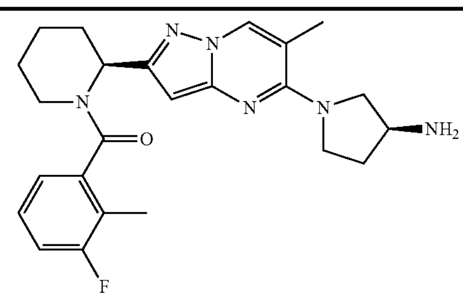 | 436.535 | 437.6 |

-continued

| Compound formula | Structure | calculated MW | observed MW |
|---|---|---|---|
| 26 | 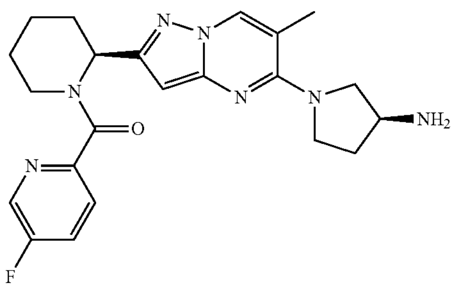 [SMILES: Cc1cn2nc([C@@H]3CCCCN3C(=O)c3ccc(F)cn3)cc2nc1N1CC[C@H](N)C1] | 423.496 | 424.5 |
| 27 | 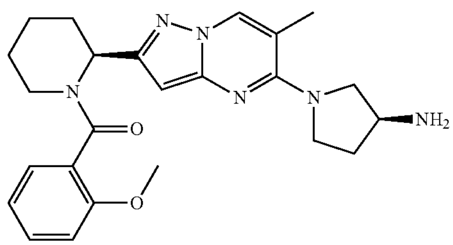 [SMILES: COc1ccccc1C(=O)N1CCCC[C@H]1c1cc2nc(N3CC[C@H](N)C3)c(C)cn2n1] | 434.544 | 435.6 |
| 28 | 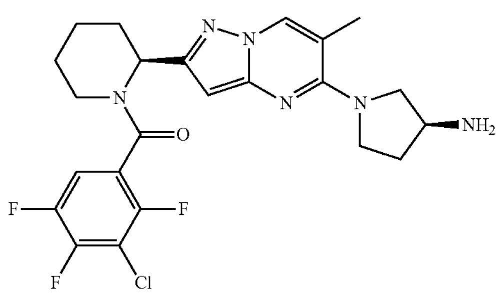 [SMILES: Cc1cn2nc([C@@H]3CCCCN3C(=O)c3cc(F)c(F)c(Cl)c3F)cc2nc1N1CC[C@H](N)C1] | 492.933 | 493.5 |
| 29 | 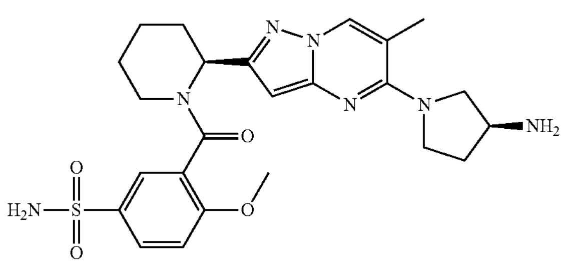 [SMILES: COc1ccc(S(N)(=O)=O)cc1C(=O)N1CCCC[C@H]1c1cc2nc(N3CC[C@H](N)C3)c(C)cn2n1] | 513.621 | 514.6 |
| 30 | 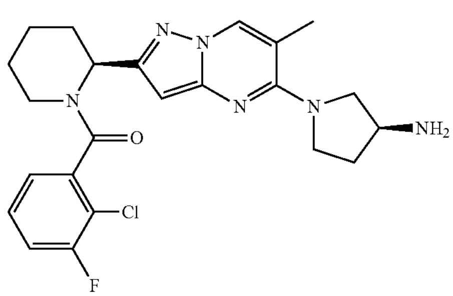 | 456.953 | 457.5 |

-continued

| Compound formula | Structure | calculated MW | observed MW |
|---|---|---|---|
| 31 | 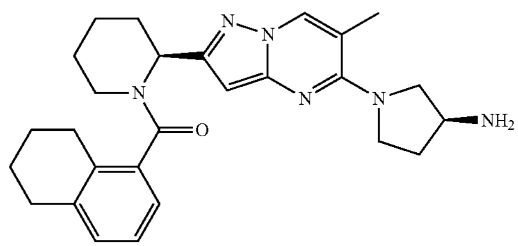 | 458.61 | 459.6 |
| 32 | 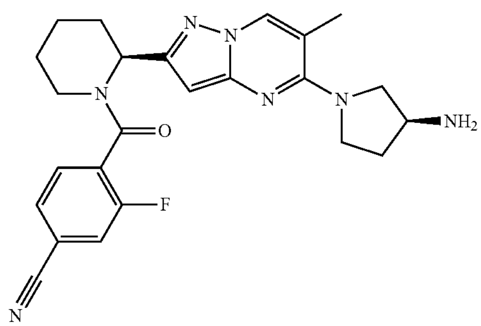 [SMILES: Cc1cn2nc([C@@H]3CCCCN3C(=O)c3ccc(C#N)cc3F)cc2nc1N1CC[C@H](N)C1] | 447.518 | 448.6 |
| 33 | 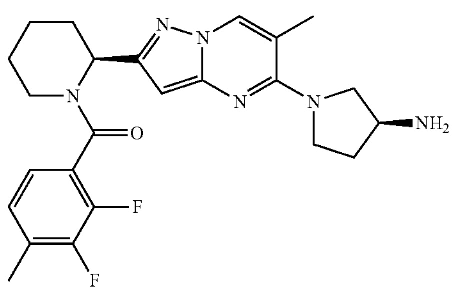 [SMILES: Cc1cn2nc([C@@H]3CCCCN3C(=O)c3ccc(C)c(F)c3F)cc2nc1N1CC[C@H](N)C1] | 454.525 | 455.5 |
| 34 | 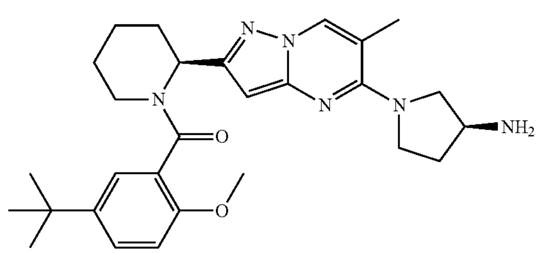 [SMILES: COc1ccc(C(C)(C)C)cc1C(=O)N1CCCC[C@H]1c1cc2nc(N3CC[C@H](N)C3)c(C)cn2n1] | 490.652 | 491.7 |
| 35 | 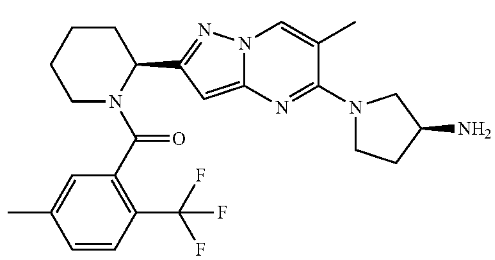 [SMILES: Cc1ccc(C(F)(F)F)c(C(=O)N2CCCC[C@H]2c2cc3nc(N4CC[C@H](N)C4)c(C)cn3n2)c1] | 486.542 | 487.6 |

-continued
| Compound formula | Structure | calculated MW | observed MW |
|---|---|---|---|
| 36 | 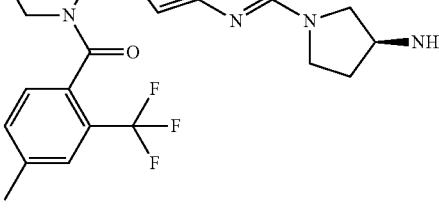 | 486.542 | 487.6 |
| 37 | 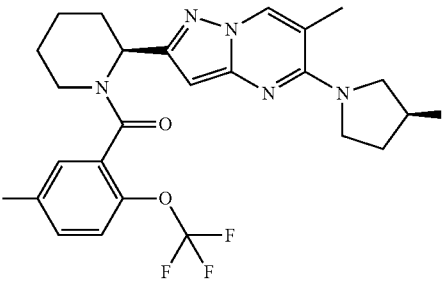 | 506.504 | 507.6 |
| 38 | 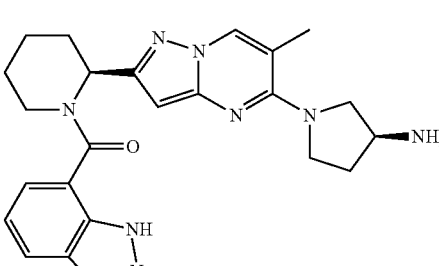 | 444.543 | 445.6 |
| 39 | 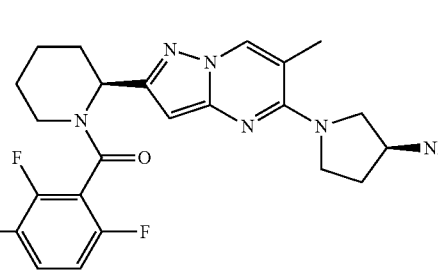 | 454.525 | 455.5 |
| 40 | 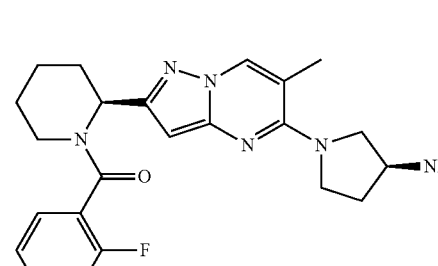 | 478.988 | 479.6 |

-continued

| Compound formula | Structure | calculated MW | observed MW |
|---|---|---|---|
| 41 | 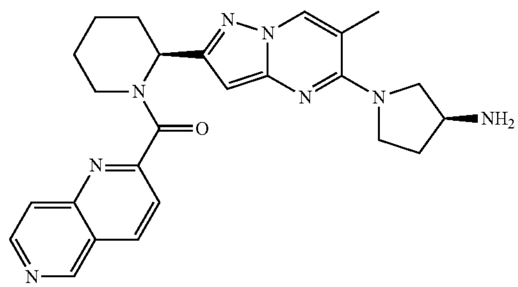 [SMILES: Cc1cn2nc([C@@H]3CCCCN3C(=O)c3ccc4cnccc4n3)cc2nc1N1CC[C@H](N)C1] | 456.554 | 457.6 |
| 42 | 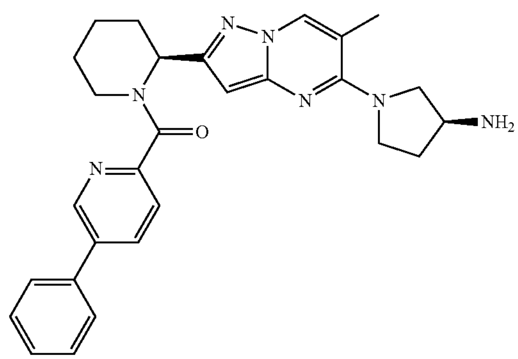 [SMILES: Cc1cn2nc([C@@H]3CCCCN3C(=O)c3ccc(-c4ccccc4)cn3)cc2nc1N1CC[C@H](N)C1] | 481.604 | 482.6 |
| 43 | 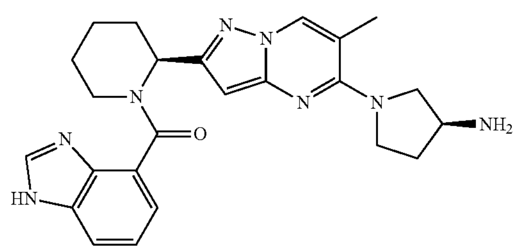 [SMILES: Cc1cn2nc([C@@H]3CCCCN3C(=O)c3cccc4[nH]cnc34)cc2nc1N1CC[C@H](N)C1] | 444.543 | 445.5 |
| 44 | 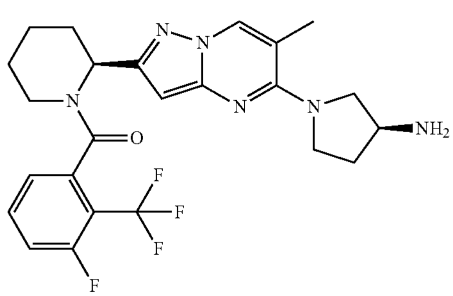 [SMILES: Cc1cn2nc([C@@H]3CCCCN3C(=O)c3cccc(F)c3C(F)(F)F)cc2nc1N1CC[C@H](N)C1] | 490.505 | 491.5 |
| 45 | 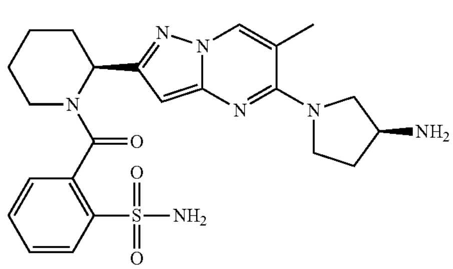 [SMILES: Cc1cn2nc([C@@H]3CCCCN3C(=O)c3ccccc3S(N)(=O)=O)cc2nc1N1CC[C@H](N)C1] | 483.595 | 484.6 |

-continued

| Compound formula | Structure | calculated MW | observed MW |
|---|---|---|---|
| 46 | 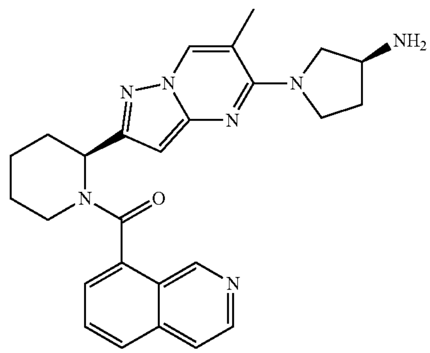 [SMILES: Cc1cn2nc([C@@H]3CCCCN3C(=O)c3cccc4ccncc34)cc2nc1N1CC[C@H](N)C1] | 455.566 | 456.6 |
| 47 | 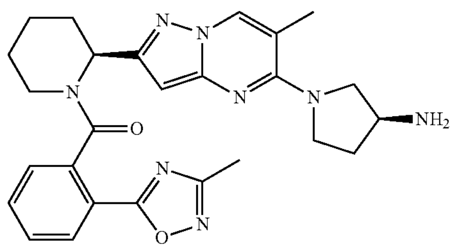 [SMILES: Cc1noc(-c2ccccc2C(=O)N2CCCC[C@H]2c2cc3nc(N4CC[C@H](N)C4)c(C)cn3n2)n1] | 486.58 | 487.6 |
| 48 | 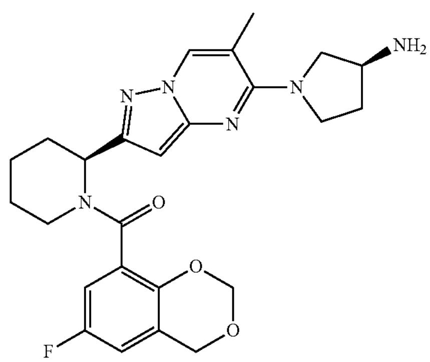 [SMILES: Cc1cn2nc([C@@H]3CCCCN3C(=O)c3cc(F)cc4c3OCOC4)cc2nc1N1CC[C@H](N)C1] | 480.544 | 481.6 |
| 49 | 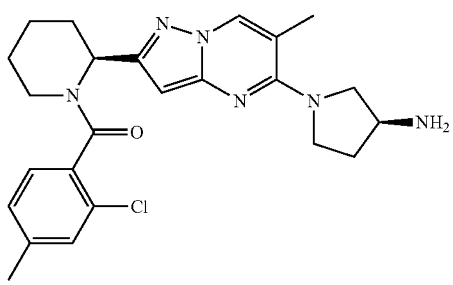 [SMILES: Cc1ccc(C(=O)N2CCCC[C@H]2c2cc3nc(N4CC[C@H](N)C4)c(C)cn3n2)c(Cl)c1] | 452.99 | 453.5 |
| 50 | 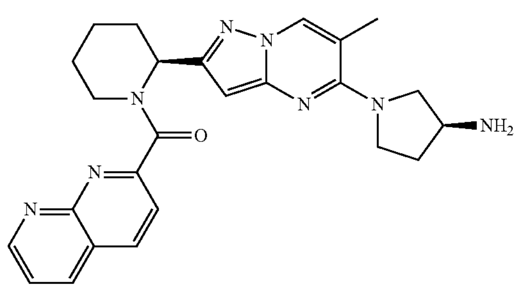 | 456.554 | 457.6 |

-continued

| Compound formula | Structure | calculated MW | observed MW |
|---|---|---|---|
| 51 | 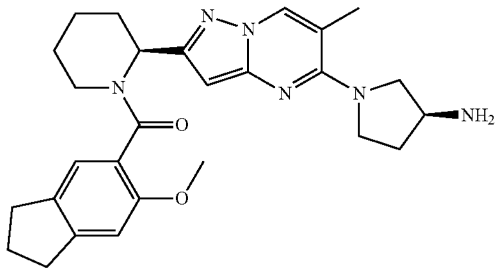 [SMILES: COc1cc2c(cc1C(=O)N1CCCC[C@H]1c1cc3nc(N4CC[C@H](N)C4)c(C)cn3n1)CCC2] | 474.609 | 475.6 |
| 52 | 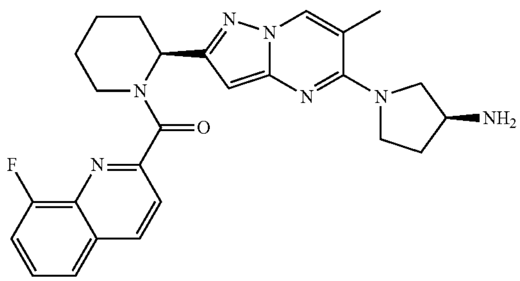 [SMILES: Cc1cn2nc([C@@H]3CCCCN3C(=O)c3ccc4cccc(F)c4n3)cc2nc1N1CC[C@H](N)C1] | 473.556 | 474.6 |
| 53 | 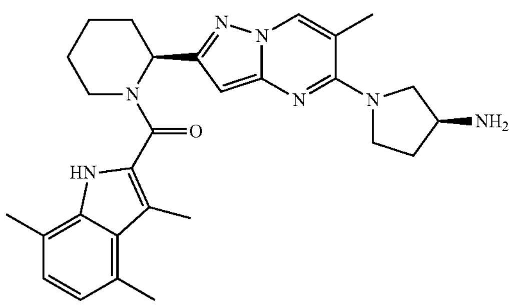 [SMILES: Cc1cn2nc([C@@H]3CCCCN3C(=O)c3[nH]c4c(C)ccc(C)c4c3C)cc2nc1N1CC[C@H](N)C1] | 485.636 | 486.6 |
| 54 | 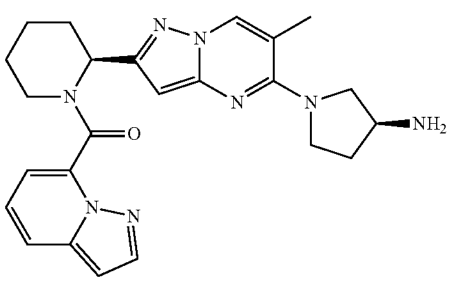 [SMILES: Cc1cn2nc([C@@H]3CCCCN3C(=O)c3cccc4ccnn34)cc2nc1N1CC[C@H](N)C1] | 444.543 | 445.6 |
| 55 | 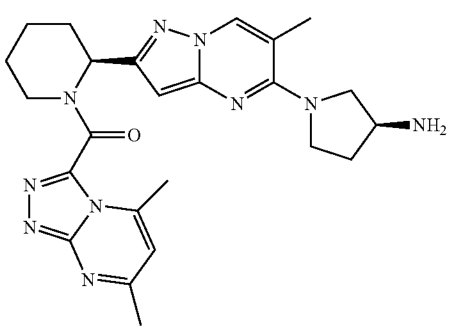 [SMILES: Cc1cc(C)n2c(C(=O)N3CCCC[C@H]3c3cc4nc(N5CC[C@H](N)C5)c(C)cn4n3)nnc2n1] | 474.573 | 475.6 |

| Compound formula | Structure | calculated MW | observed MW |
|---|---|---|---|
| 56 | 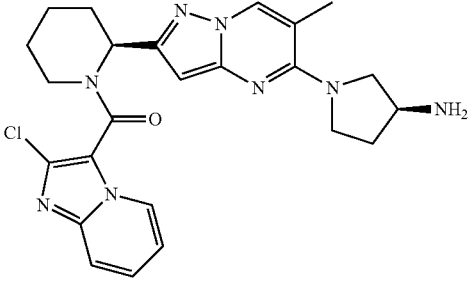 [SMILES: Cc1cn2nc([C@@H]3CCCCN3C(=O)c3c(Cl)nc4ccccn34)cc2nc1N1CC[C@H](N)C1] | 478.988 | 479.6 |
| 57 | 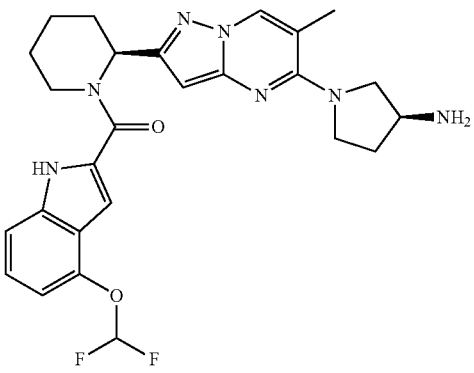 [SMILES: Cc1cn2nc([C@@H]3CCCCN3C(=O)c3cc4c(OC(F)F)cccc4[nH]3)cc2nc1N1CC[C@H](N)C1] | 509.561 | 510.6 |
| 58 | 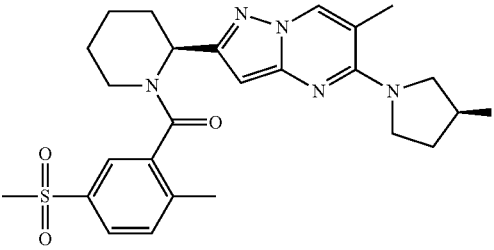 | 496.634 | 497.2 |
| 59 | 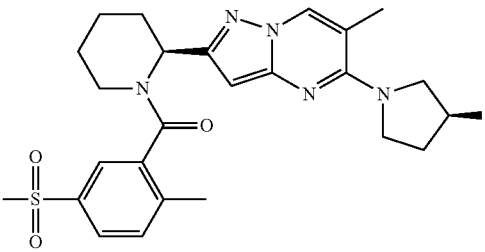 | 497.622 | 498.6 |
| 60 | 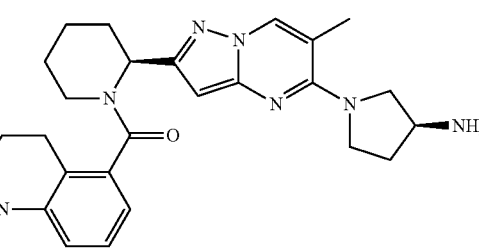 | 459.598 | 460.6 |

-continued

| Compound formula | Structure | calculated MW | observed MW |
|---|---|---|---|
| 61 | 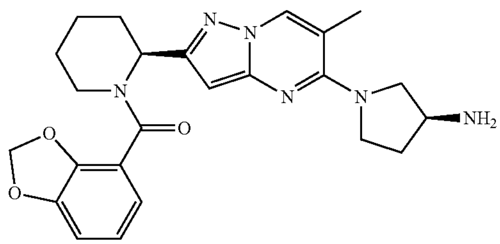 [SMILES: Cc1cn2nc([C@@H]3CCCCN3C(=O)c3cccc4c3OCO4)cc2nc1N1CC[C@H](N)C1] | 448.527 | 449.5 |
| 62 | 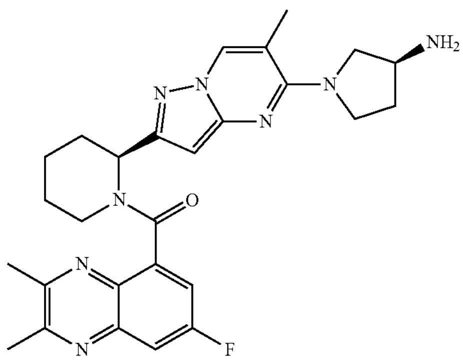 [SMILES: Cc1cn2nc([C@@H]3CCCCN3C(=O)c3cc(F)cc4nc(C)c(C)nc34)cc2nc1N1CC[C@H](N)C1] | 502.598 | 503.6 |
| 63 | 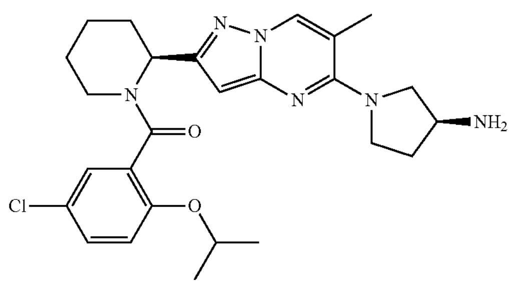 [SMILES: Cc1cn2nc([C@@H]3CCCCN3C(=O)c3cc(Cl)ccc3OC(C)C)cc2nc1N1CC[C@H](N)C1] | 497.043 | 497.6 |
| 64 | 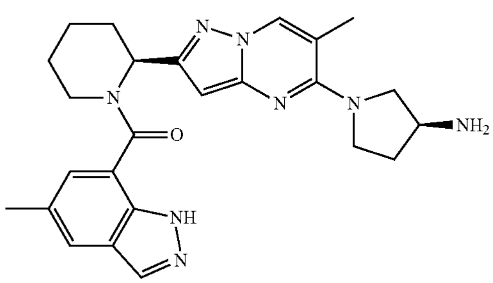 [SMILES: Cc1cc(C(=O)N2CCCC[C@H]2c2cc3nc(N4CC[C@H](N)C4)c(C)cn3n2)c2[nH]ncc2c1] | 458.57 | 459.6 |
| 65 | 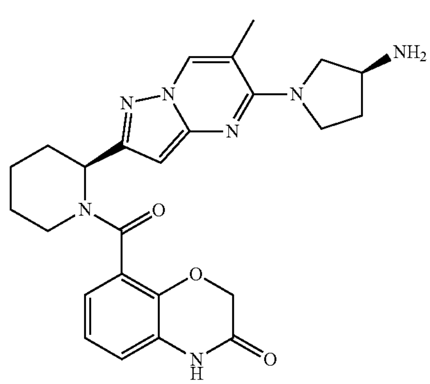 [SMILES: Cc1cn2nc([C@@H]3CCCCN3C(=O)c3cccc4c3OCC(=O)N4)cc2nc1N1CC[C@H](N)C1] | 475.553 | 476.5 |

-continued

| Compound formula | Structure | calculated MW | observed MW |
|---|---|---|---|
| 66 | 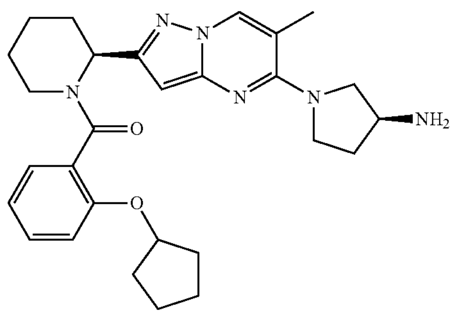 [SMILES: Cc1cn2nc([C@@H]3CCCCN3C(=O)c3ccccc3OC3CCCC3)cc2nc1N1CC[C@H](N)C1] | 488.636 | 489.6 |
| 67 | 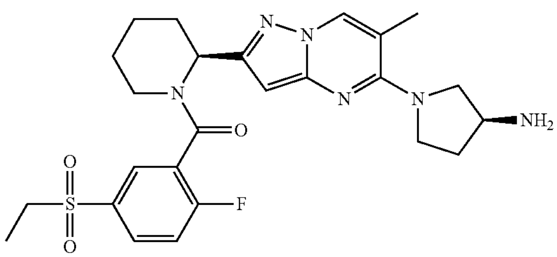 [SMILES: CCS(=O)(=O)c1ccc(F)c(C(=O)N2CCCC[C@H]2c2cc3nc(N4CC[C@H](N)C4)c(C)cn3n2)c1] | 514.624 | 515.6 |
| 68 | 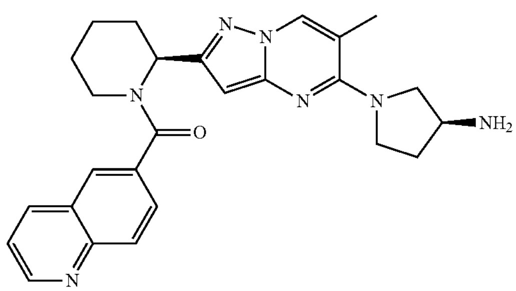 [SMILES: Cc1cn2nc([C@@H]3CCCCN3C(=O)c3ccc4ncccc4c3)cc2nc1N1CC[C@H](N)C1] | 455.566 | 456.6 |
| 69 | 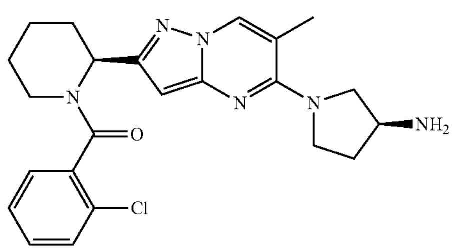 [SMILES: Cc1cn2nc([C@@H]3CCCCN3C(=O)c3ccccc3Cl)cc2nc1N1CC[C@H](N)C1] | 438.963 | 439.5 |
| 70 | 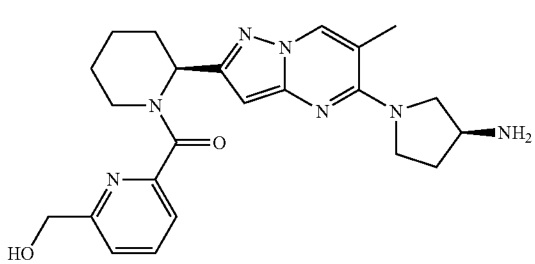 [SMILES: Cc1cn2nc([C@@H]3CCCCN3C(=O)c3cccc(CO)n3)cc2nc1N1CC[C@H](N)C1] | 435.532 | 436.6 |

-continued

| Compound formula | Structure | calculated MW | observed MW |
|---|---|---|---|
| 71 | 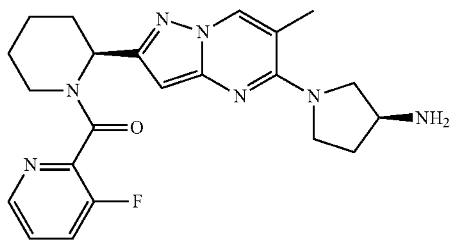 [SMILES: Cc1cn2nc([C@@H]3CCCCN3C(=O)c3ncccc3F)cc2nc1N1CC[C@H](N)C1] | 423.496 | 424.5 |
| 72 | 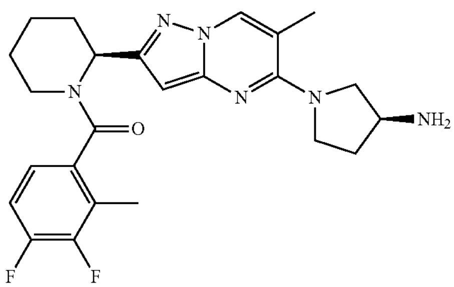 [SMILES: Cc1cn2nc([C@@H]3CCCCN3C(=O)c3ccc(F)c(F)c3C)cc2nc1N1CC[C@H](N)C1] | 454.525 | 455.6 |
| 73 | 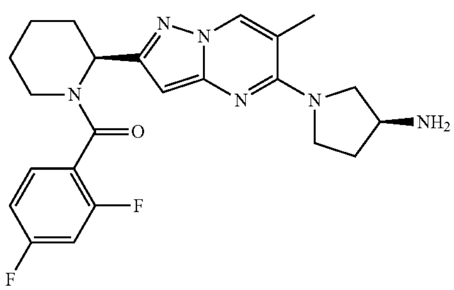 [SMILES: Cc1cn2nc([C@@H]3CCCCN3C(=O)c3ccc(F)cc3F)cc2nc1N1CC[C@H](N)C1] | 440.498 | 441.5 |
| 74 | 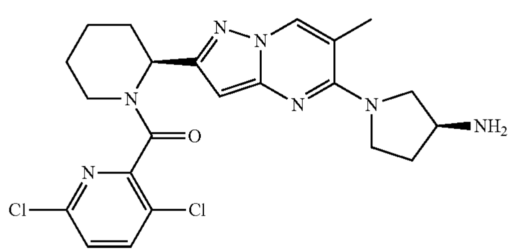 [SMILES: Cc1cn2nc([C@@H]3CCCCN3C(=O)c3nc(Cl)ccc3Cl)cc2nc1N1CC[C@H](N)C1] | 474.396 | 474.5 |
| 75 | 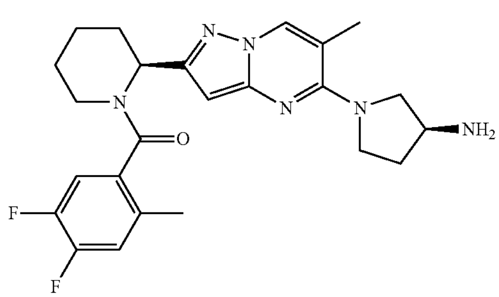 [SMILES: Cc1cc(F)c(F)cc1C(=O)N1CCCC[C@H]1c1cc2nc(N3CC[C@H](N)C3)c(C)cn2n1] | 454.525 | 455.5 |

| Compound formula | Structure | calculated MW | observed MW |
|---|---|---|---|
| 76 | 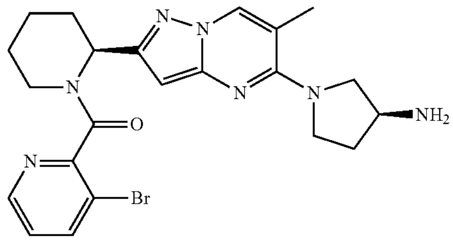 [SMILES: Cc1cn2nc([C@@H]3CCCCN3C(=O)c3ncccc3Br)cc2nc1N1CC[C@H](N)C1] | 484.407 | 484.5 |
| 77 | 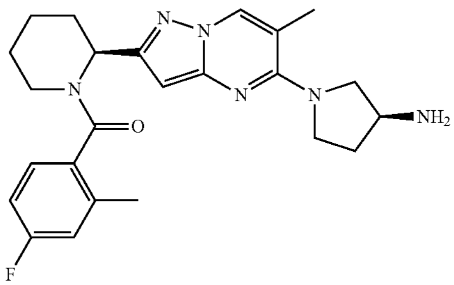 [SMILES: Cc1cc(F)ccc1C(=O)N1CCCC[C@H]1c1cc2nc(N3CC[C@H](N)C3)c(C)cn2n1] | 436.535 | 437.5 |
| 78 | 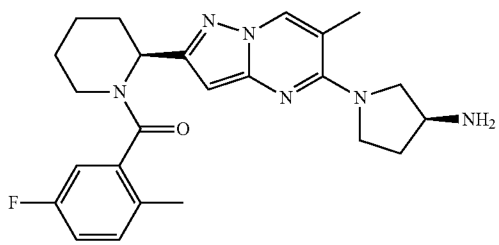 [SMILES: Cc1ccc(F)cc1C(=O)N1CCCC[C@H]1c1cc2nc(N3CC[C@H](N)C3)c(C)cn2n1] | 436.535 | 437.6 |
| 79 | 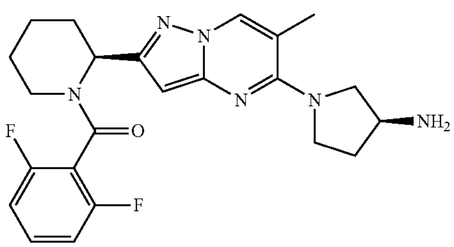 [SMILES: Cc1cn2nc([C@@H]3CCCCN3C(=O)c3c(F)cccc3F)cc2nc1N1CC[C@H](N)C1] | 440.498 | 441.5 |
| 80 | 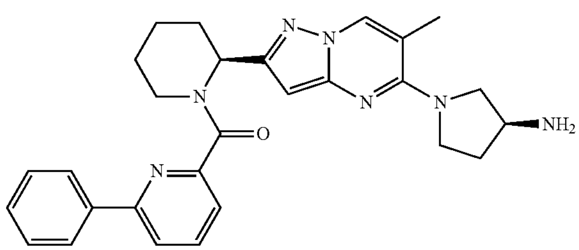 [SMILES: Cc1cn2nc([C@@H]3CCCCN3C(=O)c3cccc(-c4ccccc4)n3)cc2nc1N1CC[C@H](N)C1] | 481.604 | 482.6 |
| 81 | 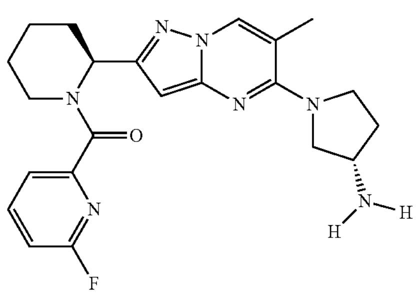 [SMILES: Cc1cn2nc([C@@H]3CCCCN3C(=O)c3cccc(F)n3)cc2nc1N1CC[C@H](N)C1] | 423.496 | 424.2 |

-continued

| Compound formula | Structure | calculated MW | observed MW |
|---|---|---|---|
| 82 | 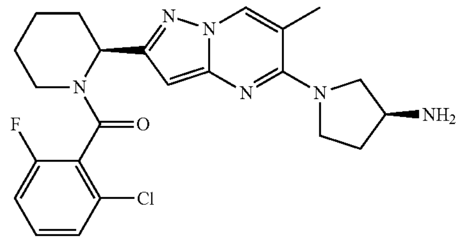 | 456.953 | 457.5 |
| 83 | 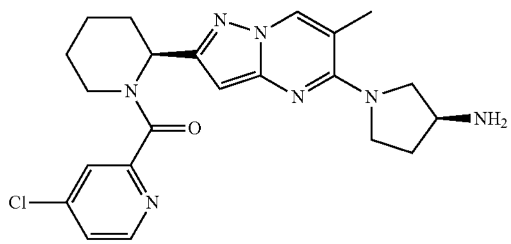 [SMILES: Cc1cn2nc([C@@H]3CCCCN3C(=O)c3cc(Cl)ccn3)cc2nc1N1CC[C@H](N)C1] | 439.951 | 440.5 |
| 84 | 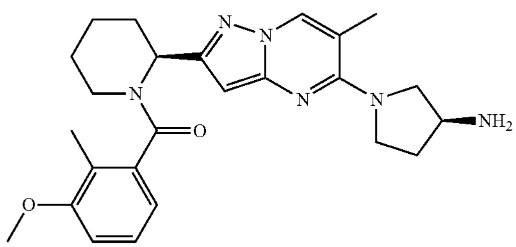 [SMILES: COc1cccc(C(=O)N2CCCC[C@H]2c2cc3nc(N4CC[C@H](N)C4)c(C)cn3n2)c1C] | 448.571 | 449.6 |
| 85 | 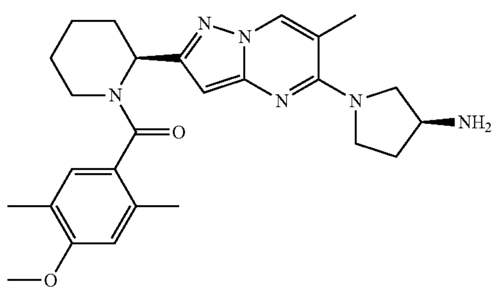 [SMILES: COc1cc(C)c(C(=O)N2CCCC[C@H]2c2cc3nc(N4CC[C@H](N)C4)c(C)cn3n2)cc1C] | 462.598 | 463.6 |
| 86 | 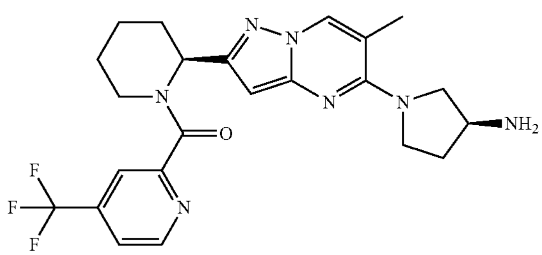 [SMILES: Cc1cn2nc([C@@H]3CCCCN3C(=O)c3cc(C(F)(F)F)ccn3)cc2nc1N1CC[C@H](N)C1] | 473.503 | 474.6 |
| 87 | 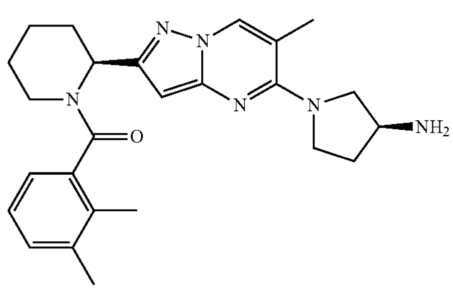 [SMILES: Cc1cn2nc([C@@H]3CCCCN3C(=O)c3cccc(C)c3C)cc2nc1N1CC[C@H](N)C1] | 432.572 | 433.6 |

-continued

| Compound formula | Structure | calculated MW | observed MW |
|---|---|---|---|
| 88 | 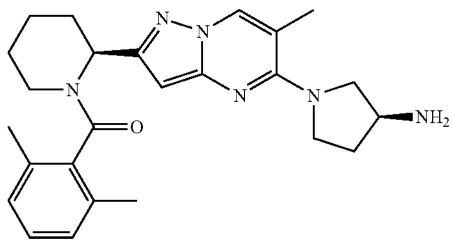 [SMILES: Cc1cn2nc([C@@H]3CCCCN3C(=O)c3c(C)cccc3C)cc2nc1N1CC[C@H](N)C1] | 432.572 | 433.6 |
| 89 | 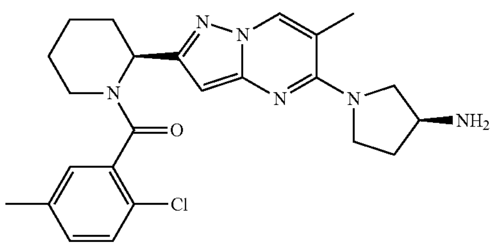 [SMILES: Cc1ccc(Cl)c(C(=O)N2CCCC[C@H]2c2cc3nc(N4CC[C@H](N)C4)c(C)cn3n2)c1] | 452.99 | 453.5 |
| 90 | 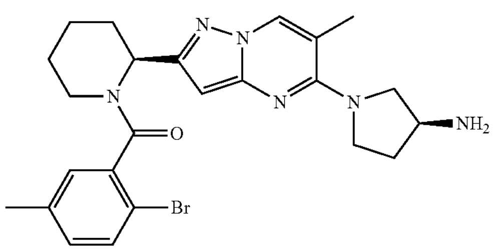 [SMILES: Cc1ccc(Br)c(C(=O)N2CCCC[C@H]2c2cc3nc(N4CC[C@H](N)C4)c(C)cn3n2)c1] | 497.446 | 497.5 |
| 91 | 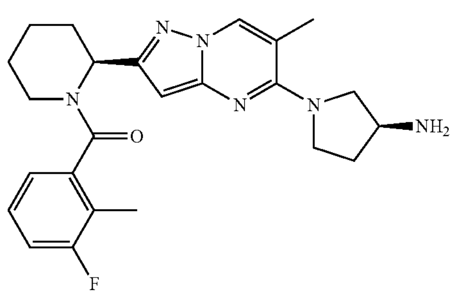 [SMILES: Cc1cn2nc([C@@H]3CCCCN3C(=O)c3cccc(F)c3C)cc2nc1N1CC[C@H](N)C1] | 436.535 | 437.6 |
| 92 | 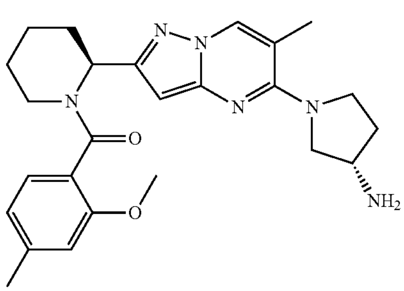 [SMILES: COc1cc(C)ccc1C(=O)N1CCCC[C@H]1c1cc2nc(N3CC[C@H](N)C3)c(C)cn2n1] | 448.571 | 449.6 |

-continued
| Compound formula | Structure | calculated MW | observed MW |
|---|---|---|---|
| 93 | 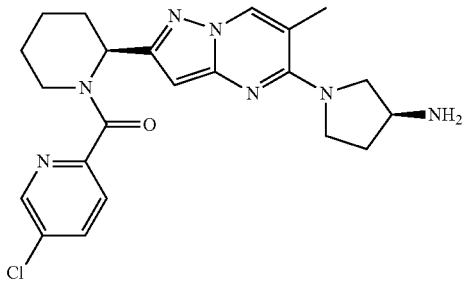 [SMILES: Cc1cn2nc([C@@H]3CCCCN3C(=O)c3ccc(Cl)cn3)cc2nc1N1CC[C@H](N)C1] | 439.951 | 440.5 |
| 94 | 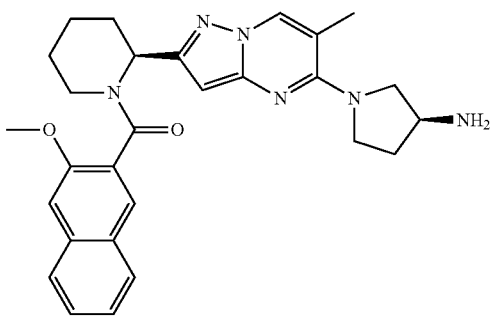 [SMILES: COc1cc2ccccc2cc1C(=O)N1CCCC[C@H]1c1cc2nc(N3CC[C@H](N)C3)c(C)cn2n1] | 484.604 | 485.6 |
| 95 | 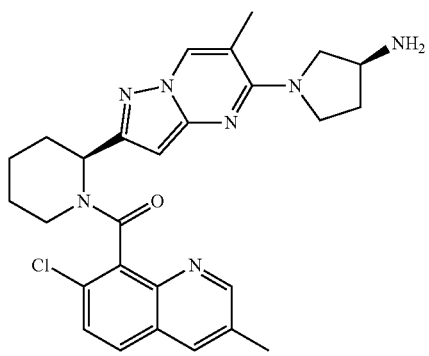 [SMILES: Cc1cnc2c(C(=O)N3CCCC[C@H]3c3cc4nc(N5CC[C@H](N)C5)c(C)cn4n3)c(Cl)ccc2c1] | 504.038 | 504.6 |
| 96 | 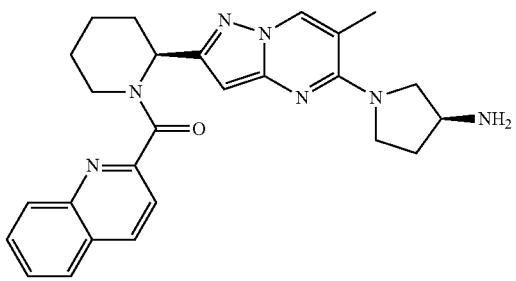 [SMILES: Cc1cn2nc([C@@H]3CCCCN3C(=O)c3ccc4ccccc4n3)cc2nc1N1CC[C@H](N)C1] | 455.566 | 456.6 |

-continued

| Compound formula | Structure | calculated MW | observed MW |
|---|---|---|---|
| 97 | 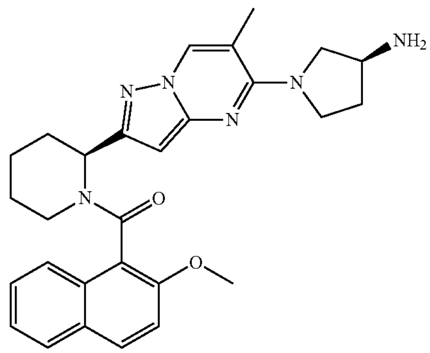 [SMILES: COc1ccc2ccccc2c1C(=O)N1CCCC[C@H]1c1cc2nc(N3CC[C@H](N)C3)c(C)cn2n1] | 484.604 | 485.6 |
| 98 | 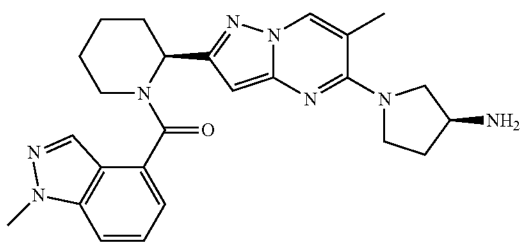 [SMILES: Cc1cn2nc([C@@H]3CCCCN3C(=O)c3cccc4c3cnn4C)cc2nc1N1CC[C@H](N)C1] | 458.57 | 459.6 |
| 99 | 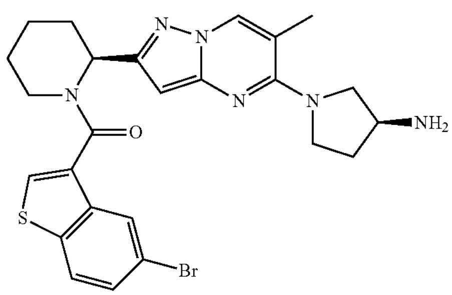 [SMILES: Cc1cn2nc([C@@H]3CCCCN3C(=O)c3csc4ccc(Br)cc34)cc2nc1N1CC[C@H](N)C1] | 539.505 | 539.5 |
| 100 | 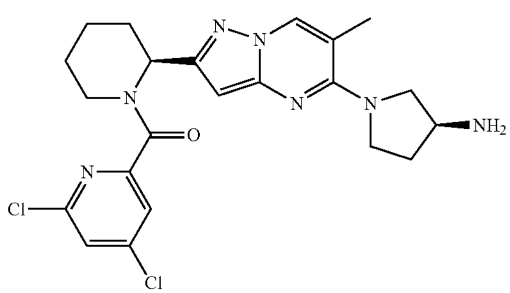 [SMILES: Cc1cn2nc([C@@H]3CCCCN3C(=O)c3cc(Cl)cc(Cl)n3)cc2nc1N1CC[C@H](N)C1] | 474.396 | 474.5 |
| 101 | 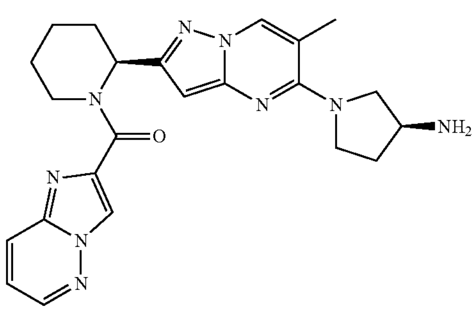 [SMILES: Cc1cn2nc([C@@H]3CCCCN3C(=O)c3cn4ncccc4n3)cc2nc1N1CC[C@H](N)C1] | 445.531 | 446.5 |

-continued

| Compound formula | Structure | calculated MW | observed MW |
|---|---|---|---|
| 102 | 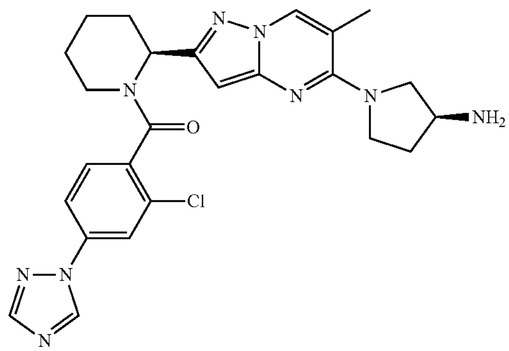 [SMILES: Cc1cn2nc([C@@H]3CCCCN3C(=O)c3ccc(-n4cncn4)cc3Cl)cc2nc1N1CC[C@H](N)C1] | 506.014 | 506.6 |
| 103 | 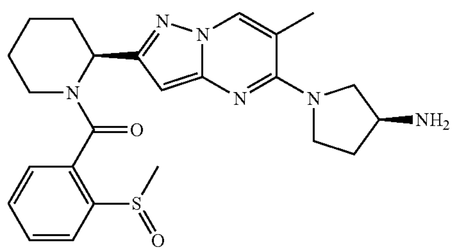 [SMILES: Cc1cn2nc([C@@H]3CCCCN3C(=O)c3ccccc3S(C)=O)cc2nc1N1CC[C@H](N)C1] | 466.608 | 467.5 |
| 104 | 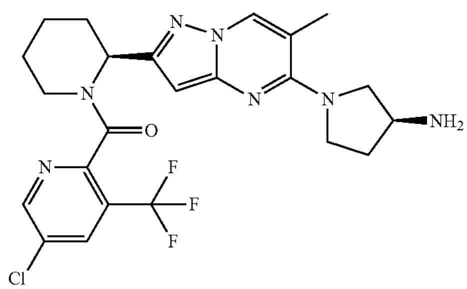 [SMILES: Cc1cn2nc([C@@H]3CCCCN3C(=O)c3ncc(Cl)cc3C(F)(F)F)cc2nc1N1CC[C@H](N)C1] | 507.948 | 508.5 |
| 105 | 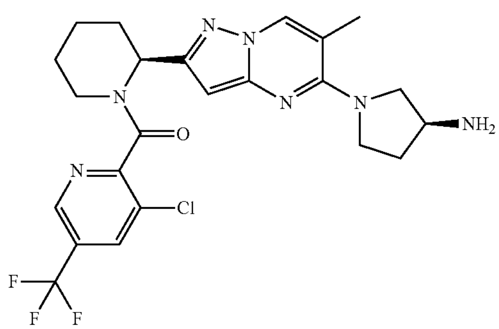 [SMILES: Cc1cn2nc([C@@H]3CCCCN3C(=O)c3ncc(C(F)(F)F)cc3Cl)cc2nc1N1CC[C@H](N)C1] | 507.948 | 508.5 |
| 106 | 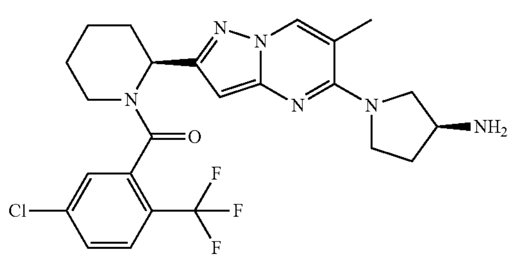 [SMILES: Cc1cn2nc([C@@H]3CCCCN3C(=O)c3cc(Cl)ccc3C(F)(F)F)cc2nc1N1CC[C@H](N)C1] | 506.96 | 507.5 |

-continued

| Compound formula | Structure | calculated MW | observed MW |
|---|---|---|---|
| 107 | 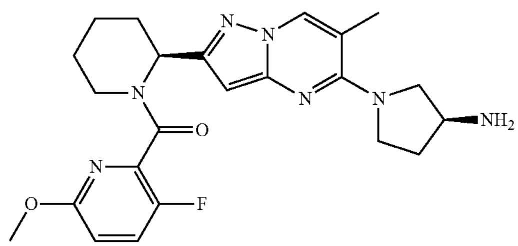 [SMILES: COc1ccc(F)c(C(=O)N2CCCC[C@H]2c2cc3nc(N4CC[C@H](N)C4)c(C)cn3n2)n1] | 453.522 | 454.6 |
| 108 | 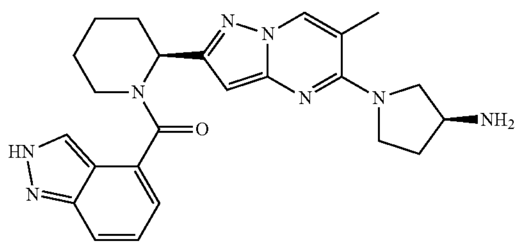 [SMILES: Cc1cn2nc([C@@H]3CCCCN3C(=O)c3cccc4n[nH]cc34)cc2nc1N1CC[C@H](N)C1] | 444.543 | 445.2 |
| 109 | 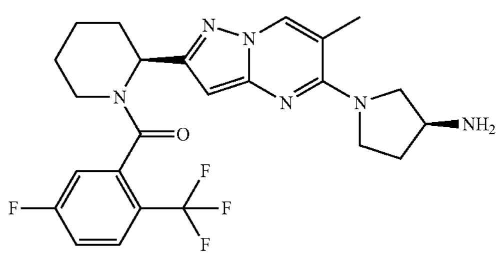 [SMILES: Cc1cn2nc([C@@H]3CCCCN3C(=O)c3cc(F)ccc3C(F)(F)F)cc2nc1N1CC[C@H](N)C1] | 490.505 | 491.6 |
| 110 | 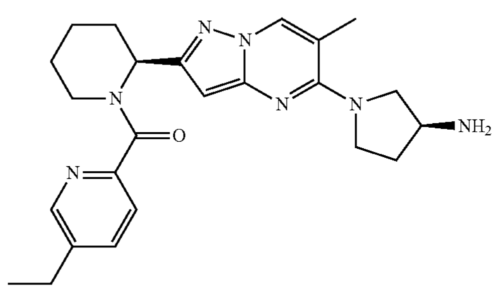 [SMILES: CCc1ccc(C(=O)N2CCCC[C@H]2c2cc3nc(N4CC[C@H](N)C4)c(C)cn3n2)nc1] | 433.56 | 434.5 |
| 111 | 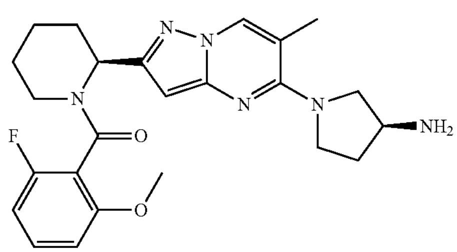 [SMILES: COc1cccc(F)c1C(=O)N1CCCC[C@H]1c1cc2nc(N3CC[C@H](N)C3)c(C)cn2n1] | 452.534 | 453.5 |

Example 3

General Procedure for the Preparation of Compounds 112-191

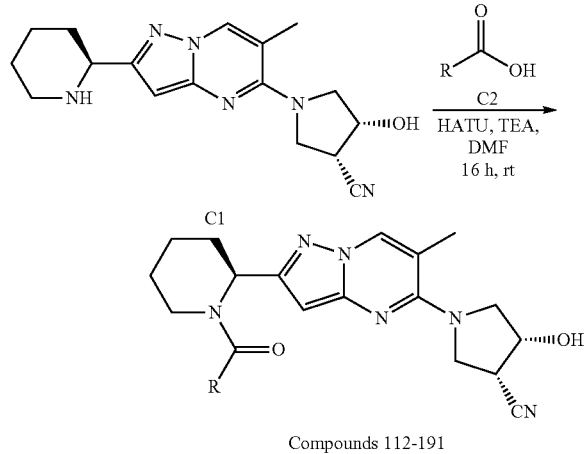

Compounds 112-191

In 50 mL, singled necked, round bottomed flask was placed tert-butyl (3S,4R)-4-hydroxy-1-(6-methyl-2-((S)-piperidin-2-yl)pyrazolo[1,5-a]pyrimidin-5-yl)pyrrolidine-3-carbonitrile (C1) (1932 mg, 5.90 mmol) and TEA (1.64 mL, 11.8 mmol) in DMF (13 mL). The carboxylic acids C2 0.040 mmol) were placed in separate 2-ml vials. Then, into each vial was dispensed a solution of C1 (0.037 mmol) followed by the addition of HATU (15.2 mg, 0.04 mmol). The resulting reaction mixtures were placed on an orbital shaker at room temperature for 16 h. Then, to each reaction mixture was added EtOAc (4 mL), washed with sat. NaHCO$_3$ (2 mL×2), and concentrated in Genevac. Then, it was loaded onto the CUSIL column, washed with EtOAc:Hexane (1:1, 4 mL), eluted with MeOH:EtOAc (5:95, 3 mL), and concentrated in Genevac to give the final compound (i.e. compounds 112-191).

| Compound formula | Compound | calculated MW | observed MW |
|---|---|---|---|
| 112 | | 523.44 | 523.4 |
| 113 | | 460.538 | 461.5 |
| 114 | | 518.927 | 519.4 |

-continued

| Compound formula | Compound | calculated MW | observed MW |
|---|---|---|---|
| 115 | | 465.945 | 466.4 |
| 116 | | 482.947 | 483.4 |
| 117 | | 473.512 | 474.5 |
| 118 | | 480.519 | 481.5 |
| 119 | | 516.646 | 517.6 |

-continued

| Compound formula | Compound | calculated MW | observed MW |
|---|---|---|---|
| 120 | | 512.536 | 513.5 |
| 121 | | 512.536 | 513.5 |
| 122 | | 532.498 | 533.5 |
| 123 | | 470.537 | 471.5 |
| 124 | | 480.519 | 481.5 |

| Compound formula | Compound | calculated MW | observed MW |
|---|---|---|---|
| 125 | | 507.598 | 508.5 |
| 126 | | 478.528 | 479.5 |
| 127 | | 482.548 | 483.5 |
| 128 | | 507.598 | 508.5 |
| 129 | | 512.574 | 513.5 |

-continued

| Compound formula | Compound | calculated MW | observed MW |
|---|---|---|---|
| 130 | | 506.538 | 507.5 |
| 131 | | 478.984 | 479.5 |
| 132 | | 500.603 | 501.5 |
| 133 | | 499.55 | 500.5 |
| 134 | | 511.63 | 512.5 |

-continued

| Compound formula | Compound | calculated MW | observed MW |
|---|---|---|---|
| 135 | | 470.537 | 471.5 |
| 136 | | 504.982 | 505.4 |
| 137 | | 535.555 | 536.5 |
| 138 | | 522.628 | 523.5 |
| 139 | | 485.592 | 486.5 |

-continued

| Compound formula | Compound | calculated MW | observed MW |
|---|---|---|---|
| 140 | | 474.521 | 475.5 |
| 141 | | 528.592 | 528.5 |
| 142 | | 523.037 | 523.5 |
| 143 | | 484.564 | 485.5 |
| 144 | | 514.63 | 515.6 |

-continued

| Compound formula | Compound | calculated MW | observed MW |
|---|---|---|---|
| 145 | | 540.618 | 541.5 |
| 146 | | 464.957 | 465.4 |
| 147 | | 461.526 | 462.4 |
| 148 | | 499.497 | 500.5 |
| 149 | | 480.519 | 481.5 |
| 150 | | 466.492 | 467.5 |

| Compound formula | Compound | calculated MW | observed MW |
|---|---|---|---|
| 151 | | 469.549 | 470.5 |
| 152 | | 500.39 | 500.5 |
| 153 | | 480.519 | 481.5 |
| 154 | | 510.401 | 510.4 |
| 155 | | 462.529 | 463.5 |

-continued

| Compound formula | Compound | calculated MW | observed MW |
|---|---|---|---|
| 156 | | 462.529 | 463.5 |
| 157 | | 466.492 | 467.2 |
| 158 | | 507.598 | 508.5 |
| 159 | | 445.527 | 446.2 |
| 160 | | 449.49 | 450.2 |
| 161 | | 557.396 | 558.1 |

-continued

| Compound formula | Compound | calculated MW | observed MW |
|---|---|---|---|
| 162 | | 484.604 | 485.3 |
| 163 | | 481.56 | 482.2 |
| 164 | | 456.51 | 457.2 |
| 165 | | 474.565 | 475.2 |
| 166 | | 460.538 | 462.2 |

-continued

| Compound formula | Compound | calculated MW | observed MW |
|---|---|---|---|
| 167 | | 488.592 | 489.5 |
| 168 | | 499.497 | 500.5 |
| 169 | | 458.566 | 459.5 |
| 170 | | 478.984 | 479.5 |
| 171 | | 523.44 | 523.4 |

-continued

| Compound formula | Compound | calculated MW | observed MW |
|---|---|---|---|
| 172 | | 462.529 | 463.5 |
| 173 | | 474.565 | 475.5 |
| 174 | | 510.598 | 511.5 |
| 175 | | 470.537 | 471.5 |
| 176 | | 445.527 | 446.5 |

-continued
| Compound formula | Compound | calculated MW | observed MW |
|---|---|---|---|
| 177 | 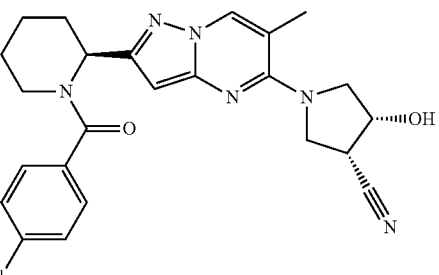 [SMILES: Cc1ccc(C(=O)N2CCCC[C@H]2c2cc3nc(N4C[C@@H](C#N)[C@@H](O)C4)c(C)cn3n2)c(Cl)c1] | 499.402 | 499.4 |
| 178 | 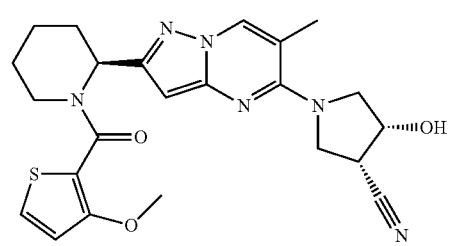 [SMILES: COc1ccsc1C(=O)N1CCCC[C@H]1c1cc2nc(N3C[C@@H](C#N)[C@@H](O)C3)c(C)cn2n1] | 466.564 | 467.5 |
| 179 | 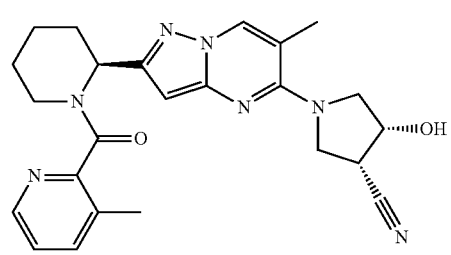 [SMILES: Cc1cccnc1C(=O)N1CCCC[C@H]1c1cc2nc(N3C[C@@H](C#N)[C@@H](O)C3)c(C)cn2n1] | 445.527 | 446.5 |
| 180 | 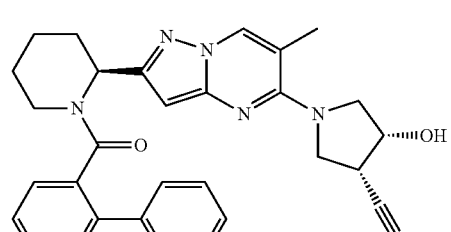 | 506.61 | 507.5 |
| 181 | 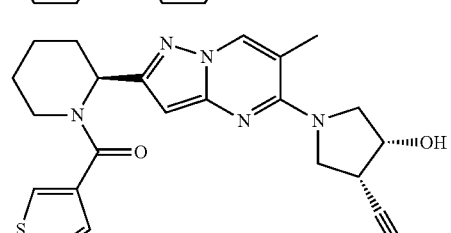 | 436.538 | 437.4 |
| 182 | 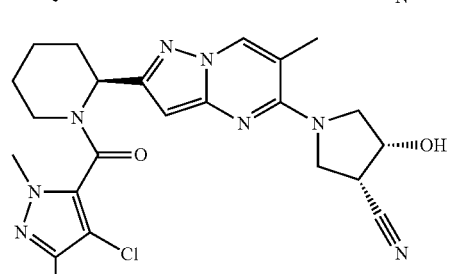 | 482.976 | 483.5 |

-continued

| Compound formula | Compound | calculated MW | observed MW |
|---|---|---|---|
| 183 | | 490.63 | 491.5 |
| 184 | | 498.509 | 499.5 |
| 185 | | 483.576 | 484.5 |
| 186 | | 482.947 | 483.4 |
| 187 | | 484.564 | 485.5 |

-continued

| Compound formula | Compound | calculated MW | observed MW |
|---|---|---|---|
| 188 | | 494.983 | 495.5 |
| 189 | | 502.501 | 503.5 |
| 190 | | 497.003 | 497.5 |
| 191 | | 513.606 | 514.5 |

Example 4

Procedure for the Preparation of Intermediate A1

Intermediate 1

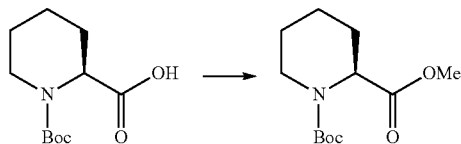 [SMILES: CC(C)(C)OC(=O)N1CCCC[C@H]1C(=O)O ; COC(=O)[C@@H]1CCCCN1C(=O)OC(C)(C)C]

N-Boc-(S)-piperidine-2-carboxylic acid (5.0 g, 22 mmol) in DMF (100 mL) was treated with $Cs_2CO_3$ (3.5 g, 10.9 mmol) and MeI (1.5 mL, 24 mmol). The mixture was stirred for 4 hours and diluted with MTBE (250 mL) The mixture was washed with water (2×100 mL) and saturated sodium chloride solution (1×100 mL) The solution was dried over anhydrous sodium sulfate and concentrated to afford the ester intermediate 1 which was used without further purification.

$^1$H NMR ($CDCl_3$, 300 MHz): δ 4.80 (m, 1H), 3.97 (m, 1H), 3.73 (s, 3H), 2.93 (m, 1H), 2.18 (app d, J=13.2 Hz, 1H), 1.67 (m, 2H), 1.45 (br s, 10H), 1.20 (app t, J=13.5 Hz, 1H).

$R_f$=0.90 (30% EtOAc-hexanes).

Intermediate 2

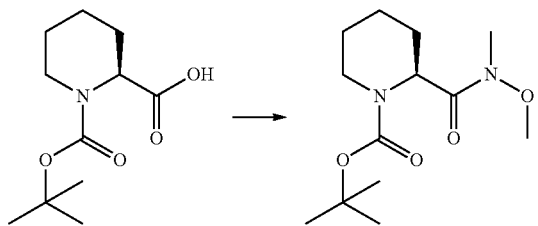 [SMILES: CC(C)(C)OC(=O)N1CCCC[C@H]1C(=O)O ; CON(C)C(=O)[C@@H]1CCCCN1C(=O)OC(C)(C)C]

(S)-1-Boc-piperidine-2-carboxylic acid (25 g, 109 mmol, Sigma-Aldrich) in DMF (500 mL) was treated sequentially with MeNHOMe.HCl (11.2 g, 115 mmol), N-methylmorpholine (36 mL, 327 mmol), HOBt (16.2 g, 120 mmol), and EDCI (23 g, 120 mmol) and stirred for 18 h. The solution was diluted with EtOAc (1000 mL) and washed with $H_2O$ (2×500 mL) and saturated NaCl solution (500 mL). The solution was dried over $MgSO_4$, filtered and concentrated. The residue was subjected to a 330 g $SiO_2$ Combiflash High Performance Gold column (0-100% EtOAc-hexanes gradient) to afford the Weinreb amide intermediate 2:

$^1$H NMR ($CDCl_3$, 300 MHz): δ 5.06 (br m, 1H), 3.93 (br m, 1H), 3.77 (br s, 3H), 3.18 (s, 3H), 2.01 (app d, J=13.5 Hz, 1H), 1.71 (m, 4H), 1.45 (s, 9H).

LCMS (ESI) m/z 273 [M+H]$^+$, $t_R$=2.31 min.

HPLC (RP: 6-98% MeCN—$H_2O$ gradient, 0.05% TFA modifier) $t_R$=4.423 min.

$R_f$=0.60 (50% EtOAc-hexanes).

Intermediate 3

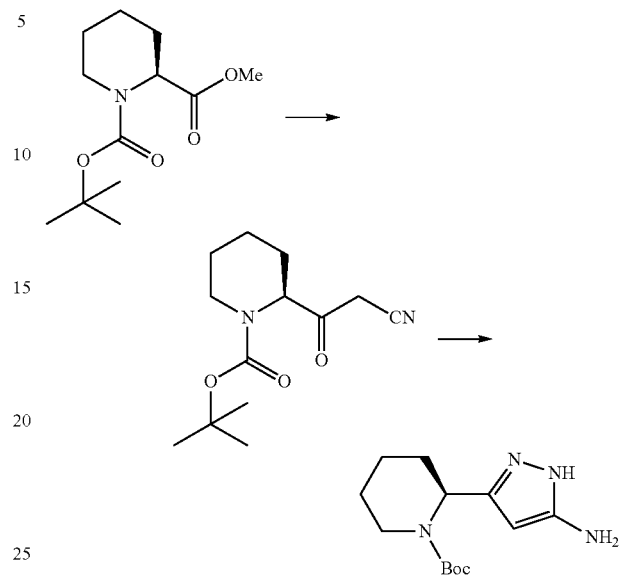

To a solution of acetonitrile (5 ml, 93.8 mmol) in dry THF (50 ml) at −78° C. was added dropwise NaN(TMS)$_2$ (34 ml, 68 mmol, 2M in hexanes). The solution was warmed up to −40° C. and stirred for 20 min. The solution was then cooled down to −78° C. and a solution of the ester (Intermediate 1) (7.6 g, 31.1 mmol) in THF (20 ml) was added dropwise. The solution was warmed up to −40° C. and stirred for 2 h. The solution was then cooled down to −78° C. and a solution of acetic acid (4.8 ml, 80 mmol) in THF (20 ml) added dropwise. The solution was then warmed to RT and volatiles were removed under reduced pressure at 40° C. The resulting residue was dissolved in EtOAc (300 mL) and the organic phase was washed with brine twice. Volatiles were removed under reduced pressure at 40° C.

$^1$H NMR (DMSO, 300 MHz) δ 4.63 (br s, 1H), 4.18-4.13 (m, 1H), 3.82-3.78 (m, 1H), 3.65 (s, 2H), 2.85-2.63 (m, 1H), 1.65-1.52 (m, 9H), 1.38 (s, 9H).

LCMS m/z: 153 [M-Boc group+H], $t_R$=2.50 min.

The residue was dissolved in EtOH (150 ml) and hydrazine acetate (4.5 g, 47 mmol) was added. The solution was stirred for 16 h at RT. Volatiles were removed under reduced pressure at 40° C., EtOAc added (200 ml) and the organic phase washed with aqueous dilute $NaHCO_3$, then $H_2O$ followed by brine. Volatiles were removed under reduced pressure at 40° C., the resulting residue was purified by silica gel column (DCM/MeOH, gradient from 0% to 20%) to afford the product intermediate.

LCMS m/z [M+H]$^+$ $C_{13}H_{22}N_4O_2$ requires: 266.34. Found 266.84.

HPLC (min, purity) $t_R$=2.13, 100%.

$^1$H NMR (DMSO, 300 MHz) 11.20 (br s, 1H), 5.09 (m, 1H), 5.07 (s, 1H), 4.67 (br s, 2H), 3.81 (app d, J=12.0 Hz, 1H), 2.72 (app br t, J=12.0 Hz, 1H), 2.08 (app d, J=12.9 Hz, 1H), 1.57 (m, 4H), 1.39 (s, 9H); MS (ESI) m/z 267 [M+H]$^+$, $t_R$=1.97 min. (3.5 min method). HPLC (Chiral: Chiralpak AD-H, isocratic n-heptane-isopropanol 70:30). $t_R$ (desired)=22.42 min, $t_R$ (enantiomer of desired isomer)=25.67 min; % ee=93.

Intermediate 3 Via Weinreb Amide

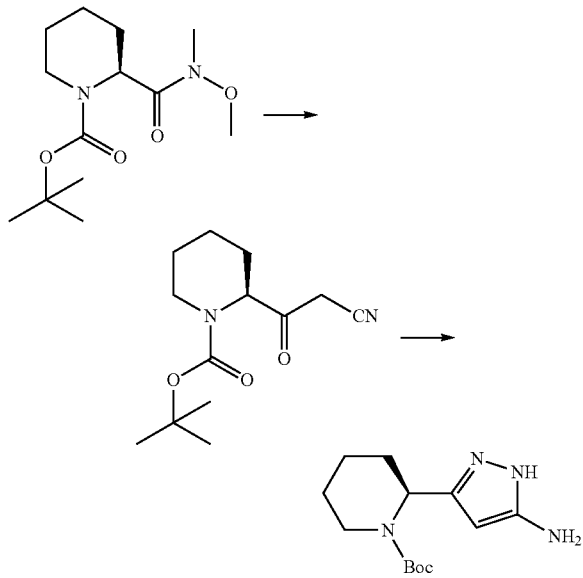

MeCN (3.20 mL, 60.7 mmol) in THF (50 mL) was cooled to −78° C. under Ar. NaHMDS solution (1.0M in THF, 36.8 mL, 36.8 mmol) was added dropwise over 5 min, during which time an off-white suspension had formed. The suspension was warmed to −20° C. and stirred for 20 min. The suspension was cooled to −78° C. and transferred via cannula to the Weinreb amide intermediate 2 (5.02 g, 18.4 mmol) in THF (50 mL) at −78° C. over 5 min. The suspension is warmed to −45° C. and stirred for 3 h, during which time the suspension became a yellow solution. The solution was cooled to −78° C. and AcOH (4.2 mL in 10 mL THF, 73.6 mmol) was added dropwise. The solution was warmed to room temperature and diluted with EtOAc (100 mL). The solution was washed with $H_2O$ (50 mL) and saturated NaCl solution (50 mL) The solution was dried over $MgSO_4$ and concentrated to afford the cyano ketone which was used without further purification.

The crude α-cyano ketone was used in the next reaction with hydrazine acetate to synthesize desired amino pyrazole intermediate 3 as described above.

MS (ESI) m/z 267 [M+H]$^+$, $t_R$=1.81 min.
HPLC (RP: 6-98% MeCN—$H_2O$ gradient, 0.05% TFA modifier) $t_R$=3.212 min (>95% purity @ 254 nM).
HPLC (Chiral: Chiralpak AD-H 250 4.6 mm, 5 micron; isocratic n-heptane-isopropanol 70:30) $t_R$ (a isomer, desired)=22.35 min, $t_R$ (b isomer)=25.78 min; α=1.15; % ee=>90%.

Intermediate 4

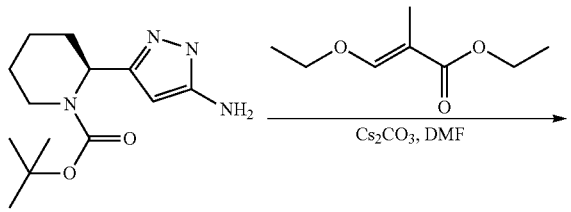

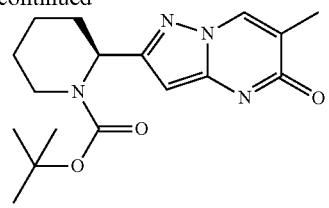

(E)-ethyl-3-Ethoxy-2-methylacrylate (Intermediate 32) (11.8 g, 67.6 mmol) and $Cs_2CO_3$ (22.0 g, 67.6 mmol) were added to a solution of intermediate 3 (12.0 g, 45.1 mmol) at room temperature and the reaction mixture was heated to 130° C. After 17 h, the reaction mixture was allowed to cool to room temperature and was concentrated under reduced pressure. The crude residue was diluted with ethyl acetate (250 mL) and was filtered. The resulting filtrate was concentrated under reduced pressure and the residue was purified via $SiO_2$ column chromatography (330 g $SiO_2$ Combiflash HP Gold Column, 0-100% ethyl acetate/hexanes) to afford intermediate 4.

$^1$H NMR ($CDCl_3$, 400 MHz): δ 12.01 (br s, 1H), 7.99 (s, 1H), 5.73 (s, 1H), 5.42 (br s, 1H), 4.01 (br d, J=12.2 Hz, 1H), 2.81 (br t, J=11.2 Hz, 1H), 2.29 (d, J=13.5 Hz, 1H), 2.07 (d, J=1.1 Hz, 3H), 1.87-1.69 (m, 1H), 1.68-1.41 (m, 4H), 1.48 (s, 9H).
$^{13}$C NMR ($CDCl_3$, 100 MHz): δ 162.87, 156.34, 155.43, 140.16, 135.00, 113.29, 86.50, 79.75, 28.41, 27.79, 25.27, 21.00, 19.88, 13.38.
LCMS (ESI) m/z 333.0 [M+H]$^+$, $t_R$=2.24 min.
HPLC $t_R$ (min), purity %: 3.969, 99%.
$R_f$=0.50 (EtOAc).
Chiral HPLC, 98% ee (Chiralpak IC 5 mM, 4.6 150 mm, 10-95% MeCN/$H_2O$, 0.05% trifluoroacetic acid modifier) (S)-isomer $t_R$=22.234 min, (R)-isomer $t_R$=20.875 min.

Intermediate 5

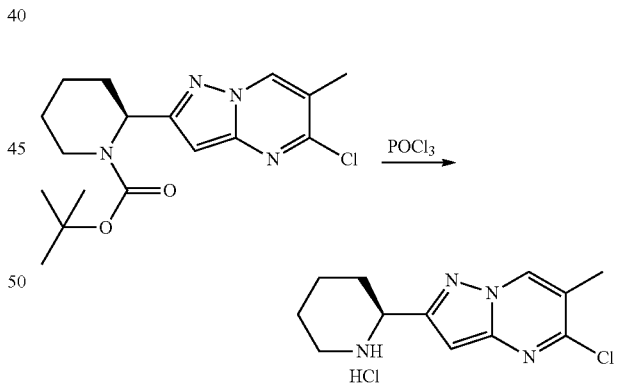

$POCl_3$ (5.60 mL, 59.8 mmol) was added to intermediate 4 (993.4 mg, 2.99 mmol) at room temperature and the reaction mixture was heated to 100° C. After 2 h, the reaction mixture was allowed to cool to room temperature and was concentrated under reduced pressure to afford intermediate 5 which was used directly in the following step.

$^1$H NMR (DMSO-$d_6$, 400 MHz): δ 9.40 (br d, J=7.6 Hz, 1H), 9.27-9.16 (m, 2H), 6.85 (s, 1H), 4.54 (t, J=112.4 Hz, 1H), 3.32 (d, J=12.8 Hz, 1H), 3.08 (q, J=8.81 Hz, 1H), 2.33 (s, 3H), 2.23-2.14 (m, 1H), 1.92-1.61 (m, 5H).
LCMS (ESI) m/z 251.1 [M+H]$^+$, $t_R$=0.21 min.
HPLC $t_R$=2.35 min.

217
Intermediate A1

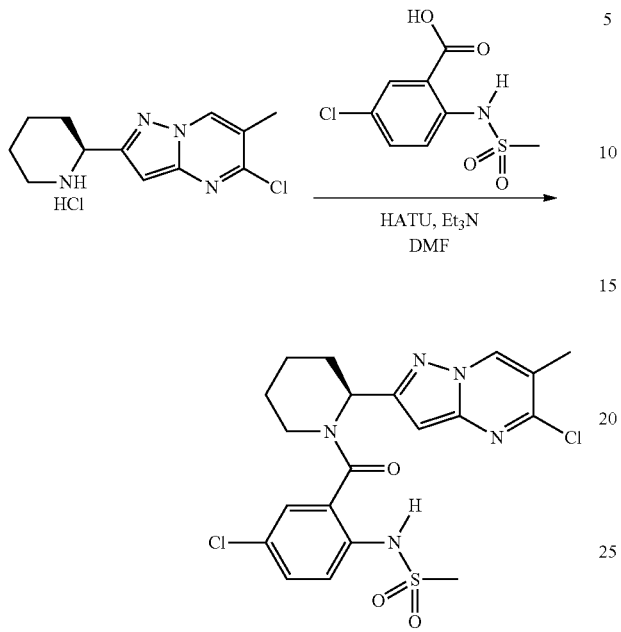

HATU (1.37 g, 3.59 mmol) was added to a solution of 5-chloro-2-(methylsulfonamido) benzoic acid (823 mg, 3.29 mmol) in DMF (15.0 mL), and the reaction mixture was stirred at room temperature. After 1 h, a solution of crude intermediate 5 (220 mg, 2.99 mmol) in DMF (1 mL) was added followed by the addition of triethylamine (2.00 mL, 14.3 mmol), and the reaction mixture was stirred at room temperature for 19 h. The reaction mixture was partitioned between ethyl acetate (250 mL) and saturated aqueous sodium bicarbonate solution (200 mL), and the layers were separated. The organic layer was washed with saturated aqueous sodium bicarbonate solution (200 mL) and saturated sodium chloride solution (200 mL), was dried over $Na_2SO_4$, and was concentrated under reduced pressure. The crude residue was purified via $SiO_2$ column chromatography (12 g $SiO_2$ Combiflash HP Gold Column, 0-100% ethyl acetate/hexanes) to afford intermediate A1 (736.2 mg, 51% (2-steps)) as a white solid.

$^1$H NMR (CDCl$_3$, 400 MHz): δ 10.05 (br s, 0.2H), 9.13 (br s, 1H), 8.95 (br s, 1H), 8.81 (br s, 0.2H), 7.70 (d, J=8.8 Hz, 1H), 7.56 (d, J=8.8 Hz, 0.2H), 7.40 (dd, J=8.8, 2.4 Hz, 1H), 7.33 (d, J=2.4 Hz, 1H), 7.31 (d, J=4.4 Hz, 0.2H), 6.45 (s, 1H), 6.40 (br s, 0.2H), 6.28 (br d, J=4.4 Hz, 1H), 5.01 (br s, 0.2H), 4.54 (br d, J=14.0 Hz, 0.2H), 3.35 (br d, J=13.2 Hz, 1H), 3.15-3.03 (m, 1H), 2.92 (s, 3H), 2.39 (s, 3H), 2.13-1.98 (m, 1H), 1.90-1.59 (m, 2H), 1.59-1.31 (m, 3H).

$^{13}$C NMR (CDCl$_3$, 100 MHz): δ 167.09, 156.12, 153.13, 147.86, 135.68, 131.79, 131.66, 131.38, 130.12, 125.91, 125.44, 117.08, 93.74, 47.65, 44.07, 39.81, 27.83, 25.47, 19.78, 16.90.

LCMS (ESI) m/z 482.1 [M+H]$^+$, $t_R$=2.79 min.

HPLC $t_R$ (min), purity %: 5.438, 99%.

$R_f$=0.47 (50% EtOAc/hexanes).

218

Chiral HPLC, 99% ee (Chiralpak IC 5 mM, 4.6 150 mm, 10-95% MeCN/H$_2$O, 0.05% trifluoroacetic acid modifier) (S)-isomer $t_R$=29.739 min, (R)-isomer $t_R$=29.495 min.

Example 5

Procedure for the Preparation of Intermediate B1

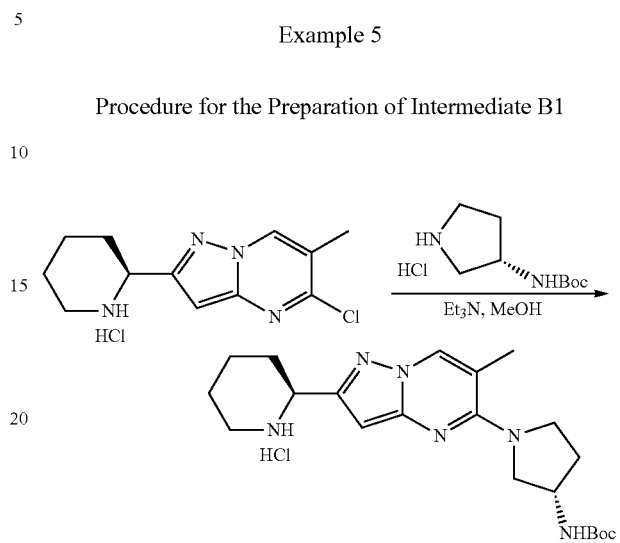

To a solution of intermediate 5 (100.0 mg, 0.35 mmol) in MeOH (1.74 mL) was added (S)-tert-butyl pyrrolidin-3-yl-carbamate (648 mg, 3.48 mmol) and triethylamine (970 μL, 6.96 mmol) at room temperature, and the reaction mixture was heated to 70° C. After 4 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford intermediate B1.

LCMS (ESI) m/z 401.23 [M+H]$^+$, $t_R$=1.86 min.

Example 6

Procedure for the Preparation of Intermediate C1

Intermediate 7

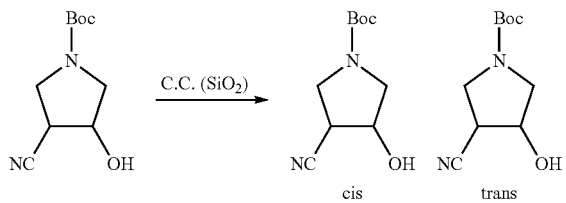 [SMILES: CC(C)(C)OC(=O)N1CC(O)C(C#N)C1 ; "C.C. (SiO2)" ; CC(C)(C)OC(=O)N1CC(O)C(C#N)C1 ; CC(C)(C)OC(=O)N1CC(O)C(C#N)C1]

A mixture of cis/trans tert-butyl 3-cyano-4-hydroxypyrrolidine-1-carboxylate was separated on a silica column (200-300) eluting with ethyl acetate:petroleum ether=1:10, ethyl acetate:petroleum ether=1:5 to give intermediate 7 (earlier eluting peak, 30 g, 46%) as white solid.

TLC (Eluent: ethyl acetate:petroleum ether=1:1): Starting material cis/trans mixture ($R_f$=0.4 and 0.45).

$^1$H NMR: (400 MHz DMSO) δ 4.60-4.48 (m, 1H), 3.8-3.65 (m, 1H), 3.51-3.63 (m, 1H), 3.5-3.3 (m, 2H), 2.9-3.1 (m, 1H), 2.70 (s, 1H), 1.3-1.45 (s, 9H).

Intermediate 8

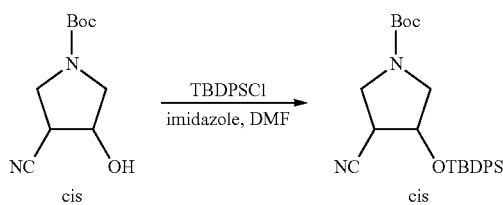

To mixture of intermediate 7 (10 g, 0.047 mol) and imidazole (6.4 g, 0.094 mol) in DMF (100 ml) was added TBDPSCl (14.2 g, 0.05 mol) dropwise and the mixture was stirred at room temperature overnight. 10% citric acid was added and extracted with ethyl acetate, dried and concentrated, purified by silica gel column chromatography (ethyl acetate:petroleum ether=1:50 to 1:25) to give intermediate 8.

TLC Information (Eluent: petroleum ether:ethyl acetate=1:1), starting material $R_f$=0.40, product $R_f$=0.90.

$^1$H NMR (400 MHz DMSO) δ 7.74-7.62 (m, 4H), 7.47-7.41 (m, 6H), 4.51 (m, 1H), 3.8-3.65 (m, 1H), 3.51-3.63 (m, 1H), 3.5-3.3 (m, 2H), 2.9-3.1 (m, 1H), 1.3-1.45 (s, 9H).

Intermediates 9a and 9b

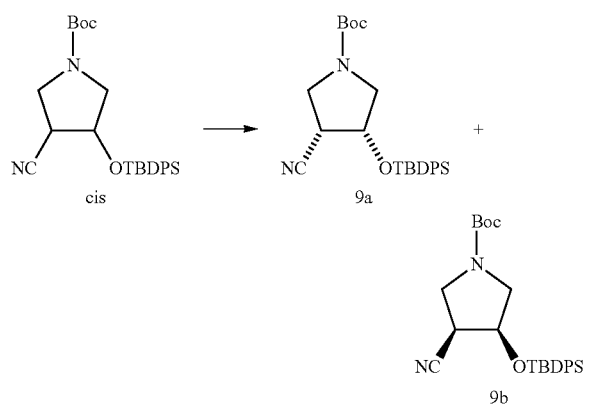

Intermediate 8 was separated by chiral SFC (see below) to give intermediate 9a (earlier eluting) and intermediate 9b (later eluting).

Column: ChiralPak IC-H, 250 50 mmI.D, mobile Phase: CO$_2$/iPrOH (35% isocratic), retention time (9a) 1.94 min, retention time (9b): 2.73 min.

Intermediate 10a

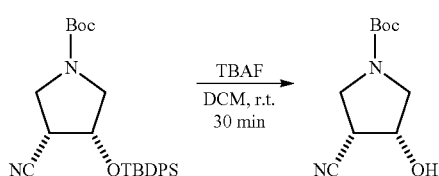

A solution of intermediate 9a (16.3 g, 0.036 mol) in CH$_2$Cl$_2$ (200 mL) at r.t was added TBAF (8.0 g, 0.025 mol).

The reaction mixture was stirred at r.t for 30 min, then diluted with CH$_2$Cl$_2$ (500 mL), and washed with saturated aq. NH4Cl and brine, dried over MgSO$_4$, filtered, and concentrated. The crude product was purified by silica gel chromatography (petroleum ether:ethyl acetate=10:1 to 2:1) to afford intermediate 10a.

TLC Information (10a) (Eluent: petroleum ether:ethyl acetate=1:1).

1. Starting material ($R_f$=0.90).
2. Reaction Mixture (Product: $R_f$=0.4).

$^1$H NMR (10a): 400 MHz DMSO 14.60-4.58 (m, 1H), 3.87-3.79 (m, 1H), 3.69-3.64 (m, 1H), 3.56-3.49 (m, 2H), 2.9-3.1 (m, 1H), 1.4-1.5 (s, 9H).

Intermediate C1

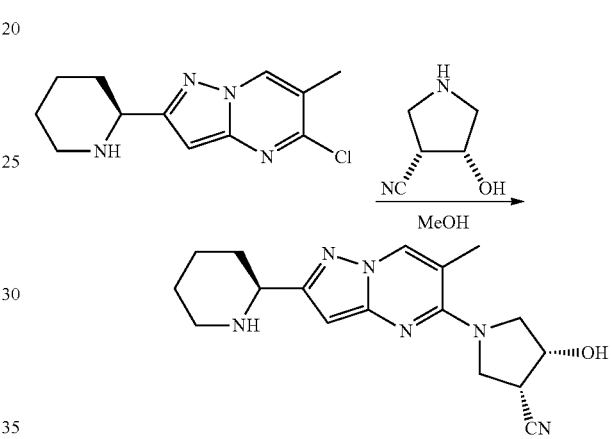

A solution of intermediate 17 (Example 18: prepared from 1 g BOC intermediate 10a) was dissolved in MeOH (10 ml), to the solution was added intermediate 5 (944 mg, 3.76 mmol) and NEt$_3$ (2 ml). The reaction mixture was heated at 70° overnight. The solvent was evaporated and the residue was purified with purified by combi-flash column chromatography (0-100% MeOH/DCM) to afford intermediate C1.

LCMS (m/z) 327.40[M+H]$^+$

MW 326.19.

Example 7

Preparation of Phosphate (—P(O)OH$_2$) Compound 192

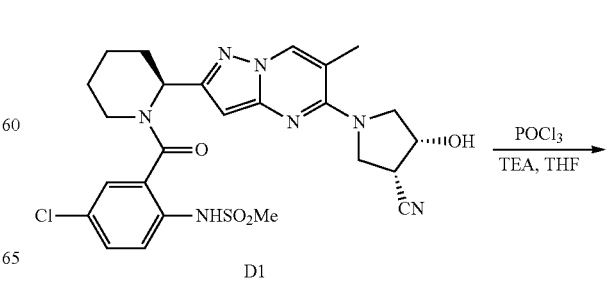

D1

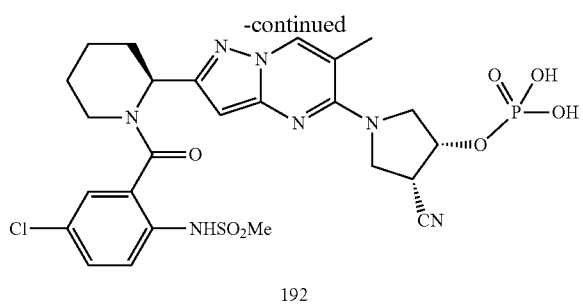

192

Compound 192 can be prepared from intermediate D1 (preparation described directly below) by treating a solution of D1 in THF at about 0° C. with POCl₃ and triethylamine. The reaction mixture can be stirred at about 0° C. for a period of time and quenched with triethylammonium bicarbonate buffer (1M). The mixture can then be concentrated and purified by HPLC to give the desired product.

Compound 192 can also be prepared by the following protocol.

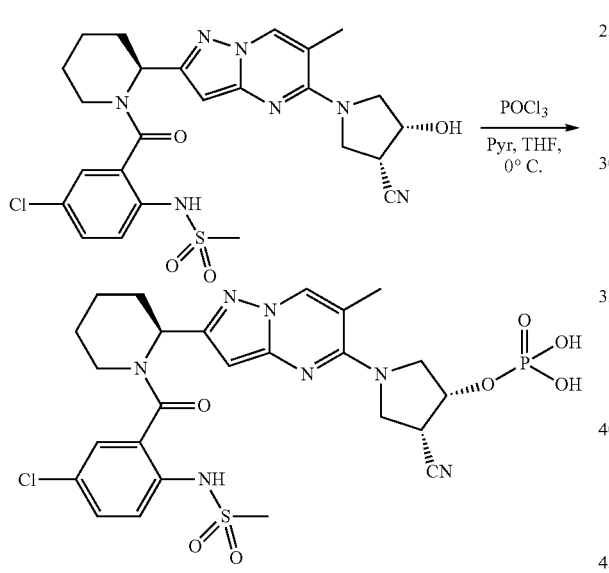

Intermediate D1 (100 mg, 0.18 mmol) was dissolved in THF (2 ml), and the reaction mixture was cooled to 0° C. using an ice bath. To the above solution was added POCl₃ (110 mg, 0.72 mmol) followed by pyridine (71 mg, 0.9 mmol). The reaction mixture was stirred at 0° C. for 30 mins before it was quenched with saturated NaHCO₃. Washed the aqueous layer with DCM twice (20 mL), the aqueous layer was lyopholized and the residue was then purified by prep HPLC (Gemini C18, 100 30 mm, 5 micron column) using a gradient of water/acetonitrile 0-100 to afford the title compound 192.

LCMS (m/z) 638.12 [M+H], Tr=2.87 min.
CALC. MW 638.03.

Accordingly one embodiment includes compound 192 and salts thereof, as well as methods and intermediates that are useful for the preparation of compound 192 and intermediate D1.

In a similar manner the corresponding phosphate prodrugs (—P(O)OH₂) of the compounds of formulas I, Ia, II, IIa, III, IIIa, IV and IVa can also be prepared. Accordingly, one embodiment includes the phosphate compounds (—P(O)OH₂) of the compounds of formulas I, Ia, II, IIa, III, IIIa, IV and IVa and salts thereof.

Preparation of Intermediate D1

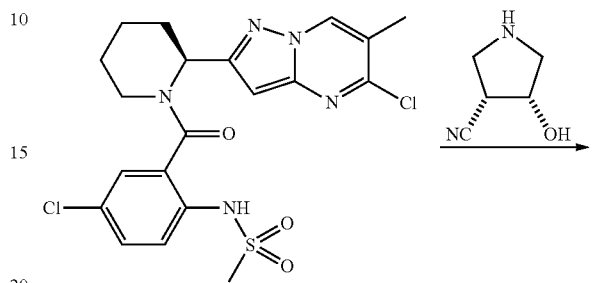

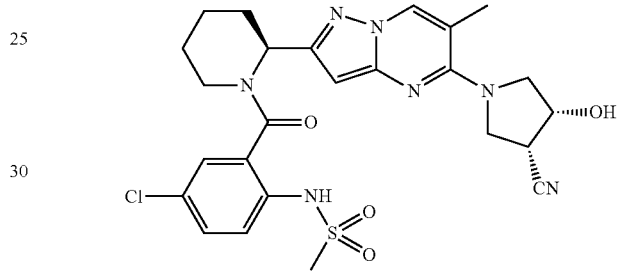

The starting chloride intermediate A1 (0.92 g, 1.9 mmol) was dissolved in iPrOH (10 mL) and treated with triethylamine (0.45 mL, 0.33 g) and the intermediate 17 (0.45 g) and then heated to a gentle reflux under nitrogen. After heating overnight the solution was cooled and diluted with ethyl acetate and brine. The organic layer was separated and concentrated under reduced pressure. The crude product was purified by silica gel chromatography (50-100% ethyl acetate in hexanes) to afford the product as a white solid (1.15 g). LCMS (ESI) m/z 558.2 [M+H]⁺, t_R=2.17 min.

Using similar procedures the corresponding compounds 193, 194 and 195 can also be prepared. Accordingly, one embodiment includes compounds 193, 194 and 195 and salts thereof.

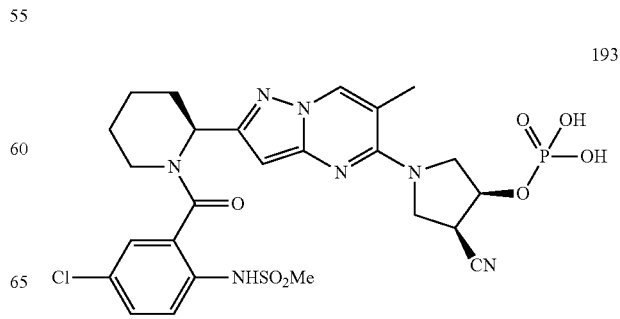

193

194

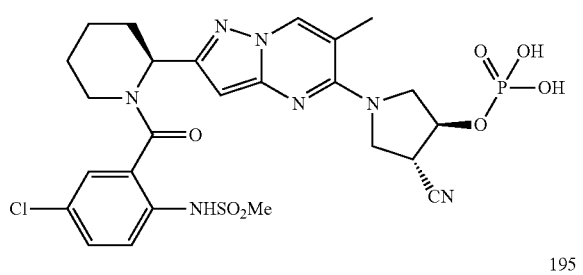

195

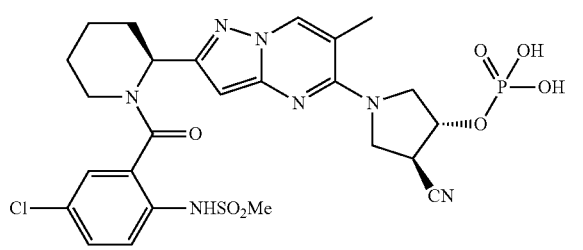

Example 8

Preparation of Compound 196

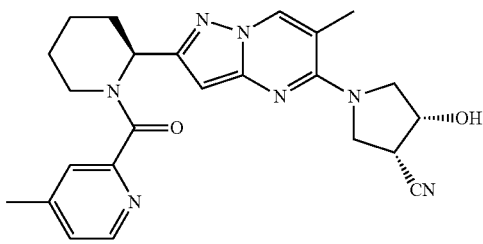 [SMILES: Cc1ccnc(C(=O)N2CCCC[C@H]2c2cc3nc(N4C[C@@H](C#N)[C@@H](O)C4)c(C)cn3n2)c1]

Compound 196 was prepared according to the general procedure cited below LCMS (m/z)
446.04 [M+H]+
MW 445.22
General Procedure

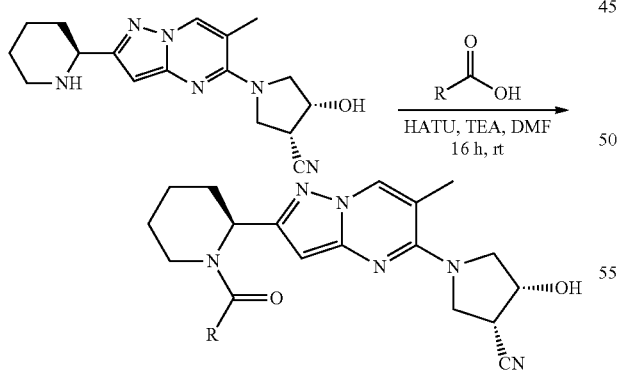

In 50 mL, singled necked, round bottomed flask was placed intermediate C1 (1932 mg, 5.90 mmol) and TEA (1.64 mL, 11.8 mmol) in DMF (13 mL) The carboxylic acid (0.040 mmol) was placed in a separate 2-ml vial. Then, into the vial was dispensed a solution of intermediate C1 (0.037 mmol) followed by the addition of HATU (15.2 mg, 0.04 mmol). The resulting reaction mixture was placed on an orbital shaker at room temperature for 16 h. Then, to the reaction mixture was added EtOAc (4 mL), washed with sat. NaHCO$_3$ (2 mL×2), and concentrated in Genevac. The crude residue was loaded onto the CUSIL column, washed with EtOAc:Hexane (1:1, 4 mL), eluted with MeOH:EtOAc (5:95, 3 mL), and concentrated in Genevac to give the final compound 196.

Example 9

Preparation of Intermediate 11

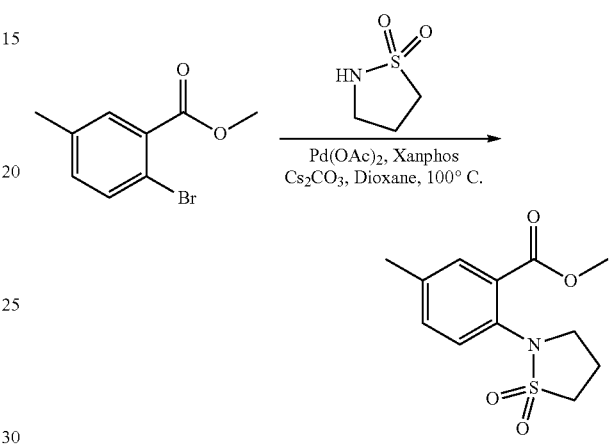

To an oven dried 50 mL round-bottom flask, methyl 2-bromo-5-methylbenzoate (352 mg, 1.54 mmol), sultam (236 mg, 1.95 mmol), cesium carbonate (732 mg, 2.25 mmol), palladium acetate (40.4 mg, 0.18 mmol), and Xanphos (136 mg, 0.235 mmol) were added and flask was placed under argon. Reagents were suspended in 8 mL of anhydrous dioxane and mixture was heated at 100° C. overnight. After cooling to room temperature, reaction mixture was filtered, washing with ethyl acetate. Combined filtrate was concentrated under reduced pressure and resulting film was purified by silica gel column chromatography (25-100% Ethyl Acetate in Hexanes) to yield intermediate 11.

$^1$H-NMR (DMSO, 400 MHz): δ 7.75 (d, 1H), 7.44 (m, 1H), 7.35 (m, 1H), 3.89 (s, 3H), 3.81 (t, 2H), 3.28 (t, 2H), 2.55 (m, 2H), 2.39 (s, 3H).

LCMS m/z [M+H]+ $C_{12}H_{15}NO_4S$ requires: 270.07. Found 270.12.

Example 10

Preparation of Intermediate 12

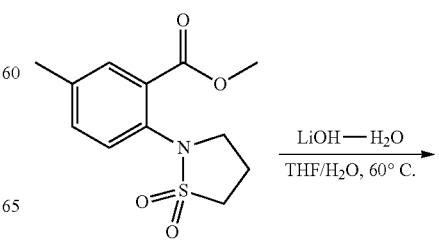

-continued

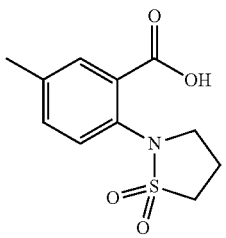

Lithium hydroxide monohydrate (496 mg, 11.8 mmol) was added to a solution of intermediate 11 (316 mg, 1.17 mmol) in 22 mL of THF and 12 mL of water at room temperature. Reaction mixture was heated at 60° C. for two hours. After cooling to room temperature, reaction mixture was acidified with 40 mL of 1N $HCl_{(aq)}$ and extracted with ethyl acetate (3×30 mL). The combined organic layers were washed 50 mL of Brine, separated, dried ($MgSO_4$), filtered, and concentrated under reduced pressure to yield intermediate 12.

$^1$H-NMR (DMSO, 400 MHz): δ 12.9 (s, 1H), 7.57 (d, J=1.6 Hz, 1H), 7.41-7.34 (m, 2H), 3.66 (t, J=6.8 Hz, 2H), 3.28 (m, 2H), 2.37 (m, 2H), 2.33 (s, 3H).

LCMS m/z [M+H]$^-$ $C_{11}H_{13}NO_4S$ requires: 254.06. Found 254.18.

Example 11

Preparation of Compound 197

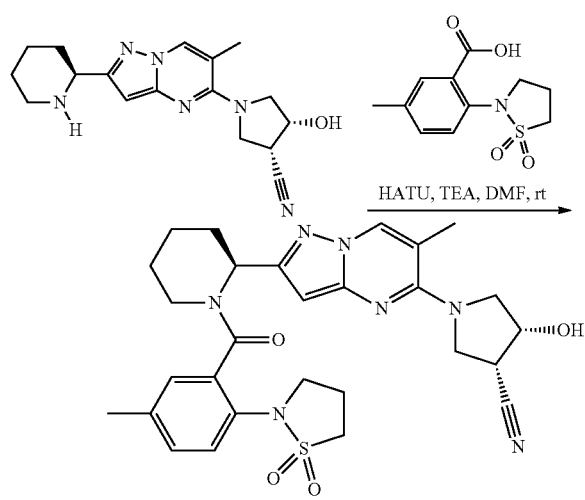

HATU (70 mg, 0.185 mmol) was added to a solution of intermediate 12 (40 mg, 0.16 mmol) in 3 mL of anhydrous DMF at room temperature. After 60 minutes of stirring, intermediate C1 (40 mg, 0.123 mmol) was added followed immediately by triethylamine (0.030 mL, 0.213 mmol). Reaction mixture stirred at room temperature overnight under argon. Mixture was then poured into 30 mL of $H_2O$ and extracted three times with 30 mL of ethyl acetate. The combined organic layers were washed with 50 mL brine, dried ($MgSO_4$), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 197 as a trifluoroacetic acid salt, after lyophilization.

LCMS m/z [M+H]$^+$ $C_{28}H_{33}N_7O_4S$ requires: 564.23. Found 564.13.

HPLC Tr (min), purity %: 5.33, 99%

Example 12

Preparation of Intermediate 13

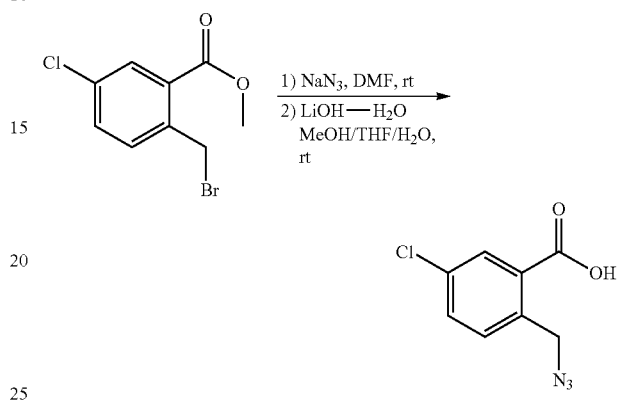

Step 1: Sodium azide (158 mg, 2.43 mmol) was added to a solution of methyl 2-(bromomethyl)-5-chlorobenzoate (518 mg, 1.97 mmol) in 3 mL of DMF at room temperature. After stirring overnight, reaction mixture was quenched with 25 mL of water. Aqueous was extracted with ethyl acetate (3×30 mL) and combined organics were washed with water (2×40 mL) and 50 mL of brine. Organics were dried ($Na_2SO_4$), filtered, and concentrated under reduced pressure to yield methyl 2-(azidomethyl)-5-chlorobenzoate which was used in the next step without further purification.

Step 2: Lithium hydroxide monohydrate (794 mg, 18.9 mmol) was added to a solution of methyl 2-(azidomethyl)-5-chlorobenzoate (426 mg, 1.88 mmol), from the previous step, in 27 mL of 1:1:1 THF:methanol:water at room temperature. After stirring overnight, reaction mixture was quenched with 20 mL of 2N $HCl_{(aq)}$, and extracted with ethyl acetate (3×30 mL) Combined organics were washed with brine, dried ($MgSO_4$), filtered, and concentrated under reduced pressure to yield intermediate 13.

$^1$H-NMR (DMSO, 400 MHz): 7.88 (m, 1H), 7.70-7.65 (m, 1H), 7.54 (m, 1H), 4.78 (s, 2H).

Example 13

Preparation of Compound 198

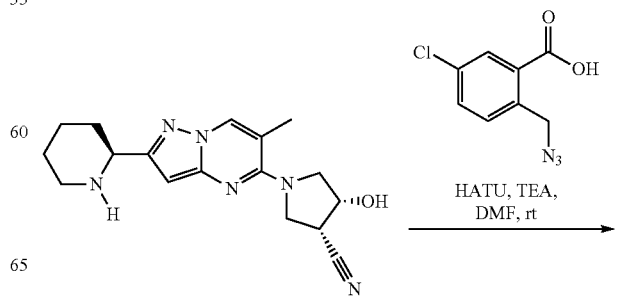

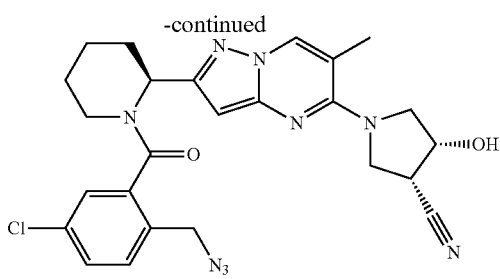

Following the procedure for the synthesis of compound 197, beginning with intermediate 13 (36.2 mg, 0.171 mmol) and intermediate C1 (40 mg, 0.123 mmol), compound 198 was synthesized as a trifluoroacetic acid salt after lyophilization.

LCMS m/z [M+H]⁺ $C_{25}H_{26}ClN_9O_2$ requires: 520.19. Found 520.03.

HPLC Tr (min), purity %: 6.34, 97%.

Example 14

Preparation of Intermediate 14

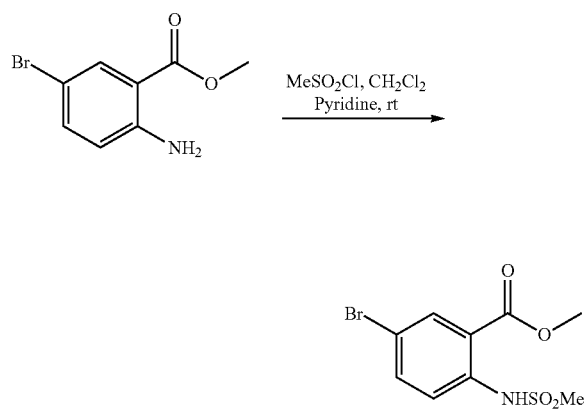

To a solution of methyl 2-amino-5-bromobenzoate (7.38 g, 32.0 mmol) and pyridine (6.3 mL, 81.5 mmol) in 100 mL of anhydrous $CH_2Cl_2$, was added slowly methane sulfonylchloride (6.5 mL, 79.9 mmol). After stirring overnight, reaction mixture was quenched with 100 mL of 1N $HCl_{(aq)}$. Aqueous mixture was extracted with ethyl acetate (3×120 mL) and combined organic layers were washed 200 mL brine. Organics were dried ($MgSO_4$), filtered, and concentrated under reduced pressure to yield intermediate 14. Silica gel column chromatography (0-30% Ethyl Acetate in Hexanes), yielded intermediate 14.

¹H-NMR (CDCl₃, 300 MHz): δ 10.4 (s, 1H), 8.22 (s, 1H), 7.63 (s, 2H), 3.96 (s, 3H), 3.05 (s, 3H)

LCMS m/z [M+H]⁺ $C_9H_{10}BrNO_4S$ requires: 307.95. Found 308.06.

Example 15

Preparation of Intermediate 15

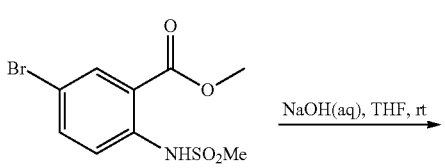

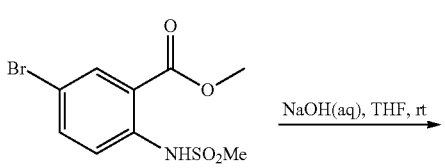

A 2.65M solution of NaOH in water (2.65 mL, 7.02 mmol) was added to a solution of intermediate 14 in 9 mL of THF with strong stirring. The reaction mixture was stirred at room temperature over night. The mixture was then acidified with 10 mL of 1N HCl and extracted with ethyl acetate (3×20 mL). The combined organic layers were washed 30 mL of brine, separated, dried ($MgSO_4$), filtered, and concentrated under reduced pressure to yield intermediate 15.

¹H-NMR (DMSO, 300 MHz): δ 10.6 (s, 1H), 8.05 (s, 1H), 7.79 (d, 1H), 7.55 (d, 1H), 3.18 (s, 3H).

LCMS m/z [M+H]⁻ $C_8H_8BrNO_4S$ requires: 291.94. Found 291.90.

Example 16

Preparation of Compound 199

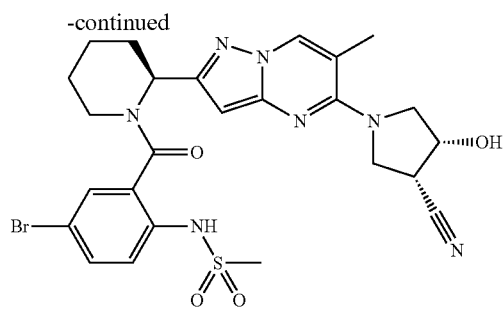

Following the procedure for the synthesis of compound 197, beginning with intermediate 15 (47 mg, 0.160 mmol) and intermediate C1 (40 mg, 0.123 mmol), compound 199 was synthesized as a trifluoroacetic acid salt, after lyophilization.

LCMS m/z [M+H]$^+$ C$_{25}$H$_{28}$BrN$_7$O$_4$S requires: 602.11. Found 602.78

HPLC Tr (min), purity %: 6.52, 80%

Example 17

Preparation of Intermediate 16

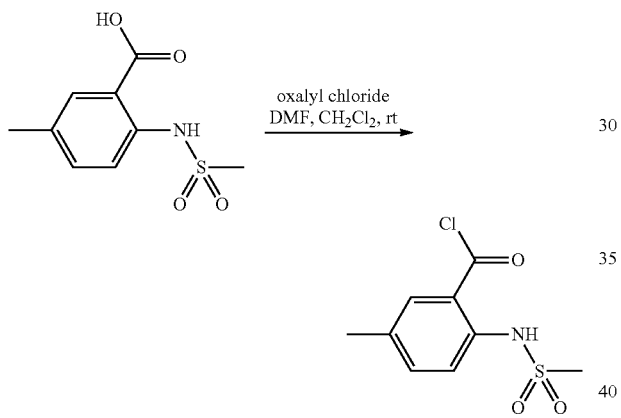

DMF (0.070 mL, 0.908 mmol) was added slowly to a suspension of 5-methyl-2-(methylsulfonamido)benzoic acid (1.01 g, 4.59 mmol) and oxalyl chloride (1.6 mL, 18.3 mmol) in 11 mL of anhydrous dichloromethane. After 3 hours, reaction mixture was concentrated and dried in-vacuo to yield intermediate 16 which was used in the next step without further purification.

$^1$H-NMR (CDCl$_3$, 400 MHz): δ 10.2 (s, 1H), 7.92 (s, 1H), 7.64 (m, 1H), 7.39 (m, 1H), 3.03 (s, 3H), 2.35 (s, 3H).

Example 18

Preparation of Intermediate 17

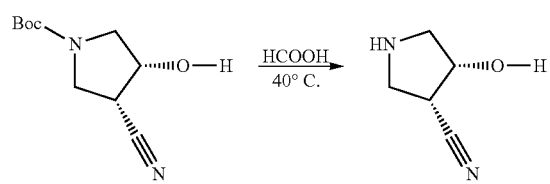 [SMILES: CC(C)(C)OC(=O)N1C[C@@H](C#N)[C@@H](O)C1 ; "HCOOH" ; N#C[C@@H]1CNC[C@@H]1O]

The BOC pyrollidine intermediate 10a (1 g, 4.7 mmol) was added to HCOOH (5 ml) and was heated at 40° C. for 2 h. The solvent was evaporated under reduced pressure and preheated IPA (100° C.) was added to dissolve the residue, white precipitate formed after the IPA solution cooled down. The product was filtered and washed with IPA to give intermediate 17 that was used without further purification in subsequent reactions.

Example 19

Preparation of Intermediate 18

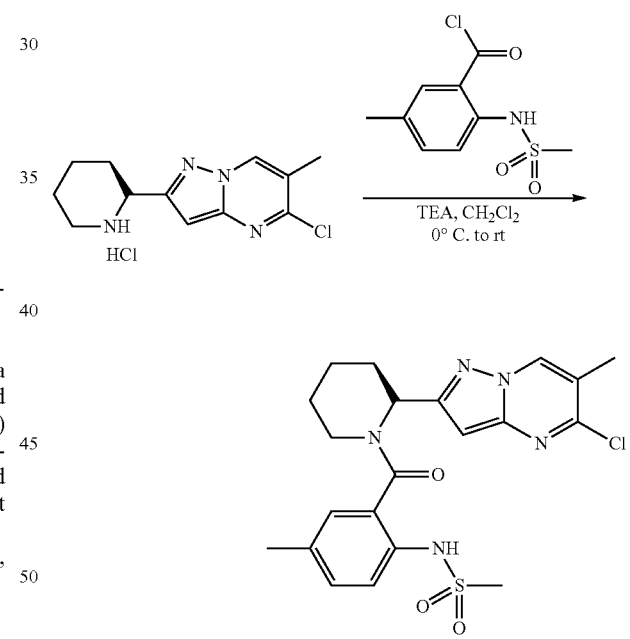

Triethylamine (0.58 mL, 4.16 mmol) was added slowly to a mixture of intermediate 17 (479 mg, 2.01 mmol) and intermediate 5 (573 mg, 2.00 mmol) in 10 mL of dichloromethane under argon at 0° C. After 3 hours, LC/MS indicated full conversion to desired product. The reaction mixture was concentrated and dried in-vacuo to yield intermediate 18 that was used in the next steps without further purification.

LCMS m/z [M+11]$^+$ C$_{21}$H$_{24}$ClN$_5$O$_3$S requires: 462.13. Found 462.32.

Example 20

Preparation of Compound 200

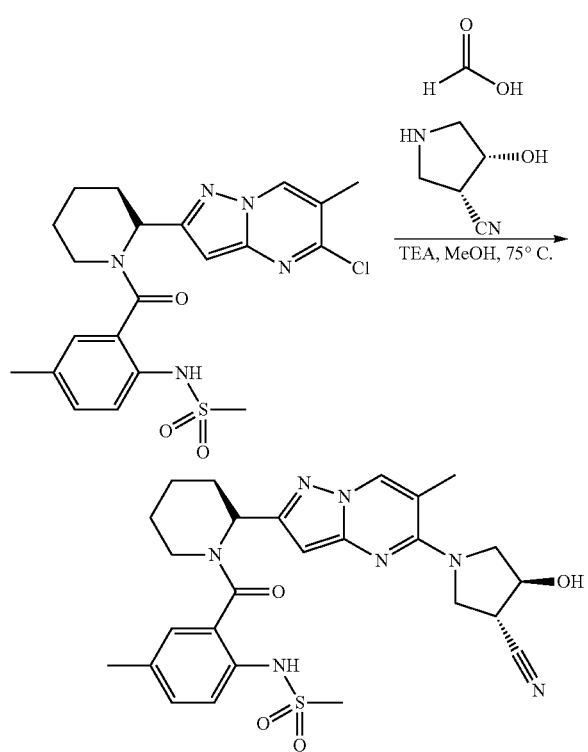

Triethylamine (0.100 mL, 0.717 mmol) was added to a mixture of intermediate 18 (102 mg, 0.221 mmol) and intermediate 17 (50 mg, 0.316 mmol) in 3 mL of methanol at room temperature. After heating at 75° C. overnight, reaction mixture was cooled to room temperature and concentrated under reduced pressure. The remaining residue was purified by silica gel column chromatography (10-75% ethyl acetate in hexanes) to yield compound 200.

LCMS m/z $[M+H]^+$ $C_{26}H_{31}H_7O_4S$ requires: 538.22. Found 538.01.

HPLC Tr (min), purity %: 6.10, 97%.

Example 21

Preparation of Compound 201

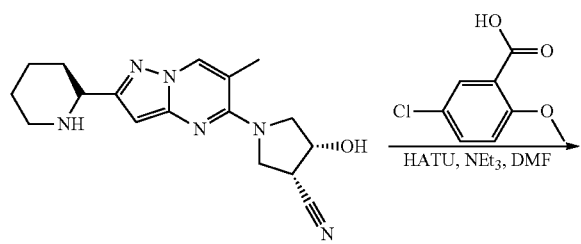

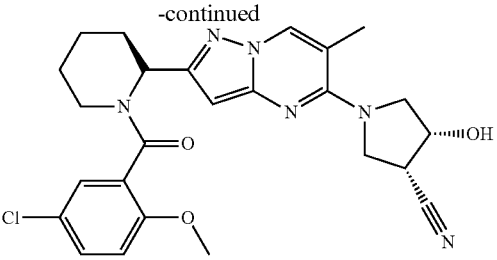

2-Methoxy-5-chlorobenzoic acid (29 mg, 0.17 mmol) and HATU (76 mg, 0.2 mmol) were dissolved in DMF (2 ml). The reaction mixture was stirred at room temperature for 10 mins. To the above solution was added intermediate C1 (35 mg, 0.1 mmol) and $NEt_3$ (55 µl). The reaction was stirred at room temperature for 30 mins and was quenched with brine (10 ml) and then extracted with EtOAc (20 ml). The organic layer was washed with brine twice (10 ml) and then was evaporated under reduced pressure. The residue was purified with prep HPLC (0-100% $CH_3CN/H_2O$) to afford compound 201.

LCMS (m/z) 495.17 $[M+H]^+$.

MW 493.97.

Example 22

Preparation of Compound 202

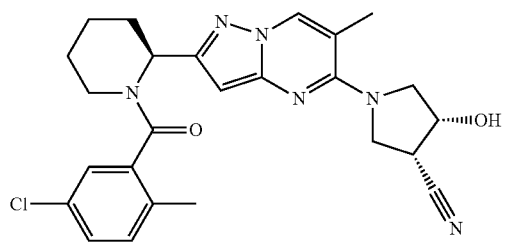 [SMILES: Cc1ccc(Cl)cc1C(=O)N1CCCC[C@H]1c1cc2nc(N3C[C@@H](C#N)[C@@H](O)C3)c(C)cn2n1]

The title compound was prepared according to the procedure for compound 201 starting from intermediate C1 and 2-methyl-5-chlorobenzoic acid.

LCMS (m/z) 479.20 $[M+H]^+$.

MW 477.97.

Example 23

Preparation of Intermediate 19

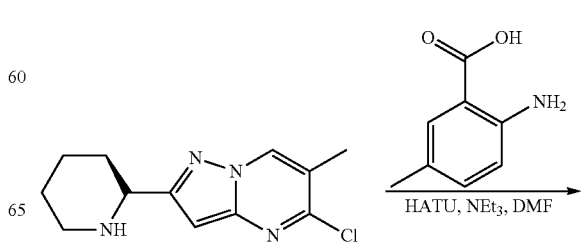

-continued

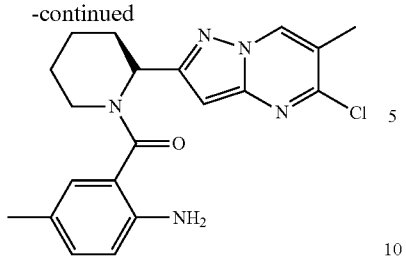

2-Amino-5-methylbenzoic acid (316 mg, 2.09 mmol), HATU (992 mg, 2.61 mmol) were dissolved in anhydrous DMF (2 ml). After activation for 1 hour, intermediate 5 (500 mg, 1.74 mmol) and triethylamine (0.7 ml) was added to the above solution. The reaction was stirred under nitrogen for 2 hours. Solvents were removed by rotary evaporation. The residue was purified with silica gel column chromatography to provide intermediate 19.

LCMS m/z [M+H]$^+$ C$_{20}$H$_{22}$ClN$_5$O requires: 384.15. Found 383.99.

HPLC Tr (min), purity %: 2.00, 98%.

Example 24

Preparation of Intermediate 20

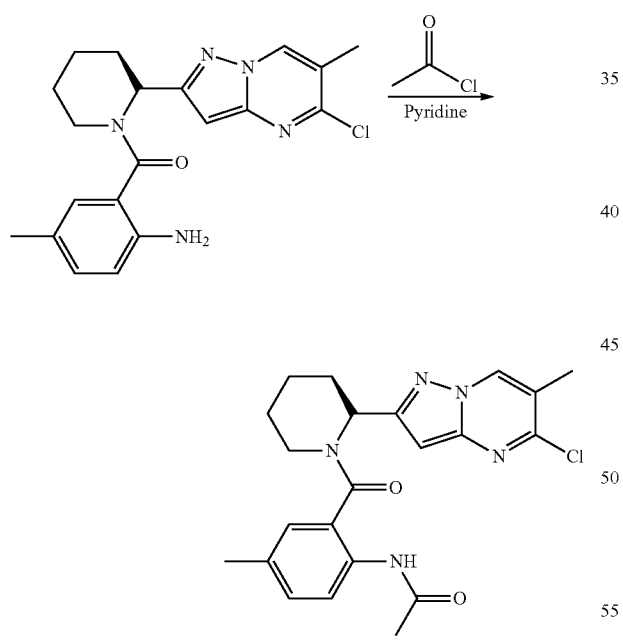

Intermediate 19 (320 mg, 0.84 mmol) was dissolved in pyridine (2 ml). Then acetyl chloride (78 mg, 1.0 mmol) was added to the above solution. The reaction was stirred under nitrogen for 30 mins. Solvents were removed by rotary evaporation. The residue was purified with silica gel column chromatography to provide intermediate 20.

LCMS m/z [M+H]$^+$ C$_{22}$H$_{24}$ClN$_5$O$_2$ requires: 426.16. Found 425.89.

HPLC Tr (min), purity %: 2.40, 98%.

Example 25

Preparation of Compound 203

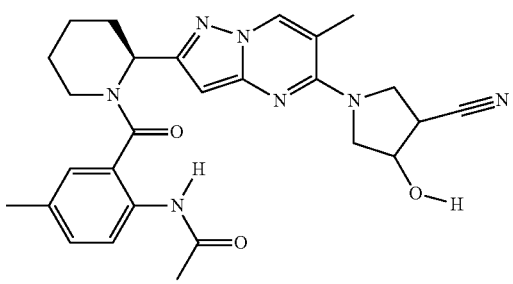 [SMILES: CC(=O)Nc1ccc(C)cc1C(=O)N1CCCC[C@H]1c1cc2nc(N3CC(O)C(C#N)C3)c(C)cn2n1]

The title compound was prepared in 25% yield according to the procedure for compound 201 starting from intermediate 20 and the cis and trans mixture of 3-cyano-4-hydroxy-pyrrolidine. Compound 203 was obtained as a mixture of all 4 isomers at the pyrrolidine.

LCMS (m/z) 501.87 [M+H]$^+$.

MW 500.58.

Example 26

Preparation of Compound 204

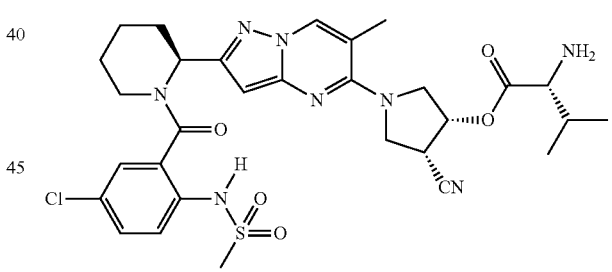

Intermediate D1 (Example 7) (0.100 g) was dissolved in DMF (2 ml) and Boc-L-valine (0.075 g), DMAP (0.02 g) and HATU (0.096 g) added with stirring at room temperature. After 5 h, the solution was diluted with MeCN (2 ml) and water (4 ml) and was purified with preparatory HPLC to yield the corresponding ester. The ester was dissolved in dioxane (2 ml) and HCl (4M in dioxane, 2 ml) was added with stirring. After 2 h, volatiles were removed at room temperature and the crude product was purified with preparatory HPLC to yield compound 204.

LCMS (m/z) 657.23, Tr=1.64 min.

MW 657.18.

Example 27

Preparation of Compound 205

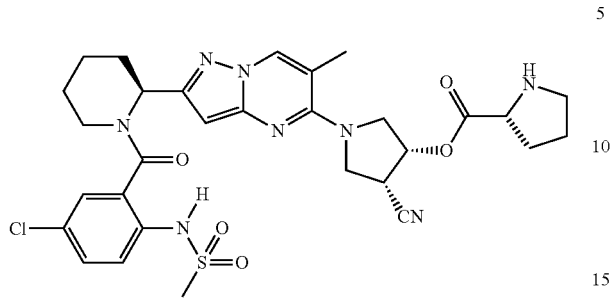

The title compound was prepared in an analogous way as described for compound 204 above utilizing proline to afford the product compound 205.

LCMS (m/z) 655.21, Tr=1.58 min.
CALC. MW 655.17.

Example 28

Preparation of Compound 206

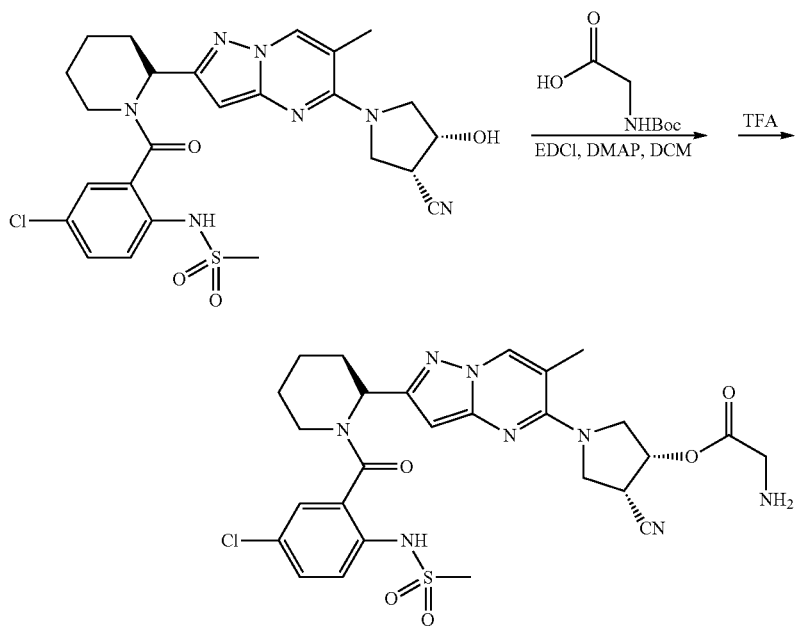

Intermediate D1 (Example 7) (200 mg, 0.36 mmol) was dissolved in DCM (2 ml), to the above solution was added Boc-Glycine (90 mg, 0.6 mmol) and EDCI (111 mg, 0.58 mmol) followed by DMAP (23 mg, 0.18 mmol). The reaction mixture was stirred at room temperature for 3 hours. To the above reaction mixture was added TFA (0.1 ml) and stirred at room temperature for 1 h. The solvent was evaporated under reduced pressure and purified with prep HPLC (Gemini C18, 100 30 mm, 5 micron column) using a gradient of water/acetonitrile 0-100 to afford the title compound 206.

LCMS (m/z) 615.24 [M+H], Tr=2.67 min.
CALC. MW 615.22.

Example 29

Preparation of Compound 207

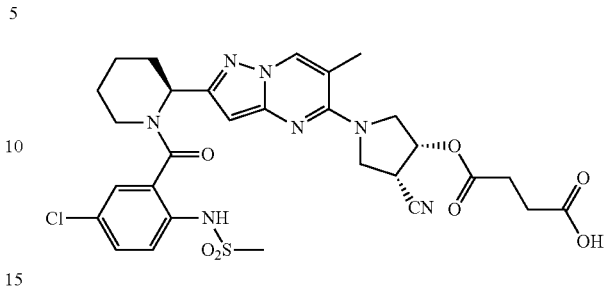

Into oven-dried, argon purged flask were placed intermediate D1 (Example 7) (140 mg, 0.25 mmol), succinic anhydride (55 mg, 0.55 mmol) and catalytic amount (1 mg) of 4-dimethylaminopyridine. The flask was sealed with septa and repurged with argon three times. Dry tetrahydrofuran (20 mL) was added into the reaction mixture via syringe, followed by diisopropylethylamine (72 mg, 0.56 mmol). This reaction mixture was heated for 14 hours at 70° C. to achieve the full conversion. The solvent was evaporated, the residue was dissolved in ethyl acetate (30 mL) and this solution was washed twice with 10% solution of citric acid (30 mL), brine (30 mL), dried over magnesium sulfate, filtered and evaporated. The residue was purified by silica gel chromatography using gradient of dichloromethane/methanol (from 10/0 to 9/1) to afford the title compound 207.

TLC $R_f$=0.49 (10% methanol in dichloromethane, silica gel).

LCMS (m/z) 658.2 (100%) and 660.2 (44%) [M+H]$^+$; 655.8 (100%) and 657.9 (40%) [M−H]$^+$, Tr=3.96 min., purity>99%.

For $C_{29}H_{32}ClN_7O_7S$ Calc. MW 657.2 (100%) and 659.2 (37%).

$^1$H-NMR (CDCl$_3$, 400 MHz): 9.19 (s, 1H), 8.73 (s, 1H), 7.61 (d, J=8.8 Hz, 1H), 7.31 (d, J=8.8 Hz, 1H), 7.25 (s, 1H), 6.14 (s, 1H), 6.03 (s, 1H), 5.51 (s, 1H), 5.23 (s, 1H), 4.04 (m, 3H), 3.75 (m, 1H), 3.34 (m, 1H), 3.19 (m, 1H), 3.06 (m, 1H), 2.84 (m, 2H), 2.66 (m, 3H), 2.29 (m, 3H), 2.00-1.22 (m, 6H).

Example 30

Preparation of Compound 208

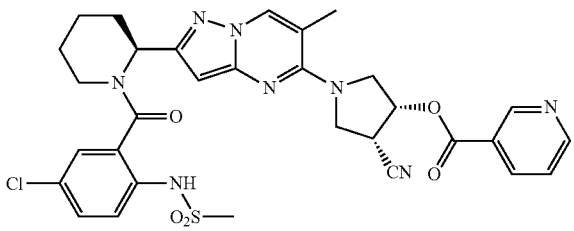 [SMILES: Cc1cn2nc([C@@H]3CCCCN3C(=O)c3cc(Cl)ccc3NS(C)(=O)=O)cc2nc1N1C[C@@H](C#N)[C@@H](OC(=O)c2cccnc2)C1]

Into oven-dried, argon purged flask were placed intermediate D1 (Example 7) (56 mg, 0.1 mmol), niacin (19 mg, 0.15 mmol) and 4-dimethylaminopyridine (18 mg, 0.15 mmol). The flask was sealed with septa and repurged with argon three times. Dry dichloromethane (20 mL) was added into the reaction mixture via syringe, followed by 1-ethyl-3-(3-dimethylaminopropyl)carbodiimide hydrochloride (67 mg, 0.3 mmol). This reaction mixture was repurged with argon three times and stirred at room temperature for 10 minutes to achieve the full conversion. The solvent was evaporated, the residue was dissolved in ethyl acetate (30 mL) and this solution was washed twice with 5% solution of citric acid (30 mL), saturated solution of NaHCO$_3$ (30 mL), water (30 mL), brine (30 mL), dried over magnesium sulfate, filtered and evaporated. The residue was purified by silica gel chromatography using gradient of dichloromethane/methanol (from 10/0 to 95/5) to afford the title compound.

TLC R$_f$=0.78 (5% methanol in dichloromethane, silica gel).

LCMS (m/z) 663.3 (100%) and 665.2 (43%) [M+H]$^+$; 661.2 (100%) and 663.2 (38%) [M−H]$^+$, Tr=4.19 min., purity>99%.

For C$_{31}$H$_{31}$ClN$_8$O$_5$S Calc. MW 662.2 (100%) and 664.2 (38%).

$^1$H-NMR (CDCl$_3$, 400 MHz): 9.21 (s, 1H), 8.77 (d, J=4.2 Hz, 1H), 8.74 (s, 1H), 8.31 (d, J=7.9 Hz, 1H), 7.61 (d, J=8.8 Hz, 1H), 7.39 (dd, J=7.9 Hz, J=4.2 Hz, 1H), 7.31 (d, J=8.8 Hz, 1H), 7.24 (s, 1H), 6.14 (m, 1H), 6.02 (s, 1H), 5.73 (m, 1H), 4.16 (m, 4H), 3.88 (m, 1H), 3.47 (m, 1H), 3.00 (s, 1H), 3.06 (m, 1H), 2.82 (s, 3H), 2.31 (s, 3H), 1.60-1.22 (m, 6H).

Example 31

Preparation of Compound 209

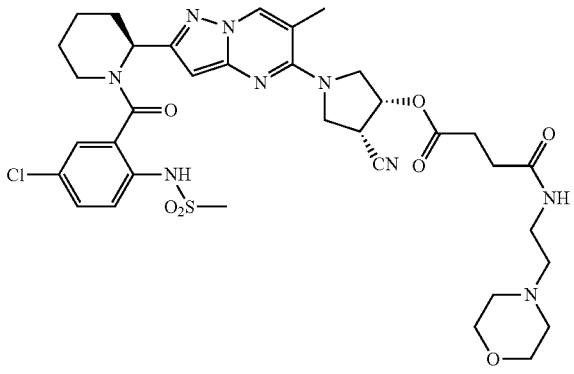 [SMILES: Cc1cn2nc([C@@H]3CCCCN3C(=O)c3cc(Cl)ccc3NS(C)(=O)=O)cc2nc1N1C[C@@H](C#N)[C@@H](OC(=O)CCC(=O)NCCN2CCOCC2)C1]

Into oven-dried, argon purged flask were placed compound 207 (123 mg, 0.19 mmol) and 2-morpholinoethanamine (27 mg, 0.21 mmol). The flask was sealed with septa and repurged with argon three times. Reaction flask was placed in an ice-bath. 6 mL of dry acetonitrile were added into the reaction mixture via syringe, followed by diisopropylethylamine (97 mg, 0.75 mmol) and O-(7-azabenzotriazol-1-yl)-N,N,N',N'-tetramethyluronium hexafluorophosphate (107 mg, 0.28 mmol). This reaction mixture was repurged three times with argon, the ice-bath was removed and the reaction mixture was stirred at room temperature for 5 minutes to achieve the full conversion. The solvent was evaporated and the residue was purified by silica gel chromatography (triethylamine neutralized silica gel) using gradient of dichloromethane/methanol (from 10/0 to 9/1) to afford the title compound 209.

TLC R$_f$=0.57 (10% methanol in dichloromethane, silica gel).

LCMS (m/z) 770.3 (100%) and 772.2 (51%) [M+H]$^+$; 768.2 (100%) and 770.1 (43%) [M−H]$^+$, Tr=2.95 min., purity>99%.

For C$_{35}$H$_{44}$ClN$_9$O$_7$S Calc. MW 769.3 (100%) 771.3 (37%).

$^1$H-NMR (CDCl$_3$, 400 MHz): 9.23 (s, 1H), 8.72 (s, 1H), 7.62 (d, J=8.7 Hz, 1H), 7.31 (d, J=8.7 Hz, 1H), 7.25 (m, 1H), 6.14 (m, 1H), 6.00 (s, 2H), 5.51 (m, 1H), 5.23 (s, 2H), 4.03 (m, 1H), 3.75 (m, 1H), 3.64 (m, 6H), 3.26 (m, 2H), 3.19 (m, 1H), 3.06 (m, 2H), 2.80 (s, 3H), 2.73 (m, 2H), 2.45 (m, 2H), 2.38 (m, 3H), 2.28 (s, 3H), 1.94-1.22 (m, 4H).

Example 32

Preparation of Intermediate 32

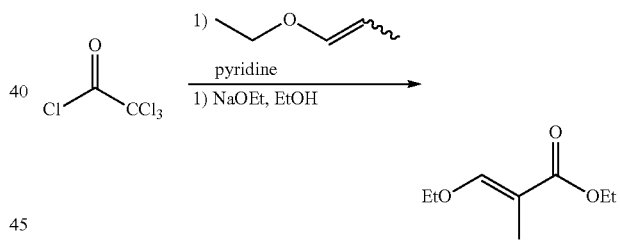

A solution of 1-ethoxy-propene (5.1 mL, 46 mmol) in pyridine (3.4 mL) was added slowly via addition funnel (~1 drop/sec) to neat trichloroacetyl chloride (4.7 mL, 42 mmol) at −10° C. under an argon atmosphere. The reaction mixture was then allowed to slowly warm to 23° C. After 20 h, the reaction mixture was diluted with dichloromethane (50 mL) and the resulting mixture was washed with 0.01N HCl (3 50 mL) and brine (50 m L), was dried over anhydrous sodium sulfate, and was concentrated under reduced pressure. To the crude residue was added sodium ethoxide (21 wt % in ethanol, 7.1 g, 44 mmol) slowly via syringe. After 30 min, the reaction mixture was partitioned between dichloromethane (500 mL) and water (500 mL). The phases were split and the aqueous layer was extracted with dichloromethane (500 mL). The combined organic extracts were dried over anhydrous sodium sulfate, and were concentrated to afford intermediate 32.

$^1$H-NMR (CDCl$_3$, 400 MHz): 7.28 (app s, 1H), 4.09 (q, J=7.1 Hz, 2H), 3.96 (q, J=7.1 Hz, 2H), 1.66 (s, 3H), 1.25 (t, J=7.1 Hz, 3H), 1.20 (t, J=7.1 Hz, 3H).

Antiviral Activity

Another embodiment relates to methods of inhibiting viral infections, comprising the step of treating a sample or subject suspected of needing such inhibition with a composition of the invention.

Samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and manmade materials such as cell cultures.

If desired, the anti-virus activity of a compound described herein after application of the composition can be observed by any method including direct and indirect methods of detecting such activity. Quantitative, qualitative, and semi-quantitative methods of determining such activity are all contemplated. Typically one of the screening methods described above are applied, however, any other method such as observation of the physiological properties of a living organism are also applicable.

The antiviral activity of a compound described herein can be measured using standard screening protocols that are known. For example, the antiviral activity of a compound can be measured using the following general protocols.

Respiratory Syncytial Virus (RSV) Antiviral Activity and Cytotoxicity Assays

Anti-RSV Activity

Antiviral activity against RSV was determined using an in vitro cytoprotection assay in Hep2 cells. In this assay, compounds inhibiting the virus replication exhibit cytoprotective effect against the virus-induced cell killing were quantified using a cell viability reagent. The method used was similar to methods previously described in published literature (Chapman et al., *Antimicrob Agents Chemother.* 2007, 51(9):3346-53.)

Hep2 cells were obtained from ATCC (Manassas, VI) and maintained in MEM media supplemented with 10% fetal bovine serum and penicillin/streptomycin. Cells were passaged twice a week and kept at subconfluent stage. Commercial stock of RSV strain A2 (Advanced Biotechnologies, Columbia, Md.) was titered before compound testing to determine the appropriate dilution of the virus stock that generated desirable cytopathic effect in Hep2 cells.

For antiviral tests, Hep2 cells were seeded into 96-well plates 24 hours before the assay at a density of 3,000 cells/well. On a separate 96well plate, compounds to be tested were serially diluted in cell culture media. Eight concentrations in 3-fold serial dilution increments were prepared for each tested compound and 100 uL/well of each dilution was transferred in duplicate onto plates with seeded Hep2 cells. Subsequently, appropriate dilution of virus stock previously determined by titration was prepared in cell culture media and 100 uL/well was added to test plates containing cells and serially diluted compounds. Each plate included three wells of infected untreated cells and three wells of uninfected cells that served as 0% and 100% virus inhibition control, respectively. Following the infection with RSV, testing plates were incubated for 4 days in a tissue culture incubator. After the incubation, RSV-induced cytopathic effect was determined using a Cell TiterGlo reagent (Promega, Madison, Wis.) followed by a luminescence read-out. The percentage inhibition was calculated for each tested concentration relative to the 0% and 100% inhibition controls and the EC50 value for each compound was determined by non-linear regression as a concentration inhibiting the RSV-induced cytopathic effect by 50%. Ribavirin (purchased from Sigma, St. Louis, Mo.) was used as a positive control for antiviral activity.

Compounds were also tested for antiviral activity against RSV in Hep2 cells using a 384 well format. Compounds were diluted in DMSO using a 10-step serial dilution in 3-fold increments via automation in 4 adjacent replicates each. Eight compounds were tested per dilution plate. 0.4 uL of diluted compounds were then stamped via Biomek into 384-well plates (Nunc 142761 or 164730 w/lid 264616) containing 20 µL of media (Mediatech Inc. MEM supplemented with Glutamine, 10% FBS and Pen/Strep). DMSO and a suitable positive control compound, such as 80 µM GS-329467 or 10 µM 427346 was used for the 100% and 0% cell killing controls, respectively.

Hep2 cells ($1.0 \times 10^5$ cells/ml) were prepared as above in batch to at least 40 mls excess of the number of sample plates (8 mls cell mix per plate) and infected with vendor supplied (ABI) RSV strain A2 to arrive at an MOI of 1:1000 (virus:cell #) or 1:3000 (vol virus:cell vol). Immediately after addition of virus, the RSV infected Hep2 cell suspension was added to each stamped 384-well plate at 20 µl per well using a uFlow dispenser, giving a final volume of 40 µL/well, each with 2000 infected cells. The plates were then incubated for 5 days at 37° C. and 5% $CO_2$. Following incubation, the plates were equilibrated to room temperature in a biosafety cabinet hood for 1.5 hrs and 40 µL of Cell-Titer Glo viability reagent (Promega) was added to each well via uFlow. Following a 10-20 minute incubation, the plates were read using an EnVision or Victor Luminescence plate reader (Perkin-Elmer). The data was then uploaded and analyzed on the Bioinformatics portal under the RSV Cell Infectivity and 8-plate EC50-Hep2-384 or 8-plate EC50-Hep2-Envision protocols.

Multiple point data generated in the assay was analysed using Pipeline Pilot (Accelrys, Inc., Version 7.0) to generate a dose response curve based on least squares fit to a 4-parameter curve. The generated formula for the curve was then used to calculate the % inhibition at a given concentration. The % inhibition reported in the table was then adjusted based on the normalization of the bottom and top of the curve % inhibition values to 0% and 100% respectively.

Representative activities for the compounds of the invention against RSV-induced cytopathic effects are shown in the Table below.

| Compound formula | Percent inhibition at 0.5 µM |
|---|---|
| 1 | 100 |
| 2 | 100 |
| 3 | 100 |
| 4 | 100 |
| 5 | 100 |
| 6 | 100 |
| 7 | 100 |
| 8 | 90 |
| 9 | 99 |
| 10 | 95 |
| 11 | 92 |
| 12 | 89 |
| 13 | 82 |
| 14 | 81 |

| Compound formula | Percent inhibition at 0.5 μM |
|---|---|
| 15 | 82 |
| 16 | 71 |
| 17 | 70 |
| 18 | 70 |
| 19 | 70 |
| 20 | 63 |
| 21 | 58 |
| 22 | 55 |
| 23 | 48 |
| 24 | 30 |
| 25 | 100 |
| 26 | 84 |
| 27 | 100 |
| 28 | 100 |
| 29 | 71 |
| 30 | 100 |
| 31 | 100 |
| 32 | 79 |
| 33 | 99 |
| 34 | 13 |
| 35 | 100 |
| 36 | 98 |
| 37 | 100 |
| 38 | 100 |
| 39 | 100 |
| 40 | 95 |
| 41 | 4 |
| 42 | 9 |
| 43 | 88 |
| 44 | 100 |
| 45 | 45 |
| 46 | 100 |
| 47 | 90 |
| 48 | 100 |
| 49 | 99 |
| 50 | 15 |
| 51 | 100 |
| 52 | 71 |
| 53 | 25 |
| 54 | 100 |
| 55 | 5 |
| 56 | 84 |
| 57 | 13 |
| 58 | 61 |
| 59 | 52 |
| 60 | 100 |
| 61 | 100 |
| 62 | 11 |
| 63 | 100 |
| 64 | 100 |
| 65 | 97 |
| 66 | 95 |
| 67 | 21 |
| 68 | 37 |
| 69 | 100 |
| 70 | 56 |
| 71 | 98 |
| 72 | 100 |
| 73 | 99 |
| 74 | 100 |
| 75 | 100 |
| 76 | 99 |
| 77 | 100 |
| 78 | 100 |
| 79 | 100 |
| 80 | 14 |
| 81 | 96 |
| 82 | 100 |
| 83 | 99 |
| 84 | 100 |
| 85 | 100 |
| 86 | 80 |
| 87 | 100 |
| 88 | 100 |
| 89 | 100 |
| 90 | 100 |
| 91 | 100 |
| 92 | 100 |
| 93 | 44 |
| 94 | 88 |
| 95 | 21 |
| 96 | 65 |
| 97 | 100 |
| 98 | 97 |
| 99 | 100 |
| 100 | 100 |
| 101 | 16 |
| 102 | 16 |
| 103 | 100 |
| 104 | 56 |
| 105 | 31 |
| 106 | 100 |
| 107 | 100 |
| 108 | 99 |
| 109 | 100 |
| 110 | 36 |
| 111 | n.d. |
| 112 | 100 |
| 113 | 100 |
| 114 | 100 |
| 115 | 98 |
| 116 | 100 |
| 117 | 46 |
| 118 | 99 |
| 119 | n.d. |
| 120 | 100 |
| 121 | 92 |
| 122 | 100 |
| 123 | 98 |
| 124 | 100 |
| 125 | n.d. |
| 126 | 82 |
| 127 | n.d. |
| 128 | n.d. |
| 129 | 87 |
| 130 | 100 |
| 131 | 96 |
| 132 | 97 |
| 133 | 56 |
| 134 | 35 |
| 135 | 100 |
| 136 | 83 |
| 137 | n.d. |
| 138 | 65 |
| 139 | 100 |
| 140 | 100 |
| 141 | n.d. |
| 142 | 100 |
| 143 | 100 |
| 144 | 80 |
| 145 | 60 |
| 146 | 100 |
| 147 | n.d. |
| 148 | 77 |
| 149 | 100 |
| 150 | 99 |
| 151 | 100 |
| 152 | 100 |
| 153 | 100 |
| 154 | 90 |
| 155 | 100 |
| 156 | 100 |
| 157 | 98 |
| 158 | n.d. |
| 159 | 91 |
| 160 | 71 |
| 161 | 61 |
| 162 | 100 |
| 163 | 100 |
| 164 | n.d. |
| 165 | 92 |
| 166 | 100 |

-continued

| Compound formula | Percent inhibition at 0.5 μM |
|---|---|
| 167 | 100 |
| 168 | 44 |
| 169 | 100 |
| 170 | 100 |
| 171 | 100 |
| 172 | 100 |
| 173 | 98 |
| 174 | 58 |
| 175 | 91 |
| 176 | 97 |
| 177 | 99 |
| 178 | 100 |
| 179 | 93 |
| 180 | 94 |
| 181 | 83 |
| 182 | 93 |
| 183 | 100 |
| 184 | 100 |
| 185 | 100 |
| 186 | 100 |
| 187 | 100 |
| 188 | 100 |
| 189 | 89 |
| 190 | 100 |
| 191 | n.d. |
| 192 | 100 |
| 193 | n.d |
| 194 | n.d |
| 195 | n.d |
| 196 | 96 |
| 197 | 100 |
| 198 | 100 |
| 199 | 100 |
| 200 | 100 |
| 201 | 100 |
| 202 | 100 |
| 203 | 100 |
| 204 | 100 |
| 205 | 100 |
| 206 | 100 |
| 207 | 100 |
| 208 | 100 |
| 209 | 100 |

(n.d. not determined)

Cytotoxicity

Cytotoxicity of tested compounds was determined in uninfected Hep2 cells in parallel with the antiviral activity using the cell viability reagent in a similar fashion as described before for other cell types (Cihlar et al., *Antimicrob Agents Chemother.* 2008, 52(2):655-65). The same protocol as for the determination of antiviral activity was used for the measurement of compound cytotoxicity except that the cells were not infected with RSV. Instead, fresh cell culture media (100 uL/well) without the virus was added to tested plates with cells and prediluted compounds. Cells were then incubated for 4 days followed by a cell viability test using CellTiter Glo reagent and a luminescence read-out. Untreated cell and cells treated with 50 ug/mL puromycin (Sigma, St. Louis, Mo.) were used as 100% and 0% cell viability control, respectively. The percent of cell viability was calculated for each tested compound concentration relative to the 0% and 100% controls and the CC50 value was determined by non-linear regression as a compound concentration reducing the cell viability by 50%.

To test for compound cytotoxicity in Hep2 cells using a 384 well format, compounds were diluted in DMSO using a 10-step serial dilution in 3-fold increments via automation in 4 adjacent replicates each. Eight compounds were tested per dilution plate. 0.4 uL of diluted compounds were then stamped via Biomek into 384-well plates (Nunc 142761 or 164730 w/lid 264616) containing 20 μL of media (Mediatech Inc. MEM supplemented with Glutamine, 10% FBS and Pen/Strep). 50 μg/mL puromycin and DMSO were used for the 100% and 0% cytotoxicity controls, respectively.

Hep2 cells ($1.0 \times 10^5$ cells/nil) were added to each stamped plate at 20 ul per well to give a total of 2000 cells/well and a final volume of 40 μL/well. Usually, the cells were batch prediluted to $1.0 \times 10^5$ cells/mL in excess of the number of sample plates and added at 20 ul per well into each assay plate using a uFlow dispenser. The plates were then incubated for 4 days at 37° C. and 5% $CO_2$. Following incubation, the plates were equilibrated to room temperature in a biosafety cabinet hood for 1.5 hrs and 40 μL of Cell-Titer Glo viability reagent (Promega) was added to each well via uFlow. Following a 10-20 minute incubation, the plates were read using an EnVision or Victor Luminescence plate reader (Perkin-Elmer). The data was then uploaded and analyzed on the Bioinformatics portal (Pipeline Pilot) under the Cytotoxicity assay using the 8-plate CC50-Hep2 or 8-plate CC50-Hep2 Envision protocols. Compounds tested for Anti-RSV activity were also tested in this cyctotoxicity assay.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A compound of the formula:

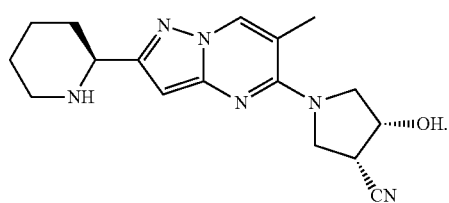 [SMILES: Cc1cn2nc([C@@H]3CCCCN3)cc2nc1N1C[C@@H](C#N)[C@@H](O)C1]

* * * * *